US011820774B2

(12) United States Patent
Blass et al.

(10) Patent No.: US 11,820,774 B2
(45) Date of Patent: *Nov. 21, 2023

(54) MODULATORS OF THE SIGMA-2 RECEPTOR AND THEIR METHOD OF USE

(71) Applicant: Temple University—Of the Commonwealth System of Higher Education, Philadelphia, PA (US)

(72) Inventors: Benjamin E. Blass, Eagleville, PA (US); Daniel J. Canney, Ambler, PA (US); Kevin M. Blattner, Folsom, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 10 days.

This patent is subject to a terminal disclaimer.

(21) Appl. No.: 17/154,761

(22) Filed: Jan. 21, 2021

(65) Prior Publication Data
US 2021/0363145 A1 Nov. 25, 2021

Related U.S. Application Data

(63) Continuation of application No. 16/496,073, filed as application No. PCT/US2018/022574 on Mar. 15, 2018, now Pat. No. 10,961,249.

(60) Provisional application No. 62/474,277, filed on Mar. 21, 2017.

(51) Int. Cl.
C07D 487/04 (2006.01)

(52) U.S. Cl.
CPC .................. C07D 487/04 (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,148,408 B2 | 4/2012 | Bunnelle et al. | |
| 10,961,249 B2 * | 3/2021 | Blass | C07D 203/00 |
| 2009/0170824 A1 | 7/2009 | Castro Pineiro et al. | |
| 2013/0178458 A1 | 7/2013 | Lindsley et al. | |
| 2015/0291539 A1 | 10/2015 | Canney et al. | |
| 2016/0016941 A1 | 1/2016 | Canney et al. | |
| 2016/0185785 A1 | 6/2016 | Ioannidis et al. | |
| 2016/0303084 A1 | 10/2016 | Chen et al. | |
| 2017/0298037 A1 | 10/2017 | Canney et al. | |
| 2018/0221365 A1 | 8/2018 | Canney et al. | |
| 2019/0367528 A1 | 12/2019 | Canney et al. | |

FOREIGN PATENT DOCUMENTS

| | | |
|---|---|---|
| JP | 2007-526333 A | 9/2007 |
| JP | 2010-509402 A | 3/2010 |
| JP | 2011-519936 A | 7/2011 |
| JP | 2016-540792 A | 12/2016 |
| JP | 2019-535825 | 12/2019 |
| JP | 2020-511515 | 4/2020 |
| WO | WO 2009/137308 A1 | 11/2009 |
| WO | WO 2014/160592 A2 | 10/2014 |
| WO | WO 2014/164756 A1 | 10/2014 |
| WO | WO 2016/040554 A1 | 3/2016 |
| WO | WO 2016/055394 A1 | 4/2016 |
| WO | WO 2016/183150 A1 | 11/2016 |
| WO | WO 2018/093818 A1 | 5/2018 |
| WO | WO 2018175188 | 9/2018 |
| WO | WO 2018175190 | 9/2018 |
| WO | WO 2019217890 | 11/2019 |
| WO | WO 2021/097116 A1 | 5/2021 |
| WO | WO 2021/097117 A2 | 5/2021 |

OTHER PUBLICATIONS

Li, @ 2016 International Society for Neurochemistry, J. Neurochem. (2017) 140, 561-575.*
Bhandare et al., "Modifications to five-substituted 3,3-diethyl-4,5-dihydro-2(3H)-furanones en route to novel muscarinic receptor ligands.", Medicinal Chemistry Research, vol. 20, No. 5, 2011, pp. 558-565, XP055283393.
Bhandare et al., "Bioisosteric Replacement and Related Analogs in the Design, Synthesis and Evaluation of Ligands for Muscarinic Acetylcholine Receptors," Med. Chem. (2014) 10:361-375.
Gao et al., "Homologation as a lead modification approach en route to a series of lactone-based muscarinic ligands", Medicinal Chemistry Research., vol. 23, No. 2, Aug. 22, 2013 (Aug. 22, 2013), pp. 1023-1030, XP055305444, US, ISSN: 1054-2523, DOI: 10.1007/s00044-013-0692-3.
Guo, Lin, and Xuechu Zhen. "Sigma-2 receptor ligands: neurobiological effects." Current medicinal chemistry 22.8 (2015): 989-1003.
Hellewell, Susan B., and Wayne D. Bowen. "A sigma-like binding site in rat pheochromocytoma (PC12) cells: decreased affinity for (+)-benzomorphans and lower molecular weight suggest a different sigma receptor form from that of guinea pig brain." Brain research 527.2 (1990): 244-253.
International Preliminary Report on Patentability dated Sep. 24, 2019 for PCT/US2018/022574.
International Search Report dated May 4, 2018 for PCT/US2018/022574.
Izzo, Nicholas J., et al. "Alzheimer's therapeutics targeting amyloid beta 1-42 oligomers I: Abeta 42 oligomer binding to specific neuronal receptors is displaced by drug candidates that improve cognitive deficits." PloS one 9.11 (2014).
Izzo, Nicholas J., et al. "Alzheimer's therapeutics targeting amyloid beta 1-42 oligomers II: Sigma-2/PGRMC1 receptors mediate Abeta 42 oligomer binding and synaptotoxicity." PloS one 9.11 (2014).
Lee Collier, Thomas, Rikki N. Waterhouse, and Michael Kassiou. "Imaging sigma receptors: applications in drug development." Current pharmaceutical design 13.1 (2007): 51-72.

(Continued)

*Primary Examiner* — Nizal S Chandrakumar
(74) *Attorney, Agent, or Firm* — Proskauer Rose LLP

(57) ABSTRACT

Pharmaceutical compositions of the invention comprise functionalized lactone derivatives having a disease-modifying action in the treatment of diseases associated with dysregulation of sigma-2 receptor activity.

6 Claims, No Drawings

(56) References Cited

OTHER PUBLICATIONS

Martin, W. R., and C. G. Eades. "Thompson, JA, Huppler, RE and Gilbert." *PE: The effects of morphine-and nalorphine-like drugs in the nondependent and morphine-dependent chronic spinal dog. J. Pharmacol. Exp. Ther* 197 (1976): 517-532.

Matsumoto, Rae R. "σ Receptors: historical perspective and background." *Sigma Receptors.* Springer, Boston, MA, 2007. 1-23.

Skuza, Grazyna. "Pharmacology of sigma (σ) receptor ligands from a behavioral perspective." *Current pharmaceutical design* 18.7 (2012): 863-874.

Written Opinion of the International Searching Authority dated May 4, 2018 for PCT/US2018/022574.

Xu, Jinbin, et al. "Identification of the PGRMC1 protein complex as the putative sigma-2 receptor binding site." *Nature communications* 2.1 (2011): 1-7.

\* cited by examiner

MODULATORS OF THE SIGMA-2 RECEPTOR AND THEIR METHOD OF USE

CROSS-REFERENCE TO RELATED APPLICATIONS

This application is a continuation application of U.S. application Ser. No. 16/496,073, filed Sep. 20, 2019, which is a 35 U.S.C. § 371 National Stage Application of International Application No. PCT/US2018/022574, filed Mar. 15, 2018, which claims priority to U.S. Provisional Patent Application No. 62/474,277, filed Mar. 21, 2017, the contents of which are incorporated herein by reference in their entireties.

STATEMENT REGARDING FEDERALLY SPONSORED RESEARCH OR DEVELOPMENT

This invention was made with government support under grant number HHSN-271-2008-00025-C awarded by the National Institute of Mental Health and grant number 1R41AG052249-01 awarded by the National Institute on Aging. The government has certain rights in the invention.

FIELD OF INVENTION

Embodiments of the invention are directed to novel compounds useful as sigma-2 receptor binders and their method of use. Embodiments are further directed to a novel chemotype useful for the treatment diseases that are associated with dysregulation of sigma-2 receptor activity.

BACKGROUND OF THE INVENTION

The sigma-1 and sigma-2 receptors were first identified in the mid-1970's based on their interaction with radioligands. In 1976, a study of the physiological properties of (±)-SKF-10,047 (N-allylnormetazocine) and it structurally related benzomorphan analogues, morphine and ketazocine, in the chronic spinal dog model identified three receptor sub-types, the μ-opioid receptor, the κ-opioid receptor, and the σ-receptor (sigma receptor) (Martin, W. R.; Eades, C. G.; Thompson, J. A.; Huppler, R. E.; Gilbert, P. E. The effects of morphine- and nalorphine-like drugs in the nondependent and morphine-dependent chronic spinal dog. J. Pharmacol. Exp. Ther. 1976, 197, 517-532). It subsequently determined that (−)-SKF-10,047 binds to the μ-opioid receptor and the κ-opioid receptor, while (+)-SKF-10,047 selectively to the 6-receptor (sigma receptor), although the true function of the 6-receptor remained unknown (Matsumoto, R. R. Sigma Receptors: Historical Perspective and Background. In Sigma Receptors: Chemistry, Cell Biology and Clinical Implications; Matsumoto, R. R., Bowen, W. D., Su, T.-P., Eds.; Springer Science: New York, NY, 2007; pp 1-23. Collier, T. L.; Waterhouse, R. N.; Kassiou, M. Imaging sigma receptors: applications in drug development. Curr. Pharm. Des. 2007, 13, 51-72.) The availability of the σ-receptor selective radioligand [³H]o-ditolylguanidine (DTG) facilitated more detailed binding studies of ligand for the σ-receptor, and eventually lead to the identification of two distinct subtypes, the $\sigma_1$-receptor and the $\sigma_2$-receptor (Hellewell, S. B.; Bowen, W. D. A sigma-like binding site in rat pheochromocytoma (PC12) cells: decreased affinity for (+)-benzomorphans and lower molecular weight suggest a different sigma receptor form from that of guinea pig brain. Brain Res. 1990, 527, 244-253.) Although the exact structure of the $\sigma_2$-receptor is unknown, recent studies have photoaffinity labeling studies have suggested that the $\sigma_2$-receptor is synonymous with the progesterone receptor membrane component-1 (PGRMC1) (Xu, J. et al. Identification of the PGRMC1 protein complex as the putative sigma-2 receptor binding site. Nat. Commun. 2, 380 (2011).

The therapeutic utility of compounds capable of binding to the $\sigma_2$-receptor or modulating activity of the $\sigma_2$-receptor has also been explored. It has recently been discovered, for example, that compounds capable of binding to the $\sigma_2$-receptor can prevent the binding of beta amyloid protein (Aβ) oligomers to neurons, thereby preventing downstream synaptotoxicity. This aspect of $\sigma_2$-receptor binders provides an opportunity for the application of $\sigma_2$-receptor binders as treatment for Alzheimer's disease, mild cognitive impairments, and memory disorders. It has further been demonstrated that compounds capable of binding to the $\sigma_2$-receptor can displace beta amyloid protein (Aβ) oligomers from neurons, thereby preventing downstream synaptotoxicity. This aspect of $\sigma_2$-receptor binders also provides an opportunity for the application of $\sigma_2$-receptor binders as treatment for Alzheimer's disease, mild cognitive impairments, and memory disorders (Izzo, N. J. et al. Alzheimer's therapeutics targeting amyloid Beta 1-42 oligomers I: abeta 42 oligomer binding to specific neuronal receptors is displaced by drug candidates that improve cognitive deficits. PLoS One 9, e111898 (2014). Izzo, N. J. et al. Alzheimer's Therapeutics Targeting Amyloid Beta 1-42 Oligomers II: Sigma-2/PGRMC1 Receptors Mediate Abeta 42 Oligomer Binding and Synaptotoxicity. PLoS One 9, e111899 (2014).

Separately, it is has demonstrated that expression of the $\sigma_2$-receptor is elevated in tumor cells as compared with normal cells. Cancer cells in which overexpression of the $\sigma_2$-receptor occurs, but is not limited to, pancreatic cancer, lung cancer, breast cancer, melanoma, prostate cancer, and ovarian cancer. It has been further discovered that compounds capable of binding to the $\sigma_2$-receptor modulate its activity and induce cancer cell death. As such, the $\sigma_2$-receptor is a viable target for the identification of anti-cancer agents, and compounds capable of binding to the $\sigma_2$-receptor represent an opportunity to develop new anti-cancer agents.

The dysregulation of sigma-2 receptor activity has also been implacted in a number of neuropsychiatric disorders including but not limited to generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia (Guo, L.; Zhen, X. Simga-2 Receptor ligands: Neurobiological effects. Current Medicincal Chemistry, 2015, 22, 8, 989-1003. Skuza, G. Pharmacology of sigma (σ) receptor ligands from a behavioral perspective. Current Pharmaceutical Design, 2012, 18, 7, 863-874.). As such, the $\sigma_2$-receptor is a viable target for the treatment of neuropsychiatric disorders including but not limited to generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia. Compounds that bind to the $\sigma_2$-receptor that are capable of modulating $\sigma_2$-receptor represent an opportunity to identify new treatments for a number of neuropsychiatric disorders including but not limited to generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia.

BRIEF SUMMARY OF THE INVENTION

The present invention is directed toward novel sigma-2 receptor binders, compounds of formula (I),

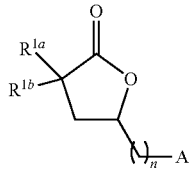

(I)

including hydrates, solvates, pharmaceutically acceptable salts, prodrugs and complexes thereof, wherein:

A is selected from a group consisting of

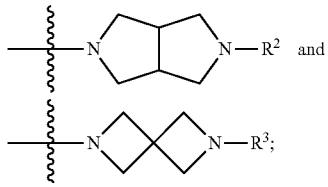

n is 1, 2, or 3;

$R^{1a}$ and $R^{1b}$ are each independently selected from the group consisting of hydrogen, $C_{1-6}$ linear alkyl, and $C_{1-6}$ branched alkyl, or $R^{1a}$ and $R^{1b}$ may be taken together with the atom to which they are bound to form a ring having from 3 to 7 ring atoms;

$R^2$ is selected from a group consisting of a benzene ring that is optionally substituted with 0 to 3 $R^4$ groups that are not hydrogen, a 4-pyridine ring that is optionally substituted with 0 to 2 $R^5$ groups that are not hydrogen, a 3-pyridine ring that is optionally substituted with 0 to 2 $R^5$ groups that are not hydrogen, and a 2-pyridine ring that is optionally substituted with 0 to 2 $R^5$ groups that are not hydrogen;

$R^3$ is selected from a group consisting of a benzene ring that is optionally substituted with 0 to 3 $R^4$ groups that are not hydrogen, a 4-pyridine ring that is optionally substituted with 0 to 2 $R^5$ groups that are not hydrogen, a 3-pyridine ring that is optionally substituted with 0 to 2 $R^5$ groups that are not hydrogen, and a 2-pyridine ring that is optionally substituted with 0 to 2 $R^5$ groups that are not hydrogen;

$R^4$ is at each occurrence independently selected from the group consisting of hydrogen, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2(C_{1-6}$ linear alkyl), $SO_2(C_{3-7}$ branched alkyl), —$SO_2(C_{3-7}$ cycloalkyl), $COR^6$, $CO_2R^7$, $CONR^{8a}R^{8b}$, $SO_2NR^{8a}R^8$, $NR^{9a}R^{9b}$, $NR^{9a}COR^{10}$, $NR^{9a}SO_2R^{11}$, and $NR^{9a}SO_2NR^{12a}R^{12b}$;

the terms $R^{4a}$, $R^{4b}$, $R^{4c}$, $R^{4d}$, and $R^{4e}$ may be used to designate individual $R^4$ groups on a benzene ring;

$R^5$ is at each occurrence independently selected from the group consisting of hydrogen, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^1$, and $NR^{9a}SO_2NR^{12a}R^{12b}$;

the terms $R^{5a}$, $R^{5b}$, $R^{5c}$, and $R^{5d}$ may be used to designate individual $R^5$ groups on a pyridine ring;

$R^6$ is at each occurrence independently selected from the group consisting of hydrogen, $C_{1-6}$ linear alkyl, $C_{3-7}$ branched alkyl, and $C_{3-7}$ cycloalkyl;

$R^7$ is at each occurrence independently selected from the group consisting of $C_{1-6}$ linear alkyl, $C_{3-7}$ branched alkyl, and $C_{3-7}$ cycloalkyl;

$R^{8a}$ is at each occurrence independently selected from the group consisting of H, $C_{1-6}$ linear alkyl, $C_{3-7}$ branched alkyl, and $C_{3-7}$ cycloalkyl;

$R^{8b}$ is at each occurrence independently selected from the group consisting of H, $C_{1-6}$ linear alkyl, $C_{3-7}$ branched alkyl, and $C_{3-7}$ cycloalkyl;

$R^{9a}$ is at each occurrence independently selected from the group consisting of H, $C_{1-6}$ linear alkyl, $C_{3-7}$ branched alkyl, and $C_{3-7}$ cycloalkyl;

$R^{9b}$ is at each occurrence independently selected from the group consisting of H, $C_{1-6}$ linear alkyl, $C_{3-7}$ branched alkyl, and $C_{3-7}$ cycloalkyl;

$R^{9a}$ and $R^{9b}$ may be taken together with the atom to which they are bound to form a ring having from 3 to 7 ring atoms optionally containing an oxygen;

$R^{10}$ is at each occurrence independently selected from the group consisting of H, $C_{1-6}$ linear alkyl, $C_{3-7}$ branched alkyl, and $C_{3-7}$ cycloalkyl;

$R^{11}$ is at each occurrence independently selected from the group consisting of $C_{1-6}$ linear alkyl, $C_{3-7}$ branched alkyl, and $C_{3-7}$ cycloalkyl;

$R^{12a}$ is at each occurrence independently selected from the group consisting of hydrogen, $C_{1-6}$ linear alkyl, $C_{3-7}$ branched alkyl, and $C_{3-7}$ cycloalkyl; and $R^{12b}$ is at each occurrence independently selected from the group consisting of hydrogen, $C_{1-6}$ linear alkyl, $C_{3-7}$ branched alkyl, and $C_{3-7}$ cycloalkyl.

The present invention further relates to compositions comprising: an effective amount of one or more compounds according to the present invention and an excipient.

The present invention also relates to a method for treating or preventing diseases that involve dysregulation of sigma-2 receptor activity, for example neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, schizophrenia, Alzheimer's disease, mild cognitive impairment, and memory disorders, as well as cancer, for example pancreatic cancer, lung cancer, breast cancer, melanoma, prostate cancer, and ovarian cancer said method comprising administering to a subject an effective amount of a compound or composition according to the present invention.

The present invention yet further relates to a method for treating or preventing diseases that involve dysregulation of sigma-2 receptor activity, for example neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, schizophrenia, Alzheimer's disease, mild cognitive impairment, and memory disorders, as well as cancer, for example pancreatic cancer, lung cancer, breast cancer, melanoma, prostate cancer, and ovarian cancer wherein said method comprises administering to a subject a composition comprising an effective amount of one or more compounds according to the present invention and an excipient.

The present invention yet further relates to a method for treating or preventing diseases that involve overexpression of the sigma-2 receptor such as cancer, for example pancreatic cancer, lung cancer, breast cancer, melanoma, prostate cancer, and ovarian cancer said method comprising administering to a subject an effective amount of a compound or composition according to the present invention.

The present invention yet further relates to a method for treating or preventing diseases that involve overexpression of the sigma-2 receptor such as cancer, for example pancreatic cancer, lung cancer, breast cancer, melanoma, prostate cancer, and ovarian cancer wherein said method comprises administering to a subject a composition comprising an effective amount of one or more compounds according to the present invention and an excipient.

The present invention also relates to a method for treating or preventing disease or conditions associated with dysregulation of sigma-2 receptor activity. Said methods comprise administering to a subject an effective amount of a compound or composition according to the present invention.

The present invention yet further relates to a method for treating or preventing disease or conditions associated with dysregulation of sigma-2 receptor activity, wherein said method comprises administering to a subject a composition comprising an effective amount of one or more compounds according to the present invention and an excipient.

The present invention further relates to a process for preparing the sigma-2 receptor binders modulators of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

There is evidence that suggests a role for the sigma-2 receptor in a number of disease states including, but not limited to neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders. Sigma-2 receptor activity modulators are likely to have a beneficial effect on patients suffering from these diseases and disorders. The disorders in which Sigma-2 receptor dysregulation plays a role and modulation of Sigma-2 receptor receptor activity by a therapeutic agent may be a viable approach to therapeutic relief include, but are not limited to, neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders.

There is a long felt need for new Sigma-2 receptor binders and Sigma-2 receptor activity modulators that will provide therapeutic relief from patients suffering from diseases associated with dysregulation of the Sigma-2 receptor. The invention addresses the need to identify novel Sigma-2 receptor binders and Sigma-2 receptor activity modulators capable to treating disease associated with dysregulation of Sigma-2 receptor activity. The present invention addresses the need to develop new therapeutic agents for the treatment and prevention of neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders.

The Sigma-2 receptor binders and Sigma-2 receptor activity modulators of the present invention are capable of treating and preventing diseases associated with dysregulation of the sigma-2 receptor, for example neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders. Without wishing to be limited by theory, it is believed that the Sigma-2 receptor binders and Sigma-2 receptor activity modulators of the present invention can ameliorate, abate, otherwise cause to be controlled, diseases and disorders associated with dysregulation of the sigma-2 receptor. The diseases and disorders include, but are not limited to neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders.

The Sigma-2 receptor binders and Sigma-2 receptor activity modulators of the present invention are also capable of treating and preventing diseases associated with overexpression of the sigma-2 receptor, for example neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders. Without wishing to be limited by theory, it is believed that the Sigma-2 receptor binders and Sigma-2 receptor activity modulators of the present invention can ameliorate, abate, otherwise cause to be controlled, diseases and disorders associated with overexpression of the sigma-2 receptor. The diseases and disorders include, but are not limited to neuropsychiatric disorders such as generalized anxiety disorder, social anxiety disorder, panic disorder, agoraphobia, obsessive-compulsive disorder post-traumatic stress disorder, depression, bipolar disorder, anorexia nervosa, bulimia nervosa, substance use disorders, and schizophrenia, cancers such as pancreatic cancer, lung cancer, breast cancer, melanoma, prostate cancer, and ovarian cancer, as well as Alzheimer's disease, mild cognitive impairments, and memory disorders.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously.

As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_{1-6}$alkyl)$_2$amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "haloalkoxy" refers to the group —O-haloalkyl, wherein the haloalkyl group is as defined above. Examples of haloalkoxy groups include, but are not limited to, fluoromethoxy, difluoromethoxy, trifluoromethoxy, and pentafluoroethoxyl.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocyclyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, 1H-benzo[d]imidazol-2(3H)-onyl, 1H-benzo[d]imidazolyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

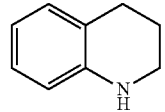

is, for the purposes of the present invention, considered a heterocyclic unit. 6,7-Dihydro-5H-cyclopentapyrimidine having the formula:

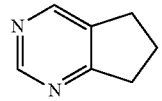

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

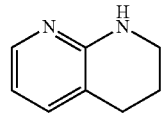

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —NO$_2$, oxo (=O), —OR$^{13}$, —SR$^{13}$, —N(R$^{13}$)$_2$, —NR$^{13}$C(O)R$^{13}$, —SO$_2$R$^{13}$, —SO$_2$OR$^{13}$, —SO$_2$N(R$^{13}$)$_2$, —C(O)R$^{13}$, —C(O)OR$^{13}$, —C(O)N(R$^{13}$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^{13}$; wherein R$^{13}$, at each occurrence, independently is hydrogen, —OR$^{14}$, —SR$^{14}$, —C(O)R$^{14}$, —C(O)OR$^{14}$, —C(O)N(R$^{14}$)$_2$, —SO$_2$R$^{14}$, —S(O)$_2$OR$^{14}$, —N(R$^{14}$)$_2$, —NR$^{14}$C(O)R$^{14}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{13}$ units taken together with the atom(s) to which they are bound form an optionally substituted carbocycle or heterocycle wherein said carbocycle or heterocycle has 3 to 7 ring atoms; wherein R$^{14}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^{14}$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^{15}$; for example, —OH, —OCH$_3$, —OCH$_2$CH$_3$, —OCH$_2$CH$_2$CH$_3$;
ii) —C(O)R$^{15}$; for example, —COCH$_3$, —COCH$_2$CH$_3$, —COCH$_2$CH$_2$CH$_3$;
iii) —C(O)OR$^{15}$; for example, —CO$_2$CH$_3$, —CO$_2$CH$_2$CH$_3$, —CO$_2$CH$_2$CH$_2$CH$_3$;
iv) —C(O)N(R$^{15}$)$_2$; for example, —CONH$_2$, —CONHCH$_3$, —CON(CH$_3$)$_2$;
v) —N(R$^{15}$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_e$X$_g$; wherein X is halogen, m is from 0 to 2, e+g=3; for example, —CH$_2$F, —CHF$_2$, —CF$_3$, —CCl$_3$, or —CBr$_3$;
viii) —SO$_2$R$^{15}$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^{15}$)C(O)R$^{15}$;
xiii) Oxo (=O);
xiv) Heterocycle; and
xv) Heteroaryl.

wherein each R$^{15}$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); two R$^{15}$ units can be taken together to form a ring comprising 3-7 ring atoms. In certain aspects, each R$^{15}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_6$, and $C_5$-$C_6$, alkyl.

For the purposes of the present invention the terms "compound," "analog," and "composition of matter" stand equally well for the sigma-2 receptor activity modulators and sigma-2 receptor binders described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^9)_2$, each $R^9$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Sigma-2 Receptor Binders and Sigma-2 Receptor Activity Modulators

The sigma-2 receptor binders and sigma-2 receptor activity modulators of the present invention include all enantiomeric and diastereomeric forms alts thereof having the formula The present invention is directed toward novel sigma-2 receptor binders, compounds of formula (I),

including hydrates, solvates, pharmaceutically acceptable salts, prodrugs and complexes thereof, wherein:

A is selected from a group consisting of

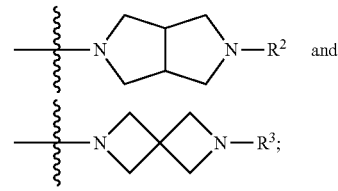

n is 1, 2, or 3;

$R^{1a}$ and $R^{1b}$ are each independently selected from the group consisting of hydrogen, $C_{1-6}$ linear alkyl, and $C_{1-6}$ branched alkyl, or $R^{1a}$ and $R^{1b}$ may be taken together with the atom to which they are bound to form a ring having from 3 to 7 ring atoms;

$R^2$ is selected from a group consisting of a benzene ring that is optionally substituted with 0 to 3 $R^4$ groups that are not hydrogen, a 4-pyridine ring that is optionally substituted with 0 to 2 $R^5$ groups that are not hydrogen, a 3-pyridine ring that is optionally substituted with 0 to 2 $R^5$ groups that are not hydrogen, and a 2-pyridine ring that is optionally substituted with 0 to 2 $R^5$ groups that are not hydrogen;

$R^3$ is selected from a group consisting of a benzene ring that is optionally substituted with 0 to 3 $R^4$ groups that are not hydrogen, a 4-pyridine ring that is optionally substituted with 0 to 2 $R^5$ groups that are not hydrogen, a 3-pyridine ring that is optionally substituted with 0 to 2 $R^5$ groups that are not hydrogen, and a 2-pyridine ring that is optionally substituted with 0 to 2 $R^5$ groups that are not hydrogen;

$R^4$ is at each occurrence independently selected from the group consisting of hydrogen, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$;

the terms $R^{4a}$, $R^{4b}$, $R^{4c}$, $R^{4d}$, and $R^{4e}$ may be used to designate individual $R^4$ groups on a benzene ring;

$R^5$ is at each occurrence independently selected from the group consisting of hydrogen, OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$;

the terms $R^{5a}$, $R^{5b}$, $R^{5c}$, and $R^{5d}$ may be used to designate individual $R^5$ groups on a pyridine ring;

$R^6$ is at each occurrence independently selected from the group consisting of hydrogen, $C_{1-6}$ linear alkyl, $C_{3-7}$ branched alkyl, and $C_{3-7}$ cycloalkyl;

$R^7$ is at each occurrence independently selected from the group consisting of $C_{1-6}$ linear alkyl, $C_{3-7}$ branched alkyl, and $C_{3-7}$ cycloalkyl;

$R^{8a}$ is at each occurrence independently selected from the group consisting of H, $C_{1-6}$ linear alkyl, $C_{3-7}$ branched alkyl, and $C_{3-7}$ cycloalkyl;

$R^{8b}$ is at each occurrence independently selected from the group consisting of H, $C_{1-6}$ linear alkyl, $C_{3-7}$ branched alkyl, and $C_{3-7}$ cycloalkyl;

$R^{9a}$ is at each occurrence independently selected from the group consisting of H, $C_{1-6}$ linear alkyl, $C_{3-7}$ branched alkyl, and $C_{3-7}$ cycloalkyl;

$R^{9b}$ is at each occurrence independently selected from the group consisting of H, $C_{1-6}$ linear alkyl, $C_{3-7}$ branched alkyl, and $C_{3-7}$ cycloalkyl;

$R^{9a}$ and $R^{9b}$ may be taken together with the atom to which they are bound to form a ring having from 3 to 7 ring atoms optionally containing an oxygen;

$R^{10}$ is at each occurrence independently selected from the group consisting of H, $C_{1-6}$ linear alkyl, $C_{3-7}$ branched alkyl, and $C_{3-7}$ cycloalkyl;

$R^{11}$ is at each occurrence independently selected from the group consisting of $C_{1-6}$ linear alkyl, $C_{3-7}$ branched alkyl, and $C_{3-7}$ cycloalkyl;

$R^{12a}$ is at each occurrence independently selected from the group consisting of hydrogen, $C_{1-6}$ linear alkyl, $C_{3-7}$ branched alkyl, and $C_{3-7}$ cycloalkyl; and $R^{12b}$ is at each occurrence independently selected from the group consisting of hydrogen, $C_{1-6}$ linear alkyl, $C_{3-7}$ branched alkyl, and $C_{3-7}$ cycloalkyl.

In one embodiment, the present invention includes compounds having formula (II):

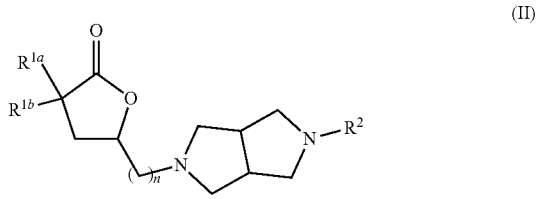

(II)

Including hydrates, solvates, enantiomers, diastereomers, pharmaceutically acceptable salts, and complexes thereof.

In one embodiment, the present invention includes compounds having formula (IIa):

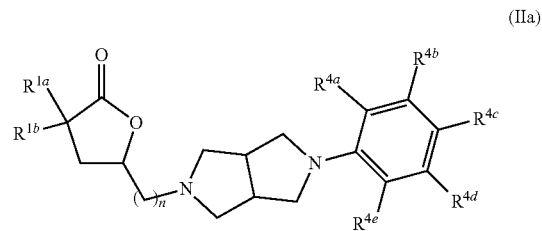

(IIa)

Including hydrates, solvates, enantiomers, diastereomers, pharmaceutically acceptable salts, and complexes thereof wherein:

at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, —S($C_{1-6}$ linear alkyl), S($C_{3-7}$ branched alkyl), heterocyclyl, —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IIb):

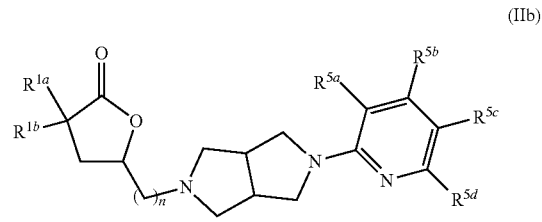

(IIb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IIc):

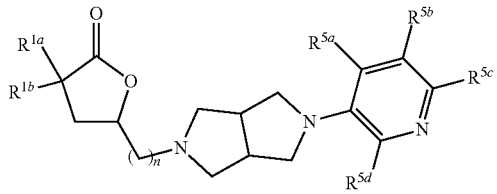

(IIc)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IId):

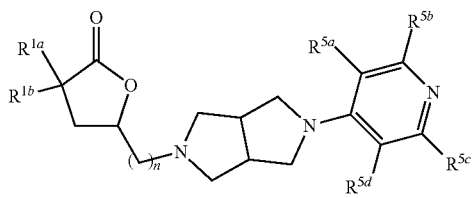

(IId)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^1$, $NR^{9a}SO_2R^{11}$, and $NR^{9a}SO_2NR^{12a}R^{12b}$.

In one embodiment, the present invention includes compounds having formula (III):

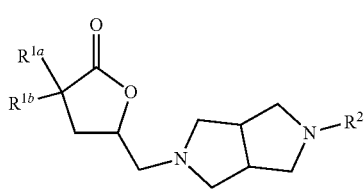

(III)

Including hydrates, solvates, enantiomers, diastereomers, pharmaceutically acceptable salts, and complexes thereof.

In one embodiment, the present invention includes compounds having formula (IIIa):

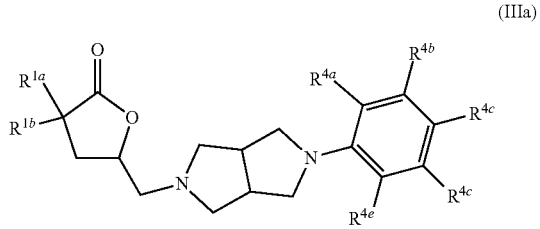

(IIIa)

Including hydrates, solvates, enantiomers, diastereomers, pharmaceutically acceptable salts, and complexes thereof wherein:
at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (ITb):

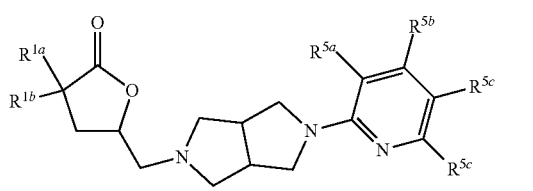

(IIIb)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IIIc):

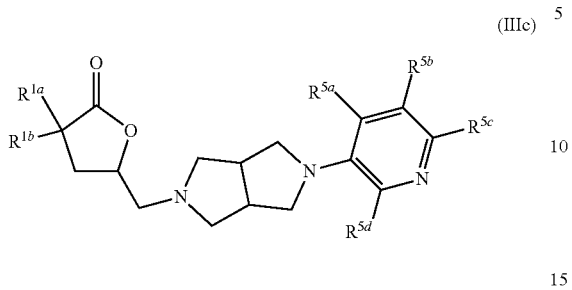

(IIIc)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IId):

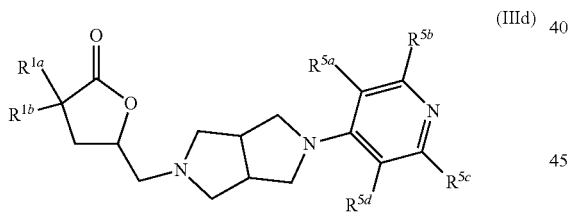

(IIId)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IV):

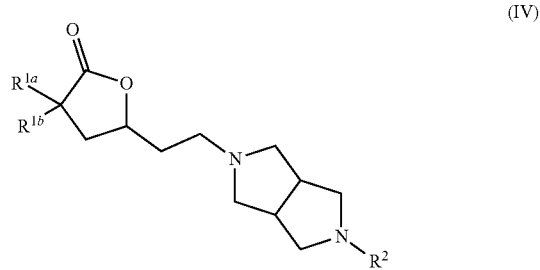

(IV)

Including hydrates, solvates, enantiomers, diastereomers, pharmaceutically acceptable salts, and complexes thereof.

In one embodiment, the present invention includes compounds having formula (IVa):

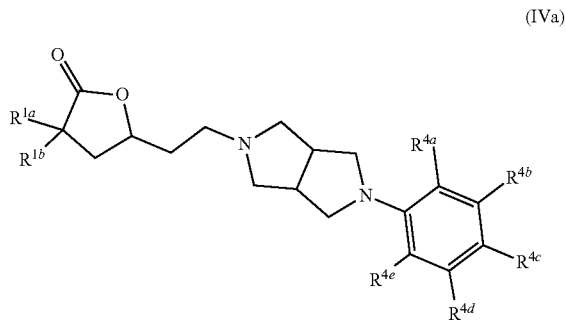

(IVa)

Including hydrates, solvates, enantiomers, diastereomers, pharmaceutically acceptable salts, and complexes thereof wherein:

at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IVb):

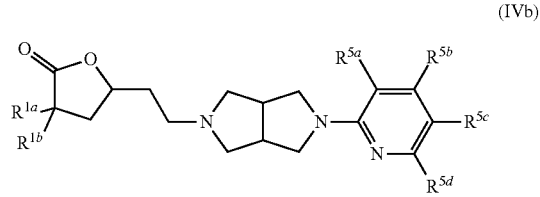

(IVb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^1$, $NR^{9a}SO_2R^{11}$, and $NR^{9a}SO_2NR^{12a}R^{12b}$.

In one embodiment, the present invention includes compounds having formula (IVc):

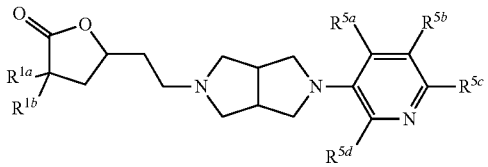

(IVb)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IVd):

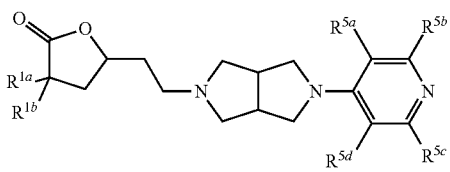

(Ivd)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{9b}$, $NR^{9a}SO_2R^{11}$, and $NR^{9a}SO_2NR^{12a}R^{12b}$.

In one embodiment, the present invention includes compounds having formula (V):

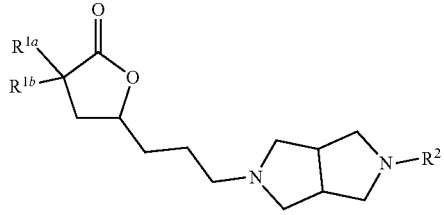

(V)

Including hydrates, solvates, enantiomers, diastereomers, pharmaceutically acceptable salts, and complexes thereof.

In one embodiment, the present invention includes compounds having formula (Va):

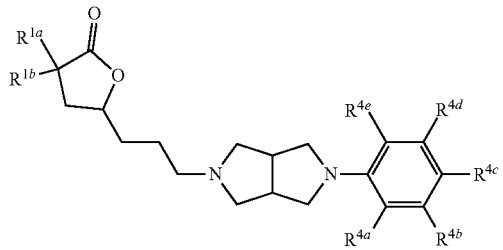

(Va)

Including hydrates, solvates, enantiomers, diastereomers, pharmaceutically acceptable salts, and complexes thereof wherein:
at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (Vb):

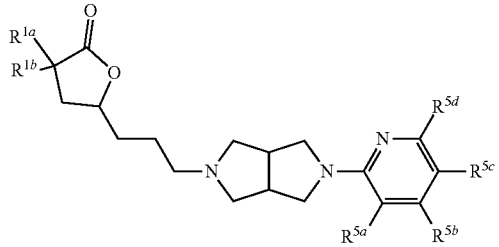

(Vb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (Vc):

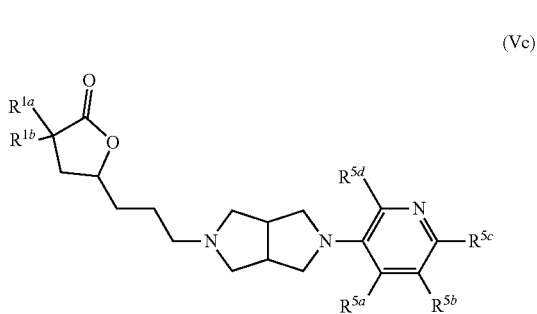

(Vc)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (Vd):

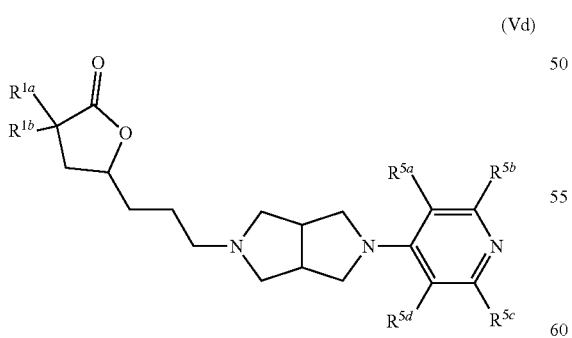

(Vd)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VI):

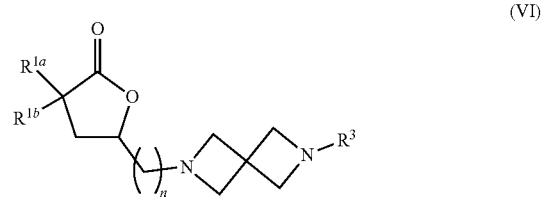

(VI)

Including hydrates, solvates, enantiomers, diastereomers, pharmaceutically acceptable salts, and complexes thereof.

In one embodiment, the present invention includes compounds having formula (VIa):

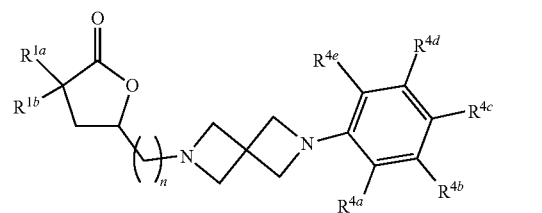

(VIa)

Including hydrates, solvates, enantiomers, diastereomers, pharmaceutically acceptable salts, and complexes thereof wherein:
at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIb):

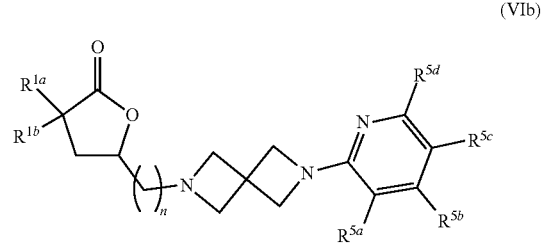

(VIb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIc):

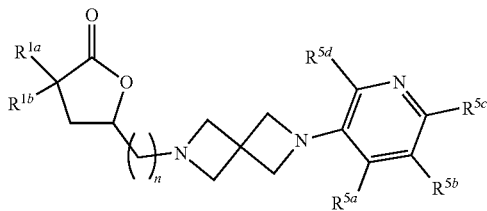

(VIc)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^1$, $NR^{9a}SO_2R^{11}$, and $NR^{9a}SO_2NR^{12a}R^{12b}$.

In one embodiment, the present invention includes compounds having formula (VId):

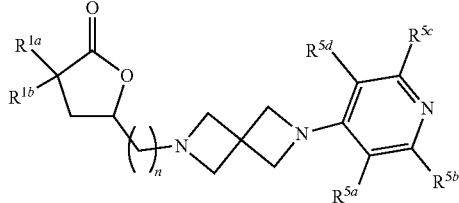

(VId)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VII):

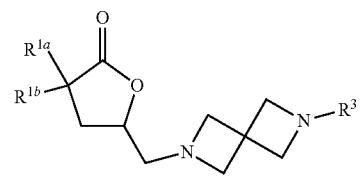

(VII)

Including hydrates, solvates, enantiomers, diastereomers, pharmaceutically acceptable salts, and complexes thereof.

In one embodiment, the present invention includes compounds having formula (VIIa):

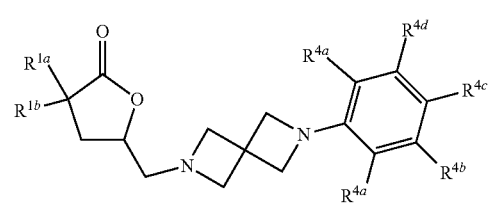

(VIIa)

Including hydrates, solvates, enantiomers, diastereomers, pharmaceutically acceptable salts, and complexes thereof wherein:

at least 2 of the group $R^{4a}$, $R^{4b}$, $R^{4c}$, $R^{4d}$, and $R^{4e}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIIb):

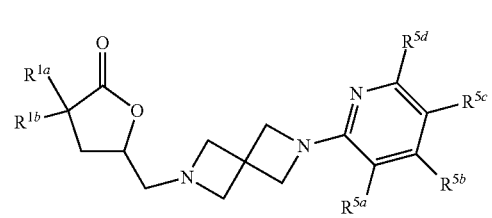

(VIIb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIIc):

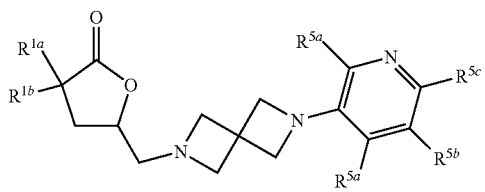

(VIIc)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^1$, $NR^{9a}SO_2R^{11}$, and $NR^{9a}SO_2NR^{12a}R^{12b}$.

In one embodiment, the present invention includes compounds having formula (VIId):

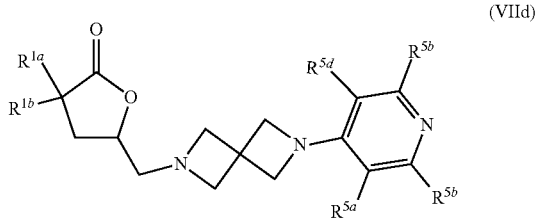

(VIId)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIII):

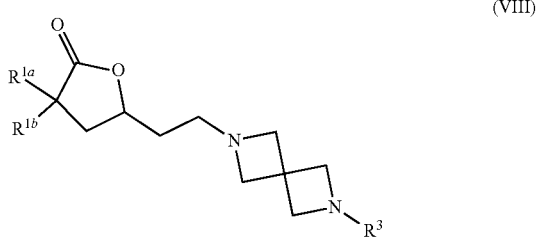

(VIII)

Including hydrates, solvates, enantiomers, diastereomers, pharmaceutically acceptable salts, and complexes thereof.

In one embodiment, the present invention includes compounds having formula (VIIIa):

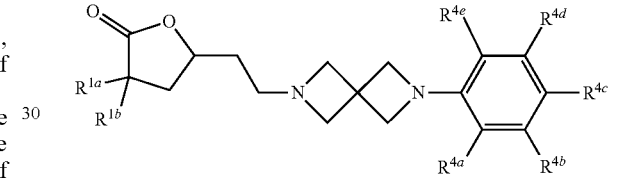

(VIIIa)

Including hydrates, solvates, enantiomers, diastereomers, pharmaceutically acceptable salts, and complexes thereof wherein:
at least 2 of the group $R^{4a}$, $R^{4b}$, $R^{4c}$, $R^{4d}$, and $R^{4'}$ are hydrogen and 0 to 3 of $R^{4a}$, $R^{4b}$, $R^{4c}$, $R^{4d}$, and $R^{4e}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —S($C_{1-6}$ linear alkyl), S($C_{3-7}$ branched alkyl), —S($C_{3-7}$ cycloalkyl), —$SO_2$($C_{1-6}$ linear alkyl), $SO_2$ ($C_{3-7}$ branched alkyl), —$SO_2$($C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (VIIIb):

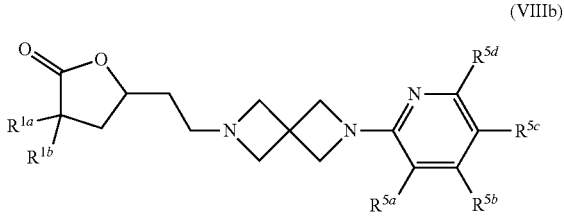

(VIIIb)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, NO$_2$, halogen, CN, C$_{1-6}$ linear alkyl, C$_{3-7}$ branched alkyl, C$_{3-7}$ cycloalkyl, C$_{1-6}$ linear alkoxy, C$_{3-7}$ branched alkoxy, C$_{3-7}$ cycloalkoxy, C$_{1-6}$ linear haloalkyl, C$_{3-7}$ branched haloalkyl, C$_{1-6}$ linear haloalkoxy, heterocyclyl, —S(C$_{1-6}$ linear alkyl), S(C$_{3-7}$ branched alkyl), —S(C$_{3-7}$ cycloalkyl), —SO$_2$(C$_{1-6}$ linear alkyl), SO$_2$(C$_{3-7}$ branched alkyl), —SO$_2$(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$COR$^{10}$, NR$^{9a}$SO$_2$R$^{11}$, and NR$^{9a}$SO$_2$NR$^{12a}$R$^{12b}$.

In one embodiment, the present invention includes compounds having formula (VIIIc):

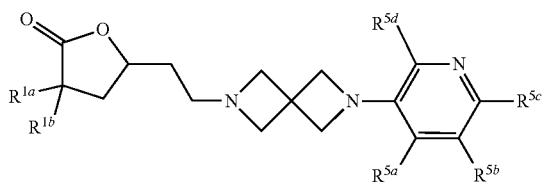

(VIIIc)

Including hydrates, solvates, enantiomers, diastereomers, pharmaceutically acceptable salts, and complexes thereof wherein:
at least 2 of the group R$^{5a}$, R$^{5b}$, R$^{5c}$, and R$^{5d}$, are hydrogen and 0 to 2 of R$^{5a}$, R$^{5b}$, R$^{5c}$, and R$^{5d}$ are independently selected from the group consisting of OH, NO$_2$, halogen, CN, C$_{1-6}$ linear alkyl, C$_{3-7}$ branched alkyl, C$_{3-7}$ cycloalkyl, C$_{1-6}$ linear alkoxy, C$_{3-7}$ branched alkoxy, C$_{3-7}$ cycloalkoxy, C$_{1-6}$ linear haloalkyl, C$_{3-7}$ branched haloalkyl, C$_{1-6}$ linear haloalkoxy, heterocyclyl, —S(C$_{1-6}$ linear alkyl), S(C$_{3-7}$ branched alkyl), —S(C$_{3-7}$ cycloalkyl), —SO$_2$(C$_{1-6}$ linear alkyl), SO$_2$(C$_{3-7}$ branched alkyl), —SO$_2$(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$COR$^{10}$, NR$^{9a}$SO$_2$R$^{11}$, and NR$^{9a}$SO$_2$NR$^{12a}$R$^{12b}$.

In one embodiment, the present invention includes compounds having formula (VIIId):

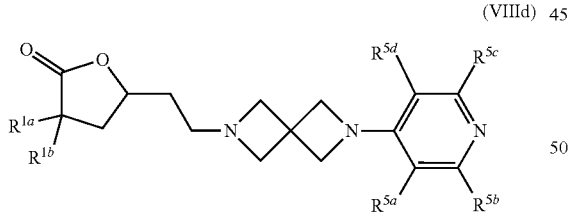

(VIIId)

Including hydrates, solvates, enantiomers, diastereomers, pharmaceutically acceptable salts, and complexes thereof wherein:
at least 2 of the group R$^{5a}$, R$^{5b}$, R$^{5c}$, and R$^{5d}$, are hydrogen and 0 to 2 of R$^{5a}$, R$^{5b}$, R$^{5c}$, and R$^{5d}$ are independently selected from the group consisting of OH, NO$_2$, halogen, CN, C$_{1-6}$ linear alkyl, C$_{3-7}$ branched alkyl, C$_{3-7}$ cycloalkyl, C$_{1-6}$ linear alkoxy, C$_{3-7}$ branched alkoxy, C$_{3-7}$ cycloalkoxy, C$_{1-6}$ linear haloalkyl, C$_{3-7}$ branched haloalkyl, C$_{1-6}$ linear haloalkoxy, heterocyclyl, —S(C$_{1-6}$ linear alkyl), S(C$_{3-7}$ branched alkyl), —S(C$_{3-7}$ cycloalkyl), —SO$_2$(C$_{1-6}$ linear alkyl), SO$_2$(C$_{3-7}$ branched alkyl), —SO$_2$(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$COR$^{10}$, NR$^{9a}$SO$_2$R$^{11}$, and NR$^{9a}$SO$_2$NR$^{12a}$R$^{12b}$.

In one embodiment, the present invention includes compounds having formula (IX):

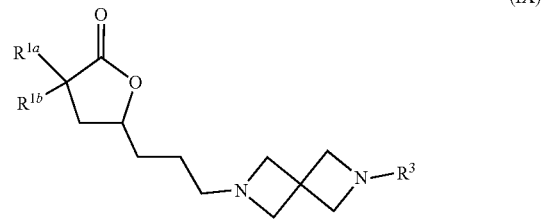

(IX)

Including hydrates, solvates, enantiomers, diastereomers, pharmaceutically acceptable salts, and complexes thereof.

In one embodiment, the present invention includes compounds having formula (IXa):

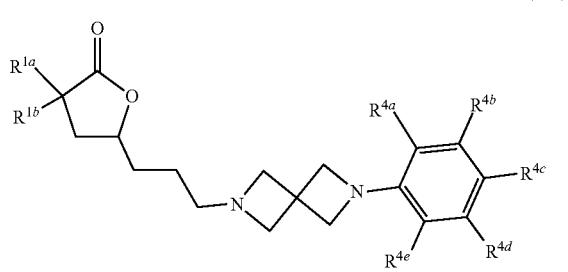

(IXa)

Including hydrates, solvates, enantiomers, diastereomers, pharmaceutically acceptable salts, and complexes thereof wherein:
at least 2 of the group R$^{4a}$, R$^{4b}$, R$^{4c}$, R$^{4d}$, and R$^{4e}$ are hydrogen and 0 to 3 of R$^{4a}$, R$^{4b}$, R$^{4c}$, R$^{4d}$, and R$^{4e}$ are independently selected from the group consisting of OH, NO$_2$, halogen, CN, C$_{1-6}$ linear alkyl, C$_{3-7}$ branched alkyl, C$_{3-7}$ cycloalkyl, C$_{1-6}$ linear alkoxy, C$_{3-7}$ branched alkoxy, C$_{3-7}$ cycloalkoxy, C$_{1-6}$ linear haloalkyl, C$_{3-7}$ branched haloalkyl, C$_{1-6}$ linear haloalkoxy, heterocyclyl, —S(C$_{1-6}$ linear alkyl), S(C$_{3-7}$ branched alkyl), —S(C$_{3-7}$ cycloalkyl), —SO$_2$(C$_{1-6}$ linear alkyl), SO$_2$(C$_{3-7}$ branched alkyl), —SO$_2$(C$_{3-7}$ cycloalkyl), COR$^6$, CO$_2$R$^7$, CONR$^{8a}$R$^{8b}$, SO$_2$NR$^{8a}$R$^{8b}$, NR$^{9a}$R$^{9b}$, NR$^{9a}$COR$^{10}$, NR$^{9a}$SO$_2$R$^{11}$, and NR$^{9a}$SO$_2$NR$^{12a}$R$^{12b}$.

In one embodiment, the present invention includes compounds having formula (IXb):

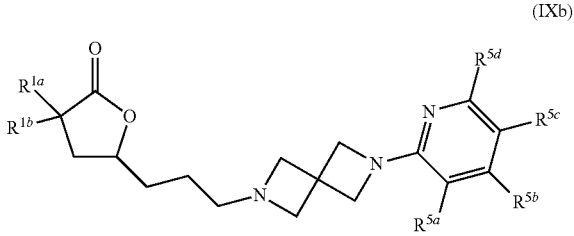

(IXb)

Including hydrates, solvates, enantiomers, diastereomers, pharmaceutically acceptable salts, and complexes thereof wherein:

at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —$S(C_{1-6}$ linear alkyl), $S(C_{3-7}$ branched alkyl), —$S(C_{3-7}$ cycloalkyl), —$SO_2(C_{1-6}$ linear alkyl), $SO_2(C_{3-7}$ branched alkyl), —$SO_2(C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IXc):

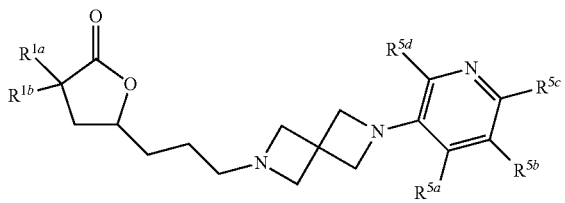

(IXc)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —$S(C_{1-6}$ linear alkyl), $S(C_{3-7}$ branched alkyl), —$S(C_{3-7}$ cycloalkyl), —$SO_2(C_{1-6}$ linear alkyl), $SO_2(C_{3-7}$ branched alkyl), —$SO_2(C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^{10}$, $NR^{9a}SO_2R^{11}$, and $NR^{9a}SO_2NR^{12a}R^{12b}$.

In one embodiment, the present invention includes compounds having formula (IXd):

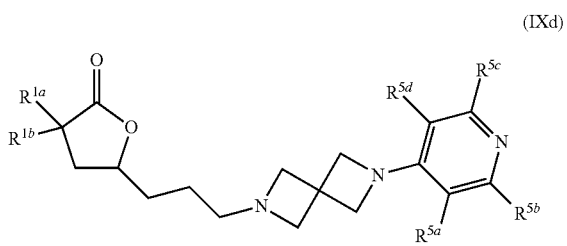

(IXd)

Including hydrates, solvates, enantiomers, diastereomers, pharmaceutically acceptable salts, and complexes thereof wherein:
at least 2 of the group $R^{5a}$, $R^{5b}$, $R^{5c}$, and $R^{5d}$, are hydrogen and 0 to 2 of $R^{5a}$, $R^{5b}$, $R^{5c}$, and $R^{5d}$ are independently selected from the group consisting of OH, $NO_2$, halogen, CN, $C_{1-6}$ linear alkyl, $C_{3-7}$ branched alkyl, $C_{3-7}$ cycloalkyl, $C_{1-6}$ linear alkoxy, $C_{3-7}$ branched alkoxy, $C_{3-7}$ cycloalkoxy, $C_{1-6}$ linear haloalkyl, $C_{3-7}$ branched haloalkyl, $C_{1-6}$ linear haloalkoxy, heterocyclyl, —$S(C_{1-6}$ linear alkyl), $S(C_{3-7}$ branched alkyl), —$S(C_{3-7}$ cycloalkyl), —$SO_2(C_{1-6}$ linear alkyl), $SO_2(C_{3-7}$ branched alkyl), —$SO_2(C_{3-7}$ cycloalkyl), $COR^6$, $CO_2R^7$, $CONR^{8a}R^{8b}$, $SO_2NR^{8a}R^{8b}$, $NR^{9a}R^{9b}$, $NR^{9a}COR^1$, $NR^{9a}SO_2R^{11}$, and $NR^{9a}SO_2NR^{12a}R^{12b}$.

In some embodiments A is

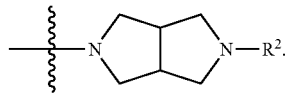

In some embodiments A is

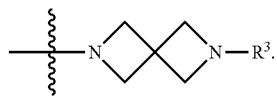

In some embodiments n is 1.
In some embodiments n is 2.
In some embodiments n is 3.
In some embodiments $R^{1a}$ is hydrogen.
In some embodiments $R^{1a}$ is $C_{1-6}$ linear alkyl.
In some embodiments $R^{1a}$ is $C_{1-6}$ branched alkyl.
In some embodiments $R^{1b}$ is hydrogen.
In some embodiments $R^{1b}$ is $C_{1-6}$ linear alkyl.
In some embodiments $R^{1b}$ is $C_{1-6}$ branched alkyl.
In some embodiments $R^{1a}$ and $R^{1b}$ are be taken together with the atom to which they are bound to form a ring having from 3 ring atoms.
In some embodiments $R^{1a}$ and $R^{1b}$ are be taken together with the atom to which they are bound to form a ring having from 4 ring atoms.
In some embodiments $R^{1a}$ and $R^{1b}$ are be taken together with the atom to which they are bound to form a ring having from 5 ring atoms.
In some embodiments $R^{1a}$ and $R^{1b}$ are be taken together with the atom to which they are bound to form a ring having from 6 ring atoms.
In some embodiments $R^{1a}$ and $R^{1b}$ are be taken together with the atom to which they are bound to form a ring having from 7 ring atoms.
In some embodiments $R^2$ is a benzene ring that is optionally substituted with 0 to 3 $R^4$ groups that are not hydrogen.
In some embodiments $R^2$ is a 4-pyridine ring that is optionally substituted with 0 to 2 $R^5$ groups that are not hydrogen.
In some embodiments $R^2$ is a 3-pyridine ring that is optionally substituted with 0 to 2 $R^5$ groups that are not hydrogen.
In some embodiments $R^2$ is a 2-pyridine ring that is optionally substituted with 0 to 2 $R^5$ groups that are not hydrogen.
In some embodiments $R^3$ is a benzene ring that is optionally substituted with 0 to 3 $R^4$ groups that are not hydrogen.
In some embodiments $R^3$ is a 4-pyridine ring that is optionally substituted with 0 to 2 $R^5$ groups that are not hydrogen.
In some embodiments $R^3$ is a 3-pyridine ring that is optionally substituted with 0 to 2 $R^5$ groups. that are not hydrogen
In some embodiments $R^3$ is a 2-pyridine ring that is optionally substituted with 0 to 2 $R^5$ groups that are not hydrogen.

In some embodiments $R^4$ is hydrogen.
In some embodiments $R^4$ is OH.
In some embodiments $R^4$ is $NO_2$.
In some embodiments $R^4$ is halogen.
In some embodiments $R^4$ is CN.
In some embodiments $R^4$ is $C_{1-6}$ linear alkyl.
In some embodiments $R^4$ is $C_{3-7}$ branched alkyl.
In some embodiments $R^4$ is $C_{3-7}$ cycloalkyl.
In some embodiments $R^4$ is $C_{1-6}$ linear alkoxy.
In some embodiments $R^4$ is $C_{3-7}$ branched alkoxy.
In some embodiments $R^4$ is $C_{3-7}$ cycloalkoxy.
In some embodiments $R^4$ is $C_{1-6}$ linear haloalkyl.
In some embodiments $R^4$ is $C_{3-7}$ branched haloalkyl.
In some embodiments $R^4$ is $C_{1-6}$ linear haloalkoxy.
In some embodiments $R^4$ is heterocyclyl.
In some embodiments $R^4$ is —S($C_{1-6}$ linear alkyl).
In some embodiments $R^4$ is —S($C_{3-7}$ branched alkyl).
In some embodiments $R^4$ is —S($C_{3-7}$ cycloalkyl).
In some embodiments $R^4$ is —$SO_2$($C_{1-6}$ linear alkyl).
In some embodiments $R^4$ is —$SO_2$($C_{3-7}$ branched alkyl).
In some embodiments $R^4$ is —$SO_2$($C_{3-7}$ cycloalkyl).
In some embodiments $R^4$ is $COR^6$.
In some embodiments $R^4$ is $CO_2R^7$.
In some embodiments $R^4$ is $CONR^{8a}R^{8b}$.
In some embodiments $R^4$ is $SO_2NR^{8a}R^{8b}$.
In some embodiments $R^4$ is $NR^{9a}R^{9b}$.
In some embodiments $R^4$ is $NR^{9a}COR^{10}$.
In some embodiments $R^4$ is $NR^{9a}SO_2R^{11}$.
In some embodiments $R^4$ is $NR^{9a}SO_2NR^{12a}R^{12b}$.
In some embodiments $R^{4a}$ is hydrogen.
In some embodiments $R^{4a}$ is OH.
In some embodiments $R^{4a}$ is $NO_2$.
In some embodiments $R^{4a}$ is halogen.
In some embodiments $R^{4a}$ is CN.
In some embodiments $R^{4a}$ is $C_{1-6}$ linear alkyl.
In some embodiments $R^{4a}$ is $C_{3-7}$ branched alkyl.
In some embodiments $R^{4a}$ is $C_{3-7}$ cycloalkyl.
In some embodiments $R^{4a}$ is $C_{1-6}$ linear alkoxy.
In some embodiments $R^{4a}$ is $C_{3-7}$ branched alkoxy.
In some embodiments $R^{4a}$ is $C_{3-7}$ cycloalkoxy.
In some embodiments $R^{4a}$ is $C_{1-6}$ linear haloalkyl.
In some embodiments $R^{4a}$ is $C_{3-7}$ branched haloalkyl.
In some embodiments $R^{4a}$ is $C_{1-6}$ linear haloalkoxy.
In some embodiments $R^{4a}$ is heterocyclyl.
In some embodiments $R^{4a}$ is —S($C_{1-6}$ linear alkyl).
In some embodiments $R^{4a}$ is —S($C_{3-7}$ branched alkyl).
In some embodiments $R^{4a}$ is —S($C_{3-7}$ cycloalkyl).
In some embodiments $R^{4a}$ is —$SO_2$($C_{1-6}$ linear alkyl).
In some embodiments $R^{4a}$ is —$SO_2$($C_{3-7}$ branched alkyl).
In some embodiments $R^{4a}$ is —$SO_2$($C_{3-7}$ cycloalkyl).
In some embodiments $R^{4a}$ is $COR^6$.
In some embodiments $R^{4a}$ is $CO_2R^7$.
In some embodiments $R^{4a}$ is $CONR^{8a}R^{8b}$.
In some embodiments $R^{4a}$ is $SO_2NR^{8a}R^{8b}$.
In some embodiments $R^{4a}$ is $NR^{9a}R^{9b}$.
In some embodiments $R^{4a}$ is $NR^{9a}COR^{10}$.
In some embodiments $R^{4a}$ is $NR^{9a}SO_2R^{11}$.
In some embodiments $R^{4a}$ is $NR^{9a}SO_2NR^{12a}R^{12b}$.
In some embodiments $R^{4b}$ is hydrogen.
In some embodiments $R^{4b}$ is OH.
In some embodiments $R^{4b}$ is $NO_2$.
In some embodiments $R^{4b}$ is halogen.
In some embodiments $R^{4b}$ is CN.
In some embodiments $R^{4b}$ is $C_{1-6}$ linear alkyl.
In some embodiments $R^{4b}$ is $C_{3-7}$ branched alkyl.
In some embodiments $R^{4b}$ is $C_{3-7}$ cycloalkyl.
In some embodiments $R^{4b}$ is $C_{1-6}$ linear alkoxy.
In some embodiments $R^{4b}$ is $C_{3-7}$ branched alkoxy.
In some embodiments $R^{4b}$ is $C_{3-7}$ cycloalkoxy.
In some embodiments $R^{4b}$ is $C_{1-6}$ linear haloalkyl.
In some embodiments $R^{4b}$ is $C_{3-7}$ branched haloalkyl.
In some embodiments $R^{4b}$ is $C_{1-6}$ linear haloalkoxy.
In some embodiments $R^b$ is heterocyclyl.
In some embodiments $R^{4b}$ is —S($C_{1-6}$ linear alkyl).
In some embodiments $R^{4b}$ is —S($C_{3-7}$ branched alkyl).
In some embodiments $R^{4b}$ is —S($C_{3-7}$ cycloalkyl).
In some embodiments $R^{4b}$ is —$SO_2$($C_{1-6}$ linear alkyl).
In some embodiments $R^{4b}$ is —$SO_2$($C_{3-7}$ branched alkyl).
In some embodiments $R^{4b}$ is —$SO_2$($C_{3-7}$ cycloalkyl).
In some embodiments $R^{4b}$ is $COR^6$.
In some embodiments $R^{4b}$ is $CO_2R^7$.
In some embodiments $R^{4b}$ is $CONR^{8a}R^{8b}$.
In some embodiments $R^{4b}$ is $SO_2NR^{8a}R^{8b}$.
In some embodiments $R^{4b}$ is $NR^{9a}R^{9b}$.
In some embodiments $R^{4b}$ is $NR^{9a}COR^{10}$.
In some embodiments $R^{4b}$ is $NR^{9a}SO_2R^{11}$.
In some embodiments $R^{4b}$ is $NR^{9a}SO_2NR^{12a}R^{12b}$.
In some embodiments $R^{4c}$ is hydrogen.
In some embodiments $R^{4c}$ is OH.
In some embodiments $R^{4c}$ is $NO_2$.
In some embodiments $R^{4c}$ is halogen.
In some embodiments $R^{4c}$ is CN.
In some embodiments $R^{4c}$ is $C_{1-6}$ linear alkyl.
In some embodiments $R^{4c}$ is $C_{3-7}$ branched alkyl.
In some embodiments $R^{4c}$ is $C_{3-7}$ cycloalkyl.
In some embodiments $R^{4c}$ is $C_{1-6}$ linear alkoxy.
In some embodiments $R^{4c}$ is $C_{3-7}$ branched alkoxy.
In some embodiments $R^{4c}$ is $C_{3-7}$ cycloalkoxy.
In some embodiments $R^{4c}$ is $C_{1-6}$ linear haloalkyl.
In some embodiments $R^{4c}$ is $C_{3-7}$ branched haloalkyl.
In some embodiments $R^{4c}$ is $C_{1-6}$ linear haloalkoxy.
In some embodiments $R^{4c}$ is heterocyclyl.
In some embodiments $R^{4c}$ is —S($C_{1-6}$ linear alkyl).
In some embodiments $R^{4c}$ is —S($C_{3-7}$ branched alkyl).
In some embodiments $R^{4c}$ is —S($C_{3-7}$ cycloalkyl).
In some embodiments $R^{4c}$ is —$SO_2$($C_{1-6}$ linear alkyl).
In some embodiments $R^{4c}$ is —$SO_2$($C_{3-7}$ branched alkyl).
In some embodiments $R^{4c}$ is —$SO_2$($C_{3-7}$ cycloalkyl).
In some embodiments $R^{4c}$ is $COR^6$.
In some embodiments $R^{4c}$ is $CO_2R^7$.
In some embodiments $R^{4c}$ is $CONR^{8a}R^{8b}$.
In some embodiments $R^{4c}$ is $SO_2NR^{8a}R^{8b}$.
In some embodiments $R^{4c}$ is $NR^{9a}R^9$.
In some embodiments $R^{4c}$ is $NR^{9a}COR^{10}$.
In some embodiments $R^{4c}$ is $NR^{9a}SO_2R^{11}$.
In some embodiments $R^{4c}$ is $NR^{9a}SO_2NR^{12a}R^{12b}$.
In some embodiments $R^{4d}$ is hydrogen.
In some embodiments $R^{4d}$ is OH.
In some embodiments $R^{4d}$ is $NO_2$.
In some embodiments $R^{4d}$ is halogen.
In some embodiments $R^{4d}$ is CN.
In some embodiments $R^{4d}$ is $C_{1-6}$ linear alkyl.
In some embodiments $R^{4d}$ is $C_{3-7}$ branched alkyl.
In some embodiments $R^{4d}$ is $C_{3-7}$ cycloalkyl.
In some embodiments $R^{4d}$ is $C_{1-6}$ linear alkoxy.
In some embodiments $R^{4d}$ is $C_{3-7}$ branched alkoxy.
In some embodiments $R^{4d}$ is $C_{3-7}$ cycloalkoxy.
In some embodiments $R^{4d}$ is $C_{1-6}$ linear haloalkyl.
In some embodiments $R^{4d}$ is $C_{3-7}$ branched haloalkyl.
In some embodiments $R^{4d}$ is $C_{1-6}$ linear haloalkoxy.
In some embodiments $R^{4d}$ is heterocyclyl.
In some embodiments $R^{4d}$ is —S($C_{1-6}$ linear alkyl).
In some embodiments $R^{4d}$ is —S($C_{3-7}$ branched alkyl).
In some embodiments $R^{4d}$ is —S($C_{3-7}$ cycloalkyl).
In some embodiments $R^{4d}$ is —$SO_2$($C_{1-6}$ linear alkyl).

In some embodiments $R^{4d}$ is —SO$_2$(C$_{3-7}$ branched alkyl).
In some embodiments $R^{4d}$ is —SO$_2$(C$_{3-7}$ cycloalkyl).
In some embodiments $R^{4d}$ is COR$^6$.
In some embodiments $R^{4d}$ is CO$_2$R$^7$.
In some embodiments $R^{4d}$ is CONR$^{8a}$R$^{8b}$.
In some embodiments $R^{4d}$ is SO$_2$NR$^{8a}$R$^{8b}$.
In some embodiments $R^{4d}$ is NR$^{9a}$R$^{9b}$.
In some embodiments $R^{4d}$ is NR$^{9a}$COR$^{10}$.
In some embodiments $R^{4d}$ is NR$^{9a}$SO$_2$R$^{11}$.
In some embodiments $R^{4d}$ is NR$^{9a}$SO$_2$NR$^{12a}$R$^{12b}$.
In some embodiments $R^{4e}$ is hydrogen.
In some embodiments $R^{4e}$ is OH.
In some embodiments $R^{4e}$ is NO$_2$.
In some embodiments $R^{4e}$ is halogen.
In some embodiments $R^{4e}$ is CN.
In some embodiments $R^{4e}$ is C$_{1-6}$ linear alkyl.
In some embodiments $R^{4e}$ is C$_{3-7}$ branched alkyl.
In some embodiments $R^{4e}$ is C$_{3-7}$ cycloalkyl.
In some embodiments $R^{4e}$ is C$_{1-6}$ linear alkoxy.
In some embodiments $R^{4e}$ is C$_{3-7}$ branched alkoxy.
In some embodiments $R^{4e}$ is C$_{3-7}$ cycloalkoxy.
In some embodiments $R^{4e}$ is C$_{1-6}$ linear haloalkyl.
In some embodiments $R^{4e}$ is C$_{3-7}$ branched haloalkyl.
In some embodiments $R^{4e}$ is C$_{1-6}$ linear haloalkoxy.
In some embodiments $R^{4e}$ is heterocyclyl.
In some embodiments $R^{4e}$ is —S(C$_{1-6}$ linear alkyl).
In some embodiments $R^{4e}$ is —S(C$_{3-7}$ branched alkyl).
In some embodiments $R^{4e}$ is —S(C$_{3-7}$ cycloalkyl).
In some embodiments $R^{4e}$ is —SO$_2$(C$_{1-6}$ linear alkyl).
In some embodiments $R^{4e}$ is —SO$_2$(C$_{3-7}$ branched alkyl).
In some embodiments $R^{4e}$ is —SO$_2$(C$_{3-7}$ cycloalkyl).
In some embodiments $R^{4e}$ is COR$^6$.
In some embodiments $R^{4e}$ is CO$_2$R$^7$.
In some embodiments $R^{4e}$ is CONR$^{8a}$R$^{8b}$.
In some embodiments $R^{4e}$ is SO$_2$NR$^{8a}$R$^{8b}$.
In some embodiments $R^{4a}$ is NR$^{9a}$R$^{9b}$.
In some embodiments $R^{4e}$ is NR$^{9a}$COR$^{10}$.
In some embodiments $R^{4e}$ is NR$^{9a}$SO$_2$R$^{11}$.
In some embodiments $R^{4e}$ is NR$^{9a}$SO$_2$NR$^{12a}$R$^{12b}$.
In some embodiments $R^5$ is hydrogen.
In some embodiments $R^5$ is OH.
In some embodiments $R^5$ is NO$_2$.
In some embodiments $R^5$ is halogen.
In some embodiments $R^5$ is CN.
In some embodiments $R^5$ is C$_{1-6}$ linear alkyl.
In some embodiments $R^5$ is C$_{3-7}$ branched alkyl.
In some embodiments $R^5$ is C$_{3-7}$ cycloalkyl.
In some embodiments $R^5$ is C$_{1-6}$ linear alkoxy.
In some embodiments $R^5$ is C$_{3-7}$ branched alkoxy.
In some embodiments $R^5$ is C$_{3-7}$ cycloalkoxy.
In some embodiments $R^5$ is C$_{1-6}$ linear haloalkyl.
In some embodiments $R^5$ is C$_{3-7}$ branched haloalkyl.
In some embodiments $R^5$ is C$_{1-6}$ linear haloalkoxy.
In some embodiments $R^5$ is —S(C$_{1-6}$ linear alkyl).
In some embodiments $R^5$ is —S(C$_{3-7}$ branched alkyl).
In some embodiments $R^5$ is —S(C$_{3-7}$ cycloalkyl).
In some embodiments $R^5$ is —SO$_2$(C$_{1-6}$ linear alkyl).
In some embodiments $R^5$ is —SO$_2$(C$_{3-7}$ branched alkyl).
In some embodiments $R^5$ is —SO$_2$(C$_{3-7}$ cycloalkyl).
In some embodiments $R^5$ is COR$^6$.
In some embodiments $R^5$ is CO$_2$R$^7$.
In some embodiments $R^5$ is CONR$^{8a}$R$^{8b}$.
In some embodiments $R^5$ is SO$_2$NR$^{8a}$R$^{8b}$.
In some embodiments $R^5$ is NR$^{9a}$R$^{9b}$.
In some embodiments $R^5$ is NR$^{9a}$COR$^{10}$.
In some embodiments $R^5$ is NR$^{9a}$SO$_2$R$^{11}$.
In some embodiments $R^5$ is NR$^{9a}$SO$_2$NR$^{12a}$R$^{12b}$.
In some embodiments $R^{5a}$ is hydrogen.
In some embodiments $R^{5a}$ is OH.
In some embodiments $R^{5a}$ is NO$_2$.
In some embodiments $R^{5a}$ is halogen.
In some embodiments $R^{5a}$ is CN.
In some embodiments $R^{5a}$ is C$_{1-6}$ linear alkyl.
In some embodiments $R^{5a}$ is C$_{3-7}$ branched alkyl.
In some embodiments $R^{5a}$ is C$_{3-7}$ cycloalkyl.
In some embodiments $R^{5a}$ is C$_{1-6}$ linear alkoxy.
In some embodiments $R^{5a}$ is C$_{3-7}$ branched alkoxy.
In some embodiments $R^{5a}$ is C$_{3-7}$ cycloalkoxy.
In some embodiments $R^{5a}$ is C$_{1-6}$ linear haloalkyl.
In some embodiments $R^{5a}$ is C$_{3-7}$ branched haloalkyl.
In some embodiments $R^{5a}$ is C$_{1-6}$ linear haloalkoxy.
In some embodiments $R^{5a}$ is —S(C$_{1-6}$ linear alkyl).
In some embodiments $R^{5a}$ is —S(C$_{3-7}$ branched alkyl).
In some embodiments $R^{5a}$ is —S(C$_{3-7}$ cycloalkyl).
In some embodiments $R^{5a}$ is —SO$_2$(C$_{1-6}$ linear alkyl).
In some embodiments $R^{5a}$ is —SO$_2$(C$_{3-7}$ branched alkyl).
In some embodiments $R^{5a}$ is —SO$_2$(C$_{3-7}$ cycloalkyl).
In some embodiments $R^{5a}$ is COR$^6$.
In some embodiments $R^{5a}$ is CO$_2$R$^7$.
In some embodiments $R^{5a}$ is CONR$^{8a}$R$^{8b}$.
In some embodiments $R^{5a}$ is SO$_2$NR$^{8a}$R$^{8b}$.
In some embodiments $R^{5a}$ is NR$^{9a}$R$^9$.
In some embodiments $R^{5a}$ is NR$^{9a}$COR$^{10}$.
In some embodiments $R^{5a}$ is NR$^{9a}$SO$_2$R$^{11}$.
In some embodiments $R^{5a}$ is NR$^{9a}$SO$_2$NR$^{12a}$R$^{12b}$.
In some embodiments $R^{5b}$ is hydrogen.
In some embodiments $R^{5b}$ is OH.
In some embodiments $R^{5b}$ is NO$_2$.
In some embodiments $R^{5b}$ is halogen.
In some embodiments $R^{5b}$ is CN.
In some embodiments $R^{5b}$ is C$_{1-6}$ linear alkyl.
In some embodiments $R^{5b}$ is C$_{3-7}$ branched alkyl.
In some embodiments $R^{5b}$ is C$_{3-7}$ cycloalkyl.
In some embodiments $R^{5b}$ is C$_{1-6}$ linear alkoxy.
In some embodiments $R^{5b}$ is C$_{3-7}$ branched alkoxy.
In some embodiments $R^{5b}$ is C$_{3-7}$ cycloalkoxy.
In some embodiments $R^{5b}$ is C$_{1-6}$ linear haloalkyl.
In some embodiments $R^{5b}$ is C$_{3-7}$ branched haloalkyl.
In some embodiments $R^{5b}$ is C$_{1-6}$ linear haloalkoxy.
In some embodiments $R^{5b}$ is —S(C$_{1-6}$ linear alkyl).
In some embodiments $R^{5b}$ is —S(C$_{3-7}$ branched alkyl).
In some embodiments $R^{5b}$ is —S(C$_{3-7}$ cycloalkyl).
In some embodiments $R^{5b}$ is —SO$_2$(C$_{1-6}$ linear alkyl).
In some embodiments $R^{5b}$ is —SO$_2$(C$_{3-7}$ branched alkyl).
In some embodiments $R^{5b}$ is —SO$_2$(C$_{3-7}$ cycloalkyl).
In some embodiments $R^{5b}$ is COR$^6$.
In some embodiments $R^{5b}$ is CO$_2$R$^7$.
In some embodiments $R^{5b}$ is CONR$^{8a}$R$^{8b}$.
In some embodiments $R^{5b}$ is SO$_2$NR$^{8a}$R$^{8b}$.
In some embodiments $R^{5b}$ is NR$^{9a}$R$^{9b}$.
In some embodiments $R^{5b}$ is NR$^{9a}$COR$^{10}$.
In some embodiments $R^{5b}$ is NR$^{9a}$SO$_2$R$^{11}$.
In some embodiments $R^{5b}$ is NR$^{9a}$SO$_2$NR$^{12a}$R$^{12b}$.
In some embodiments $R^{5c}$ is hydrogen.
In some embodiments $R^{5c}$ is OH.
In some embodiments $R^{5c}$ is NO$_2$.
In some embodiments $R^{5c}$ is halogen.
In some embodiments $R^{5c}$ is CN.
In some embodiments $R^{5c}$ is C$_{1-6}$ linear alkyl.
In some embodiments $R^{5c}$ is C$_{3-7}$ branched alkyl.
In some embodiments $R^{5c}$ is C$_{3-7}$ cycloalkyl.
In some embodiments $R^{5c}$ is C$_{1-6}$ linear alkoxy.
In some embodiments $R^{5c}$ is C$_{3-7}$ branched alkoxy.
In some embodiments $R^{5c}$ is C$_{3-7}$ cycloalkoxy.

In some embodiments $R^{5c}$ is $C_{1-6}$ linear haloalkyl.
In some embodiments $R^{5c}$ is $C_{3-7}$ branched haloalkyl.
In some embodiments $R^{5c}$ is $C_{1-6}$ linear haloalkoxy.
In some embodiments $R^{5c}$ is —S($C_{1-6}$ linear alkyl).
In some embodiments $R^{5c}$ is —S($C_{3-7}$ branched alkyl).
In some embodiments $R^{5c}$ is —S($C_{3-7}$ cycloalkyl).
In some embodiments $R^{5c}$ is —SO$_2$($C_{1-6}$ linear alkyl).
In some embodiments $R^{5c}$ is —SO$_2$($C_{3-7}$ branched alkyl).
In some embodiments $R^{5c}$ is —SO$_2$($C_{3-7}$ cycloalkyl).
In some embodiments $R^{5c}$ is COR$^6$.
In some embodiments $R^{5c}$ is CO$_2$R$^7$.
In some embodiments $R^{5c}$ is CONR$^{8a}$R$^{8b}$.
In some embodiments $R^{5c}$ is SO$_2$NR$^{8a}$R$^{8b}$.
In some embodiments $R^{5c}$ is NR$^{9a}$R$^9$.
In some embodiments $R^{5c}$ is NR$^{9a}$COR$^{10}$.
In some embodiments $R^{5c}$ is NR$^{9a}$SO$_2$R$^{11}$.
In some embodiments $R^{5c}$ is NR$^{9a}$SO$_2$NR$^{12a}$R$^{12b}$.
In some embodiments $R^{5d}$ is hydrogen.
In some embodiments $R^{5d}$ is OH.
In some embodiments $R^{5d}$ is NO$_2$.
In some embodiments $R^{5d}$ is halogen.
In some embodiments $R^{5d}$ is CN.
In some embodiments $R^{5d}$ is $C_{1-6}$ linear alkyl.
In some embodiments $R^{5d}$ is $C_{3-7}$ branched alkyl.
In some embodiments $R^{5d}$ is $C_{3-7}$ cycloalkyl.
In some embodiments $R^{5d}$ is $C_{1-6}$ linear alkoxy.
In some embodiments $R^{5d}$ is $C_{3-7}$ branched alkoxy.
In some embodiments $R^{5d}$ is $C_{3-7}$ cycloalkoxy.
In some embodiments $R^{5d}$ is $C_{1-6}$ linear haloalkyl.
In some embodiments $R^{5d}$ is $C_{3-7}$ branched haloalkyl.
In some embodiments $R^{5d}$ is $C_{1-6}$ linear haloalkoxy.
In some embodiments $R^{5d}$ is —S($C_{1-6}$ linear alkyl).
In some embodiments $R^{5d}$ is —S($C_{3-7}$ branched alkyl).
In some embodiments $R^{5d}$ is —S($C_{3-7}$ cycloalkyl).
In some embodiments $R^{5d}$ is —SO$_2$($C_{1-6}$ linear alkyl).
In some embodiments $R^{5d}$ is —SO$_2$($C_{3-7}$ branched alkyl).
In some embodiments $R^{5d}$ is —SO$_2$($C_{3-7}$ cycloalkyl).
In some embodiments $R^{5d}$ is COR$^6$.
In some embodiments $R^{5d}$ is CO$_2$R$^7$.
In some embodiments $R^{5d}$ is CONR$^{8a}$R$^{8b}$.
In some embodiments $R^{5d}$ is SO$_2$NR$^{8a}$R$^{8b}$.
In some embodiments $R^{5d}$ is NR$^{9a}$R$^{9b}$.
In some embodiments $R^{5d}$ is NR$^{9a}$COR$^{10}$.
In some embodiments $R^{5d}$ is NR$^{9a}$SO$_2$R$^{11}$.
In some embodiments $R^{5d}$ is NR$^{9a}$SO$_2$NR$^{12a}$R$^{12b}$.
In some embodiments $R^6$ is hydrogen.
In some embodiments $R^6$ is $C_{1-6}$ linear alkyl.
In some embodiments $R^6$ is $C_{3-7}$ branched alkyl.
In some embodiments $R^6$ is $C_{3-7}$ cycloalkyl.
In some embodiments $R^7$ is $C_{1-6}$ linear alkyl.
In some embodiments $R^7$ is $C_{3-7}$ branched alkyl.
In some embodiments $R^7$ is $C_{3-7}$ cycloalkyl.
In some embodiments $R^{8a}$ is hydrogen.
In some embodiments $R^{8a}$ is $C_{1-6}$ linear alkyl.
In some embodiments $R^{8a}$ is $C_{3-7}$ branched alkyl.
In some embodiments $R^{8a}$ is $C_{3-7}$ cycloalkyl.
In some embodiments $R^{8b}$ is hydrogen.
In some embodiments $R^{8b}$ is $C_{1-6}$ linear alkyl.
In some embodiments $R^{8b}$ is $C_{3-7}$ branched alkyl.
In some embodiments $R^{8b}$ is $C_{3-7}$ cycloalkyl.
In some embodiments $R^{9a}$ is hydrogen.
In some embodiments $R^{9a}$ is $C_{1-6}$ linear alkyl.
In some embodiments $R^{9a}$ is $C_{3-7}$ branched alkyl.
In some embodiments $R^{9a}$ is $C_{3-7}$ cycloalkyl.
In some embodiments $R^{9b}$ is hydrogen.
In some embodiments $R^{9b}$ is $C_{1-6}$ linear alkyl.
In some embodiments $R^{9b}$ is $C_{3-7}$ branched alkyl.
In some embodiments $R^{9b}$ is $C_{3-7}$ cycloalkyl.
In some embodiments $R^{9a}$ and $R^{9b}$ are be taken together with the atom to which they are bound to form a ring having 3 ring atoms.
In some embodiments $R^{9a}$ and $R^{9b}$ are be taken together with the atom to which they are bound to form a ring having 4 ring atoms.
In some embodiments $R^{9a}$ and $R^{9b}$ are be taken together with the atom to which they are bound to form a ring having 5 ring atoms.
In some embodiments $R^{9a}$ and $R^{9b}$ are be taken together with the atom to which they are bound to form a ring having 6 ring atoms optionally containing an oxygen.
In some embodiments $R^{9a}$ and $R^{9b}$ are be taken together with the atom to which they are bound to form a ring having 7 ring atoms optionally containing an oxygen.
In some embodiments $R^{10}$ is hydrogen.
In some embodiments $R^{10}$ is $C_{1-6}$ linear alkyl.
In some embodiments $R^{10}$ is $C_{3-7}$ branched alkyl.
In some embodiments $R^{10}$ is $C_{3-7}$ cycloalkyl.
In some embodiments $R^{11}$ is hydrogen.
In some embodiments $R^{11}$ is $C_{1-6}$ linear alkyl.
In some embodiments $R^{11}$ is $C_{3-7}$ branched alkyl.
In some embodiments $R^{11}$ is $C_{3-7}$ cycloalkyl.
In some embodiments $R^{12a}$ is hydrogen.
In some embodiments $R^{12a}$ is $C_{1-6}$ linear alkyl.
In some embodiments $R^{12a}$ is $C_{3-7}$ branched alkyl.
In some embodiments $R^{12a}$ is $C_{3-7}$ cycloalkyl.
In some embodiments $R^{12b}$ is hydrogen.
In some embodiments $R^{12b}$ is $C_{1-6}$ linear alkyl.
In some embodiments $R^{12b}$ is $C_{3-7}$ branched alkyl.
In some embodiments $R^{12b}$ is $C_{3-7}$ cycloalkyl.

Examples of compounds of the invention include, but are not limited to:

(R)-3-(2-(6-(pyridin-4-yl)-2,6-diazaspiro[3.3]heptan-2-yl)ethyl)-2-oxaspiro[4.5]decan-1-one:
(S)-3-(2-(6-(pyridin-4-yl)-2,6-diazaspiro[3.3]heptan-2-yl)ethyl)-2-oxaspiro[4.5]decan-1-one
(R)-3,3-diethyl-5-(2-(6-phenyl-2,6-diazaspiro[3.3]heptan-2-yl)ethyl)dihydrofuran-2(3H)-one;
(S)-3,3-diethyl-5-(2-(6-phenyl-2,6-diazaspiro[3.3]heptan-2-yl)ethyl)dihydrofuran-2(3H)-one;
(R)-3-(2-(6-phenyl-2,6-diazaspiro[3.3]heptan-2-yl)ethyl)-2-oxaspiro[4.5]decan-1-one;
(S)-3-(2-(6-phenyl-2,6-diazaspiro[3.3]heptan-2-yl)ethyl)-2-oxaspiro[4.5]decan-1-one;
(R)-3,3-diethyl-5-(2-(5-(2-isopropylphenyl)hexahydropyrrolo[3,4-c]pyrrol-2(1H)-yl)ethyl)dihydrofuran-2(3H)-one;
(S)-3,3-diethyl-5-(2-(5-(2-isopropylphenyl)hexahydropyrrolo[3,4-c]pyrrol-2(1H)-yl)ethyl)dihydrofuran-2(3H)-one;
(R)-3-(2-(5-(3-methylpyridin-4-yl)hexahydropyrrolo[3,4-c]pyrrol-2(1H)-yl)ethyl)-2-oxaspiro[4.5]decan-1-one;
(S)-3-(2-(5-(3-methylpyridin-4-yl)hexahydropyrrolo[3,4-c]pyrrol-2(1H)-yl)ethyl)-2-oxaspiro[4.5]decan-1-one;
(R)-3-(2-(5-(2-methylpyridin-4-yl)hexahydropyrrolo[3,4-c]pyrrol-2(1H)-yl)ethyl)-2-oxaspiro[4.5]decan-1-one;
(S)-3-(2-(5-(2-methylpyridin-4-yl)hexahydropyrrolo[3,4-c]pyrrol-2(1H)-yl)ethyl)-2-oxaspiro[4.5]decan-1-one;
(R)-3-(2-(5-(2,6-dimethylpyridin-4-yl)hexahydropyrrolo[3,4-c]pyrrol-2(1H)-yl)ethyl)-2-oxaspiro[4.5]decan-1-one;
(S)-3-(2-(5-(2,6-dimethylpyridin-4-yl)hexahydropyrrolo[3,4-c]pyrrol-2(1H)-yl)ethyl)-2-oxaspiro[4.5]decan-1-one;
(R)-3-(2-(6-(3-methylpyridin-4-yl)-2,6-diazaspiro[3.3]heptan-2-yl)ethyl)-2-oxaspiro[4.5]decan-1-one;

(S)-3-(2-(6-(3-methylpyridin-4-yl)-2,6-diazaspiro[3.3]heptan-2-yl)ethyl)-2-oxaspiro[4.5]decan-1-one;
(R)-3-(2-(6-(2-methylpyridin-4-yl)-2,6-diazaspiro[3.3]heptan-2-yl)ethyl)-2-oxaspiro[4.5]decan-1-one;
(S)-3-(2-(6-(2-methylpyridin-4-yl)-2,6-diazaspiro[3.3]heptan-2-yl)ethyl)-2-oxaspiro[4.5]decan-1-one;
(R)-3-(2-(6-(2,6-dimethylpyridin-4-yl)-2,6-diazaspiro[3.3]heptan-2-yl)ethyl)-2-oxaspiro[4.5]decan-1-one;
(S)-3-(2-(6-(2,6-dimethylpyridin-4-yl)-2,6-diazaspiro[3.3]heptan-2-yl)ethyl)-2-oxaspiro[4.5]decan-1-one;
(R)-3,3-diethyl-5-(2-(5-(o-tolyl)hexahydropyrrolo[3,4-c]pyrrol-2(1H)-yl)ethyl)dihydrofuran-2(3H)-one;
(S)-3,3-diethyl-5-(2-(5-(o-tolyl)hexahydropyrrolo[3,4-c]pyrrol-2(1H)-yl)ethyl)dihydrofuran-2(3H)-one;
(R)-3,3-diethyl-5-(2-(5-(m-tolyl)hexahydropyrrolo[3,4-c]pyrrol-2(1H)-yl)ethyl)dihydrofuran-2(3H)-one;
(S)-3,3-diethyl-5-(2-(5-(m-tolyl)hexahydropyrrolo[3,4-c]pyrrol-2(1H)-yl)ethyl)dihydrofuran-2(3H)-one;
(R)-3,3-diethyl-5-(2-(5-(p-tolyl)hexahydropyrrolo[3,4-c]pyrrol-2(1H)-yl)ethyl)dihydrofuran-2(3H)-one;
(S)-3,3-diethyl-5-(2-(5-(p-tolyl)hexahydropyrrolo[3,4-c]pyrrol-2(1H)-yl)ethyl)dihydrofuran-2(3H)-one;
(R)-2-(5-(2-(4,4-diethyl-5-oxotetrahydrofuran-2-yl)ethyl)hexahydropyrrolo[3,4-c]pyrrol-2(1H)-yl)benzonitrile;
(S)-2-(5-(2-(4,4-diethyl-5-oxotetrahydrofuran-2-yl)ethyl)hexahydropyrrolo[3,4-c]pyrrol-2(1H)-yl)benzonitrile;
(R)-3-(5-(2-(4,4-diethyl-5-oxotetrahydrofuran-2-yl)ethyl)hexahydropyrrolo[3,4-c]pyrrol-2(1H)-yl)benzonitrile;
(S)-3-(5-(2-(4,4-diethyl-5-oxotetrahydrofuran-2-yl)ethyl)hexahydropyrrolo[3,4-c]pyrrol-2(1H)-yl)benzonitrile;
(R)-4-(5-(2-(4,4-diethyl-5-oxotetrahydrofuran-2-yl)ethyl)hexahydropyrrolo[3,4-c]pyrrol-2(1H)-yl)benzonitrile;
(S)-4-(5-(2-(4,4-diethyl-5-oxotetrahydrofuran-2-yl)ethyl)hexahydropyrrolo[3,4-c]pyrrol-2(1H)-yl)benzonitrile;
(R)-3,3-diethyl-5-(2-(5-(2-methoxyphenyl)hexahydropyrrolo[3,4-c]pyrrol-2(1H)-yl)ethyl)dihydrofuran-2(3H)-one;
(S)-3,3-diethyl-5-(2-(5-(2-methoxyphenyl)hexahydropyrrolo[3,4-c]pyrrol-2(1H)-yl)ethyl)dihydrofuran-2(3H)-one;
(R)-3,3-diethyl-5-(2-(5-(3-methoxyphenyl)hexahydropyrrolo[3,4-c]pyrrol-2(1H)-yl)ethyl)dihydrofuran-2(3H)-one;
(S)-3,3-diethyl-5-(2-(5-(3-methoxyphenyl)hexahydropyrrolo[3,4-c]pyrrol-2(1H)-yl)ethyl)dihydrofuran-2(3H)-one;
(R)-3,3-diethyl-5-(2-(5-(4-methoxyphenyl)hexahydropyrrolo[3,4-c]pyrrol-2(1H)-yl)ethyl)dihydrofuran-2(3H)-one;
(S)-3,3-diethyl-5-(2-(5-(4-methoxyphenyl)hexahydropyrrolo[3,4-c]pyrrol-2(1H)-yl)ethyl)dihydrofuran-2(3H)-one;
(R)-3,3-diethyl-5-(2-(5-(2-morpholinophenyl)hexahydropyrrolo[3,4-c]pyrrol-2(1H)-yl)ethyl)dihydrofuran-2(3H)-one;
(S)-3,3-diethyl-5-(2-(5-(2-morpholinophenyl)hexahydropyrrolo[3,4-c]pyrrol-2(1H)-yl)ethyl)dihydrofuran-2(3H)-one;
(R)-3,3-diethyl-5-(2-(5-(2-hydroxyphenyl)hexahydropyrrolo[3,4-c]pyrrol-2(1H)-yl)ethyl)dihydrofuran-2(3H)-one;
(S)-3,3-diethyl-5-(2-(5-(2-hydroxyphenyl)hexahydropyrrolo[3,4-c]pyrrol-2(1H)-yl)ethyl)dihydrofuran-2(3H)-one;
(R)-3,3-diethyl-5-(2-(5-(3-hydroxyphenyl)hexahydropyrrolo[3,4-c]pyrrol-2(1H)-yl)ethyl)dihydrofuran-2(3H)-one;
(S)-3,3-diethyl-5-(2-(5-(3-hydroxyphenyl)hexahydropyrrolo[3,4-c]pyrrol-2(1H)-yl)ethyl)dihydrofuran-2(3H)-one;
(R)-3,3-diethyl-5-(2-(5-(4-hydroxyphenyl)hexahydropyrrolo[3,4-c]pyrrol-2(1H)-yl)ethyl)dihydrofuran-2(3H)-one;
(S)-3,3-diethyl-5-(2-(5-(4-hydroxyphenyl)hexahydropyrrolo[3,4-c]pyrrol-2(1H)-yl)ethyl)dihydrofuran-2(3H)-one;
(R)-3,3-diethyl-5-(2-(5-phenylhexahydropyrrolo[3,4-c]pyrrol-2(1H)-yl)ethyl)dihydrofuran-2(3H)-one;
(S)-3,3-diethyl-5-(2-(5-phenylhexahydropyrrolo[3,4-c]pyrrol-2(1H)-yl)ethyl)dihydrofuran-2(3H)-one;
or a pharmaceutically acceptable form thereof.

Exemplary embodiments include compounds having the formula (II) or a pharmaceutically acceptable salt form thereof:

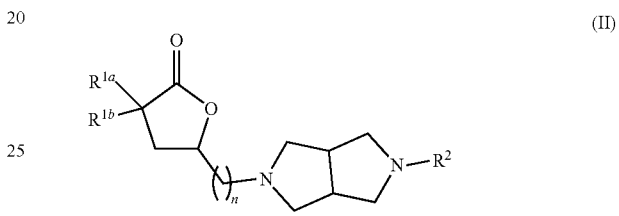

(II)

wherein non-limiting examples of $R^{1a}$, $R^{1b}$, $R^2$ and n are defined herein below in Table 1.

TABLE 1

| Entry | n | $R^{1a}$ | $R^{1b}$ | $R^2$ |
|---|---|---|---|---|
| 1 | 1 | $CH_3$ | $CH_3$ | Phenyl |
| 2 | 2 | $CH_3$ | $CH_3$ | Phenyl |
| 3 | 3 | $CH_3$ | $CH_3$ | Phenyl |
| 4 | 1 | $CH_2CH_3$ | $CH_2CH_3$ | Phenyl |
| 5 | 2 | $CH_2CH_3$ | $CH_2CH_3$ | Phenyl |
| 6 | 3 | $CH_2CH_3$ | $CH_2CH_3$ | Phenyl |
| 7 | 1 | $CH_3$ | $CH_3$ | 4-OH-phenyl |
| 8 | 2 | $CH_3$ | $CH_3$ | 4-OH-phenyl |
| 10 | 3 | $CH_3$ | $CH_3$ | 4-OH-phenyl |
| 11 | 1 | $CH_2CH_3$ | $CH_2CH_3$ | 4-OH-phenyl |
| 12 | 2 | $CH_2CH_3$ | $CH_2CH_3$ | 4-OH-phenyl |
| 13 | 3 | $CH_2CH_3$ | $CH_2CH_3$ | 4-OH-phenyl |
| 14 | 1 | $CH_3$ | $CH_3$ | 3-OH-phenyl |
| 15 | 2 | $CH_3$ | $CH_3$ | 3-OH-phenyl |
| 16 | 3 | $CH_3$ | $CH_3$ | 3-OH-phenyl |
| 17 | 1 | $CH_2CH_3$ | $CH_2CH_3$ | 3-OH-phenyl |
| 18 | 2 | $CH_2CH_3$ | $CH_2CH_3$ | 3-OH-phenyl |
| 19 | 3 | $CH_2CH_3$ | $CH_2CH_3$ | 3-OH-phenyl |
| 20 | 1 | $CH_3$ | $CH_3$ | 2-OH-phenyl |
| 21 | 2 | $CH_3$ | $CH_3$ | 2-OH-phenyl |
| 22 | 3 | $CH_3$ | $CH_3$ | 2-OH-phenyl |
| 23 | 1 | $CH_2CH_3$ | $CH_2CH_3$ | 2-OH-phenyl |
| 24 | 2 | $CH_2CH_3$ | $CH_2CH_3$ | 2-OH-phenyl |
| 25 | 3 | $CH_2CH_3$ | $CH_2CH_3$ | 2-OH-phenyl |
| 26 | 1 | $CH_3$ | $CH_3$ | 4-$CH_3$-Phenyl |
| 27 | 2 | $CH_3$ | $CH_3$ | 4-$CH_3$-Phenyl |
| 28 | 3 | $CH_3$ | $CH_3$ | 4-$CH_3$-Phenyl |
| 26 | 1 | $CH_2CH_3$ | $CH_2CH_3$ | 4-$CH_3$-Phenyl |
| 30 | 2 | $CH_2CH_3$ | $CH_2CH_3$ | 4-$CH_3$-Phenyl |
| 31 | 3 | $CH_2CH_3$ | $CH_2CH_3$ | 4-$CH_3$-Phenyl |
| 32 | 1 | $CH_3$ | $CH_3$ | 3-$CH_3$-Phenyl |
| 33 | 2 | $CH_3$ | $CH_3$ | 3-$CH_3$-Phenyl |
| 34 | 3 | $CH_3$ | $CH_3$ | 3-$CH_3$-Phenyl |
| 35 | 1 | $CH_2CH_3$ | $CH_2CH_3$ | 3-$CH_3$-Phenyl |
| 36 | 2 | $CH_2CH_3$ | $CH_2CH_3$ | 3-$CH_3$-Phenyl |
| 37 | 3 | $CH_2CH_3$ | $CH_2CH_3$ | 3-$CH_3$-Phenyl |
| 38 | 1 | $CH_3$ | $CH_3$ | 2-$CH_3$-Phenyl |
| 39 | 2 | $CH_3$ | $CH_3$ | 2-$CH_3$-Phenyl |
| 40 | 3 | $CH_3$ | $CH_3$ | 2-$CH_3$-Phenyl |

TABLE 1-continued

| Entry | n | $R^{1a}$ | $R^{1b}$ | $R^2$ |
|---|---|---|---|---|
| 41 | 1 | $CH_2CH_3$ | $CH_2CH_3$ | 2-$CH_3$-Phenyl |
| 42 | 2 | $CH_2CH_3$ | $CH_2CH_3$ | 2-$CH_3$-Phenyl |
| 43 | 3 | $CH_2CH_3$ | $CH_2CH_3$ | 2-$CH_3$-Phenyl |
| 44 | 1 | $CH_3$ | $CH_3$ | 4-$OCH_3$-Phenyl |
| 45 | 2 | $CH_3$ | $CH_3$ | 4-$OCH_3$-Phenyl |
| 46 | 3 | $CH_3$ | $CH_3$ | 4-$OCH_3$-Phenyl |
| 47 | 1 | $CH_2CH_3$ | $CH_2CH_3$ | 4-$OCH_3$-Phenyl |
| 48 | 2 | $CH_2CH_3$ | $CH_2CH_3$ | 4-$OCH_3$-Phenyl |
| 49 | 3 | $CH_2CH_3$ | $CH_2CH_3$ | 4-$OCH_3$-Phenyl |
| 50 | 1 | $CH_3$ | $CH_3$ | 3-$OCH_3$-Phenyl |
| 51 | 2 | $CH_3$ | $CH_3$ | 3-$OCH_3$-Phenyl |
| 52 | 3 | $CH_3$ | $CH_3$ | 3-$OCH_3$-Phenyl |
| 53 | 1 | $CH_2CH_3$ | $CH_2CH_3$ | 3-$OCH_3$-Phenyl |
| 54 | 2 | $CH_2CH_3$ | $CH_2CH_3$ | 3-$OCH_3$-Phenyl |
| 55 | 3 | $CH_2CH_3$ | $CH_2CH_3$ | 3-$OCH_3$-Phenyl |
| 56 | 1 | $CH_3$ | $CH_3$ | 2-$OCH_3$-Phenyl |
| 57 | 2 | $CH_3$ | $CH_3$ | 2-$OCH_3$-Phenyl |
| 58 | 3 | $CH_3$ | $CH_3$ | 2-$OCH_3$-Phenyl |
| 59 | 1 | $CH_2CH_3$ | $CH_2CH_3$ | 2-$OCH_3$-Phenyl |
| 60 | 2 | $CH_2CH_3$ | $CH_2CH_3$ | 2-$OCH_3$-Phenyl |
| 61 | 3 | $CH_2CH_3$ | $CH_2CH_3$ | 2-$OCH_3$-Phenyl |
| 62 | 1 | $CH_3$ | $CH_3$ | 4-CN-Phenyl |
| 63 | 2 | $CH_3$ | $CH_3$ | 4-CN-Phenyl |
| 64 | 3 | $CH_3$ | $CH_3$ | 4-CN-Phenyl |
| 65 | 1 | $CH_2CH_3$ | $CH_2CH_3$ | 4-CN-Phenyl |
| 66 | 2 | $CH_2CH_3$ | $CH_2CH_3$ | 4-CN-Phenyl |
| 67 | 3 | $CH_2CH_3$ | $CH_2CH_3$ | 4-CN-Phenyl |
| 68 | 1 | $CH_3$ | $CH_3$ | 3-CN-Phenyl |
| 69 | 2 | $CH_3$ | $CH_3$ | 3-CN-Phenyl |
| 70 | 3 | $CH_3$ | $CH_3$ | 3-CN-Phenyl |
| 71 | 1 | $CH_2CH_3$ | $CH_2CH_3$ | 3-CN-Phenyl |
| 72 | 2 | $CH_2CH_3$ | $CH_2CH_3$ | 3-CN-Phenyl |
| 73 | 3 | $CH_2CH_3$ | $CH_2CH_3$ | 3-CN-Phenyl |
| 74 | 1 | $CH_3$ | $CH_3$ | 2-CN-Phenyl |
| 75 | 2 | $CH_3$ | $CH_3$ | 2-CN-Phenyl |
| 76 | 3 | $CH_3$ | $CH_3$ | 2-CN-Phenyl |
| 77 | 1 | $CH_2CH_3$ | $CH_2CH_3$ | 2-CN-Phenyl |
| 78 | 2 | $CH_2CH_3$ | $CH_2CH_3$ | 2-CN-Phenyl |
| 79 | 3 | $CH_2CH_3$ | $CH_2CH_3$ | 2-CN-Phenyl |
| 80 | 1 | $CH_3$ | $CH_3$ | 4-F-Phenyl |
| 81 | 2 | $CH_3$ | $CH_3$ | 4-F-Phenyl |
| 82 | 3 | $CH_3$ | $CH_3$ | 4-F-Phenyl |
| 83 | 1 | $CH_2CH_3$ | $CH_2CH_3$ | 4-F-Phenyl |
| 84 | 2 | $CH_2CH_3$ | $CH_2CH_3$ | 4-F-Phenyl |
| 85 | 3 | $CH_2CH_3$ | $CH_2CH_3$ | 4-F-Phenyl |
| 86 | 1 | $CH_3$ | $CH_3$ | 3-F-Phenyl |
| 87 | 2 | $CH_3$ | $CH_3$ | 3-F-Phenyl |
| 88 | 3 | $CH_3$ | $CH_3$ | 3-F-Phenyl |
| 89 | 1 | $CH_2CH_3$ | $CH_2CH_3$ | 3-F-Phenyl |
| 90 | 2 | $CH_2CH_3$ | $CH_2CH_3$ | 3-F-Phenyl |
| 91 | 3 | $CH_2CH_3$ | $CH_2CH_3$ | 3-F-Phenyl |
| 92 | 1 | $CH_3$ | $CH_3$ | 2-F-Phenyl |
| 93 | 2 | $CH_3$ | $CH_3$ | 2-F-Phenyl |
| 94 | 3 | $CH_3$ | $CH_3$ | 2-F-Phenyl |
| 95 | 1 | $CH_2CH_3$ | $CH_2CH_3$ | 2-F-Phenyl |
| 96 | 2 | $CH_2CH_3$ | $CH_2CH_3$ | 2-F-Phenyl |
| 97 | 3 | $CH_2CH_3$ | $CH_2CH_3$ | 2-F-Phenyl |
| 98 | 1 | $CH_3$ | $CH_3$ | 4-Cl-Phenyl |
| 99 | 2 | $CH_3$ | $CH_3$ | 4-Cl-Phenyl |
| 100 | 3 | $CH_3$ | $CH_3$ | 4-Cl-Phenyl |
| 101 | 1 | $CH_2CH_3$ | $CH_2CH_3$ | 4-Cl-Phenyl |
| 102 | 2 | $CH_2CH_3$ | $CH_2CH_3$ | 4-Cl-Phenyl |
| 103 | 3 | $CH_2CH_3$ | $CH_2CH_3$ | 4-Cl-Phenyl |
| 104 | 1 | $CH_3$ | $CH_3$ | 3-Cl-Phenyl |
| 105 | 2 | $CH_3$ | $CH_3$ | 3-Cl-Phenyl |
| 106 | 3 | $CH_3$ | $CH_3$ | 3-Cl-Phenyl |
| 107 | 1 | $CH_2CH_3$ | $CH_2CH_3$ | 3-Cl-Phenyl |
| 108 | 2 | $CH_2CH_3$ | $CH_2CH_3$ | 3-Cl-Phenyl |
| 109 | 3 | $CH_2CH_3$ | $CH_2CH_3$ | 3-Cl-Phenyl |
| 110 | 1 | $CH_3$ | $CH_3$ | 2-Cl-Phenyl |
| 111 | 2 | $CH_3$ | $CH_3$ | 2-Cl-Phenyl |
| 112 | 3 | $CH_3$ | $CH_3$ | 2-Cl-Phenyl |
| 113 | 1 | $CH_2CH_3$ | $CH_2CH_3$ | 2-Cl-Phenyl |
| 114 | 2 | $CH_2CH_3$ | $CH_2CH_3$ | 2-Cl-Phenyl |
| 115 | 3 | $CH_2CH_3$ | $CH_2CH_3$ | 2-Cl-Phenyl |
| 116 | 1 | $CH_3$ | $CH_3$ | 4-Br-Phenyl |
| 117 | 2 | $CH_3$ | $CH_3$ | 4-Br-Phenyl |
| 118 | 3 | $CH_3$ | $CH_3$ | 4-Br-Phenyl |
| 119 | 1 | $CH_2CH_3$ | $CH_2CH_3$ | 4-Br-Phenyl |
| 120 | 2 | $CH_2CH_3$ | $CH_2CH_3$ | 4-Br-Phenyl |
| 121 | 3 | $CH_2CH_3$ | $CH_2CH_3$ | 4-Br-Phenyl |
| 122 | 1 | $CH_3$ | $CH_3$ | 4-$OCF_3$-Phenyl |
| 123 | 2 | $CH_3$ | $CH_3$ | 4-$OCF_3$-Phenyl |
| 124 | 3 | $CH_3$ | $CH_3$ | 4-$OCF_3$-Phenyl |
| 125 | 1 | $CH_2CH_3$ | $CH_2CH_3$ | 4-$OCF_3$-Phenyl |
| 126 | 2 | $CH_2CH_3$ | $CH_2CH_3$ | 4-$OCF_3$-Phenyl |
| 127 | 3 | $CH_2CH_3$ | $CH_2CH_3$ | 4-$OCF_3$-Phenyl |
| 128 | 1 | $CH_3$ | $CH_3$ | 3-$OCF_3$-Phenyl |
| 129 | 2 | $CH_3$ | $CH_3$ | 3-$OCF_3$-Phenyl |
| 130 | 3 | $CH_3$ | $CH_3$ | 3-$OCF_3$-Phenyl |
| 131 | 1 | $CH_2CH_3$ | $CH_2CH_3$ | 3-$OCF_3$-Phenyl |
| 132 | 2 | $CH_2CH_3$ | $CH_2CH_3$ | 3-$OCF_3$-Phenyl |
| 133 | 3 | $CH_2CH_3$ | $CH_2CH_3$ | 3-$OCF_3$-Phenyl |
| 134 | 1 | $CH_3$ | $CH_3$ | 2-$OCF_3$-Phenyl |
| 135 | 2 | $CH_3$ | $CH_3$ | 2-$OCF_3$-Phenyl |
| 136 | 3 | $CH_3$ | $CH_3$ | 2-$OCF_3$-Phenyl |
| 137 | 1 | $CH_2CH_3$ | $CH_2CH_3$ | 2-$OCF_3$-Phenyl |
| 138 | 2 | $CH_2CH_3$ | $CH_2CH_3$ | 2-$OCF_3$-Phenyl |
| 139 | 3 | $CH_2CH_3$ | $CH_2CH_3$ | 2-$OCF_3$-Phenyl |
| 140 | 1 | $CH_3$ | $CH_3$ | 4-isopropyl-phenyl |
| 141 | 2 | $CH_3$ | $CH_3$ | 4-isopropyl-phenyl |
| 142 | 3 | $CH_3$ | $CH_3$ | 4-isopropyl-phenyl |
| 143 | 1 | $CH_2CH_3$ | $CH_2CH_3$ | 4-isopropyl-phenyl |
| 144 | 2 | $CH_2CH_3$ | $CH_2CH_3$ | 4-isopropyl-phenyl |
| 145 | 3 | $CH_2CH_3$ | $CH_2CH_3$ | 4-isopropyl-phenyl |
| 146 | 1 | $CH_3$ | $CH_3$ | 3-isopropyl-phenyl |
| 147 | 2 | $CH_3$ | $CH_3$ | 3-isopropyl-phenyl |
| 148 | 3 | $CH_3$ | $CH_3$ | 3-isopropyl-phenyl |
| 149 | 1 | $CH_2CH_3$ | $CH_2CH_3$ | 3-isopropyl-phenyl |
| 150 | 2 | $CH_2CH_3$ | $CH_2CH_3$ | 3-isopropyl-phenyl |
| 151 | 3 | $CH_2CH_3$ | $CH_2CH_3$ | 3-isopropyl-phenyl |
| 152 | 1 | $CH_3$ | $CH_3$ | 2-isopropyl-phenyl |
| 153 | 2 | $CH_3$ | $CH_3$ | 2-isopropyl-phenyl |
| 154 | 3 | $CH_3$ | $CH_3$ | 2-isopropyl-phenyl |
| 155 | 1 | $CH_2CH_3$ | $CH_2CH_3$ | 2-isopropyl-phenyl |
| 156 | 2 | $CH_2CH_3$ | $CH_2CH_3$ | 2-isopropyl-phenyl |
| 157 | 3 | $CH_2CH_3$ | $CH_2CH_3$ | 2-isopropyl-phenyl |
| 158 | 1 | $CH_3$ | $CH_3$ | 4-cyclopropyl-phenyl |
| 159 | 2 | $CH_3$ | $CH_3$ | 4-cyclopropyl-phenyl |
| 160 | 3 | $CH_3$ | $CH_3$ | 4-cyclopropyl-phenyl |
| 161 | 1 | $CH_2CH_3$ | $CH_2CH_3$ | 4-cyclopropyl-phenyl |
| 162 | 2 | $CH_2CH_3$ | $CH_2CH_3$ | 4-cyclopropyl-phenyl |
| 163 | 3 | $CH_2CH_3$ | $CH_2CH_3$ | 4-cyclopropyl-phenyl |
| 164 | 1 | $CH_3$ | $CH_3$ | 3-cyclopropyl-phenyl |
| 165 | 2 | $CH_3$ | $CH_3$ | 3-cyclopropyl-phenyl |
| 166 | 3 | $CH_3$ | $CH_3$ | 3-cyclopropyl-phenyl |
| 167 | 1 | $CH_2CH_3$ | $CH_2CH_3$ | 3-cyclopropyl-phenyl |
| 168 | 2 | $CH_2CH_3$ | $CH_2CH_3$ | 3-cyclopropyl-phenyl |
| 169 | 3 | $CH_2CH_3$ | $CH_2CH_3$ | 3-cyclopropyl-phenyl |
| 170 | 1 | $CH_3$ | $CH_3$ | 2-cyclopropyl-phenyl |
| 171 | 2 | $CH_3$ | $CH_3$ | 2-cyclopropyl-phenyl |
| 172 | 3 | $CH_3$ | $CH_3$ | 2-cyclopropyl-phenyl |
| 173 | 1 | $CH_2CH_3$ | $CH_2CH_3$ | 2-cyclopropyl-phenyl |
| 174 | 2 | $CH_2CH_3$ | $CH_2CH_3$ | 2-cyclopropyl-phenyl |
| 175 | 3 | $CH_2CH_3$ | $CH_2CH_3$ | 2-cyclopropyl-phenyl |
| 176 | 1 | $CH_3$ | $CH_3$ | 4-morpholino-phenyl |
| 177 | 2 | $CH_3$ | $CH_3$ | 4-morpholino-phenyl |
| 178 | 3 | $CH_3$ | $CH_3$ | 4-morpholino-phenyl |
| 179 | 1 | $CH_2CH_3$ | $CH_2CH_3$ | 4-morpholino-phenyl |
| 180 | 2 | $CH_2CH_3$ | $CH_2CH_3$ | 4-morpholino-phenyl |
| 181 | 3 | $CH_2CH_3$ | $CH_2CH_3$ | 4-morpholino-phenyl |
| 182 | 1 | $CH_3$ | $CH_3$ | 3-morpholino-phenyl |
| 183 | 2 | $CH_3$ | $CH_3$ | 3-morpholino-phenyl |
| 184 | 3 | $CH_3$ | $CH_3$ | 3-morpholino-phenyl |
| 185 | 1 | $CH_2CH_3$ | $CH_2CH_3$ | 3-morpholino-phenyl |
| 186 | 2 | $CH_2CH_3$ | $CH_2CH_3$ | 3-morpholino-phenyl |
| 187 | 3 | $CH_2CH_3$ | $CH_2CH_3$ | 3-morpholino-phenyl |
| 188 | 1 | $CH_3$ | $CH_3$ | 2-morpholino-phenyl |
| 189 | 2 | $CH_3$ | $CH_3$ | 2-morpholino-phenyl |
| 190 | 3 | $CH_3$ | $CH_3$ | 2-morpholino-phenyl |
| 191 | 1 | $CH_2CH_3$ | $CH_2CH_3$ | 2-morpholino-phenyl |
| 192 | 2 | $CH_2CH_3$ | $CH_2CH_3$ | 2-morpholino-phenyl |
| 193 | 3 | $CH_2CH_3$ | $CH_2CH_3$ | 2-morpholino-phenyl |
| 194 | 1 | $CH_3$ | $CH_3$ | 2-pyridyl |
| 195 | 2 | $CH_3$ | $CH_3$ | 2-pyridyl |
| 196 | 3 | $CH_3$ | $CH_3$ | 2-pyridyl |

TABLE 1-continued

| Entry | n | R1a | R1b | R2 |
|---|---|---|---|---|
| 197 | 1 | CH2CH3 | CH2CH3 | 2-pyridyl |
| 198 | 2 | CH2CH3 | CH2CH3 | 2-pyridyl |
| 199 | 3 | CH2CH3 | CH2CH3 | 2-pyridyl |
| 200 | 1 | CH3 | CH3 | 3-pyridyl |
| 201 | 2 | CH3 | CH3 | 3-pyridyl |
| 202 | 3 | CH3 | CH3 | 3-pyridyl |
| 203 | 1 | CH2CH3 | CH2CH3 | 3-pyridyl |
| 204 | 2 | CH2CH3 | CH2CH3 | 3-pyridyl |
| 205 | 3 | CH2CH3 | CH2CH3 | 3-pyridyl |
| 206 | 1 | CH3 | CH3 | 4-pyridyl |
| 207 | 2 | CH3 | CH3 | 4-pyridyl |
| 208 | 3 | CH3 | CH3 | 4-pyridyl |
| 209 | 1 | CH2CH3 | CH2CH3 | 4-pyridyl |
| 210 | 2 | CH2CH3 | CH2CH3 | 4-pyridyl |
| 211 | 3 | CH2CH3 | CH2CH3 | 4-pyridyl |
| 212 | 1 | CH3 | CH3 | 2-CH3-4-pyridyl |
| 213 | 2 | CH3 | CH3 | 2-CH3-4-pyridyl |
| 214 | 3 | CH3 | CH3 | 2-CH3-4-pyridyl |
| 215 | 1 | CH2CH3 | CH2CH3 | 2-CH3-4-pyridyl |
| 216 | 2 | CH2CH3 | CH2CH3 | 2-CH3-4-pyridyl |
| 217 | 3 | CH2CH3 | CH2CH3 | 2-CH3-4-pyridyl |
| 218 | 1 | CH3 | CH3 | 3-CH3-4-pyridyl |
| 219 | 2 | CH3 | CH3 | 3-CH3-4-pyridyl |
| 220 | 3 | CH3 | CH3 | 3-CH3-4-pyridyl |
| 221 | 1 | CH2CH3 | CH2CH3 | 3-CH3-4-pyridyl |
| 222 | 2 | CH2CH3 | CH2CH3 | 3-CH3-4-pyridyl |
| 223 | 3 | CH2CH3 | CH2CH3 | 3-CH3-4-pyridyl |
| 224 | 1 | CH3 | CH3 | 3,5-dimethylpyridin-4-yl |
| 225 | 2 | CH3 | CH3 | 3,5-dimethylpyridin-4-yl |
| 226 | 3 | CH3 | CH3 | 3,5-dimethylpyridin-4-yl |
| 227 | 1 | CH2CH3 | CH2CH3 | 3,5-dimethylpyridin-4-yl |
| 228 | 2 | CH2CH3 | CH2CH3 | 3,5-dimethylpyridin-4-yl |
| 229 | 3 | CH2CH3 | CH2CH3 | 3,5-dimethylpyridin-4-yl |
| 230 | 1 | CH3 | CH3 | 2,6-dimethylpyridin-4-yl |
| 231 | 2 | CH3 | CH3 | 2,6-dimethylpyridin-4-yl |
| 232 | 3 | CH3 | CH3 | 2,6-dimethylpyridin-4-yl |
| 233 | 1 | CH2CH3 | CH2CH3 | 2,6-dimethylpyridin-4-yl |
| 234 | 2 | CH2CH3 | CH2CH3 | 2,6-dimethylpyridin-4-yl |
| 235 | 3 | CH2CH3 | CH2CH3 | 2,6-dimethylpyridin-4-yl |

Exemplary embodiments include compounds having the formula (X) or a pharmaceutically acceptable salt form thereof:

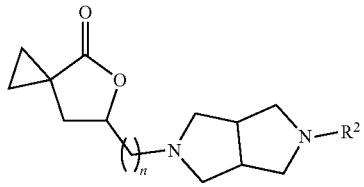

(X)

wherein non-limiting examples of $R^2$ and n are defined herein below in Table 2.

TABLE 2

| Entry | n | R2 |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH3-Phenyl |
| 14 | 2 | 4-CH3-Phenyl |
| 15 | 3 | 4-CH3-Phenyl |
| 16 | 1 | 3-CH3-Phenyl |
| 17 | 2 | 3-CH3-Phenyl |
| 18 | 3 | 3-CH3-Phenyl |
| 19 | 1 | 2-CH3-Phenyl |
| 20 | 2 | 2-CH3-Phenyl |
| 21 | 3 | 2-CH3-Phenyl |
| 22 | 1 | 4-OCH3-Phenyl |
| 23 | 2 | 4-OCH3-Phenyl |
| 24 | 3 | 4-OCH3-Phenyl |
| 25 | 1 | 3-OCH3-Phenyl |
| 26 | 2 | 3-OCH3-Phenyl |
| 27 | 3 | 3-OCH3-Phenyl |
| 28 | 1 | 2-OCH3-Phenyl |
| 29 | 2 | 2-OCH3-Phenyl |
| 30 | 3 | 2-OCH3-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF3-Phenyl |
| 62 | 2 | 4-OCF3-Phenyl |
| 63 | 3 | 4-OCF3-Phenyl |
| 64 | 1 | 4-OCF3-Phenyl |
| 65 | 2 | 4-OCF3-Phenyl |
| 66 | 3 | 4-OCF3-Phenyl |
| 67 | 1 | 4-OCF3-Phenyl |
| 68 | 2 | 4-OCF3-Phenyl |
| 69 | 3 | 4-OCF3-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |

TABLE 2-continued

| Entry | n | R² |
|---|---|---|
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (XI) or a pharmaceutically acceptable salt form thereof:

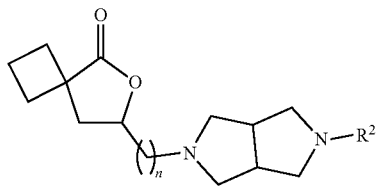

(XI)

wherein non-limiting examples of R² and n are defined herein below in Table 3.

TABLE 3

| Entry | n | R² |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |

TABLE 3-continued

| Entry | n | R² |
|---|---|---|
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (XII) or a pharmaceutically acceptable salt form thereof:

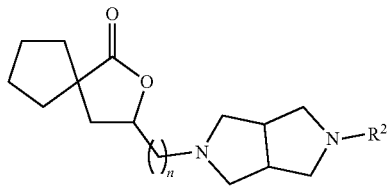

(XII)

wherein non-limiting examples of R and n are defined herein below in Table 4.

TABLE 4

| Entry | n | R² |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |

TABLE 4-continued

| Entry | n | R² |
|---|---|---|
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (XIII) or a pharmaceutically acceptable salt form thereof:

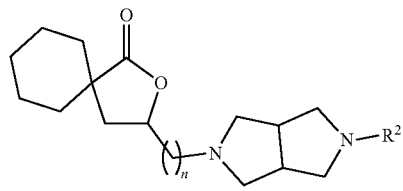

(XIII)

wherein non-limiting examples of $R^2$ and n are defined herein below in Table 5.

TABLE 5

| Entry | n | R² |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |

TABLE 5-continued

| Entry | n | R² |
|---|---|---|
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH3-4-pyridyl |
| 107 | 2 | 2-CH3-4-pyridyl |
| 108 | 3 | 2-CH3-4-pyridyl |
| 109 | 1 | 3-CH3-4-pyridyl |
| 110 | 2 | 3-CH3-4-pyridyl |
| 111 | 3 | 3-CH3-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (VI) or a pharmaceutically acceptable salt form thereof:

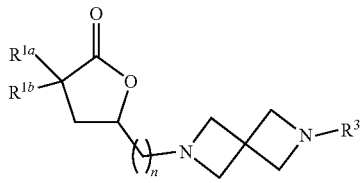

(VI)

wherein non-limiting examples of $R^{1a}$, $R^{1b}$, $R^3$ and n are defined herein below in Table 6.

TABLE 6

| Entry | n | $R^{1a}$ | $R^{1b}$ | $R^3$ |
|---|---|---|---|---|
| 1 | 1 | $CH_3$ | $CH_3$ | Phenyl |
| 2 | 2 | $CH_3$ | $CH_3$ | Phenyl |
| 3 | 3 | $CH_3$ | $CH_3$ | Phenyl |
| 4 | 1 | $CH_2CH_3$ | $CH_2CH_3$ | Phenyl |
| 5 | 2 | $CH_2CH_3$ | $CH_2CH_3$ | Phenyl |
| 6 | 3 | $CH_2CH_3$ | $CH_2CH_3$ | Phenyl |
| 7 | 1 | $CH_3$ | $CH_3$ | 4-OH-phenyl |
| 8 | 2 | $CH_3$ | $CH_3$ | 4-OH-phenyl |
| 10 | 3 | $CH_3$ | $CH_3$ | 4-OH-phenyl |
| 11 | 1 | $CH_2CH_3$ | $CH_2CH_3$ | 4-OH-phenyl |
| 12 | 2 | $CH_2CH_3$ | $CH_2CH_3$ | 4-OH-phenyl |
| 13 | 3 | $CH_2CH_3$ | $CH_2CH_3$ | 4-OH-phenyl |
| 14 | 1 | $CH_3$ | $CH_3$ | 3-OH-phenyl |
| 15 | 2 | $CH_3$ | $CH_3$ | 3-OH-phenyl |
| 16 | 3 | $CH_3$ | $CH_3$ | 3-OH-phenyl |
| 17 | 1 | $CH_2CH_3$ | $CH_2CH_3$ | 3-OH-phenyl |
| 18 | 2 | $CH_2CH_3$ | $CH_2CH_3$ | 3-OH-phenyl |
| 19 | 3 | $CH_2CH_3$ | $CH_2CH_3$ | 3-OH-phenyl |
| 20 | 1 | $CH_3$ | $CH_3$ | 2-OH-phenyl |
| 21 | 2 | $CH_3$ | $CH_3$ | 2-OH-phenyl |
| 22 | 3 | $CH_3$ | $CH_3$ | 2-OH-phenyl |
| 23 | 1 | $CH_2CH_3$ | $CH_2CH_3$ | 2-OH-phenyl |
| 24 | 2 | $CH_2CH_3$ | $CH_2CH_3$ | 2-OH-phenyl |
| 25 | 3 | $CH_2CH_3$ | $CH_2CH_3$ | 2-OH-phenyl |
| 26 | 1 | $CH_3$ | $CH_3$ | 4-$CH_3$-Phenyl |
| 27 | 2 | $CH_3$ | $CH_3$ | 4-$CH_3$-Phenyl |
| 28 | 3 | $CH_3$ | $CH_3$ | 4-$CH_3$-Phenyl |
| 26 | 1 | $CH_2CH_3$ | $CH_2CH_3$ | 4-$CH_3$-Phenyl |
| 30 | 2 | $CH_2CH_3$ | $CH_2CH_3$ | 4-$CH_3$-Phenyl |
| 31 | 3 | $CH_2CH_3$ | $CH_2CH_3$ | 4-$CH_3$-Phenyl |
| 32 | 1 | $CH_3$ | $CH_3$ | 3-$CH_3$-Phenyl |
| 33 | 2 | $CH_3$ | $CH_3$ | 3-$CH_3$-Phenyl |
| 34 | 3 | $CH_3$ | $CH_3$ | 3-$CH_3$-Phenyl |
| 35 | 1 | $CH_2CH_3$ | $CH_2CH_3$ | 3-$CH_3$-Phenyl |
| 36 | 2 | $CH_2CH_3$ | $CH_2CH_3$ | 3-$CH_3$-Phenyl |
| 37 | 3 | $CH_2CH_3$ | $CH_2CH_3$ | 3-$CH_3$-Phenyl |
| 38 | 1 | $CH_3$ | $CH_3$ | 2-$CH_3$-Phenyl |
| 39 | 2 | $CH_3$ | $CH_3$ | 2-$CH_3$-Phenyl |
| 40 | 3 | $CH_3$ | $CH_3$ | 2-$CH_3$-Phenyl |
| 41 | 1 | $CH_2CH_3$ | $CH_2CH_3$ | 2-$CH_3$-Phenyl |
| 42 | 2 | $CH_2CH_3$ | $CH_2CH_3$ | 2-$CH_3$-Phenyl |
| 43 | 3 | $CH_2CH_3$ | $CH_2CH_3$ | 2-$CH_3$-Phenyl |
| 44 | 1 | $CH_3$ | $CH_3$ | 4-$OCH_3$-Phenyl |
| 45 | 2 | $CH_3$ | $CH_3$ | 4-$OCH_3$-Phenyl |
| 46 | 3 | $CH_3$ | $CH_3$ | 4-$OCH_3$-Phenyl |
| 47 | 1 | $CH_2CH_3$ | $CH_2CH_3$ | 4-$OCH_3$-Phenyl |
| 48 | 2 | $CH_2CH_3$ | $CH_2CH_3$ | 4-$OCH_3$-Phenyl |
| 49 | 3 | $CH_2CH_3$ | $CH_2CH_3$ | 4-$OCH_3$-Phenyl |
| 50 | 1 | $CH_3$ | $CH_3$ | 3-$OCH_3$-Phenyl |
| 51 | 2 | $CH_3$ | $CH_3$ | 3-$OCH_3$-Phenyl |
| 52 | 3 | $CH_3$ | $CH_3$ | 3-$OCH_3$-Phenyl |
| 53 | 1 | $CH_2CH_3$ | $CH_2CH_3$ | 3-$OCH_3$-Phenyl |
| 54 | 2 | $CH_2CH_3$ | $CH_2CH_3$ | 3-$OCH_3$-Phenyl |
| 55 | 3 | $CH_2CH_3$ | $CH_2CH_3$ | 3-$OCH_3$-Phenyl |
| 56 | 1 | $CH_3$ | $CH_3$ | 2-$OCH_3$-Phenyl |
| 57 | 2 | $CH_3$ | $CH_3$ | 2-$OCH_3$-Phenyl |
| 58 | 3 | $CH_3$ | $CH_3$ | 2-$OCH_3$-Phenyl |
| 59 | 1 | $CH_2CH_3$ | $CH_2CH_3$ | 2-$OCH_3$-Phenyl |
| 60 | 2 | $CH_2CH_3$ | $CH_2CH_3$ | 2-$OCH_3$-Phenyl |
| 61 | 3 | $CH_2CH_3$ | $CH_2CH_3$ | 2-$OCH_3$-Phenyl |
| 62 | 1 | $CH_3$ | $CH_3$ | 4-CN-Phenyl |
| 63 | 2 | $CH_3$ | $CH_3$ | 4-CN-Phenyl |
| 64 | 3 | $CH_3$ | $CH_3$ | 4-CN-Phenyl |
| 65 | 1 | $CH_2CH_3$ | $CH_2CH_3$ | 4-CN-Phenyl |
| 66 | 2 | $CH_2CH_3$ | $CH_2CH_3$ | 4-CN-Phenyl |
| 67 | 3 | $CH_2CH_3$ | $CH_2CH_3$ | 4-CN-Phenyl |
| 68 | 1 | $CH_3$ | $CH_3$ | 3-CN-Phenyl |
| 69 | 2 | $CH_3$ | $CH_3$ | 3-CN-Phenyl |
| 70 | 3 | $CH_3$ | $CH_3$ | 3-CN-Phenyl |
| 71 | 1 | $CH_2CH_3$ | $CH_2CH_3$ | 3-CN-Phenyl |
| 72 | 2 | $CH_2CH_3$ | $CH_2CH_3$ | 3-CN-Phenyl |
| 73 | 3 | $CH_2CH_3$ | $CH_2CH_3$ | 3-CN-Phenyl |
| 74 | 1 | $CH_3$ | $CH_3$ | 2-CN-Phenyl |
| 75 | 2 | $CH_3$ | $CH_3$ | 2-CN-Phenyl |
| 76 | 3 | $CH_3$ | $CH_3$ | 2-CN-Phenyl |
| 77 | 1 | $CH_2CH_3$ | $CH_2CH_3$ | 2-CN-Phenyl |
| 78 | 2 | $CH_2CH_3$ | $CH_2CH_3$ | 2-CN-Phenyl |
| 79 | 3 | $CH_2CH_3$ | $CH_2CH_3$ | 2-CN-Phenyl |
| 80 | 1 | $CH_3$ | $CH_3$ | 4-F-Phenyl |
| 81 | 2 | $CH_3$ | $CH_3$ | 4-F-Phenyl |
| 82 | 3 | $CH_3$ | $CH_3$ | 4-F-Phenyl |
| 83 | 1 | $CH_2CH_3$ | $CH_2CH_3$ | 4-F-Phenyl |
| 84 | 2 | $CH_2CH_3$ | $CH_2CH_3$ | 4-F-Phenyl |
| 85 | 3 | $CH_2CH_3$ | $CH_2CH_3$ | 4-F-Phenyl |
| 86 | 1 | $CH_3$ | $CH_3$ | 3-F-Phenyl |
| 87 | 2 | $CH_3$ | $CH_3$ | 3-F-Phenyl |
| 88 | 3 | $CH_3$ | $CH_3$ | 3-F-Phenyl |
| 89 | 1 | $CH_2CH_3$ | $CH_2CH_3$ | 3-F-Phenyl |
| 90 | 2 | $CH_2CH_3$ | $CH_2CH_3$ | 3-F-Phenyl |
| 91 | 3 | $CH_2CH_3$ | $CH_2CH_3$ | 3-F-Phenyl |
| 92 | 1 | $CH_3$ | $CH_3$ | 2-F-Phenyl |
| 93 | 2 | $CH_3$ | $CH_3$ | 2-F-Phenyl |
| 94 | 3 | $CH_3$ | $CH_3$ | 2-F-Phenyl |
| 95 | 1 | $CH_2CH_3$ | $CH_2CH_3$ | 2-F-Phenyl |
| 96 | 2 | $CH_2CH_3$ | $CH_2CH_3$ | 2-F-Phenyl |
| 97 | 3 | $CH_2CH_3$ | $CH_2CH_3$ | 2-F-Phenyl |
| 98 | 1 | $CH_3$ | $CH_3$ | 4-Cl-Phenyl |
| 99 | 2 | $CH_3$ | $CH_3$ | 4-Cl-Phenyl |
| 100 | 3 | $CH_3$ | $CH_3$ | 4-Cl-Phenyl |
| 101 | 1 | $CH_2CH_3$ | $CH_2CH_3$ | 4-Cl-Phenyl |
| 102 | 2 | $CH_2CH_3$ | $CH_2CH_3$ | 4-Cl-Phenyl |
| 103 | 3 | $CH_2CH_3$ | $CH_2CH_3$ | 4-Cl-Phenyl |
| 104 | 1 | $CH_3$ | $CH_3$ | 3-Cl-Phenyl |
| 105 | 2 | $CH_3$ | $CH_3$ | 3-Cl-Phenyl |
| 106 | 3 | $CH_3$ | $CH_3$ | 3-Cl-Phenyl |
| 107 | 1 | $CH_2CH_3$ | $CH_2CH_3$ | 3-Cl-Phenyl |
| 108 | 2 | $CH_2CH_3$ | $CH_2CH_3$ | 3-Cl-Phenyl |
| 109 | 3 | $CH_2CH_3$ | $CH_2CH_3$ | 3-Cl-Phenyl |
| 110 | 1 | $CH_3$ | $CH_3$ | 2-Cl-Phenyl |
| 111 | 2 | $CH_3$ | $CH_3$ | 2-Cl-Phenyl |
| 112 | 3 | $CH_3$ | $CH_3$ | 2-Cl-Phenyl |
| 113 | 1 | $CH_2CH_3$ | $CH_2CH_3$ | 2-Cl-Phenyl |
| 114 | 2 | $CH_2CH_3$ | $CH_2CH_3$ | 2-Cl-Phenyl |
| 115 | 3 | $CH_2CH_3$ | $CH_2CH_3$ | 2-Cl-Phenyl |
| 116 | 1 | $CH_3$ | $CH_3$ | 4-Br-Phenyl |
| 117 | 2 | $CH_3$ | $CH_3$ | 4-Br-Phenyl |
| 118 | 3 | $CH_3$ | $CH_3$ | 4-Br-Phenyl |
| 119 | 1 | $CH_2CH_3$ | $CH_2CH_3$ | 4-Br-Phenyl |
| 120 | 2 | $CH_2CH_3$ | $CH_2CH_3$ | 4-Br-Phenyl |
| 121 | 3 | $CH_2CH_3$ | $CH_2CH_3$ | 4-Br-Phenyl |
| 122 | 1 | $CH_3$ | $CH_3$ | 4-$OCF_3$-Phenyl |
| 123 | 2 | $CH_3$ | $CH_3$ | 4-$OCF_3$-Phenyl |
| 124 | 3 | $CH_3$ | $CH_3$ | 4-$OCF_3$-Phenyl |
| 125 | 1 | $CH_2CH_3$ | $CH_2CH_3$ | 4-$OCF_3$-Phenyl |
| 126 | 2 | $CH_2CH_3$ | $CH_2CH_3$ | 4-$OCF_3$-Phenyl |
| 127 | 3 | $CH_2CH_3$ | $CH_2CH_3$ | 4-$OCF_3$-Phenyl |
| 128 | 1 | $CH_3$ | $CH_3$ | 3-$OCF_3$-Phenyl |
| 129 | 2 | $CH_3$ | $CH_3$ | 3-$OCF_3$-Phenyl |
| 130 | 3 | $CH_3$ | $CH_3$ | 3-$OCF_3$-Phenyl |
| 131 | 1 | $CH_2CH_3$ | $CH_2CH_3$ | 3-$OCF_3$-Phenyl |
| 132 | 2 | $CH_2CH_3$ | $CH_2CH_3$ | 3-$OCF_3$-Phenyl |
| 133 | 3 | $CH_2CH_3$ | $CH_2CH_3$ | 3-$OCF_3$-Phenyl |
| 134 | 1 | $CH_3$ | $CH_3$ | 2-$OCF_3$-Phenyl |
| 135 | 2 | $CH_3$ | $CH_3$ | 2-$OCF_3$-Phenyl |
| 136 | 3 | $CH_3$ | $CH_3$ | 2-$OCF_3$-Phenyl |
| 137 | 1 | $CH_2CH_3$ | $CH_2CH_3$ | 2-$OCF_3$-Phenyl |
| 138 | 2 | $CH_2CH_3$ | $CH_2CH_3$ | 2-$OCF_3$-Phenyl |
| 139 | 3 | $CH_2CH_3$ | $CH_2CH_3$ | 2-$OCF_3$-Phenyl |
| 140 | 1 | $CH_3$ | $CH_3$ | 4-isopropyl-phenyl |
| 141 | 2 | $CH_3$ | $CH_3$ | 4-isopropyl-phenyl |

TABLE 6-continued

| Entry | n | R$^{1a}$ | R$^{1b}$ | R$^3$ |
|---|---|---|---|---|
| 142 | 3 | CH$_3$ | CH$_3$ | 4-isopropyl-phenyl |
| 143 | 1 | CH2CH3 | CH2CH3 | 4-isopropyl-phenyl |
| 144 | 2 | CH2CH3 | CH2CH3 | 4-isopropyl-phenyl |
| 145 | 3 | CH2CH3 | CH2CH3 | 4-isopropyl-phenyl |
| 146 | 1 | CH$_3$ | CH$_3$ | 3-isopropyl-phenyl |
| 147 | 2 | CH$_3$ | CH$_3$ | 3-isopropyl-phenyl |
| 148 | 3 | CH$_3$ | CH$_3$ | 3-isopropyl-phenyl |
| 149 | 1 | CH$_2$CH$_3$ | CH$_2$CH$_3$ | 3-isopropyl-phenyl |
| 150 | 2 | CH$_2$CH$_3$ | CH$_2$CH$_3$ | 3-isopropyl-phenyl |
| 151 | 3 | CH$_2$CH$_3$ | CH$_2$CH$_3$ | 3-isopropyl-phenyl |
| 152 | 1 | CH$_3$ | CH$_3$ | 2-isopropyl-phenyl |
| 153 | 2 | CH$_3$ | CH$_3$ | 2-isopropyl-phenyl |
| 154 | 3 | CH$_3$ | CH$_3$ | 2-isopropyl-phenyl |
| 155 | 1 | CH$_2$CH$_3$ | CH$_2$CH$_3$ | 2-isopropyl-phenyl |
| 156 | 2 | CH$_2$CH$_3$ | CH$_2$CH$_3$ | 2-isopropyl-phenyl |
| 157 | 3 | CH$_2$CH$_3$ | CH$_2$CH$_3$ | 2-isopropyl-phenyl |
| 158 | 1 | CH$_3$ | CH$_3$ | 4-cyclopropyl-phenyl |
| 159 | 2 | CH$_3$ | CH$_3$ | 4-cyclopropyl-phenyl |
| 160 | 3 | CH$_3$ | CH$_3$ | 4-cyclopropyl-phenyl |
| 161 | 1 | CH$_2$CH$_3$ | CH$_2$CH$_3$ | 4-cyclopropyl-phenyl |
| 162 | 2 | CH$_2$CH$_3$ | CH$_2$CH$_3$ | 4-cyclopropyl-phenyl |
| 163 | 3 | CH$_2$CH$_3$ | CH$_2$CH$_3$ | 4-cyclopropyl-phenyl |
| 164 | 1 | CH$_3$ | CH$_3$ | 3-cyclopropyl-phenyl |
| 165 | 2 | CH$_3$ | CH$_3$ | 3-cyclopropyl-phenyl |
| 166 | 3 | CH$_3$ | CH$_3$ | 3-cyclopropyl-phenyl |
| 167 | 1 | CH$_2$CH$_3$ | CH$_2$CH$_3$ | 3-cyclopropyl-phenyl |
| 168 | 2 | CH$_2$CH$_3$ | CH$_2$CH$_3$ | 3-cyclopropyl-phenyl |
| 169 | 3 | CH$_2$CH$_3$ | CH$_2$CH$_3$ | 3-cyclopropyl-phenyl |
| 170 | 1 | CH$_3$ | CH$_3$ | 2-cyclopropyl-phenyl |
| 171 | 2 | CH$_3$ | CH$_3$ | 2-cyclopropyl-phenyl |
| 172 | 3 | CH$_3$ | CH$_3$ | 2-cyclopropyl-phenyl |
| 173 | 1 | CH$_2$CH$_3$ | CH$_2$CH$_3$ | 2-cyclopropyl-phenyl |
| 174 | 2 | CH$_2$CH$_3$ | CH$_2$CH$_3$ | 2-cyclopropyl-phenyl |
| 175 | 3 | CH$_2$CH$_3$ | CH$_2$CH$_3$ | 2-cyclopropyl-phenyl |
| 176 | 1 | CH$_3$ | CH$_3$ | 4-morpholino-phenyl |
| 177 | 2 | CH$_3$ | CH$_3$ | 4-morpholino-phenyl |
| 178 | 3 | CH$_3$ | CH$_3$ | 4-morpholino-phenyl |
| 179 | 1 | CH$_2$CH$_3$ | CH$_2$CH$_3$ | 4-morpholino-phenyl |
| 180 | 2 | CH$_2$CH$_3$ | CH$_2$CH$_3$ | 4-morpholino-phenyl |
| 181 | 3 | CH$_2$CH$_3$ | CH$_2$CH$_3$ | 4-morpholino-phenyl |
| 182 | 1 | CH$_3$ | CH$_3$ | 3-morpholino-phenyl |
| 183 | 2 | CH$_3$ | CH$_3$ | 3-morpholino-phenyl |
| 184 | 3 | CH$_3$ | CH$_3$ | 3-morpholino-phenyl |
| 185 | 1 | CH$_2$CH$_3$ | CH$_2$CH$_3$ | 3-morpholino-phenyl |
| 186 | 2 | CH$_2$CH$_3$ | CH$_2$CH$_3$ | 3-morpholino-phenyl |
| 187 | 3 | CH$_2$CH$_3$ | CH$_2$CH$_3$ | 3-morpholino-phenyl |
| 188 | 1 | CH$_3$ | CH$_3$ | 2-morpholino-phenyl |
| 189 | 2 | CH$_3$ | CH$_3$ | 2-morpholino-phenyl |
| 190 | 3 | CH$_3$ | CH$_3$ | 2-morpholino-phenyl |
| 191 | 1 | CH$_2$CH$_3$ | CH$_2$CH$_3$ | 2-morpholino-phenyl |
| 192 | 2 | CH$_2$CH$_3$ | CH$_2$CH$_3$ | 2-morpholino-phenyl |
| 193 | 3 | CH$_2$CH$_3$ | CH$_2$CH$_3$ | 2-morpholino-phenyl |
| 194 | 1 | CH$_3$ | CH$_3$ | 2-pyridyl |
| 195 | 2 | CH$_3$ | CH$_3$ | 2-pyridyl |
| 196 | 3 | CH$_3$ | CH$_3$ | 2-pyridyl |
| 197 | 1 | CH$_2$CH$_3$ | CH$_2$CH$_3$ | 2-pyridyl |
| 198 | 2 | CH$_2$CH$_3$ | CH$_2$CH$_3$ | 2-pyridyl |
| 199 | 3 | CH$_2$CH$_3$ | CH$_2$CH$_3$ | 2-pyridyl |
| 200 | 1 | CH$_3$ | CH$_3$ | 3-pyridyl |
| 201 | 2 | CH$_3$ | CH$_3$ | 3-pyridyl |
| 202 | 3 | CH$_3$ | CH$_3$ | 3-pyridyl |
| 203 | 1 | CH$_2$CH$_3$ | CH$_2$CH$_3$ | 3-pyridyl |
| 204 | 2 | CH$_2$CH$_3$ | CH$_2$CH$_3$ | 3-pyridyl |
| 205 | 3 | CH$_2$CH$_3$ | CH$_2$CH$_3$ | 3-pyridyl |
| 206 | 1 | CH$_3$ | CH$_3$ | 4-pyridyl |
| 207 | 2 | CH$_3$ | CH$_3$ | 4-pyridyl |
| 208 | 3 | CH$_3$ | CH$_3$ | 4-pyridyl |
| 209 | 1 | CH$_2$CH$_3$ | CH$_2$CH$_3$ | 4-pyridyl |
| 210 | 2 | CH$_2$CH$_3$ | CH$_2$CH$_3$ | 4-pyridyl |
| 211 | 3 | CH$_2$CH$_3$ | CH$_2$CH$_3$ | 4-pyridyl |
| 212 | 1 | CH$_3$ | CH$_3$ | 2-CH$_3$-4-pyridyl |
| 213 | 2 | CH$_3$ | CH$_3$ | 2-CH$_3$-4-pyridyl |
| 214 | 3 | CH$_3$ | CH$_3$ | 2-CH$_3$-4-pyridyl |
| 215 | 1 | CH$_2$CH$_3$ | CH$_2$CH$_3$ | 2-CH$_3$-4-pyridyl |
| 216 | 2 | CH$_2$CH$_3$ | CH$_2$CH$_3$ | 2-CH$_3$-4-pyridyl |
| 217 | 3 | CH$_2$CH$_3$ | CH$_2$CH$_3$ | 2-CH$_3$-4-pyridyl |
| 218 | 1 | CH$_3$ | CH$_3$ | 3-CH$_3$-4-pyridyl |
| 219 | 2 | CH$_3$ | CH$_3$ | 3-CH$_3$-4-pyridyl |
| 220 | 3 | CH$_3$ | CH$_3$ | 3-CH$_3$-4-pyridyl |
| 221 | 1 | CH$_2$CH$_3$ | CH$_2$CH$_3$ | 3-CH$_3$-4-pyridyl |
| 222 | 2 | CH$_2$CH$_3$ | CH$_2$CH$_3$ | 3-CH$_3$-4-pyridyl |
| 223 | 3 | CH$_2$CH$_3$ | CH$_2$CH$_3$ | 3-CH$_3$-4-pyridyl |
| 224 | 1 | CH$_3$ | CH$_3$ | 3,5-dimethylpyridin-4-yl |
| 225 | 2 | CH$_3$ | CH$_3$ | 3,5-dimethylpyridin-4-yl |
| 226 | 3 | CH$_3$ | CH$_3$ | 3,5-dimethylpyridin-4-yl |
| 227 | 1 | CH$_2$CH$_3$ | CH$_2$CH$_3$ | 3,5-dimethylpyridin-4-yl |
| 228 | 2 | CH$_2$CH$_3$ | CH$_2$CH$_3$ | 3,5-dimethylpyridin-4-yl |
| 229 | 3 | CH$_2$CH$_3$ | CH$_2$CH$_3$ | 3,5-dimethylpyridin-4-yl |
| 230 | 1 | CH$_3$ | CH$_3$ | 2,6-dimethylpyridin-4-yl |
| 231 | 2 | CH$_3$ | CH$_3$ | 2,6-dimethylpyridin-4-yl |
| 232 | 3 | CH$_3$ | CH$_3$ | 2,6-dimethylpyridin-4-yl |
| 233 | 1 | CH$_2$CH$_3$ | CH$_2$CH$_3$ | 2,6-dimethylpyridin-4-yl |
| 234 | 2 | CH$_2$CH$_3$ | CH$_2$CH$_3$ | 2,6-dimethylpyridin-4-yl |
| 235 | 3 | CH$_2$CH$_3$ | CH$_2$CH$_3$ | 2,6-dimethylpyridin-4-yl |

Exemplary embodiments include compounds having the formula (XIV) or a pharmaceutically acceptable salt form thereof:

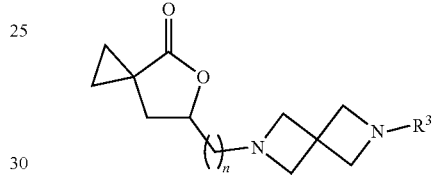

(XIV)

wherein non-limiting examples of R$^3$ and n are defined herein below in Table 7.

TABLE 7

| Entry | n | R$^3$ |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH$_3$-Phenyl |
| 14 | 2 | 4-CH$_3$-Phenyl |
| 15 | 3 | 4-CH$_3$-Phenyl |
| 16 | 1 | 3-CH$_3$-Phenyl |
| 17 | 2 | 3-CH$_3$-Phenyl |
| 18 | 3 | 3-CH$_3$-Phenyl |
| 19 | 1 | 2-CH$_3$-Phenyl |
| 20 | 2 | 2-CH$_3$-Phenyl |
| 21 | 3 | 2-CH$_3$-Phenyl |
| 22 | 1 | 4-OCH$_3$-Phenyl |
| 23 | 2 | 4-OCH$_3$-Phenyl |
| 24 | 3 | 4-OCH$_3$-Phenyl |
| 25 | 1 | 3-OCH$_3$-Phenyl |
| 26 | 2 | 3-OCH$_3$-Phenyl |
| 27 | 3 | 3-OCH$_3$-Phenyl |
| 28 | 1 | 2-OCH$_3$-Phenyl |
| 29 | 2 | 2-OCH$_3$-Phenyl |
| 30 | 3 | 2-OCH$_3$-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |

TABLE 7-continued

| Entry | n | R³ |
|---|---|---|
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |

TABLE 7-continued

| Entry | n | R³ |
|---|---|---|
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |
| 61 | 1 | |
| 62 | 2 | |
| 63 | 3 | |

Exemplary embodiments include compounds having the formula (XV) or a pharmaceutically acceptable salt form thereof:

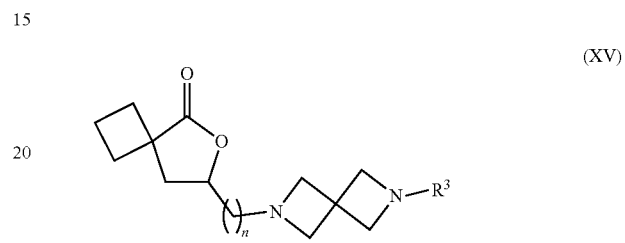

(XV)

wherein non-limiting examples of R³ and n are defined herein below in Table 8.

TABLE 8

| Entry | n | R³ |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |

TABLE 8-continued

| Entry | n | R³ |
|---|---|---|
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (XVI) or a pharmaceutically acceptable salt form thereof:

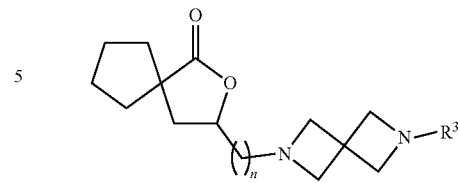

(XVI)

wherein non-limiting examples of R³ and n are defined herein below in Table 9.

TABLE 9

| Entry | n | R³ |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |

TABLE 9-continued

| Entry | n | R³ |
|---|---|---|
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (XVII) or a pharmaceutically acceptable salt form thereof:

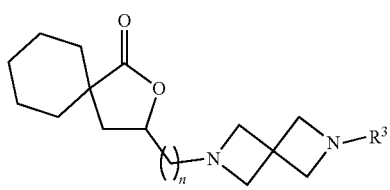

(XVII)

wherein non-limiting examples of R³ and n are defined herein below in Table 10.

TABLE 10

| Entry | n | R³ |
|---|---|---|
| 1 | 1 | Phenyl |
| 2 | 2 | Phenyl |
| 3 | 3 | Phenyl |
| 4 | 1 | 4-OH-phenyl |
| 5 | 2 | 4-OH-phenyl |
| 6 | 3 | 4-OH-phenyl |
| 7 | 1 | 3-OH-phenyl |
| 8 | 2 | 3-OH-phenyl |
| 9 | 3 | 3-OH-phenyl |
| 10 | 1 | 2-OH-phenyl |
| 11 | 2 | 2-OH-phenyl |
| 12 | 3 | 2-OH-phenyl |
| 13 | 1 | 4-CH₃-Phenyl |
| 14 | 2 | 4-CH₃-Phenyl |
| 15 | 3 | 4-CH₃-Phenyl |
| 16 | 1 | 3-CH₃-Phenyl |
| 17 | 2 | 3-CH₃-Phenyl |
| 18 | 3 | 3-CH₃-Phenyl |
| 19 | 1 | 2-CH₃-Phenyl |
| 20 | 2 | 2-CH₃-Phenyl |
| 21 | 3 | 2-CH₃-Phenyl |
| 22 | 1 | 4-OCH₃-Phenyl |
| 23 | 2 | 4-OCH₃-Phenyl |
| 24 | 3 | 4-OCH₃-Phenyl |
| 25 | 1 | 3-OCH₃-Phenyl |
| 26 | 2 | 3-OCH₃-Phenyl |
| 27 | 3 | 3-OCH₃-Phenyl |
| 28 | 1 | 2-OCH₃-Phenyl |
| 29 | 2 | 2-OCH₃-Phenyl |
| 30 | 3 | 2-OCH₃-Phenyl |
| 31 | 1 | 4-CN-Phenyl |
| 32 | 2 | 4-CN-Phenyl |
| 33 | 3 | 4-CN-Phenyl |
| 34 | 1 | 3-CN-Phenyl |
| 35 | 2 | 3-CN-Phenyl |
| 36 | 3 | 3-CN-Phenyl |
| 37 | 1 | 2-CN-Phenyl |
| 38 | 2 | 2-CN-Phenyl |
| 39 | 3 | 2-CN-Phenyl |
| 40 | 1 | 4-F-Phenyl |
| 41 | 2 | 4-F-Phenyl |
| 42 | 3 | 4-F-Phenyl |
| 43 | 1 | 3-F-Phenyl |
| 44 | 2 | 3-F-Phenyl |
| 45 | 3 | 3-F-Phenyl |
| 46 | 1 | 2-F-Phenyl |
| 47 | 2 | 2-F-Phenyl |
| 48 | 3 | 2-F-Phenyl |
| 49 | 1 | 4-Cl-Phenyl |
| 50 | 2 | 4-Cl-Phenyl |
| 51 | 3 | 4-Cl-Phenyl |
| 52 | 1 | 3-Cl-Phenyl |
| 53 | 2 | 3-Cl-Phenyl |
| 54 | 3 | 3-Cl-Phenyl |
| 55 | 1 | 2-Cl-Phenyl |
| 56 | 2 | 2-Cl-Phenyl |
| 57 | 3 | 2-Cl-Phenyl |
| 58 | 1 | 4-Br-Phenyl |
| 59 | 2 | 4-Br-Phenyl |
| 60 | 3 | 4-Br-Phenyl |
| 61 | 1 | 4-OCF₃-Phenyl |
| 62 | 2 | 4-OCF₃-Phenyl |
| 63 | 3 | 4-OCF₃-Phenyl |
| 64 | 1 | 3-OCF₃-Phenyl |
| 65 | 2 | 3-OCF₃-Phenyl |
| 66 | 3 | 3-OCF₃-Phenyl |
| 67 | 1 | 2-OCF₃-Phenyl |
| 68 | 2 | 2-OCF₃-Phenyl |
| 69 | 3 | 2-OCF₃-Phenyl |
| 70 | 1 | 4-isopropyl-phenyl |
| 71 | 2 | 4-isopropyl-phenyl |
| 72 | 3 | 4-isopropyl-phenyl |
| 73 | 1 | 3-isopropyl-phenyl |
| 74 | 2 | 3-isopropyl-phenyl |
| 75 | 3 | 3-isopropyl-phenyl |
| 76 | 1 | 2-isopropyl-phenyl |
| 77 | 2 | 2-isopropyl-phenyl |
| 78 | 3 | 2-isopropyl-phenyl |

TABLE 10-continued

| Entry | n | R³ |
|---|---|---|
| 79 | 1 | 4-cyclopropyl-phenyl |
| 80 | 2 | 4-cyclopropyl-phenyl |
| 81 | 3 | 4-cyclopropyl-phenyl |
| 82 | 1 | 3-cyclopropyl-phenyl |
| 83 | 2 | 3-cyclopropyl-phenyl |
| 84 | 3 | 3-cyclopropyl-phenyl |
| 85 | 1 | 2-cyclopropyl-phenyl |
| 86 | 2 | 2-cyclopropyl-phenyl |
| 87 | 3 | 2-cyclopropyl-phenyl |
| 88 | 1 | 4-morpholino-phenyl |
| 89 | 2 | 4-morpholino-phenyl |
| 90 | 3 | 4-morpholino-phenyl |
| 91 | 1 | 3-morpholino-phenyl |
| 92 | 2 | 3-morpholino-phenyl |
| 93 | 3 | 3-morpholino-phenyl |
| 94 | 1 | 2-morpholino-phenyl |
| 95 | 2 | 2-morpholino-phenyl |
| 96 | 3 | 2-morpholino-phenyl |
| 97 | 1 | 2-pyridyl |
| 98 | 2 | 2-pyridyl |
| 99 | 3 | 2-pyridyl |
| 100 | 1 | 3-pyridyl |
| 101 | 2 | 3-pyridyl |
| 102 | 3 | 3-pyridyl |
| 103 | 1 | 4-pyridyl |
| 104 | 2 | 4-pyridyl |
| 105 | 3 | 4-pyridyl |
| 106 | 1 | 2-CH₃-4-pyridyl |
| 107 | 2 | 2-CH₃-4-pyridyl |
| 108 | 3 | 2-CH₃-4-pyridyl |
| 109 | 1 | 3-CH₃-4-pyridyl |
| 110 | 2 | 3-CH₃-4-pyridyl |
| 111 | 3 | 3-CH₃-4-pyridyl |
| 112 | 1 | 3,5-dimethylpyridin-4-yl |
| 113 | 2 | 3,5-dimethylpyridin-4-yl |
| 114 | 3 | 3,5-dimethylpyridin-4-yl |
| 115 | 1 | 2,6-dimethylpyridin-4-yl |
| 116 | 2 | 2,6-dimethylpyridin-4-yl |
| 117 | 3 | 2,6-dimethylpyridin-4-yl |

Exemplary embodiments include compounds having the formula (II) or a pharmaceutically acceptable salt form thereof:

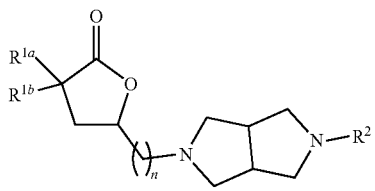

(II)

wherein non-limiting examples of $R^{1a}$, $R^{1b}$, $R^2$ and n are defined herein below in Table 11.

TABLE 11

| Entry | n | R1ᵃ | R1ᵇ | R² |
|---|---|---|---|---|
| 1 | 1 | CH₃ | CH₃ | 2-CF₃-Phenyl |
| 2 | 2 | CH₃ | CH₃ | 2-CF₃-Phenyl |
| 3 | 3 | CH₃ | CH₃ | 2-CF₃-Phenyl |
| 4 | 1 | CH₂CH₃ | CH₂CH₃ | 2-CF₃-Phenyl |
| 5 | 2 | CH₂CH₃ | CH₂CH₃ | 2-CF₃-Phenyl |
| 6 | 3 | CH₂CH₃ | CH₂CH₃ | 2-CF₃-Phenyl |
| 7 | 1 | CH₃ | CH₃ | 3-CF₃-Phenyl |
| 8 | 2 | CH₃ | CH₃ | 3-CF₃-Phenyl |
| 9 | 3 | CH₃ | CH₃ | 3-CF₃-Phenyl |
| 10 | 1 | CH₂CH₃ | CH₂CH₃ | 3-CF₃-Phenyl |
| 11 | 2 | CH₂CH₃ | CH₂CH₃ | 3-CF₃-Phenyl |
| 12 | 3 | CH₂CH₃ | CH₂CH₃ | 3-CF₃-Phenyl |
| 13 | 1 | CH₃ | CH₃ | 4-CF₃-Phenyl |
| 14 | 2 | CH₃ | CH₃ | 4-CF₃-Phenyl |
| 15 | 3 | CH₃ | CH₃ | 4-CF₃-Phenyl |
| 16 | 1 | CH₂CH₃ | CH₂CH₃ | 4-CF₃-Phenyl |
| 17 | 2 | CH₂CH₃ | CH₂CH₃ | 4-CF₃-Phenyl |
| 18 | 3 | CH₂CH₃ | CH₂CH₃ | 4-CF₃-Phenyl |
| 19 | 1 | CH₃ | CH₃ | 2-NH₂-Phenyl |
| 20 | 2 | CH₃ | CH₃ | 2-NH₂-Phenyl |
| 21 | 3 | CH₃ | CH₃ | 2-NH₂-Phenyl |
| 22 | 1 | CH₂CH₃ | CH₂CH₃ | 2-NH₂-Phenyl |
| 23 | 2 | CH₂CH₃ | CH₂CH₃ | 2-NH₂-Phenyl |
| 24 | 3 | CH₂CH₃ | CH₂CH₃ | 2-NH₂-Phenyl |
| 25 | 1 | CH₃ | CH₃ | 3-NH₂-Phenyl |
| 26 | 2 | CH₃ | CH₃ | 3-NH₂-Phenyl |
| 27 | 3 | CH₃ | CH₃ | 3-NH₂-Phenyl |
| 28 | 1 | CH₂CH₃ | CH₂CH₃ | 3-NH₂-Phenyl |
| 29 | 2 | CH₂CH₃ | CH₂CH₃ | 3-NH₂-Phenyl |
| 30 | 3 | CH₂CH₃ | CH₂CH₃ | 3-NH₂-Phenyl |
| 31 | 1 | CH₃ | CH₃ | 4-NH₂-Phenyl |
| 32 | 2 | CH₃ | CH₃ | 4-NH₂-Phenyl |
| 33 | 3 | CH₃ | CH₃ | 4-NH₂-Phenyl |
| 34 | 1 | CH₂CH₃ | CH₂CH₃ | 4-NH₂-Phenyl |
| 35 | 2 | CH₂CH₃ | CH₂CH₃ | 4-NH₂-Phenyl |
| 36 | 3 | CH₂CH₃ | CH₂CH₃ | 4-NH₂-Phenyl |
| 37 | 1 | CH₃ | CH₃ | 2-tBu-Phenyl |
| 38 | 2 | CH₃ | CH₃ | 2-tBu-Phenyl |
| 39 | 3 | CH₃ | CH₃ | 2-tBu-Phenyl |
| 40 | 1 | CH₂CH₃ | CH₂CH₃ | 2-tBu-Phenyl |
| 41 | 2 | CH₂CH₃ | CH₂CH₃ | 2-tBu-Phenyl |
| 42 | 3 | CH₂CH₃ | CH₂CH₃ | 2-tBu-Phenyl |
| 43 | 1 | CH₃ | CH₃ | 3-tBu-Phenyl |
| 44 | 2 | CH₃ | CH₃ | 3-tBu-Phenyl |
| 45 | 3 | CH₃ | CH₃ | 3-tBu-Phenyl |
| 46 | 1 | CH₂CH₃ | CH₂CH₃ | 3-tBu-Phenyl |
| 47 | 2 | CH₂CH₃ | CH₂CH₃ | 3-tBu-Phenyl |
| 48 | 3 | CH₂CH₃ | CH₂CH₃ | 3-tBu-Phenyl |
| 49 | 1 | CH₃ | CH₃ | 4-tBu-Phenyl |
| 50 | 2 | CH₃ | CH₃ | 4-tBu-Phenyl |
| 51 | 3 | CH₃ | CH₃ | 4-tBu-Phenyl |
| 52 | 1 | CH₂CH₃ | CH₂CH₃ | 4-tBu-Phenyl |
| 53 | 2 | CH₂CH₃ | CH₂CH₃ | 4-tBu-Phenyl |
| 54 | 3 | CH₂CH₃ | CH₂CH₃ | 4-tBu-Phenyl |
| 55 | 1 | CH₃ | CH₃ | 2-NO₂-Phenyl |
| 56 | 2 | CH₃ | CH₃ | 2-NO₂-Phenyl |
| 57 | 3 | CH₃ | CH₃ | 2-NO₂-Phenyl |
| 58 | 1 | CH₂CH₃ | CH₂CH₃ | 2-NO₂-Phenyl |
| 59 | 2 | CH₂CH₃ | CH₂CH₃ | 2-NO₂-Phenyl |
| 60 | 3 | CH₂CH₃ | CH₂CH₃ | 2-NO₂-Phenyl |
| 61 | 1 | CH₃ | CH₃ | 3-NO₂-Phenyl |
| 62 | 2 | CH₃ | CH₃ | 3-NO₂-Phenyl |
| 63 | 3 | CH₃ | CH₃ | 3-NO₂-Phenyl |
| 64 | 1 | CH₂CH₃ | CH₂CH₃ | 3-NO₂-Phenyl |
| 65 | 2 | CH₂CH₃ | CH₂CH₃ | 3-NO₂-Phenyl |
| 66 | 3 | CH₂CH₃ | CH₂CH₃ | 3-NO₂-Phenyl |
| 67 | 1 | CH₃ | CH₃ | 4-NO₂-Phenyl |
| 68 | 2 | CH₃ | CH₃ | 4-NO₂-Phenyl |
| 69 | 3 | CH₃ | CH₃ | 4-NO₂-Phenyl |
| 70 | 1 | CH₂CH₃ | CH₂CH₃ | 4-NO₂-Phenyl |
| 71 | 2 | CH₂CH₃ | CH₂CH₃ | 4-NO₂-Phenyl |
| 72 | 3 | CH₂CH₃ | CH₂CH₃ | 4-NO₂-Phenyl |
| 73 | 1 | CH₃ | CH₃ | 2-SCH₃-Phenyl |
| 74 | 2 | CH₃ | CH₃ | 2-SCH₃-Phenyl |
| 75 | 3 | CH₃ | CH₃ | 2-SCH₃-Phenyl |
| 76 | 1 | CH₂CH₃ | CH₂CH₃ | 2-SCH₃-Phenyl |
| 77 | 2 | CH₂CH₃ | CH₂CH₃ | 2-SCH₃-Phenyl |
| 78 | 3 | CH₂CH₃ | CH₂CH₃ | 2-SCH₃-Phenyl |
| 79 | 1 | CH₃ | CH₃ | 3-SCH₃-Phenyl |
| 80 | 2 | CH₃ | CH₃ | 3-SCH₃-Phenyl |
| 81 | 3 | CH₃ | CH₃ | 3-SCH₃-Phenyl |
| 82 | 1 | CH₂CH₃ | CH₂CH₃ | 3-SCH₃-Phenyl |
| 83 | 2 | CH₂CH₃ | CH₂CH₃ | 3-SCH₃-Phenyl |
| 84 | 3 | CH₂CH₃ | CH₂CH₃ | 3-SCH₃-Phenyl |
| 85 | 1 | CH₃ | CH₃ | 4-SCH₃-Phenyl |
| 86 | 2 | CH₃ | CH₃ | 4-SCH₃-Phenyl |
| 87 | 3 | CH₃ | CH₃ | 4-SCH₃-Phenyl |
| 88 | 1 | CH₂CH₃ | CH₂CH₃ | 4-SCH₃-Phenyl |
| 89 | 2 | CH₂CH₃ | CH₂CH₃ | 4-SCH₃-Phenyl |
| 90 | 3 | CH₂CH₃ | CH₂CH₃ | 4-SCH₃-Phenyl |

TABLE 11-continued

| Entry | n | R1[a] | R1[b] | R2 |
|---|---|---|---|---|
| 91 | 1 | CH$_3$ | CH$_3$ | 2-SO$_2$CH$_3$-Phenyl |
| 92 | 2 | CH$_3$ | CH$_3$ | 2-SO$_2$CH$_3$-Phenyl |
| 93 | 3 | CH$_3$ | CH$_3$ | 2-SO$_2$CH$_3$-Phenyl |
| 94 | 1 | CH$_2$CH$_3$ | CH$_2$CH$_3$ | 2-SO$_2$CH$_3$-Phenyl |
| 95 | 2 | CH$_2$CH$_3$ | CH$_2$CH$_3$ | 2-SO$_2$CH$_3$-Phenyl |
| 96 | 3 | CH$_2$CH$_3$ | CH$_2$CH$_3$ | 2-SO$_2$CH$_3$-Phenyl |
| 97 | 1 | CH$_3$ | CH$_3$ | 3-SO$_2$CH$_3$-Phenyl |
| 98 | 2 | CH$_3$ | CH$_3$ | 3-SO$_2$CH$_3$-Phenyl |
| 99 | 3 | CH$_3$ | CH$_3$ | 3-SO$_2$CH$_3$-Phenyl |
| 100 | 1 | CH$_2$CH$_3$ | CH$_2$CH$_3$ | 3-SO$_2$CH$_3$-Phenyl |
| 101 | 2 | CH$_2$CH$_3$ | CH$_2$CH$_3$ | 3-SO$_2$CH$_3$-Phenyl |
| 102 | 3 | CH$_2$CH$_3$ | CH$_2$CH$_3$ | 3-SO$_2$CH$_3$-Phenyl |
| 103 | 1 | CH$_3$ | CH$_3$ | 4-SO$_2$CH$_3$-Phenyl |
| 104 | 2 | CH$_3$ | CH$_3$ | 4-SO$_2$CH$_3$-Phenyl |
| 105 | 3 | CH$_3$ | CH$_3$ | 4-SO$_2$CH$_3$-Phenyl |
| 106 | 1 | CH$_2$CH$_3$ | CH$_2$CH$_3$ | 4-SO$_2$CH$_3$-Phenyl |
| 107 | 2 | CH$_2$CH$_3$ | CH$_2$CH$_3$ | 4-SO$_2$CH$_3$-Phenyl |
| 108 | 3 | CH$_2$CH$_3$ | CH$_2$CH$_3$ | 4-SO$_2$CH$_3$-Phenyl |
| 109 | 1 | CH$_3$ | CH$_3$ | 2-SO$_2$NH$_2$-Phenyl |
| 110 | 2 | CH$_3$ | CH$_3$ | 2-SO$_2$NH$_2$-Phenyl |
| 111 | 3 | CH$_3$ | CH$_3$ | 2-SO$_2$NH$_2$-Phenyl |
| 112 | 1 | CH$_2$CH$_3$ | CH$_2$CH$_3$ | 2-SO$_2$NH$_2$-Phenyl |
| 113 | 2 | CH$_2$CH$_3$ | CH$_2$CH$_3$ | 2-SO$_2$NH$_2$-Phenyl |
| 114 | 3 | CH$_2$CH$_3$ | CH$_2$CH$_3$ | 2-SO$_2$NH$_2$-Phenyl |
| 115 | 1 | CH$_3$ | CH$_3$ | 3-SO$_2$NH$_2$-Phenyl |
| 116 | 2 | CH$_3$ | CH$_3$ | 3-SO$_2$NH$_2$-Phenyl |
| 117 | 3 | CH$_3$ | CH$_3$ | 3-SO$_2$NH$_2$-Phenyl |
| 118 | 1 | CH$_2$CH$_3$ | CH$_2$CH$_3$ | 3-SO$_2$NH$_2$-Phenyl |
| 119 | 2 | CH$_2$CH$_3$ | CH$_2$CH$_3$ | 3-SO$_2$NH$_2$-Phenyl |
| 120 | 3 | CH$_2$CH$_3$ | CH$_2$CH$_3$ | 3-SO$_2$NH$_2$-Phenyl |
| 121 | 1 | CH$_3$ | CH$_3$ | 4-SO$_2$NH$_2$-Phenyl |
| 122 | 2 | CH$_3$ | CH$_3$ | 4-SO$_2$NH$_2$-Phenyl |
| 123 | 3 | CH$_3$ | CH$_3$ | 4-SO$_2$NH$_2$-Phenyl |
| 124 | 1 | CH$_2$CH$_3$ | CH$_2$CH$_3$ | 4-SO$_2$NH$_2$-Phenyl |
| 125 | 2 | CH$_2$CH$_3$ | CH$_2$CH$_3$ | 4-SO$_2$NH$_2$-Phenyl |
| 126 | 3 | CH$_2$CH$_3$ | CH$_2$CH$_3$ | 4-SO$_2$NH$_2$-Phenyl |
| 127 | 1 | CH$_3$ | CH$_3$ | 2-CONH$_2$-Phenyl |
| 128 | 2 | CH$_3$ | CH$_3$ | 2-CONH$_2$-Phenyl |
| 129 | 3 | CH$_3$ | CH$_3$ | 2-CONH$_2$-Phenyl |
| 130 | 1 | CH$_2$CH$_3$ | CH$_2$CH$_3$ | 2-CONH$_2$-Phenyl |
| 131 | 2 | CH$_2$CH$_3$ | CH$_2$CH$_3$ | 2-CONH$_2$-Phenyl |
| 132 | 3 | CH$_2$CH$_3$ | CH$_2$CH$_3$ | 2-CONH$_2$-Phenyl |
| 133 | 1 | CH$_3$ | CH$_3$ | 3-CONH$_2$-Phenyl |
| 134 | 2 | CH$_3$ | CH$_3$ | 3-CONH$_2$-Phenyl |
| 135 | 3 | CH$_3$ | CH$_3$ | 3-CONH$_2$-Phenyl |
| 136 | 1 | CH$_2$CH$_3$ | CH$_2$CH$_3$ | 3-CONH$_2$-Phenyl |
| 137 | 2 | CH$_2$CH$_3$ | CH$_2$CH$_3$ | 3-CONH$_2$-Phenyl |
| 138 | 3 | CH$_2$CH$_3$ | CH$_2$CH$_3$ | 3-CONH$_2$-Phenyl |
| 139 | 1 | CH$_3$ | CH$_3$ | 4-CONH$_2$-Phenyl |
| 140 | 2 | CH$_3$ | CH$_3$ | 4-CONH$_2$-Phenyl |
| 141 | 3 | CH$_3$ | CH$_3$ | 4-CONH$_2$-Phenyl |
| 142 | 1 | CH$_2$CH$_3$ | CH$_2$CH$_3$ | 4-CONH$_2$-Phenyl |
| 143 | 2 | CH$_2$CH$_3$ | CH$_2$CH$_3$ | 4-CONH$_2$-Phenyl |
| 144 | 3 | CH$_2$CH$_3$ | CH$_2$CH$_3$ | 4-CONH$_2$-Phenyl |
| 145 | 1 | CH$_3$ | CH$_3$ | 2-Br-Phenyl |
| 146 | 2 | CH$_3$ | CH$_3$ | 2-Br-Phenyl |
| 147 | 3 | CH$_3$ | CH$_3$ | 2-Br-Phenyl |
| 148 | 1 | CH$_2$CH$_3$ | CH$_2$CH$_3$ | 2-Br-Phenyl |
| 149 | 2 | CH$_2$CH$_3$ | CH$_2$CH$_3$ | 2-Br-Phenyl |
| 150 | 3 | CH$_2$CH$_3$ | CH$_2$CH$_3$ | 2-Br-Phenyl |
| 151 | 1 | CH$_3$ | CH$_3$ | 3-Br-Phenyl |
| 152 | 2 | CH$_3$ | CH$_3$ | 3-Br-Phenyl |
| 153 | 3 | CH$_3$ | CH$_3$ | 3-Br-Phenyl |
| 154 | 1 | CH$_2$CH$_3$ | CH$_2$CH$_3$ | 3-Br-Phenyl |
| 155 | 2 | CH$_2$CH$_3$ | CH$_2$CH$_3$ | 3-Br-Phenyl |
| 156 | 3 | CH$_2$CH$_3$ | CH$_2$CH$_3$ | 3-Br-Phenyl |
| 157 | 1 | CH$_3$ | CH$_3$ | 2,3-di-CH$_3$-phenyl |
| 158 | 2 | CH$_3$ | CH$_3$ | 2,3-di-CH$_3$-phenyl |
| 159 | 3 | CH$_3$ | CH$_3$ | 2,3-di-CH$_3$-phenyl |
| 160 | 1 | CH$_2$CH$_3$ | CH$_2$CH$_3$ | 2,3-di-CH$_3$-phenyl |
| 161 | 2 | CH$_2$CH$_3$ | CH$_2$CH$_3$ | 2,3-di-CH$_3$-phenyl |
| 162 | 3 | CH$_2$CH$_3$ | CH$_2$CH$_3$ | 2,3-di-CH$_3$-phenyl |
| 163 | 1 | CH$_3$ | CH$_3$ | 2,4-di-CH$_3$-phenyl |
| 164 | 2 | CH$_3$ | CH$_3$ | 2,4-di-CH$_3$-phenyl |
| 165 | 3 | CH$_3$ | CH$_3$ | 2,4-di-CH$_3$-phenyl |
| 166 | 1 | CH$_2$CH$_3$ | CH$_2$CH$_3$ | 2,4-di-CH$_3$-phenyl |
| 167 | 2 | CH$_2$CH$_3$ | CH$_2$CH$_3$ | 2,4-di-CH$_3$-phenyl |
| 168 | 3 | CH$_2$CH$_3$ | CH$_2$CH$_3$ | 2,4-di-CH$_3$-phenyl |
| 169 | 1 | CH$_3$ | CH$_3$ | 2,5-di-CH$_3$-phenyl |
| 170 | 2 | CH$_3$ | CH$_3$ | 2,5-di-CH$_3$-phenyl |
| 171 | 3 | CH$_3$ | CH$_3$ | 2,5-di-CH$_3$-phenyl |
| 172 | 1 | CH$_2$CH$_3$ | CH$_2$CH$_3$ | 2,5-di-CH$_3$-phenyl |
| 173 | 2 | CH$_2$CH$_3$ | CH$_2$CH$_3$ | 2,5-di-CH$_3$-phenyl |
| 174 | 3 | CH$_2$CH$_3$ | CH$_2$CH$_3$ | 2,5-di-CH$_3$-phenyl |
| 175 | 1 | CH$_3$ | CH$_3$ | 2,6-di-CH$_3$-phenyl |
| 176 | 2 | CH$_3$ | CH$_3$ | 2,6-di-CH$_3$-phenyl |
| 177 | 3 | CH$_3$ | CH$_3$ | 2,6-di-CH$_3$-phenyl |
| 178 | 1 | CH$_2$CH$_3$ | CH$_2$CH$_3$ | 2,6-di-CH$_3$-phenyl |
| 179 | 2 | CH$_2$CH$_3$ | CH$_2$CH$_3$ | 2,6-di-CH$_3$-phenyl |
| 180 | 3 | CH$_2$CH$_3$ | CH$_2$CH$_3$ | 2,6-di-CH$_3$-phenyl |
| 181 | 1 | CH$_3$ | CH$_3$ | 3,4-di-CH$_3$-phenyl |
| 182 | 2 | CH$_3$ | CH$_3$ | 3,4-di-CH$_3$-phenyl |
| 183 | 3 | CH$_3$ | CH$_3$ | 3,4-di-CH$_3$-phenyl |
| 184 | 1 | CH$_2$CH$_3$ | CH$_2$CH$_3$ | 3,4-di-CH$_3$-phenyl |
| 185 | 2 | CH$_2$CH$_3$ | CH$_2$CH$_3$ | 3,4-di-CH$_3$-phenyl |
| 186 | 3 | CH$_2$CH$_3$ | CH$_2$CH$_3$ | 3,4-di-CH$_3$-phenyl |
| 187 | 1 | CH$_3$ | CH$_3$ | 3,5-di-CH$_3$-phenyl |
| 188 | 2 | CH$_3$ | CH$_3$ | 3,5-di-CH$_3$-phenyl |
| 189 | 3 | CH$_3$ | CH$_3$ | 3,5-di-CH$_3$-phenyl |
| 190 | 1 | CH$_2$CH$_3$ | CH$_2$CH$_3$ | 3,5-di-CH$_3$-phenyl |
| 191 | 2 | CH$_2$CH$_3$ | CH$_2$CH$_3$ | 3,5-di-CH$_3$-phenyl |
| 192 | 3 | CH$_2$CH$_3$ | CH$_2$CH$_3$ | 3,5-di-CH$_3$-phenyl |
| 193 | 1 | CH$_3$ | CH$_3$ | 2,3-di-Cl-phenyl |
| 194 | 2 | CH$_3$ | CH$_3$ | 2,3-di-Cl-phenyl |
| 195 | 3 | CH$_3$ | CH$_3$ | 2,3-di-Cl-phenyl |
| 196 | 1 | CH$_2$CH$_3$ | CH$_2$CH$_3$ | 2,3-di-Cl-phenyl |
| 197 | 2 | CH$_2$CH$_3$ | CH$_2$CH$_3$ | 2,3-di-Cl-phenyl |
| 198 | 3 | CH$_2$CH$_3$ | CH$_2$CH$_3$ | 2,3-di-Cl-phenyl |
| 199 | 1 | CH$_3$ | CH$_3$ | 2,4-di-Cl-phenyl |
| 200 | 2 | CH$_3$ | CH$_3$ | 2,4-di-Cl-phenyl |
| 201 | 3 | CH$_3$ | CH$_3$ | 2,4-di-Cl-phenyl |
| 202 | 1 | CH$_2$CH$_3$ | CH$_2$CH$_3$ | 2,4-di-Cl-phenyl |
| 203 | 2 | CH$_2$CH$_3$ | CH$_2$CH$_3$ | 2,4-di-Cl-phenyl |
| 204 | 3 | CH$_2$CH$_3$ | CH$_2$CH$_3$ | 2,4-di-Cl-phenyl |
| 205 | 1 | CH$_3$ | CH$_3$ | 2,5-di-Cl-phenyl |
| 206 | 2 | CH$_3$ | CH$_3$ | 2,5-di-Cl-phenyl |
| 207 | 3 | CH$_3$ | CH$_3$ | 2,5-di-Cl-phenyl |
| 280 | 1 | CH$_2$CH$_3$ | CH$_2$CH$_3$ | 2,5-di-Cl-phenyl |
| 209 | 2 | CH$_2$CH$_3$ | CH$_2$CH$_3$ | 2,5-di-Cl-phenyl |
| 210 | 3 | CH$_2$CH$_3$ | CH$_2$CH$_3$ | 2,5-di-Cl-phenyl |
| 211 | 1 | CH$_3$ | CH$_3$ | 2,6-di-Cl-phenyl |
| 212 | 2 | CH$_3$ | CH$_3$ | 2,6-di-Cl-phenyl |
| 213 | 3 | CH$_3$ | CH$_3$ | 2,6-di-Cl-phenyl |
| 214 | 1 | CH$_2$CH$_3$ | CH$_2$CH$_3$ | 2,6-di-Cl-phenyl |
| 215 | 2 | CH$_2$CH$_3$ | CH$_2$CH$_3$ | 2,6-di-Cl-phenyl |
| 216 | 3 | CH$_2$CH$_3$ | CH$_2$CH$_3$ | 2,6-di-Cl-phenyl |
| 217 | 1 | CH$_3$ | CH$_3$ | 3,4-di-Cl-phenyl |
| 218 | 2 | CH$_3$ | CH$_3$ | 3,4-di-Cl-phenyl |
| 219 | 3 | CH$_3$ | CH$_3$ | 3,4-di-Cl-phenyl |
| 220 | 1 | CH$_2$CH$_3$ | CH$_2$CH$_3$ | 3,4-di-Cl-phenyl |
| 221 | 2 | CH$_2$CH$_3$ | CH$_2$CH$_3$ | 3,4-di-Cl-phenyl |
| 222 | 3 | CH$_2$CH$_3$ | CH$_2$CH$_3$ | 3,4-di-Cl-phenyl |
| 223 | 1 | CH$_3$ | CH$_3$ | 3,5-di-Cl-phenyl |
| 224 | 2 | CH$_3$ | CH$_3$ | 3,5-di-Cl-phenyl |
| 225 | 3 | CH$_3$ | CH$_3$ | 3,5-di-Cl-phenyl |
| 226 | 1 | CH$_2$CH$_3$ | CH$_2$CH$_3$ | 3,5-di-Cl-phenyl |
| 227 | 2 | CH$_2$CH$_3$ | CH$_2$CH$_3$ | 3,5-di-Cl-phenyl |
| 228 | 3 | CH$_2$CH$_3$ | CH$_2$CH$_3$ | 3,5-di-Cl-phenyl |
| 229 | 1 | CH$_3$ | CH$_3$ | 2-morpholino-4-CH$_3$-phenyl |
| 230 | 2 | CH$_3$ | CH$_3$ | 2-morpholino-4-CH$_3$-phenyl |
| 231 | 3 | CH$_3$ | CH$_3$ | 2-morpholino-4-CH$_3$-phenyl |
| 232 | 1 | CH$_2$CH$_3$ | CH$_2$CH$_3$ | 2-morpholino-4-CH$_3$-phenyl |
| 233 | 2 | CH$_2$CH$_3$ | CH$_2$CH$_3$ | 2-morpholino-4-CH$_3$-phenyl |
| 234 | 3 | CH$_2$CH$_3$ | CH$_2$CH$_3$ | 2-morpholino-4-CH$_3$-phenyl |
| 235 | 1 | CH$_3$ | CH$_3$ | 2-morpholino-4-CN-phenyl |
| 236 | 2 | CH$_3$ | CH$_3$ | 2-morpholino-4-CN-phenyl |
| 237 | 3 | CH$_3$ | CH$_3$ | 2-morpholino-4-CN-phenyl |
| 238 | 1 | CH$_2$CH$_3$ | CH$_2$CH$_3$ | 2-morpholino-4-CN-phenyl |
| 239 | 2 | CH$_2$CH$_3$ | CH$_2$CH$_3$ | 2-morpholino-4-CN-phenyl |
| 240 | 3 | CH$_2$CH$_3$ | CH$_2$CH$_3$ | 2-morpholino-4-CN-phenyl |
| 241 | 1 | CH$_3$ | CH$_3$ | 2-morpholino-4-OH-phenyl |
| 242 | 2 | CH$_3$ | CH$_3$ | 2-morpholino-4-OH-phenyl |
| 243 | 3 | CH$_3$ | CH$_3$ | 2-morpholino-4-OH-phenyl |
| 244 | 1 | CH$_2$CH$_3$ | CH$_2$CH$_3$ | 2-morpholino-4-OH-phenyl |
| 245 | 2 | CH$_2$CH$_3$ | CH$_2$CH$_3$ | 2-morpholino-4-OH-phenyl |
| 246 | 3 | CH$_2$CH$_3$ | CH$_2$CH$_3$ | 2-morpholino-4-OH-phenyl |

TABLE 11-continued

| Entry | n | R1$^a$ | R1$^b$ | R$^2$ |
|---|---|---|---|---|
| 247 | 1 | CH$_3$ | CH$_3$ | 2,3-dimethylpyridin-4-yl |
| 248 | 2 | CH$_3$ | CH$_3$ | 2,3-dimethylpyridin-4-yl |
| 249 | 3 | CH$_3$ | CH$_3$ | 2,3-dimethylpyridin-4-yl |
| 250 | 1 | CH$_2$CH$_3$ | CH$_2$CH$_3$ | 2,3-dimethylpyridin-4-yl |
| 251 | 2 | CH$_2$CH$_3$ | CH$_2$CH$_3$ | 2,3-dimethylpyridin-4-yl |
| 252 | 3 | CH$_2$CH$_3$ | CH$_2$CH$_3$ | 2,3-dimethylpyridin-4-yl |
| 253 | 1 | CH$_3$ | CH$_3$ | 3,6-dimethy1pyridin-4-yl |
| 254 | 2 | CH$_3$ | CH$_3$ | 3,6-dimethy1pyridin-4-yl |
| 255 | 3 | CH$_3$ | CH$_3$ | 3,6-dimethy1pyridin-4-yl |
| 256 | 1 | CH$_2$CH$_3$ | CH$_2$CH$_3$ | 3,6-dimethy1pyridin-4-yl |
| 257 | 2 | CH$_2$CH$_3$ | CH$_2$CH$_3$ | 3,6-dimethy1pyridin-4-yl |
| 258 | 3 | CH$_2$CH$_3$ | CH$_2$CH$_3$ | 3,6-dimethylpyridin-4-yl |

Exemplary embodiments include compounds having the formula (X) or a pharmaceutically acceptable salt form thereof:

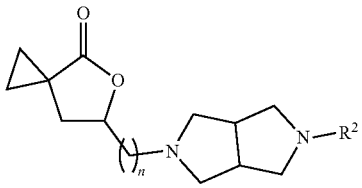

(X)

wherein non-limiting examples of R$^2$ and n are defined herein below in Table 12.

TABLE 12

| Entry | n | R$^2$ |
|---|---|---|
| 1 | 1 | 2-CF$_3$-Phenyl |
| 2 | 2 | 2-CF$_3$-Phenyl |
| 3 | 3 | 2-CF$_3$-Phenyl |
| 4 | 1 | 3-CF$_3$-Phenyl |
| 5 | 2 | 3-CF$_3$-Phenyl |
| 6 | 3 | 3-CF$_3$-Phenyl |
| 7 | 1 | 4-CF$_3$-Phenyl |
| 8 | 2 | 4-CF$_3$-Phenyl |
| 9 | 3 | 4-CF$_3$-Phenyl |
| 10 | 1 | 2-NH$_2$-Phenyl |
| 11 | 2 | 2-NH$_2$-Phenyl |
| 12 | 3 | 2-NH$_2$-Phenyl |
| 13 | 1 | 3-NH$_2$-Phenyl |
| 14 | 2 | 3-NH$_2$-Phenyl |
| 15 | 3 | 3-NH$_2$-Phenyl |
| 16 | 1 | 4-NH$_2$-Phenyl |
| 17 | 2 | 4-NH$_2$-Phenyl |
| 18 | 3 | 4-NH$_2$-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO$_2$-Phenyl |
| 29 | 2 | 2-NO$_2$-Phenyl |
| 30 | 3 | 2-NO$_2$-Phenyl |
| 31 | 1 | 3-NO$_2$-Phenyl |
| 32 | 2 | 3-NO$_2$-Phenyl |
| 33 | 3 | 3-NO$_2$-Phenyl |
| 34 | 1 | 4-NO$_2$-Phenyl |
| 35 | 2 | 4-NO$_2$-Phenyl |
| 36 | 3 | 4-NO$_2$-Phenyl |
| 37 | 1 | 2-SCH$_3$-Phenyl |
| 38 | 2 | 2-SCH$_3$-Phenyl |
| 39 | 3 | 2-SCH$_3$-Phenyl |
| 40 | 1 | 3-SCH$_3$-Phenyl |
| 41 | 2 | 3-SCH$_3$-Phenyl |
| 42 | 3 | 3-SCH$_3$-Phenyl |
| 43 | 1 | 4-SCH$_3$-Phenyl |
| 44 | 2 | 4-SCH$_3$-Phenyl |
| 45 | 3 | 4-SCH$_3$-Phenyl |
| 46 | 1 | 2-SO$_2$CH$_3$-Phenyl |
| 47 | 2 | 2-SO$_2$CH$_3$-Phenyl |
| 48 | 3 | 2-SO$_2$CH$_3$-Phenyl |
| 49 | 1 | 3-SO$_2$CH$_3$-Phenyl |
| 50 | 2 | 3-SO$_2$CH$_3$-Phenyl |
| 51 | 3 | 3-SO$_2$CH$_3$-Phenyl |
| 52 | 1 | 4-SO$_2$CH$_3$-Phenyl |
| 53 | 2 | 4-SO$_2$CH$_3$-Phenyl |
| 54 | 3 | 4-SO$_2$CH$_3$-Phenyl |
| 55 | 1 | 2-SO$_2$NH$_2$-Phenyl |
| 56 | 2 | 2-SO$_2$NH$_2$-Phenyl |
| 57 | 3 | 2-SO$_2$NH$_2$-Phenyl |
| 58 | 1 | 3-SO$_2$NH$_2$-Phenyl |
| 59 | 2 | 3-SO$_2$NH$_2$-Phenyl |
| 60 | 3 | 3-SO$_2$NH$_2$-Phenyl |
| 61 | 1 | 4-SO$_2$NH$_2$-Phenyl |
| 62 | 2 | 4-SO$_2$NH$_2$-Phenyl |
| 63 | 3 | 4-SO$_2$NH$_2$-Phenyl |
| 64 | 1 | 2-CONH$_2$-Phenyl |
| 65 | 2 | 2-CONH$_2$-Phenyl |
| 66 | 3 | 2-CONH$_2$-Phenyl |
| 67 | 1 | 3-CONH$_2$-Phenyl |
| 68 | 2 | 3-CONH$_2$-Phenyl |
| 69 | 3 | 3-CONH$_2$-Phenyl |
| 70 | 1 | 4-CONH$_2$-Phenyl |
| 71 | 2 | 4-CONH$_2$-Phenyl |
| 72 | 3 | 4-CONH$_2$-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH$_3$-phenyl |
| 80 | 2 | 2,3-di-CH$_3$-phenyl |
| 81 | 3 | 2,3-di-CH$_3$-phenyl |
| 82 | 1 | 2,4-di-CH$_3$-phenyl |
| 83 | 2 | 2,4-di-CH$_3$-phenyl |
| 84 | 3 | 2,4-di-CH$_3$-phenyl |
| 85 | 1 | 2,5-di-CH$_3$-phenyl |
| 86 | 2 | 2,5-di-CH$_3$-phenyl |
| 87 | 3 | 2,5-di-CH$_3$-phenyl |
| 88 | 1 | 2,6-di-CH$_3$-phenyl |
| 89 | 2 | 2,6-di-CH$_3$-phenyl |
| 90 | 3 | 2,6-di-CH$_3$-phenyl |
| 91 | 1 | 3,4-di-CH$_3$-phenyl |
| 92 | 2 | 3,4-di-CH$_3$-phenyl |
| 93 | 3 | 3,4-di-CH$_3$-phenyl |
| 94 | 1 | 3,5-di-CH$_3$-phenyl |
| 95 | 2 | 3,5-di-CH$_3$-phenyl |
| 96 | 3 | 3,5-di-CH$_3$-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH$_3$-phenyl |
| 116 | 2 | 2-morpholino-4-CH$_3$-phenyl |

TABLE 12-continued

| Entry | n | R² |
|---|---|---|
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XI) or a pharmaceutically acceptable salt form thereof:

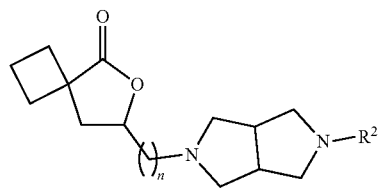

(XI)

wherein non-limiting examples of R and n are defined herein below in Table 13.

TABLE 13

| Entry | n | R² |
|---|---|---|
| 1 | 1 | 2-CF₃-Phenyl |
| 2 | 2 | 2-CF₃-Phenyl |
| 3 | 3 | 2-CF₃-Phenyl |
| 4 | 1 | 3-CF₃-Phenyl |
| 5 | 2 | 3-CF₃-Phenyl |
| 6 | 3 | 3-CF₃-Phenyl |
| 7 | 1 | 4-CF₃-Phenyl |
| 8 | 2 | 4-CF₃-Phenyl |
| 9 | 3 | 4-CF₃-Phenyl |
| 10 | 1 | 2-NH₂-Phenyl |
| 11 | 2 | 2-NH₂-Phenyl |
| 12 | 3 | 2-NH₂-Phenyl |
| 13 | 1 | 3-NH₂-Phenyl |
| 14 | 2 | 3-NH₂-Phenyl |
| 15 | 3 | 3-NH₂-Phenyl |
| 16 | 1 | 4-NH₂-Phenyl |
| 17 | 2 | 4-NH₂-Phenyl |
| 18 | 3 | 4-NH₂-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO₂-Phenyl |
| 29 | 2 | 2-NO₂-Phenyl |
| 30 | 3 | 2-NO₂-Phenyl |
| 31 | 1 | 3-NO₂-Phenyl |
| 32 | 2 | 3-NO₂-Phenyl |
| 33 | 3 | 3-NO₂-Phenyl |
| 34 | 1 | 4-NO₂-Phenyl |
| 35 | 2 | 4-NO₂-Phenyl |
| 36 | 3 | 4-NO₂-Phenyl |
| 37 | 1 | 2-SCH₃-Phenyl |
| 38 | 2 | 2-SCH₃-Phenyl |
| 39 | 3 | 2-SCH₃-Phenyl |
| 40 | 1 | 3-SCH₃-Phenyl |
| 41 | 2 | 3-SCH₃-Phenyl |
| 42 | 3 | 3-SCH₃-Phenyl |
| 43 | 1 | 4-SCH₃-Phenyl |
| 44 | 2 | 4-SCH₃-Phenyl |
| 45 | 3 | 4-SCH₃-Phenyl |
| 46 | 1 | 2-SO₂CH₃-Phenyl |
| 47 | 2 | 2-SO₂CH₃-Phenyl |
| 48 | 3 | 2-SO₂CH₃-Phenyl |
| 49 | 1 | 3-SO₂CH₃-Phenyl |
| 50 | 2 | 3-SO₂CH₃-Phenyl |
| 51 | 3 | 3-SO₂CH₃-Phenyl |
| 52 | 1 | 4-SO₂CH₃-Phenyl |
| 53 | 2 | 4-SO₂CH₃-Phenyl |
| 54 | 3 | 4-SO₂CH₃-Phenyl |
| 55 | 1 | 2-SO₂NH₂-Phenyl |
| 56 | 2 | 2-SO₂NH₂-Phenyl |
| 57 | 3 | 2-SO₂NH₂-Phenyl |
| 58 | 1 | 3-SO₂NH₂-Phenyl |
| 59 | 2 | 3-SO₂NH₂-Phenyl |
| 60 | 3 | 3-SO₂NH₂-Phenyl |
| 61 | 1 | 4-SO₂NH₂-Phenyl |
| 62 | 2 | 4-SO₂NH₂-Phenyl |
| 63 | 3 | 4-SO₂NH₂-Phenyl |
| 64 | 1 | 2-CONH₂-Phenyl |
| 65 | 2 | 2-CONH₂-Phenyl |
| 66 | 3 | 2-CONH₂-Phenyl |
| 67 | 1 | 3-CONH₂-Phenyl |
| 68 | 2 | 3-CONH₂-Phenyl |
| 69 | 3 | 3-CONH₂-Phenyl |
| 70 | 1 | 4-CONH₂-Phenyl |
| 71 | 2 | 4-CONH₂-Phenyl |
| 72 | 3 | 4-CONH₂-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH₃-phenyl |
| 80 | 2 | 2,3-di-CH₃-phenyl |
| 81 | 3 | 2,3-di-CH₃-phenyl |
| 82 | 1 | 2,4-di-CH₃-phenyl |
| 83 | 2 | 2,4-di-CH₃-phenyl |
| 84 | 3 | 2,4-di-CH₃-phenyl |
| 85 | 1 | 2,5-di-CH₃-phenyl |
| 86 | 2 | 2,5-di-CH₃-phenyl |
| 87 | 3 | 2,5-di-CH₃-phenyl |
| 88 | 1 | 2,6-di-CH₃-phenyl |
| 89 | 2 | 2,6-di-CH₃-phenyl |
| 90 | 3 | 2,6-di-CH₃-phenyl |
| 91 | 1 | 3,4-di-CH₃-phenyl |
| 92 | 2 | 3,4-di-CH₃-phenyl |
| 93 | 3 | 3,4-di-CH₃-phenyl |
| 94 | 1 | 3,5-di-CH₃-phenyl |
| 95 | 2 | 3,5-di-CH₃-phenyl |
| 96 | 3 | 3,5-di-CH₃-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH₃-phenyl |

TABLE 13-continued

| Entry | n | R² |
|---|---|---|
| 116 | 2 | 2-morpholino-4-CH₃-phenyl |
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XII) or a pharmaceutically acceptable salt form thereof:

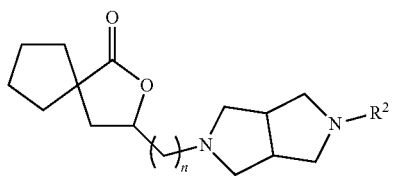

(XII)

wherein non-limiting examples of R² and n are defined herein below in Table 14.

TABLE 14

| Entry | n | R² |
|---|---|---|
| 1 | 1 | 2-CF₃-Phenyl |
| 2 | 2 | 2-CF₃-Phenyl |
| 3 | 3 | 2-CF₃-Phenyl |
| 4 | 1 | 3-CF₃-Phenyl |
| 5 | 2 | 3-CF₃-Phenyl |
| 6 | 3 | 3-CF₃-Phenyl |
| 7 | 1 | 4-CF₃-Phenyl |
| 8 | 2 | 4-CF₃-Phenyl |
| 9 | 3 | 4-CF₃-Phenyl |
| 10 | 1 | 2-NH₂-Phenyl |
| 11 | 2 | 2-NH₂-Phenyl |
| 12 | 3 | 2-NH₂-Phenyl |
| 13 | 1 | 3-NH₂-Phenyl |
| 14 | 2 | 3-NH₂-Phenyl |
| 15 | 3 | 3-NH₂-Phenyl |
| 16 | 1 | 4-NH₂-Phenyl |
| 17 | 2 | 4-NH₂-Phenyl |
| 18 | 3 | 4-NH₂-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO₂-Phenyl |
| 29 | 2 | 2-NO₂-Phenyl |
| 30 | 3 | 2-NO₂-Phenyl |
| 31 | 1 | 3-NO₂-Phenyl |
| 32 | 2 | 3-NO₂-Phenyl |
| 33 | 3 | 3-NO₂-Phenyl |
| 34 | 1 | 4-NO₂-Phenyl |
| 35 | 2 | 4-NO₂-Phenyl |
| 36 | 3 | 4-NO₂-Phenyl |
| 37 | 1 | 2-SCH₃-Phenyl |
| 38 | 2 | 2-SCH₃-Phenyl |
| 39 | 3 | 2-SCH₃-Phenyl |
| 40 | 1 | 3-SCH₃-Phenyl |
| 41 | 2 | 3-SCH₃-Phenyl |
| 42 | 3 | 3-SCH₃-Phenyl |
| 43 | 1 | 4-SCH₃-Phenyl |
| 44 | 2 | 4-SCH₃-Phenyl |
| 45 | 3 | 4-SCH₃-Phenyl |
| 46 | 1 | 2-SO₂CH₃-Phenyl |
| 47 | 2 | 2-SO₂CH₃-Phenyl |
| 48 | 3 | 2-SO₂CH₃-Phenyl |
| 49 | 1 | 3-SO₂CH₃-Phenyl |
| 50 | 2 | 3-SO₂CH₃-Phenyl |
| 51 | 3 | 3-SO₂CH₃-Phenyl |
| 52 | 1 | 4-SO₂CH₃-Phenyl |
| 53 | 2 | 4-SO₂CH₃-Phenyl |
| 54 | 3 | 4-SO₂CH₃-Phenyl |
| 55 | 1 | 2-SO₂NH₂-Phenyl |
| 56 | 2 | 2-SO₂NH₂-Phenyl |
| 57 | 3 | 2-SO₂NH₂-Phenyl |
| 58 | 1 | 3-SO₂NH₂-Phenyl |
| 59 | 2 | 3-SO₂NH₂-Phenyl |
| 60 | 3 | 3-SO₂NH₂-Phenyl |
| 61 | 1 | 4-SO₂NH₂-Phenyl |
| 62 | 2 | 4-SO₂NH₂-Phenyl |
| 63 | 3 | 4-SO₂NH₂-Phenyl |
| 64 | 1 | 2-CONH₂-Phenyl |
| 65 | 2 | 2-CONH₂-Phenyl |
| 66 | 3 | 2-CONH₂-Phenyl |
| 67 | 1 | 3-CONH₂-Phenyl |
| 68 | 2 | 3-CONH₂-Phenyl |
| 69 | 3 | 3-CONH₂-Phenyl |
| 70 | 1 | 4-CONH₂-Phenyl |
| 71 | 2 | 4-CONH₂-Phenyl |
| 72 | 3 | 4-CONH₂-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH₃-phenyl |
| 80 | 2 | 2,3-di-CH₃-phenyl |
| 81 | 3 | 2,3-di-CH₃-phenyl |
| 82 | 1 | 2,4-di-CH₃-phenyl |
| 83 | 2 | 2,4-di-CH₃-phenyl |
| 84 | 3 | 2,4-di-CH₃-phenyl |
| 85 | 1 | 2,5-di-CH₃-phenyl |
| 86 | 2 | 2,5-di-CH₃-phenyl |
| 87 | 3 | 2,5-di-CH₃-phenyl |
| 88 | 1 | 2,6-di-CH₃-phenyl |
| 89 | 2 | 2,6-di-CH₃-phenyl |
| 90 | 3 | 2,6-di-CH₃-phenyl |
| 91 | 1 | 3,4-di-CH₃-phenyl |
| 92 | 2 | 3,4-di-CH₃-phenyl |
| 93 | 3 | 3,4-di-CH₃-phenyl |
| 94 | 1 | 3,5-di-CH₃-phenyl |
| 95 | 2 | 3,5-di-CH₃-phenyl |
| 96 | 3 | 3,5-di-CH₃-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH₃-phenyl |

TABLE 14-continued

| Entry | n | R² |
|---|---|---|
| 116 | 2 | 2-morpholino-4-CH₃-phenyl |
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XIII) or a pharmaceutically acceptable salt form thereof:

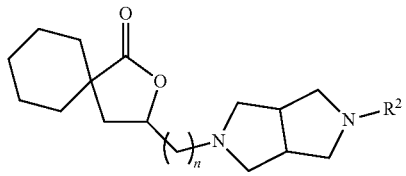

(XIII)

wherein non-limiting examples of R² and n are defined herein below in Table 15.

TABLE 15

| Entry | n | R² |
|---|---|---|
| 1 | 1 | 2-CF₃-Phenyl |
| 2 | 2 | 2-CF₃-Phenyl |
| 3 | 3 | 2-CF₃-Phenyl |
| 4 | 1 | 3-CF₃-Phenyl |
| 5 | 2 | 3-CF₃-Phenyl |
| 6 | 3 | 3-CF₃-Phenyl |
| 7 | 1 | 4-CF₃-Phenyl |
| 8 | 2 | 4-CF₃-Phenyl |
| 9 | 3 | 4-CF₃-Phenyl |
| 10 | 1 | 2-NH₂-Phenyl |
| 11 | 2 | 2-NH₂-Phenyl |
| 12 | 3 | 2-NH₂-Phenyl |
| 13 | 1 | 3-NH₂-Phenyl |
| 14 | 2 | 3-NH₂-Phenyl |
| 15 | 3 | 3-NH₂-Phenyl |
| 16 | 1 | 4-NH₂-Phenyl |
| 17 | 2 | 4-NH₂-Phenyl |
| 18 | 3 | 4-NH₂-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO₂-Phenyl |
| 29 | 2 | 2-NO₂-Phenyl |
| 30 | 3 | 2-NO₂-Phenyl |
| 31 | 1 | 3-NO₂-Phenyl |
| 32 | 2 | 3-NO₂-Phenyl |
| 33 | 3 | 3-NO₂-Phenyl |
| 34 | 1 | 4-NO₂-Phenyl |
| 35 | 2 | 4-NO₂-Phenyl |
| 36 | 3 | 4-NO₂-Phenyl |
| 37 | 1 | 2-SCH₃-Phenyl |

TABLE 15-continued

| Entry | n | R² |
|---|---|---|
| 38 | 2 | 2-SCH₃-Phenyl |
| 39 | 3 | 2-SCH₃-Phenyl |
| 40 | 1 | 3-SCH₃-Phenyl |
| 41 | 2 | 3-SCH₃-Phenyl |
| 42 | 3 | 3-SCH₃-Phenyl |
| 43 | 1 | 4-SCH₃-Phenyl |
| 44 | 2 | 4-SCH₃-Phenyl |
| 45 | 3 | 4-SCH₃-Phenyl |
| 46 | 1 | 2-SO₂CH₃-Phenyl |
| 47 | 2 | 2-SO₂CH₃-Phenyl |
| 48 | 3 | 2-SO₂CH₃-Phenyl |
| 49 | 1 | 3-SO₂CH₃-Phenyl |
| 50 | 2 | 3-SO₂CH₃-Phenyl |
| 51 | 3 | 3-SO₂CH₃-Phenyl |
| 52 | 1 | 4-SO₂CH₃-Phenyl |
| 53 | 2 | 4-SO₂CH₃-Phenyl |
| 54 | 3 | 4-SO₂CH₃-Phenyl |
| 55 | 1 | 2-SO₂NH₂-Phenyl |
| 56 | 2 | 2-SO₂NH₂-Phenyl |
| 57 | 3 | 2-SO₂NH₂-Phenyl |
| 58 | 1 | 3-SO₂NH₂-Phenyl |
| 59 | 2 | 3-SO₂NH₂-Phenyl |
| 60 | 3 | 3-SO₂NH₂-Phenyl |
| 61 | 1 | 4-SO₂NH₂-Phenyl |
| 62 | 2 | 4-SO₂NH₂-Phenyl |
| 63 | 3 | 4-SO₂NH₂-Phenyl |
| 64 | 1 | 2-CONH₂-Phenyl |
| 65 | 2 | 2-CONH₂-Phenyl |
| 66 | 3 | 2-CONH₂-Phenyl |
| 67 | 1 | 3-CONH₂-Phenyl |
| 68 | 2 | 3-CONH₂-Phenyl |
| 69 | 3 | 3-CONH₂-Phenyl |
| 70 | 1 | 4-CONH₂-Phenyl |
| 71 | 2 | 4-CONH₂-Phenyl |
| 72 | 3 | 4-CONH₂-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH₃-phenyl |
| 80 | 2 | 2,3-di-CH₃-phenyl |
| 81 | 3 | 2,3-di-CH₃-phenyl |
| 82 | 1 | 2,4-di-CH₃-phenyl |
| 83 | 2 | 2,4-di-CH₃-phenyl |
| 84 | 3 | 2,4-di-CH₃-phenyl |
| 85 | 1 | 2,5-di-CH₃-phenyl |
| 86 | 2 | 2,5-di-CH₃-phenyl |
| 87 | 3 | 2,5-di-CH₃-phenyl |
| 88 | 1 | 2,6-di-CH₃-phenyl |
| 89 | 2 | 2,6-di-CH₃-phenyl |
| 90 | 3 | 2,6-di-CH₃-phenyl |
| 91 | 1 | 3,4-di-CH₃-phenyl |
| 92 | 2 | 3,4-di-CH₃-phenyl |
| 93 | 3 | 3,4-di-CH₃-phenyl |
| 94 | 1 | 3,5-di-CH₃-phenyl |
| 95 | 2 | 3,5-di-CH₃-phenyl |
| 96 | 3 | 3,5-di-CH₃-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH₃-phenyl |

TABLE 15-continued

| Entry | n | R² |
|---|---|---|
| 116 | 2 | 2-morpholino-4-CH₃-phenyl |
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (VI) or a pharmaceutically acceptable salt form thereof:

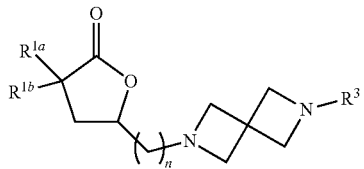

(VI)

wherein non-limiting examples of $R^{1a}$, $R^{1b}$, $R^3$ and n are defined herein below in Table 16.

TABLE 16

| Entry | n | $R^{1a}$ | $R^{1b}$ | R² |
|---|---|---|---|---|
| 1 | 1 | CH₃ | CH₃ | 2-CF₃-Phenyl |
| 2 | 2 | CH₃ | CH₃ | 2-CF₃-Phenyl |
| 3 | 3 | CH₃ | CH₃ | 2-CF₃-Phenyl |
| 4 | 1 | CH₂CH₃ | CH₂CH₃ | 2-CF₃-Phenyl |
| 5 | 2 | CH₂CH₃ | CH₂CH₃ | 2-CF₃-Phenyl |
| 6 | 3 | CH₂CH₃ | CH₂CH₃ | 2-CF₃-Phenyl |
| 7 | 1 | CH₃ | CH₃ | 3-CF₃-Phenyl |
| 8 | 2 | CH₃ | CH₃ | 3-CF₃-Phenyl |
| 9 | 3 | CH₃ | CH₃ | 3-CF₃-Phenyl |
| 10 | 1 | CH₂CH₃ | CH₂CH₃ | 3-CF₃-Phenyl |
| 11 | 2 | CH₂CH₃ | CH₂CH₃ | 3-CF₃-Phenyl |
| 12 | 3 | CH₂CH₃ | CH₂CH₃ | 3-CF₃-Phenyl |
| 13 | 1 | CH₃ | CH₃ | 4-CF₃-Phenyl |
| 14 | 2 | CH₃ | CH₃ | 4-CF₃-Phenyl |
| 15 | 3 | CH₃ | CH₃ | 4-CF₃-Phenyl |
| 16 | 1 | CH₂CH₃ | CH₂CH₃ | 4-CF₃-Phenyl |
| 17 | 2 | CH₂CH₃ | CH₂CH₃ | 4-CF₃-Phenyl |
| 18 | 3 | CH₂CH₃ | CH₂CH₃ | 4-CF₃-Phenyl |
| 19 | 1 | CH₃ | CH₃ | 2-NH₂-Phenyl |
| 20 | 2 | CH₃ | CH₃ | 2-NH₂-Phenyl |
| 21 | 3 | CH₃ | CH₃ | 2-NH₂-Phenyl |
| 22 | 1 | CH₂CH₃ | CH₂CH₃ | 2-NH₂-Phenyl |
| 23 | 2 | CH₂CH₃ | CH₂CH₃ | 2-NH₂-Phenyl |
| 24 | 3 | CH₂CH₃ | CH₂CH₃ | 2-NH₂-Phenyl |
| 25 | 1 | CH₃ | CH₃ | 3-NH₂-Phenyl |
| 26 | 2 | CH₃ | CH₃ | 3-NH₂-Phenyl |
| 27 | 3 | CH₃ | CH₃ | 3-NH₂-Phenyl |
| 28 | 1 | CH₂CH₃ | CH₂CH₃ | 3-NH₂-Phenyl |
| 29 | 2 | CH₂CH₃ | CH₂CH₃ | 3-NH₂-Phenyl |
| 30 | 3 | CH₂CH₃ | CH₂CH₃ | 3-NH₂-Phenyl |
| 31 | 1 | CH₃ | CH₃ | 4-NH₂-Phenyl |
| 32 | 2 | CH₃ | CH₃ | 4-NH₂-Phenyl |
| 33 | 3 | CH₃ | CH₃ | 4-NH₂-Phenyl |
| 34 | 1 | CH₂CH₃ | CH₂CH₃ | 4-NH₂-Phenyl |
| 35 | 2 | CH₂CH₃ | CH₂CH₃ | 4-NH₂-Phenyl |
| 36 | 3 | CH₂CH₃ | CH₂CH₃ | 4-NH₂-Phenyl |
| 37 | 1 | CH₃ | CH₃ | 2-tBu-Phenyl |
| 38 | 2 | CH₃ | CH₃ | 2-tBu-Phenyl |
| 39 | 3 | CH₃ | CH₃ | 2-tBu-Phenyl |
| 40 | 1 | CH₂CH₃ | CH₂CH₃ | 2-tBu-Phenyl |
| 41 | 2 | CH₂CH₃ | CH₂CH₃ | 2-tBu-Phenyl |
| 42 | 3 | CH₂CH₃ | CH₂CH₃ | 2-tBu-Phenyl |
| 43 | 1 | CH₃ | CH₃ | 3-tBu-Phenyl |
| 44 | 2 | CH₃ | CH₃ | 3-tBu-Phenyl |
| 45 | 3 | CH₃ | CH₃ | 3-tBu-Phenyl |
| 46 | 1 | CH₂CH₃ | CH₂CH₃ | 3-tBu-Phenyl |
| 47 | 2 | CH₂CH₃ | CH₂CH₃ | 3-tBu-Phenyl |
| 48 | 3 | CH₂CH₃ | CH₂CH₃ | 3-tBu-Phenyl |
| 49 | 1 | CH₃ | CH₃ | 4-tBu-Phenyl |
| 50 | 2 | CH₃ | CH₃ | 4-tBu-Phenyl |
| 51 | 3 | CH₃ | CH₃ | 4-tBu-Phenyl |
| 52 | 1 | CH₂CH₃ | CH₂CH₃ | 4-tBu-Phenyl |
| 53 | 2 | CH₂CH₃ | CH₂CH₃ | 4-tBu-Phenyl |
| 54 | 3 | CH₂CH₃ | CH₂CH₃ | 4-tBu-Phenyl |
| 55 | 1 | CH₃ | CH₃ | 2-NO₂-Phenyl |
| 56 | 2 | CH₃ | CH₃ | 2-NO₂-Phenyl |
| 57 | 3 | CH₃ | CH₃ | 2-NO₂-Phenyl |
| 58 | 1 | CH₂CH₃ | CH₂CH₃ | 2-NO₂-Phenyl |
| 59 | 2 | CH₂CH₃ | CH₂CH₃ | 2-NO₂-Phenyl |
| 60 | 3 | CH₂CH₃ | CH₂CH₃ | 2-NO₂-Phenyl |
| 61 | 1 | CH₃ | CH₃ | 3-NO₂-Phenyl |
| 62 | 2 | CH₃ | CH₃ | 3-NO₂-Phenyl |
| 63 | 3 | CH₃ | CH₃ | 3-NO₂-Phenyl |
| 64 | 1 | CH₂CH₃ | CH₂CH₃ | 3-NO₂-Phenyl |
| 65 | 2 | CH₂CH₃ | CH₂CH₃ | 3-NO₂-Phenyl |
| 66 | 3 | CH₂CH₃ | CH₂CH₃ | 3-NO₂-Phenyl |
| 67 | 1 | CH₃ | CH₃ | 4-NO₂-Phenyl |
| 68 | 2 | CH₃ | CH₃ | 4-NO₂-Phenyl |
| 69 | 3 | CH₃ | CH₃ | 4-NO₂-Phenyl |
| 70 | 1 | CH₂CH₃ | CH₂CH₃ | 4-NO₂-Phenyl |
| 71 | 2 | CH₂CH₃ | CH₂CH₃ | 4-NO₂-Phenyl |
| 72 | 3 | CH₂CH₃ | CH₂CH₃ | 4-NO₂-Phenyl |
| 73 | 1 | CH₃ | CH₃ | 2-SCH₃-Phenyl |
| 74 | 2 | CH₃ | CH₃ | 2-SCH₃-Phenyl |
| 75 | 3 | CH₃ | CH₃ | 2-SCH₃-Phenyl |
| 76 | 1 | CH₂CH₃ | CH₂CH₃ | 2-SCH₃-Phenyl |
| 77 | 2 | CH₂CH₃ | CH₂CH₃ | 2-SCH₃-Phenyl |
| 78 | 3 | CH₂CH₃ | CH₂CH₃ | 2-SCH₃-Phenyl |
| 79 | 1 | CH₃ | CH₃ | 3-SCH₃-Phenyl |
| 80 | 2 | CH₃ | CH₃ | 3-SCH₃-Phenyl |
| 81 | 3 | CH₃ | CH₃ | 3-SCH₃-Phenyl |
| 82 | 1 | CH₂CH₃ | CH₂CH₃ | 3-SCH₃-Phenyl |
| 83 | 2 | CH₂CH₃ | CH₂CH₃ | 3-SCH₃-Phenyl |
| 84 | 3 | CH₂CH₃ | CH₂CH₃ | 3-SCH₃-Phenyl |
| 85 | 1 | CH₃ | CH₃ | 4-SCH₃-Phenyl |
| 86 | 2 | CH₃ | CH₃ | 4-SCH₃-Phenyl |
| 87 | 3 | CH₃ | CH₃ | 4-SCH₃-Phenyl |
| 88 | 1 | CH₂CH₃ | CH₂CH₃ | 4-SCH₃-Phenyl |
| 89 | 2 | CH₂CH₃ | CH₂CH₃ | 4-SCH₃-Phenyl |
| 90 | 3 | CH₂CH₃ | CH₂CH₃ | 4-SCH₃-Phenyl |
| 91 | 1 | CH₃ | CH₃ | 2-SO₂CH₃-Phenyl |
| 92 | 2 | CH₃ | CH₃ | 2-SO₂CH₃-Phenyl |
| 93 | 3 | CH₃ | CH₃ | 2-SO₂CH₃-Phenyl |
| 94 | 1 | CH₂CH₃ | CH₂CH₃ | 2-SO₂CH₃-Phenyl |
| 95 | 2 | CH₂CH₃ | CH₂CH₃ | 2-SO₂CH₃-Phenyl |
| 96 | 3 | CH₂CH₃ | CH₂CH₃ | 2-SO₂CH₃-Phenyl |
| 97 | 1 | CH₃ | CH₃ | 3-SO₂CH₃-Phenyl |
| 98 | 2 | CH₃ | CH₃ | 3-SO₂CH₃-Phenyl |
| 99 | 3 | CH₃ | CH₃ | 3-SO₂CH₃-Phenyl |
| 100 | 1 | CH₂CH₃ | CH₂CH₃ | 3-SO₂CH₃-Phenyl |
| 101 | 2 | CH₂CH₃ | CH₂CH₃ | 3-SO₂CH₃-Phenyl |
| 102 | 3 | CH₂CH₃ | CH₂CH₃ | 3-SO₂CH₃-Phenyl |
| 103 | 1 | CH₃ | CH₃ | 4-SO₂CH₃-Phenyl |
| 104 | 2 | CH₃ | CH₃ | 4-SO₂CH₃-Phenyl |
| 105 | 3 | CH₃ | CH₃ | 4-SO₂CH₃-Phenyl |
| 106 | 1 | CH₂CH₃ | CH₂CH₃ | 4-SO₂CH₃-Phenyl |
| 107 | 2 | CH₂CH₃ | CH₂CH₃ | 4-SO₂CH₃-Phenyl |
| 108 | 3 | CH₂CH₃ | CH₂CH₃ | 4-SO₂CH₃-Phenyl |
| 109 | 1 | CH₃ | CH₃ | 2-SO₂NH₂-Phenyl |
| 110 | 2 | CH₃ | CH₃ | 2-SO₂NH₂-Phenyl |
| 111 | 3 | CH₃ | CH₃ | 2-SO₂NH₂-Phenyl |
| 112 | 1 | CH₂CH₃ | CH₂CH₃ | 2-SO₂NH₂-Phenyl |
| 113 | 2 | CH₂CH₃ | CH₂CH₃ | 2-SO₂NH₂-Phenyl |
| 114 | 3 | CH₂CH₃ | CH₂CH₃ | 2-SO₂NH₂-Phenyl |
| 115 | 1 | CH₃ | CH₃ | 3-SO₂NH₂-Phenyl |

TABLE 16-continued

| Entry | n | $R^{1a}$ | $R^{1b}$ | $R^2$ |
|---|---|---|---|---|
| 116 | 2 | $CH_3$ | $CH_3$ | 3-$SO_2NH_2$-Phenyl |
| 117 | 3 | $CH_3$ | $CH_3$ | 3-$SO_2NH_2$-Phenyl |
| 118 | 1 | $CH_2CH_3$ | $CH_2CH_3$ | 3-$SO_2NH_2$-Phenyl |
| 119 | 2 | $CH_2CH_3$ | $CH_2CH_3$ | 3-$SO_2NH_2$-Phenyl |
| 120 | 3 | $CH_2CH_3$ | $CH_2CH_3$ | 3-$SO_2NH_2$-Phenyl |
| 121 | 1 | $CH_3$ | $CH_3$ | 4-$SO_2NH_2$-Phenyl |
| 122 | 2 | $CH_3$ | $CH_3$ | 4-$SO_2NH_2$-Phenyl |
| 123 | 3 | $CH_3$ | $CH_3$ | 4-$SO_2NH_2$-Phenyl |
| 124 | 1 | $CH_2CH_3$ | $CH_2CH_3$ | 4-$SO_2NH_2$-Phenyl |
| 125 | 2 | $CH_2CH_3$ | $CH_2CH_3$ | 4-$SO_2NH_2$-Phenyl |
| 126 | 3 | $CH_2CH_3$ | $CH_2CH_3$ | 4-$SO_2NH_2$-Phenyl |
| 127 | 1 | $CH_3$ | $CH_3$ | 2-$CONH_2$-Phenyl |
| 128 | 2 | $CH_3$ | $CH_3$ | 2-$CONH_2$-Phenyl |
| 129 | 3 | $CH_3$ | $CH_3$ | 2-$CONH_2$-Phenyl |
| 130 | 1 | $CH_2CH_3$ | $CH_2CH_3$ | 2-$CONH_2$-Phenyl |
| 131 | 2 | $CH_2CH_3$ | $CH_2CH_3$ | 2-$CONH_2$-Phenyl |
| 132 | 3 | $CH_2CH_3$ | $CH_2CH_3$ | 2-$CONH_2$-Phenyl |
| 133 | 1 | $CH_3$ | $CH_3$ | 3-$CONH_2$-Phenyl |
| 134 | 2 | $CH_3$ | $CH_3$ | 3-$CONH_2$-Phenyl |
| 135 | 3 | $CH_3$ | $CH_3$ | 3-$CONH_2$-Phenyl |
| 136 | 1 | $CH_2CH_3$ | $CH_2CH_3$ | 3-$CONH_2$-Phenyl |
| 137 | 2 | $CH_2CH_3$ | $CH_2CH_3$ | 3-$CONH_2$-Phenyl |
| 138 | 3 | $CH_2CH_3$ | $CH_2CH_3$ | 3-$CONH_2$-Phenyl |
| 139 | 1 | $CH_3$ | $CH_3$ | 4-$CONH_2$-Phenyl |
| 140 | 2 | $CH_3$ | $CH_3$ | 4-$CONH_2$-Phenyl |
| 141 | 3 | $CH_3$ | $CH_3$ | 4-$CONH_2$-Phenyl |
| 142 | 1 | $CH_2CH_3$ | $CH_2CH_3$ | 4-$CONH_2$-Phenyl |
| 143 | 2 | $CH_2CH_3$ | $CH_2CH_3$ | 4-$CONH_2$-Phenyl |
| 144 | 3 | $CH_2CH_3$ | $CH_2CH_3$ | 4-$CONH_2$-Phenyl |
| 145 | 1 | $CH_3$ | $CH_3$ | 2-Br-Phenyl |
| 146 | 2 | $CH_3$ | $CH_3$ | 2-Br-Phenyl |
| 147 | 3 | $CH_3$ | $CH_3$ | 2-Br-Phenyl |
| 148 | 1 | $CH_2CH_3$ | $CH_2CH_3$ | 2-Br-Phenyl |
| 149 | 2 | $CH_2CH_3$ | $CH_2CH_3$ | 2-Br-Phenyl |
| 150 | 3 | $CH_2CH_3$ | $CH_2CH_3$ | 2-Br-Phenyl |
| 151 | 1 | $CH_3$ | $CH_3$ | 3-Br-Phenyl |
| 152 | 2 | $CH_3$ | $CH_3$ | 3-Br-Phenyl |
| 153 | 3 | $CH_3$ | $CH_3$ | 3-Br-Phenyl |
| 154 | 1 | $CH_2CH_3$ | $CH_2CH_3$ | 3-Br-Phenyl |
| 155 | 2 | $CH_2CH_3$ | $CH_2CH_3$ | 3-Br-Phenyl |
| 156 | 3 | $CH_2CH_3$ | $CH_2CH_3$ | 3-Br-Phenyl |
| 157 | 1 | $CH_3$ | $CH_3$ | 2,3-di-$CH_3$-phenyl |
| 158 | 2 | $CH_3$ | $CH_3$ | 2,3-di-$CH_3$-phenyl |
| 159 | 3 | $CH_3$ | $CH_3$ | 2,3-di-$CH_3$-phenyl |
| 160 | 1 | $CH_2CH_3$ | $CH_2CH_3$ | 2,3-di-$CH_3$-phenyl |
| 161 | 2 | $CH_2CH_3$ | $CH_2CH_3$ | 2,3-di-$CH_3$-phenyl |
| 162 | 3 | $CH_2CH_3$ | $CH_2CH_3$ | 2,3-di-$CH_3$-phenyl |
| 163 | 1 | $CH_3$ | $CH_3$ | 2,4-di-$CH_3$-phenyl |
| 164 | 2 | $CH_3$ | $CH_3$ | 2,4-di-$CH_3$-phenyl |
| 165 | 3 | $CH_3$ | $CH_3$ | 2,4-di-$CH_3$-phenyl |
| 166 | 1 | $CH_2CH_3$ | $CH_2CH_3$ | 2,4-di-$CH_3$-phenyl |
| 167 | 2 | $CH_2CH_3$ | $CH_2CH_3$ | 2,4-di-$CH_3$-phenyl |
| 168 | 3 | $CH_2CH_3$ | $CH_2CH_3$ | 2,4-di-$CH_3$-phenyl |
| 169 | 1 | $CH_3$ | $CH_3$ | 2,5-di-$CH_3$-phenyl |
| 170 | 2 | $CH_3$ | $CH_3$ | 2,5-di-$CH_3$-phenyl |
| 171 | 3 | $CH_3$ | $CH_3$ | 2,5-di-$CH_3$-phenyl |
| 172 | 1 | $CH_2CH_3$ | $CH_2CH_3$ | 2,5-di-$CH_3$-phenyl |
| 173 | 2 | $CH_2CH_3$ | $CH_2CH_3$ | 2,5-di-$CH_3$-phenyl |
| 174 | 3 | $CH_2CH_3$ | $CH_2CH_3$ | 2,5-di-$CH_3$-phenyl |
| 175 | 1 | $CH_3$ | $CH_3$ | 2,6-di-$CH_3$-phenyl |
| 176 | 2 | $CH_3$ | $CH_3$ | 2,6-di-$CH_3$-phenyl |
| 177 | 3 | $CH_3$ | $CH_3$ | 2,6-di-$CH_3$-phenyl |
| 178 | 1 | $CH_2CH_3$ | $CH_2CH_3$ | 2,6-di-$CH_3$-phenyl |
| 179 | 2 | $CH_2CH_3$ | $CH_2CH_3$ | 2,6-di-$CH_3$-phenyl |
| 180 | 3 | $CH_2CH_3$ | $CH_2CH_3$ | 2,6-di-$CH_3$-phenyl |
| 181 | 1 | $CH_3$ | $CH_3$ | 3,4-di-$CH_3$-phenyl |
| 182 | 2 | $CH_3$ | $CH_3$ | 3,4-di-$CH_3$-phenyl |
| 183 | 3 | $CH_3$ | $CH_3$ | 3,4-di-$CH_3$-phenyl |
| 184 | 1 | $CH_2CH_3$ | $CH_2CH_3$ | 3,4-di-$CH_3$-phenyl |
| 185 | 2 | $CH_2CH_3$ | $CH_2CH_3$ | 3,4-di-$CH_3$-phenyl |
| 186 | 3 | $CH_2CH_3$ | $CH_2CH_3$ | 3,4-di-$CH_3$-phenyl |
| 187 | 1 | $CH_3$ | $CH_3$ | 3,5-di-$CH_3$-phenyl |
| 188 | 2 | $CH_3$ | $CH_3$ | 3,5-di-$CH_3$-phenyl |
| 189 | 3 | $CH_3$ | $CH_3$ | 3,5-di-$CH_3$-phenyl |
| 190 | 1 | $CH_2CH_3$ | $CH_2CH_3$ | 3,5-di-$CH_3$-phenyl |
| 191 | 2 | $CH_2CH_3$ | $CH_2CH_3$ | 3,5-di-$CH_3$-phenyl |
| 192 | 3 | $CH_2CH_3$ | $CH_2CH_3$ | 3,5-di-$CH_3$-phenyl |
| 193 | 1 | $CH_3$ | $CH_3$ | 2,3-di-Cl-phenyl |
| 194 | 2 | $CH_3$ | $CH_3$ | 2,3-di-Cl-phenyl |
| 195 | 3 | $CH_3$ | $CH_3$ | 2,3-di-Cl-phenyl |
| 196 | 1 | $CH_2CH_3$ | $CH_2CH_3$ | 2,3-di-Cl-phenyl |
| 197 | 2 | $CH_2CH_3$ | $CH_2CH_3$ | 2,3-di-Cl-phenyl |
| 198 | 3 | $CH_2CH_3$ | $CH_2CH_3$ | 2,3-di-Cl-phenyl |
| 199 | 1 | $CH_3$ | $CH_3$ | 2,4-di-Cl-phenyl |
| 200 | 2 | $CH_3$ | $CH_3$ | 2,4-di-Cl-phenyl |
| 201 | 3 | $CH_3$ | $CH_3$ | 2,4-di-Cl-phenyl |
| 202 | 1 | $CH_2CH_3$ | $CH_2CH_3$ | 2,4-di-Cl-phenyl |
| 203 | 2 | $CH_2CH_3$ | $CH_2CH_3$ | 2,4-di-Cl-phenyl |
| 204 | 3 | $CH_2CH_3$ | $CH_2CH_3$ | 2,4-di-Cl-phenyl |
| 205 | 1 | $CH_3$ | $CH_3$ | 2,5-di-Cl-phenyl |
| 206 | 2 | $CH_3$ | $CH_3$ | 2,5-di-Cl-phenyl |
| 207 | 3 | $CH_3$ | $CH_3$ | 2,5-di-Cl-phenyl |
| 280 | 1 | $CH_2CH_3$ | $CH_2CH_3$ | 2,5-di-Cl-phenyl |
| 209 | 2 | $CH_2CH_3$ | $CH_2CH_3$ | 2,5-di-Cl-phenyl |
| 210 | 3 | $CH_2CH_3$ | $CH_2CH_3$ | 2,5-di-Cl-phenyl |
| 211 | 1 | $CH_3$ | $CH_3$ | 2,6-di-Cl-phenyl |
| 212 | 2 | $CH_3$ | $CH_3$ | 2,6-di-Cl-phenyl |
| 213 | 3 | $CH_3$ | $CH_3$ | 2,6-di-Cl-phenyl |
| 214 | 1 | $CH_2CH_3$ | $CH_2CH_3$ | 2,6-di-Cl-phenyl |
| 215 | 2 | $CH_2CH_3$ | $CH_2CH_3$ | 2,6-di-Cl-phenyl |
| 216 | 3 | $CH_2CH_3$ | $CH_2CH_3$ | 2,6-di-Cl-phenyl |
| 217 | 1 | $CH_3$ | $CH_3$ | 3,4-di-Cl-phenyl |
| 218 | 2 | $CH_3$ | $CH_3$ | 3,4-di-Cl-phenyl |
| 219 | 3 | $CH_3$ | $CH_3$ | 3,4-di-Cl-phenyl |
| 220 | 1 | $CH_2CH_3$ | $CH_2CH_3$ | 3,4-di-Cl-phenyl |
| 221 | 2 | $CH_2CH_3$ | $CH_2CH_3$ | 3,4-di-Cl-phenyl |
| 222 | 3 | $CH_2CH_3$ | $CH_2CH_3$ | 3,4-di-Cl-phenyl |
| 223 | 1 | $CH_3$ | $CH_3$ | 3,5-di-Cl-phenyl |
| 224 | 2 | $CH_3$ | $CH_3$ | 3,5-di-Cl-phenyl |
| 225 | 3 | $CH_3$ | $CH_3$ | 3,5-di-Cl-phenyl |
| 226 | 1 | $CH_2CH_3$ | $CH_2CH_3$ | 3,5-di-Cl-phenyl |
| 227 | 2 | $CH_2CH_3$ | $CH_2CH_3$ | 3,5-di-Cl-phenyl |
| 228 | 3 | $CH_2CH_3$ | $CH_2CH_3$ | 3,5-di-Cl-phenyl |
| 229 | 1 | $CH_3$ | $CH_3$ | 2-morpholino-4-$CH_3$-phenyl |
| 230 | 2 | $CH_3$ | $CH_3$ | 2-morpholino-4-$CH_3$-phenyl |
| 231 | 3 | $CH_3$ | $CH_3$ | 2-morpholino-4-$CH_3$-phenyl |
| 232 | 1 | $CH_2CH_3$ | $CH_2CH_3$ | 2-morpholino-4-$CH_3$-phenyl |
| 233 | 2 | $CH_2CH_3$ | $CH_2CH_3$ | 2-morpholino-4-$CH_3$-phenyl |
| 234 | 3 | $CH_2CH_3$ | $CH_2CH_3$ | 2-morpholino-4-$CH_3$-phenyl |
| 235 | 1 | $CH_3$ | $CH_3$ | 2-morpholino-4-CN-phenyl |
| 236 | 2 | $CH_3$ | $CH_3$ | 2-morpholino-4-CN-phenyl |
| 237 | 3 | $CH_3$ | $CH_3$ | 2-morpholino-4-CN-phenyl |
| 238 | 1 | $CH_2CH_3$ | $CH_2CH_3$ | 2-morpholino-4-CN-phenyl |
| 239 | 2 | $CH_2CH_3$ | $CH_2CH_3$ | 2-morpholino-4-CN-phenyl |
| 240 | 3 | $CH_2CH_3$ | $CH_2CH_3$ | 2-morpholino-4-CN-phenyl |
| 241 | 1 | $CH_3$ | $CH_3$ | 2-morpholino-4-OH-phenyl |
| 242 | 2 | $CH_3$ | $CH_3$ | 2-morpholino-4-OH-phenyl |
| 243 | 3 | $CH_3$ | $CH_3$ | 2-morpholino-4-OH-phenyl |
| 244 | 1 | $CH_2CH_3$ | $CH_2CH_3$ | 2-morpholino-4-OH-phenyl |
| 245 | 2 | $CH_2CH_3$ | $CH_2CH_3$ | 2-morpholino-4-OH-phenyl |
| 246 | 3 | $CH_2CH_3$ | $CH_2CH_3$ | 2-morpholino-4-OH-phenyl |
| 247 | 1 | $CH_3$ | $CH_3$ | 2,3-dimethylpyridin-4-yl |
| 248 | 2 | $CH_3$ | $CH_3$ | 2,3-dimethylpyridin-4-yl |
| 249 | 3 | $CH_3$ | $CH_3$ | 2,3-dimethylpyridin-4-yl |
| 250 | 1 | $CH_2CH_3$ | $CH_2CH_3$ | 2,3-dimethylpyridin-4-yl |
| 251 | 2 | $CH_2CH_3$ | $CH_2CH_3$ | 2,3-dimethylpyridin-4-yl |
| 252 | 3 | $CH_2CH_3$ | $CH_2CH_3$ | 2,3-dimethylpyridin-4-yl |
| 253 | 1 | $CH_3$ | $CH_3$ | 3,6-dimethy 1pyridin-4-yl |
| 254 | 2 | $CH_3$ | $CH_3$ | 3,6-dimethy 1pyridin-4-yl |
| 255 | 3 | $CH_3$ | $CH_3$ | 3,6-dimethy 1pyridin-4-yl |
| 256 | 1 | $CH_2CH_3$ | $CH_2CH_3$ | 3,6-dimethy 1pyridin-4-yl |
| 257 | 2 | $CH_2CH_3$ | $CH_2CH_3$ | 3,63-dimethylpyridin-4-yl |
| 258 | 3 | $CH_2CH_3$ | $CH_2CH_3$ | 3,6-dimethy 1pyridin-4-yl |

Exemplary embodiments include compounds having the formula (XIV) or a pharmaceutically acceptable salt form thereof:

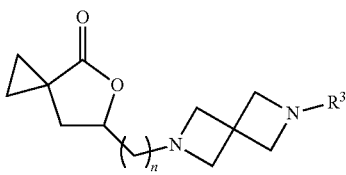

(XIV)

wherein non-limiting examples of R³ and n are defined herein below in Table 17.

TABLE 17

| Entry | n | R² |
|---|---|---|
| 1 | 1 | 2-CF₃-Phenyl |
| 2 | 2 | 2-CF₃-Phenyl |
| 3 | 3 | 2-CF₃-Phenyl |
| 4 | 1 | 3-CF₃-Phenyl |
| 5 | 2 | 3-CF₃-Phenyl |
| 6 | 3 | 3-CF₃-Phenyl |
| 7 | 1 | 4-CF₃-Phenyl |
| 8 | 2 | 4-CF₃-Phenyl |
| 9 | 3 | 4-CF₃-Phenyl |
| 10 | 1 | 2-NH₂-Phenyl |
| 11 | 2 | 2-NH₂-Phenyl |
| 12 | 3 | 2-NH₂-Phenyl |
| 13 | 1 | 3-NH₂-Phenyl |
| 14 | 2 | 3-NH₂-Phenyl |
| 15 | 3 | 3-NH₂-Phenyl |
| 16 | 1 | 4-NH₂-Phenyl |
| 17 | 2 | 4-NH₂-Phenyl |
| 18 | 3 | 4-NH₂-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO₂-Phenyl |
| 29 | 2 | 2-NO₂-Phenyl |
| 30 | 3 | 2-NO₂-Phenyl |
| 31 | 1 | 3-NO₂-Phenyl |
| 32 | 2 | 3-NO₂-Phenyl |
| 33 | 3 | 3-NO₂-Phenyl |
| 34 | 1 | 4-NO₂-Phenyl |
| 35 | 2 | 4-NO₂-Phenyl |
| 36 | 3 | 4-NO₂-Phenyl |
| 37 | 1 | 2-SCH₃-Phenyl |
| 38 | 2 | 2-SCH₃-Phenyl |
| 39 | 3 | 2-SCH₃-Phenyl |
| 40 | 1 | 3-SCH₃-Phenyl |
| 41 | 2 | 3-SCH₃-Phenyl |
| 42 | 3 | 3-SCH₃-Phenyl |
| 43 | 1 | 4-SCH₃-Phenyl |
| 44 | 2 | 4-SCH₃-Phenyl |
| 45 | 3 | 4-SCH₃-Phenyl |
| 46 | 1 | 2-SO₂CH₃-Phenyl |
| 47 | 2 | 2-SO₂CH₃-Phenyl |
| 48 | 3 | 2-SO₂CH₃-Phenyl |
| 49 | 1 | 3-SO₂CH₃-Phenyl |
| 50 | 2 | 3-SO₂CH₃-Phenyl |
| 51 | 3 | 3-SO₂CH₃-Phenyl |
| 52 | 1 | 4-SO₂CH₃-Phenyl |
| 53 | 2 | 4-SO₂CH₃-Phenyl |
| 54 | 3 | 4-SO₂CH₃-Phenyl |
| 55 | 1 | 2-SO₂NH₂-Phenyl |
| 56 | 2 | 2-SO₂NH₂-Phenyl |
| 57 | 3 | 2-SO₂NH₂-Phenyl |
| 58 | 1 | 3-SO₂NH₂-Phenyl |
| 59 | 2 | 3-SO₂NH₂-Phenyl |
| 60 | 3 | 3-SO₂NH₂-Phenyl |
| 61 | 1 | 4-SO₂NH₂-Phenyl |
| 62 | 2 | 4-SO₂NH₂-Phenyl |

TABLE 17-continued

| Entry | n | R² |
|---|---|---|
| 63 | 3 | 4-SO₂NH₂-Phenyl |
| 64 | 1 | 2-CONH₂-Phenyl |
| 65 | 2 | 2-CONH₂-Phenyl |
| 66 | 3 | 2-CONH₂-Phenyl |
| 67 | 1 | 3-CONH₂-Phenyl |
| 68 | 2 | 3-CONH₂-Phenyl |
| 69 | 3 | 3-CONH₂-Phenyl |
| 70 | 1 | 4-CONH₂-Phenyl |
| 71 | 2 | 4-CONH₂-Phenyl |
| 72 | 3 | 4-CONH₂-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH₃-phenyl |
| 80 | 2 | 2,3-di-CH₃-phenyl |
| 81 | 3 | 2,3-di-CH₃-phenyl |
| 82 | 1 | 2,4-di-CH₃-phenyl |
| 83 | 2 | 2,4-di-CH₃-phenyl |
| 84 | 3 | 2,4-di-CH₃-phenyl |
| 85 | 1 | 2,5-di-CH₃-phenyl |
| 86 | 2 | 2,5-di-CH₃-phenyl |
| 87 | 3 | 2,5-di-CH₃-phenyl |
| 88 | 1 | 2,6-di-CH₃-phenyl |
| 89 | 2 | 2,6-di-CH₃-phenyl |
| 90 | 3 | 2,6-di-CH₃-phenyl |
| 91 | 1 | 3,4-di-CH₃-phenyl |
| 92 | 2 | 3,4-di-CH₃-phenyl |
| 93 | 3 | 3,4-di-CH₃-phenyl |
| 94 | 1 | 3,5-di-CH₃-phenyl |
| 95 | 2 | 3,5-di-CH₃-phenyl |
| 96 | 3 | 3,5-di-CH₃-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH₃-phenyl |
| 116 | 2 | 2-morpholino-4-CH₃-phenyl |
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XV) or a pharmaceutically acceptable salt form thereof:

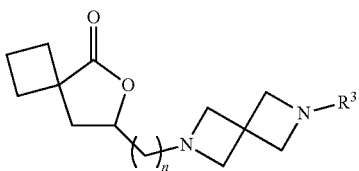

(XV)

wherein non-limiting examples of $R^3$ and n are defined herein below in Table 18.

TABLE 18

| Entry | n | $R^2$ |
|---|---|---|
| 1 | 1 | 2-$CF_3$-Phenyl |
| 2 | 2 | 2-$CF_3$-Phenyl |
| 3 | 3 | 2-$CF_3$-Phenyl |
| 4 | 1 | 3-$CF_3$-Phenyl |
| 5 | 2 | 3-$CF_3$-Phenyl |
| 6 | 3 | 3-$CF_3$-Phenyl |
| 7 | 1 | 4-$CF_3$-Phenyl |
| 8 | 2 | 4-$CF_3$-Phenyl |
| 9 | 3 | 4-$CF_3$-Phenyl |
| 10 | 1 | 2-$NH_2$-Phenyl |
| 11 | 2 | 2-$NH_2$-Phenyl |
| 12 | 3 | 2-$NH_2$-Phenyl |
| 13 | 1 | 3-$NH_2$-Phenyl |
| 14 | 2 | 3-$NH_2$-Phenyl |
| 15 | 3 | 3-$NH_2$-Phenyl |
| 16 | 1 | 4-$NH_2$-Phenyl |
| 17 | 2 | 4-$NH_2$-Phenyl |
| 18 | 3 | 4-$NH_2$-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-$NO_2$-Phenyl |
| 29 | 2 | 2-$NO_2$-Phenyl |
| 30 | 3 | 2-$NO_2$-Phenyl |
| 31 | 1 | 3-$NO_2$-Phenyl |
| 32 | 2 | 3-$NO_2$-Phenyl |
| 33 | 3 | 3-$NO_2$-Phenyl |
| 34 | 1 | 4-$NO_2$-Phenyl |
| 35 | 2 | 4-$NO_2$-Phenyl |
| 36 | 3 | 4-$NO_2$-Phenyl |
| 37 | 1 | 2-$SCH_3$-Phenyl |
| 38 | 2 | 2-$SCH_3$-Phenyl |
| 39 | 3 | 2-$SCH_3$-Phenyl |
| 40 | 1 | 3-$SCH_3$-Phenyl |
| 41 | 2 | 3-$SCH_3$-Phenyl |
| 42 | 3 | 3-$SCH_3$-Phenyl |
| 43 | 1 | 4-$SCH_3$-Phenyl |
| 44 | 2 | 4-$SCH_3$-Phenyl |
| 45 | 3 | 4-$SCH_3$-Phenyl |
| 46 | 1 | 2-$SO_2CH_3$-Phenyl |
| 47 | 2 | 2-$SO_2CH_3$-Phenyl |
| 48 | 3 | 2-$SO_2CH_3$-Phenyl |
| 49 | 1 | 3-$SO_2CH_3$-Phenyl |
| 50 | 2 | 3-$SO_2CH_3$-Phenyl |
| 51 | 3 | 3-$SO_2CH_3$-Phenyl |
| 52 | 1 | 4-$SO_2CH_3$-Phenyl |
| 53 | 2 | 4-$SO_2CH_3$-Phenyl |
| 54 | 3 | 4-$SO_2CH_3$-Phenyl |
| 55 | 1 | 2-$SO_2NH_2$-Phenyl |
| 56 | 2 | 2-$SO_2NH_2$-Phenyl |
| 57 | 3 | 2-$SO_2NH_2$-Phenyl |
| 58 | 1 | 3-$SO_2NH_2$-Phenyl |
| 59 | 2 | 3-$SO_2NH_2$-Phenyl |
| 60 | 3 | 3-$SO_2NH_2$-Phenyl |
| 61 | 1 | 4-$SO_2NH_2$-Phenyl |
| 62 | 2 | 4-$SO_2NH_2$-Phenyl |
| 63 | 3 | 4-$SO_2NH_2$-Phenyl |
| 64 | 1 | 2-$CONH_2$-Phenyl |
| 65 | 2 | 2-$CONH_2$-Phenyl |
| 66 | 3 | 2-$CONH_2$-Phenyl |
| 67 | 1 | 3-$CONH_2$-Phenyl |
| 68 | 2 | 3-$CONH_2$-Phenyl |
| 69 | 3 | 3-$CONH_2$-Phenyl |
| 70 | 1 | 4-$CONH_2$-Phenyl |
| 71 | 2 | 4-$CONH_2$-Phenyl |
| 72 | 3 | 4-$CONH_2$-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-$CH_3$-phenyl |
| 80 | 2 | 2,3-di-$CH_3$-phenyl |
| 81 | 3 | 2,3-di-$CH_3$-phenyl |
| 82 | 1 | 2,4-di-$CH_3$-phenyl |
| 83 | 2 | 2,4-di-$CH_3$-phenyl |
| 84 | 3 | 2,4-di-$CH_3$-phenyl |
| 85 | 1 | 2,5-di-$CH_3$-phenyl |
| 86 | 2 | 2,5-di-$CH_3$-phenyl |
| 87 | 3 | 2,5-di-$CH_3$-phenyl |
| 88 | 1 | 2,6-di-$CH_3$-phenyl |
| 89 | 2 | 2,6-di-$CH_3$-phenyl |
| 90 | 3 | 2,6-di-$CH_3$-phenyl |
| 91 | 1 | 3,4-di-$CH_3$-phenyl |
| 92 | 2 | 3,4-di-$CH_3$-phenyl |
| 93 | 3 | 3,4-di-$CH_3$-phenyl |
| 94 | 1 | 3,5-di-$CH_3$-phenyl |
| 95 | 2 | 3,5-di-$CH_3$-phenyl |
| 96 | 3 | 3,5-di-$CH_3$-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-$CH_3$-phenyl |
| 116 | 2 | 2-morpholino-4-$CH_3$-phenyl |
| 117 | 3 | 2-morpholino-4-$CH_3$-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XVI) or a pharmaceutically acceptable salt form thereof:

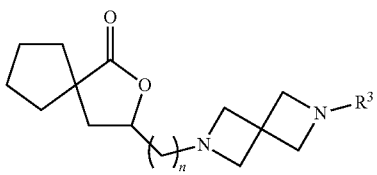

(XVI)

wherein non-limiting examples of R³ and n are defined herein below in Table 19.

TABLE 19

| Entry | n | R² |
|---|---|---|
| 1 | 1 | 2-CF₃-Phenyl |
| 2 | 2 | 2-CF₃-Phenyl |
| 3 | 3 | 2-CF₃-Phenyl |
| 4 | 1 | 3-CF₃-Phenyl |
| 5 | 2 | 3-CF₃-Phenyl |
| 6 | 3 | 3-CF₃-Phenyl |
| 7 | 1 | 4-CF₃-Phenyl |
| 8 | 2 | 4-CF₃-Phenyl |
| 9 | 3 | 4-CF₃-Phenyl |
| 10 | 1 | 2-NH₂-Phenyl |
| 11 | 2 | 2-NH₂-Phenyl |
| 12 | 3 | 2-NH₂-Phenyl |
| 13 | 1 | 3-NH₂-Phenyl |
| 14 | 2 | 3-NH₂-Phenyl |
| 15 | 3 | 3-NH₂-Phenyl |
| 16 | 1 | 4-NH₂-Phenyl |
| 17 | 2 | 4-NH₂-Phenyl |
| 18 | 3 | 4-NH₂-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-NO₂-Phenyl |
| 29 | 2 | 2-NO₂-Phenyl |
| 30 | 3 | 2-NO₂-Phenyl |
| 31 | 1 | 3-NO₂-Phenyl |
| 32 | 2 | 3-NO₂-Phenyl |
| 33 | 3 | 3-NO₂-Phenyl |
| 34 | 1 | 4-NO₂-Phenyl |
| 35 | 2 | 4-NO₂-Phenyl |
| 36 | 3 | 4-NO₂-Phenyl |
| 37 | 1 | 2-SCH₃-Phenyl |
| 38 | 2 | 2-SCH₃-Phenyl |
| 39 | 3 | 2-SCH₃-Phenyl |
| 40 | 1 | 3-SCH₃-Phenyl |
| 41 | 2 | 3-SCH₃-Phenyl |
| 42 | 3 | 3-SCH₃-Phenyl |
| 43 | 1 | 4-SCH₃-Phenyl |
| 44 | 2 | 4-SCH₃-Phenyl |
| 45 | 3 | 4-SCH₃-Phenyl |
| 46 | 1 | 2-SO₂CH₃-Phenyl |
| 47 | 2 | 2-SO₂CH₃-Phenyl |
| 48 | 3 | 2-SO₂CH₃-Phenyl |
| 49 | 1 | 3-SO₂CH₃-Phenyl |
| 50 | 2 | 3-SO₂CH₃-Phenyl |
| 51 | 3 | 3-SO₂CH₃-Phenyl |
| 52 | 1 | 4-SO₂CH₃-Phenyl |
| 53 | 2 | 4-SO₂CH₃-Phenyl |
| 54 | 3 | 4-SO₂CH₃-Phenyl |
| 55 | 1 | 2-SO₂NH₂-Phenyl |
| 56 | 2 | 2-SO₂NH₂-Phenyl |
| 57 | 3 | 2-SO₂NH₂-Phenyl |
| 58 | 1 | 3-SO₂NH₂-Phenyl |
| 59 | 2 | 3-SO₂NH₂-Phenyl |
| 60 | 3 | 3-SO₂NH₂-Phenyl |
| 61 | 1 | 4-SO₂NH₂-Phenyl |
| 62 | 2 | 4-SO₂NH₂-Phenyl |
| 63 | 3 | 4-SO₂NH₂-Phenyl |
| 64 | 1 | 2-CONH₂-Phenyl |
| 65 | 2 | 2-CONH₂-Phenyl |
| 66 | 3 | 2-CONH₂-Phenyl |
| 67 | 1 | 3-CONH₂-Phenyl |
| 68 | 2 | 3-CONH₂-Phenyl |
| 69 | 3 | 3-CONH₂-Phenyl |
| 70 | 1 | 4-CONH₂-Phenyl |
| 71 | 2 | 4-CONH₂-Phenyl |
| 72 | 3 | 4-CONH₂-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-CH₃-phenyl |
| 80 | 2 | 2,3-di-CH₃-phenyl |
| 81 | 3 | 2,3-di-CH₃-phenyl |
| 82 | 1 | 2,4-di-CH₃-phenyl |
| 83 | 2 | 2,4-di-CH₃-phenyl |
| 84 | 3 | 2,4-di-CH₃-phenyl |
| 85 | 1 | 2,5-di-CH₃-phenyl |
| 86 | 2 | 2,5-di-CH₃-phenyl |
| 87 | 3 | 2,5-di-CH₃-phenyl |
| 88 | 1 | 2,6-di-CH₃-phenyl |
| 89 | 2 | 2,6-di-CH₃-phenyl |
| 90 | 3 | 2,6-di-CH₃-phenyl |
| 91 | 1 | 3,4-di-CH₃-phenyl |
| 92 | 2 | 3,4-di-CH₃-phenyl |
| 93 | 3 | 3,4-di-CH₃-phenyl |
| 94 | 1 | 3,5-di-CH₃-phenyl |
| 95 | 2 | 3,5-di-CH₃-phenyl |
| 96 | 3 | 3,5-di-CH₃-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-CH₃-phenyl |
| 116 | 2 | 2-morpholino-4-CH₃-phenyl |
| 117 | 3 | 2-morpholino-4-CH₃-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

Exemplary embodiments include compounds having the formula (XVII) or a pharmaceutically acceptable salt form thereof:

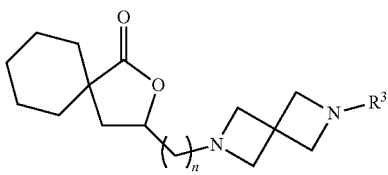

(XVII)

wherein non-limiting examples of $R^3$ and n are defined herein below in Table 20.

TABLE 20

| Entry | n | $R^2$ |
|---|---|---|
| 1 | 1 | 2-$CF_3$-Phenyl |
| 2 | 2 | 2-$CF_3$-Phenyl |
| 3 | 3 | 2-$CF_3$-Phenyl |
| 4 | 1 | 3-$CF_3$-Phenyl |
| 5 | 2 | 3-$CF_3$-Phenyl |
| 6 | 3 | 3-$CF_3$-Phenyl |
| 7 | 1 | 4-$CF_3$-Phenyl |
| 8 | 2 | 4-$CF_3$-Phenyl |
| 9 | 3 | 4-$CF_3$-Phenyl |
| 10 | 1 | 2-$NH_2$-Phenyl |
| 11 | 2 | 2-$NH_2$-Phenyl |
| 12 | 3 | 2-$NH_2$-Phenyl |
| 13 | 1 | 3-$NH_2$-Phenyl |
| 14 | 2 | 3-$NH_2$-Phenyl |
| 15 | 3 | 3-$NH_2$-Phenyl |
| 16 | 1 | 4-$NH_2$-Phenyl |
| 17 | 2 | 4-$NH_2$-Phenyl |
| 18 | 3 | 4-$NH_2$-Phenyl |
| 19 | 1 | 2-tBu-Phenyl |
| 20 | 2 | 2-tBu-Phenyl |
| 21 | 3 | 2-tBu-Phenyl |
| 22 | 1 | 3-tBu-Phenyl |
| 23 | 2 | 3-tBu-Phenyl |
| 24 | 3 | 3-tBu-Phenyl |
| 25 | 1 | 4-tBu-Phenyl |
| 26 | 2 | 4-tBu-Phenyl |
| 27 | 3 | 4-tBu-Phenyl |
| 28 | 1 | 2-$NO_2$-Phenyl |
| 29 | 2 | 2-$NO_2$-Phenyl |
| 30 | 3 | 2-$NO_2$-Phenyl |
| 31 | 1 | 3-$NO_2$-Phenyl |
| 32 | 2 | 3-$NO_2$-Phenyl |
| 33 | 3 | 3-$NO_2$-Phenyl |
| 34 | 1 | 4-$NO_2$-Phenyl |
| 35 | 2 | 4-$NO_2$-Phenyl |
| 36 | 3 | 4-$NO_2$-Phenyl |
| 37 | 1 | 2-$SCH_3$-Phenyl |
| 38 | 2 | 2-$SCH_3$-Phenyl |
| 39 | 3 | 2-$SCH_3$-Phenyl |
| 40 | 1 | 3-$SCH_3$-Phenyl |
| 41 | 2 | 3-$SCH_3$-Phenyl |
| 42 | 3 | 3-$SCH_3$-Phenyl |
| 43 | 1 | 4-$SCH_3$-Phenyl |
| 44 | 2 | 4-$SCH_3$-Phenyl |
| 45 | 3 | 4-$SCH_3$-Phenyl |
| 46 | 1 | 2-$SO_2CH_3$-Phenyl |
| 47 | 2 | 2-$SO_2CH_3$-Phenyl |
| 48 | 3 | 2-$SO_2CH_3$-Phenyl |
| 49 | 1 | 3-$SO_2CH_3$-Phenyl |
| 50 | 2 | 3-$SO_2CH_3$-Phenyl |
| 51 | 3 | 3-$SO_2CH_3$-Phenyl |
| 52 | 1 | 4-$SO_2CH_3$-Phenyl |
| 53 | 2 | 4-$SO_2CH_3$-Phenyl |
| 54 | 3 | 4-$SO_2CH_3$-Phenyl |
| 55 | 1 | 2-$SO_2NH_2$-Phenyl |
| 56 | 2 | 2-$SO_2NH_2$-Phenyl |
| 57 | 3 | 2-$SO_2NH_2$-Phenyl |
| 58 | 1 | 3-$SO_2NH_2$-Phenyl |
| 59 | 2 | 3-$SO_2NH_2$-Phenyl |
| 60 | 3 | 3-$SO_2NH_2$-Phenyl |
| 61 | 1 | 4-$SO_2NH_2$-Phenyl |
| 62 | 2 | 4-$SO_2NH_2$-Phenyl |
| 63 | 3 | 4-$SO_2NH_2$-Phenyl |
| 64 | 1 | 2-$CONH_2$-Phenyl |
| 65 | 2 | 2-$CONH_2$-Phenyl |
| 66 | 3 | 2-$CONH_2$-Phenyl |
| 67 | 1 | 3-$CONH_2$-Phenyl |
| 68 | 2 | 3-$CONH_2$-Phenyl |
| 69 | 3 | 3-$CONH_2$-Phenyl |
| 70 | 1 | 4-$CONH_2$-Phenyl |
| 71 | 2 | 4-$CONH_2$-Phenyl |
| 72 | 3 | 4-$CONH_2$-Phenyl |
| 73 | 1 | 2-Br-Phenyl |
| 74 | 2 | 2-Br-Phenyl |
| 75 | 3 | 2-Br-Phenyl |
| 76 | 1 | 3-Br-Phenyl |
| 77 | 2 | 3-Br-Phenyl |
| 78 | 3 | 3-Br-Phenyl |
| 79 | 1 | 2,3-di-$CH_3$-phenyl |
| 80 | 2 | 2,3-di-$CH_3$-phenyl |
| 81 | 3 | 2,3-di-$CH_3$-phenyl |
| 82 | 1 | 2,4-di-$CH_3$-phenyl |
| 83 | 2 | 2,4-di-$CH_3$-phenyl |
| 84 | 3 | 2,4-di-$CH_3$-phenyl |
| 85 | 1 | 2,5-di-$CH_3$-phenyl |
| 86 | 2 | 2,5-di-$CH_3$-phenyl |
| 87 | 3 | 2,5-di-$CH_3$-phenyl |
| 88 | 1 | 2,6-di-$CH_3$-phenyl |
| 89 | 2 | 2,6-di-$CH_3$-phenyl |
| 90 | 3 | 2,6-di-$CH_3$-phenyl |
| 91 | 1 | 3,4-di-$CH_3$-phenyl |
| 92 | 2 | 3,4-di-$CH_3$-phenyl |
| 93 | 3 | 3,4-di-$CH_3$-phenyl |
| 94 | 1 | 3,5-di-$CH_3$-phenyl |
| 95 | 2 | 3,5-di-$CH_3$-phenyl |
| 96 | 3 | 3,5-di-$CH_3$-phenyl |
| 97 | 1 | 2,3-di-Cl-phenyl |
| 98 | 2 | 2,3-di-Cl-phenyl |
| 99 | 3 | 2,3-di-Cl-phenyl |
| 100 | 1 | 2,4-di-Cl-phenyl |
| 101 | 2 | 2,4-di-Cl-phenyl |
| 102 | 3 | 2,4-di-Cl-phenyl |
| 103 | 1 | 2,5-di-Cl-phenyl |
| 104 | 2 | 2,5-di-Cl-phenyl |
| 105 | 3 | 2,5-di-Cl-phenyl |
| 106 | 1 | 2,6-di-Cl-phenyl |
| 107 | 2 | 2,6-di-Cl-phenyl |
| 108 | 3 | 2,6-di-Cl-phenyl |
| 109 | 1 | 3,4-di-Cl-phenyl |
| 110 | 2 | 3,4-di-Cl-phenyl |
| 111 | 3 | 3,4-di-Cl-phenyl |
| 112 | 1 | 3,5-di-Cl-phenyl |
| 113 | 2 | 3,5-di-Cl-phenyl |
| 114 | 3 | 3,5-di-Cl-phenyl |
| 115 | 1 | 2-morpholino-4-$CH_3$-phenyl |
| 116 | 2 | 2-morpholino-4-$CH_3$-phenyl |
| 117 | 3 | 2-morpholino-4-$CH_3$-phenyl |
| 118 | 1 | 2-morpholino-4-CN-phenyl |
| 119 | 2 | 2-morpholino-4-CN-phenyl |
| 120 | 3 | 2-morpholino-4-CN-phenyl |
| 121 | 1 | 2-morpholino-4-OH-phenyl |
| 122 | 2 | 2-morpholino-4-OH-phenyl |
| 123 | 3 | 2-morpholino-4-OH-phenyl |
| 124 | 1 | 2,3-dimethylpyridin-4-yl |
| 125 | 2 | 2,3-dimethylpyridin-4-yl |
| 126 | 3 | 2,3-dimethylpyridin-4-yl |
| 127 | 1 | 3,6-dimethylpyridin-4-yl |
| 128 | 2 | 3,6-dimethylpyridin-4-yl |
| 129 | 3 | 3,6-dimethylpyridin-4-yl |

For the purposes of demonstrating the manner in which the compounds of the present invention are named and referred to herein, the compound having the formula:

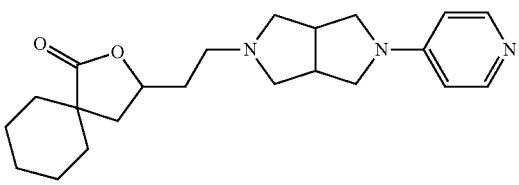

has the chemical name 3-(2-(5-(pyridin-4-yl)hexahydropyrrolo[3,4-c]pyrrol-2(1H)-yl)ethyl)-2-oxaspiro[4.5]decan-1-one.

For the purposes of demonstrating the manner in which the compounds of the present invention are named and referred to herein, the compound having the formula:

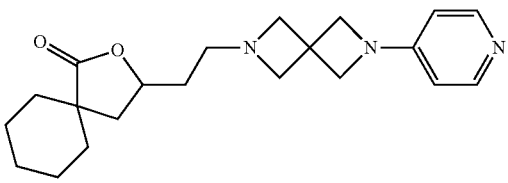 [SMILES: O=C1OC(CCN2CC3(C2)CN(c2ccncc2)C3)CC12CCCCC2]

has the chemical name 3-(2-(6-(pyridin-4-yl)-2,6-diazaspiro[3.3]heptan-2-yl)ethyl)-2-oxaspiro[4.5]decan-1-one.

For the purposes of the present invention, a compound depicted by the racemic formula, for example:

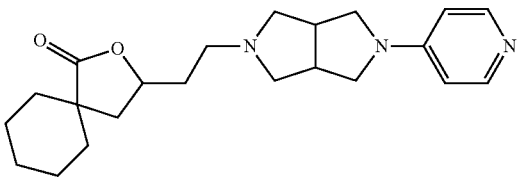 [SMILES: O=C1OC(CCN2CC3CN(c4ccncc4)CC3C2)CC12CCCCC2]

will stand equally well for either of the two enantiomers having the formula:

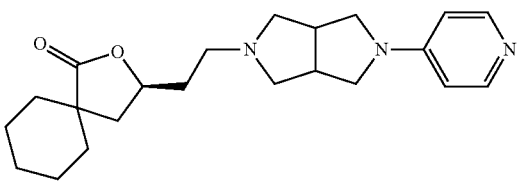 [SMILES: O=C1O[C@@H](CCN2CC3CN(c4ccncc4)CC3C2)CC12CCCCC2]

or the formula:

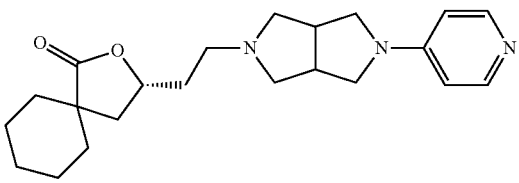 [SMILES: O=C1O[C@H](CCN2CC3CN(c4ccncc4)CC3C2)CC12CCCCC2]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the sigma-2 receptor binders and sigma-2 receptor activity modulators of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of the disclosure may be prepared according to any of the process outlined in Schemes 1-8.

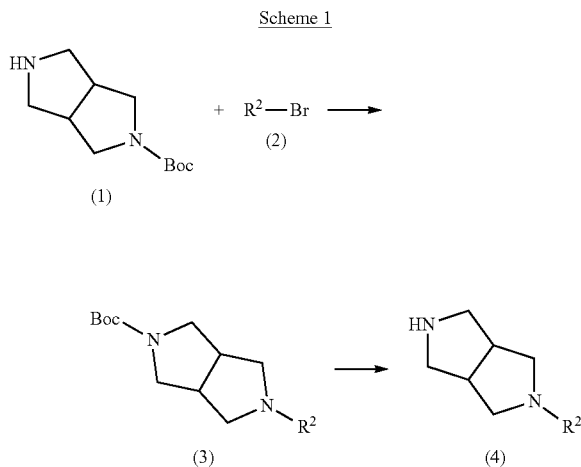

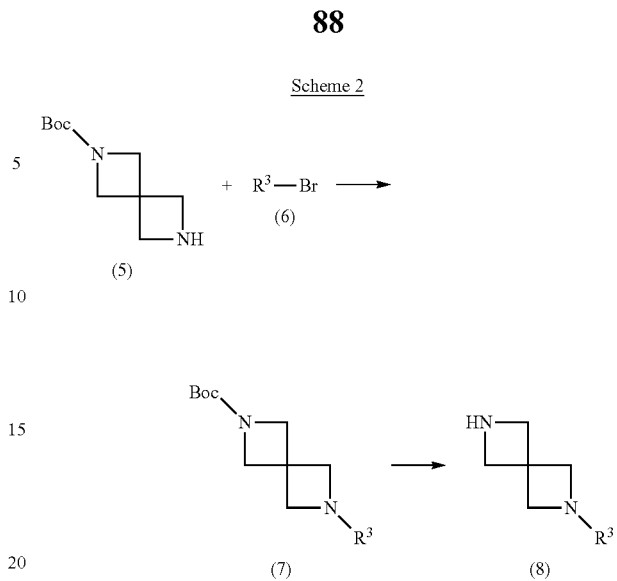

Accordingly, a suitably substituted compound (1) a known compound or compound prepared by known methods, is reacted with a compound of the formula (2), a known compound or a compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, Tris(dibenzylideneacetone)dipalladium(0), and the like, in the presence of a base such as potassium t-butoxide, sodium t-butoxide, lithium t-butoxide, potassium carbonate, sodium carbonate, lithium carbonate, cesium carbonate, sodium hydroxide, lithium hydroxide, potassium hydroxide, and the like, optionally in the presence of an organic base such as triethylamine, diisopropylethyl amine, pyridine, and the like, optionally in the presence of a bis(diphenylphosphino) derived compound such as 2,2'-bis(diphenylphosphino)-1,1'-binaphthalene, 2,2'-bis(di-p-tolylphosphino)-1,1'-binaphthyl, 1,1'-binaphthalene-2,2'-diyl)bis[bis(3,5-dimethylphenyl)phosphine], 5,5'-bis[di(3,5-xylyl) phosphino]-4,4'-bi-1,3-benzodioxole, 5,5'-bis[di(3,5-di-tert-butyl-4-methoxyphenyl) phosphino]-4,4'-bi-1,3-benzodioxole, and the like, in a solvent such as toluene, benzene, xylene, 1,4-dioxane, tetrahydrofuran, methylene chloride, 1,2-dichloroethane, N,N-dimethylformamide, N,N-dimethylacetamide, and the like, optionally with heating, optionally with microwave irradiation to provide a compound of the formula (3). A compound of the formula (3) is reacted with an acid such as trifluoroacetic acid, hydrochloric acid, sulfuric acid, and the like, optionally in the presence of an organic solvent such as methylene chloride, dichloroethane, 1,4-dioxane, tetrahydrofuran, methanol, ethanol, and the like, to provide a compound of the formula (4).

A suitably substituted compound (5) a known compound or compound prepared by known methods, is reacted with a compound of the formula (6), a known compound or a compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis(diphenylphosphino) ferrocene]dichloropalladium, Tris(dibenzylideneacetone)dipalladium(0), and the like, in the presence of a base such as potassium t-butoxide, sodium t-butoxide, lithium t-butoxide, potassium carbonate, sodium carbonate, lithium carbonate, cesium carbonate, sodium hydroxide, lithium hydroxide, potassium hydroxide, and the like, optionally in the presence of an organic base such as triethylamine, diisopropylethyl amine, pyridine, and the like, optionally in the presence of a bis(diphenylphosphino) derived compound such as 2,2'-bis(diphenylphosphino)-1, 1'-binaphthalene, 2,2'-bis(di-p-tolylphosphino)-1,1'-binaphthyl, 1,1'-binaphthalene-2,2'-diyl)bis[bis(3,5-dimethylphenyl)phosphine], 5,5'-bis[di(3,5-xylyl) phosphino]-4,4'-bi-1, 3-benzodioxole, 5,5'-bis[di(3,5-di-tert-butyl-4-methoxy phenyl)phosphino]-4,4'-bi-1,3-benzodioxole, and the like, in a solvent such as toluene, benzene, xylene, 1,4-dioxane, tetrahydrofuran, methylene chloride, 1,2-dichloroethane, N,N-dimethylformamide, N,N-dimethylacetamide, and the like, optionally with heating, optionally with microwave irradiation to provide a compound of the formula (7). A compound of the formula (7) is reacted with an acid such as trifluoroacetic acid, hydrochloric acid, sulfuric acid, and the like, optionally in the presence of an organic solvent such as methylene chloride, dichloroethane, 1,4-dioxane, tetrahydrofuran, methanol, ethanol, and the like, to provide a compound of the formula (8).

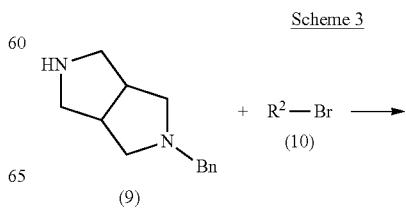

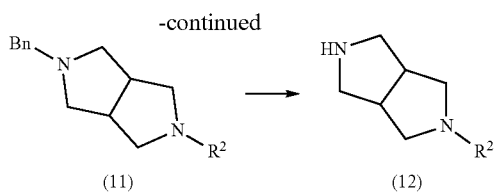

A suitably substituted compound (9) a known compound or compound prepared by known methods, is reacted with a compound of the formula (10), a known compound or a compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, Tris (dibenzylideneacetone)dipalladium(0), and the like, in the presence of a base such as potassium t-butoxide, sodium t-butoxide, lithium t-butoxide, potassium carbonate, sodium carbonate, lithium carbonate, cesium carbonate, sodium hydroxide, lithium hydroxide, potassium hydroxide, and the like, optionally in the presence of an organic base such as triethylamine, diisopropylethyl amine, pyridine, and the like, optionally in the presence of a bis(diphenylphosphino) derived compound such as 2,2'-bis(diphenylphosphino)-1, 1'-binaphthalene, 2,2'-bis(di-p-tolylphosphino)-1,1'-binaphthyl, 1,1'-binaphthalene-2,2'-diyl)bis[bis(3,5-dimethylphenyl)phosphine], 5,5'-bis[di(3,5-xylyl) phosphino]-4,4'-bi-1, 3-benzodioxole, 5,5'-bis[di(3,5-di-tert-butyl-4-methoxyphenyl)phosphino]-4,4'-bi-1,3-benzodioxole, and the like, in a solvent such as toluene, benzene, xylene, 1,4-dioxane, tetrahydrofuran, methylene chloride, 1,2-dichloroethane, N,N-dimethylformamide, N,N-dimethylacetamide, and the like, optionally with heating, optionally with microwave irradiation to provide a compound of the formula (11). A compound of the formula (11) is reacted with hydrogen in the presence of a palladium catalyst such as palladium on carbon, palladium on celite, palladium on barium sulfate, palladium acetate, palladium bis(triphenylphosphine) dichloride, palladium tetrakis(triphenylphospine), and the like, in a solvent such as methanol, ethanol, isopropanol, ethyl acetate, tetrahydrofuran, 1,4-dioxane, and the like to provide a compound of the formula (12).

Scheme 4

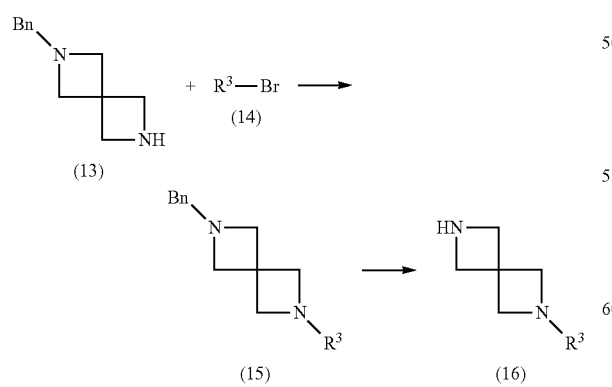

A suitably substituted compound (13) a known compound or compound prepared by known methods, is reacted with a compound of the formula (14), a known compound or a compound prepared by known methods, in the presence of a palladium catalyst such as palladium acetate, palladium bis(triphenylphosphine) dichloride, palladium tetrakis(triphenylphospine), bis(acetonitrile) dichloropalladium [1,1'-Bis (diphenylphosphino) ferrocene]dichloropalladium, Tris (dibenzylideneacetone)dipalladium(0), and the like, in the presence of a base such as potassium t-butoxide, sodium t-butoxide, lithium t-butoxide, potassium carbonate, sodium carbonate, lithium carbonate, cesium carbonate, sodium hydroxide, lithium hydroxide, potassium hydroxide, and the like, optionally in the presence of an organic base such as triethylamine, diisopropylethyl amine, pyridine, and the like, optionally in the presence of a bis(diphenylphosphino) derived compound such as 2,2'-bis(diphenylphosphino)-1, 1'-binaphthalene, 2,2'-bis(di-p-tolylphosphino)-1,1'-binaphthyl, 1,1'-binaphthalene-2,2'-diyl)bis[bis(3,5-dimethylphenyl)phosphine], 5,5'-bis[di(3,5-xylyl) phosphino]-4,4'-bi-1, 3-benzodioxole, 5,5'-bis[di(3,5-di-tert-butyl-4-methoxy phenyl)phosphino]-4,4'-bi-1,3-benzodioxole, and the like, in a solvent such as toluene, benzene, xylene, 1,4-dioxane, tetrahydrofuran, methylene chloride, 1,2-dichloroethane, N,N-dimethylformamide, N,N-dimethylacetamide, and the like, optionally with heating, optionally with microwave irradiation to provide a compound of the formula (15). A compound of the formula (15) is reacted with hydrogen in the presence of a palladium catalyst such as palladium on carbon, palladium on celite, palladium on barium sulfate, palladium acetate, palladium bis(triphenylphosphine) dichloride, palladium tetrakis(triphenylphospine), and the like, in a solvent such as methanol, ethanol, isopropanol, ethyl acetate, tetrahydrofuran, 1,4-dioxane, and the like to provide a compound of the formula (16).

Scheme 5

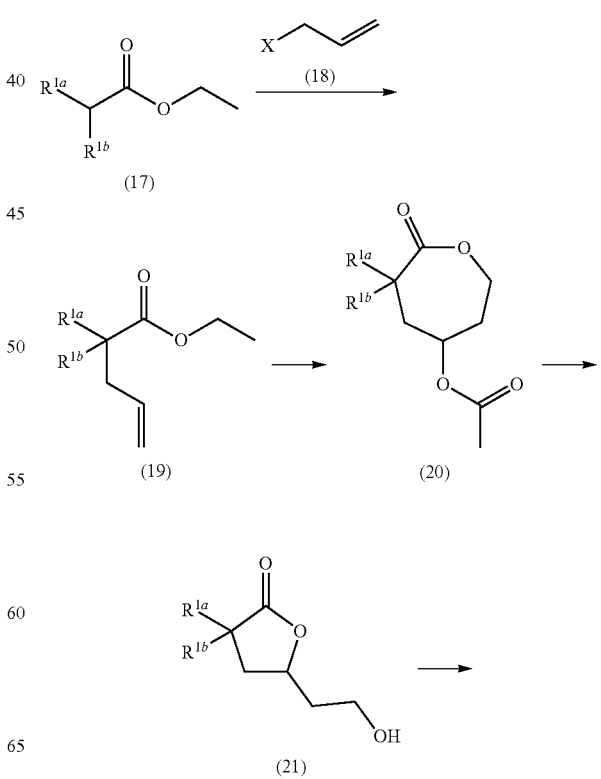

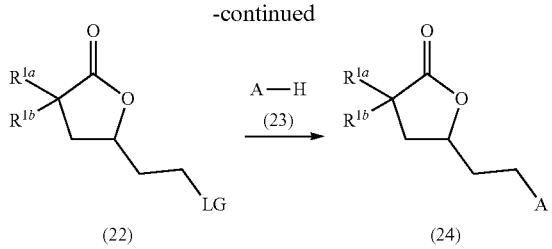

A suitably substituted compound of formula (17), a known compound or compound prepared by known methods, is reacted with a compound of the formula (18), wherein X is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, and the like in an organic solvent such as tetrahydrofuran, 1,4-dioxane, 1,2-dimethoxyethane, dimethylformamide, dimethylacetamide, and the like, to provide a compound of the formula (19). A compound of the formula (19) is then treated with paraformaldehyde in the presence of an acid such as sulfuric acid, hydrochloric acid, and the like, in an the presence of acetic acid, and optionally in an organic solvent such as methanol, ethanol, tetrahydrofuran, 1,4-dioxane, 1,2-dimethoxyethane, dimethylformamide, dimethylacetamide, and the like, optionally with heating, optionally with microwave irradiation to provide a compound of the formula (20). A compound of the formula (20) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, to provide a compound of the formula (21). A compound of the formula (21) is then converted to a compound of the formula (22), wherein LG is a leaving group such as mesylate, tosylate, nosylate, bromide, and the like, using methods that are known to one skilled in the art. Thus, a compound of the formula (21) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N,N-dimethylformamide, tetrahydrofuran, 1,4-dioxane and the like to provide a compound of the formula (22). Alternatively, a compound of the formula (21) is reacted with carbon tetrabromide in the presence of triphenylphosphine in a solvent such as methylene chloride, dichloroethane, tetrahydrofuran, 1,4-dioxane, N,N-dimethylformamide, tetrahydrofuran, 1,4-dioxane and the like, optionally with heating, optionally with microwave irradiation, to provide a compound of the formula (22). A compound of the formula (22) is reacted with a compound of the formula (23), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (24).

Scheme 6

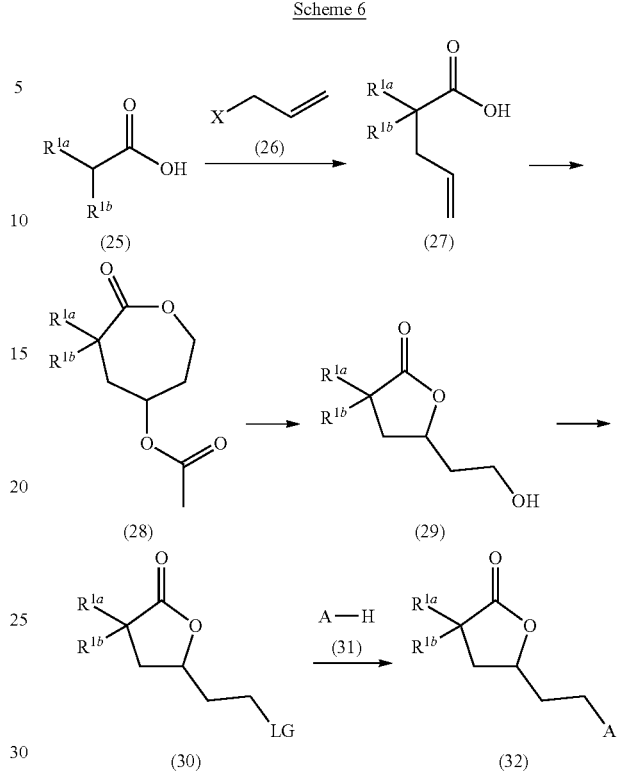

A suitably substituted compound of formula (25), a known compound or compound prepared by known methods, is reacted with a compound of the formula (26), wherein X is a leaving group such as chlorine, bromine, iodine, mesylate, tosylate, and the like, in the presence of a base such as lithium diisopropylamide, sodium diisopropylamide, potassium diisopropylamide, lithium bis(trimethylsilyl)amide, sodium bis(trimethylsilyl)amide, potassium bis(trimethylsilyl)amide, sodium hydride, n-butyl lithium, sec-butyl lithium, tert-butyl lithium, and the like in an organic solvent such as tetrahydrofuran, 1,4-dioxane, 1,2-dimethoxyethane, dimethylformamide, dimethylacetamide, and the like, to provide a compound of the formula (27). A compound of the formula (27) is then treated with paraformaldehyde in the presence of an acid such as sulfuric acid, hydrochloric acid, and the like, in the presence of acetic acid, and optionally in an organic solvent such as methanol, ethanol, tetrahydrofuran, 1,4-dioxane, 1,2-dimethoxyethane, dimethylformamide, dimethylacetamide, and the like, optionally with heating, optionally with microwave irradiation to provide a compound of the formula (28). A compound of the formula (28) is then treated with a base such as sodium hydroxide, potassium hydroxide, lithium hydroxide, and the like, in an solvent such as water, methanol, ethanol, isopropanol, and the like, optionally with heating, and then treated with an acid such as sulfuric acid, hydrochloric acid, and the like, in a solvent such as water, methanol, ethanol, isopropanol, and the like, optionally with heating, to provide a compound of the formula (29). A compound of the formula (29) is then converted to a compound of the formula (30), wherein LG is a leaving group such as mesylate, tosylate, nosylate, bromide, and the like, using methods that are known to one skilled in the art. Thus, a compound of the formula (29) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N,N-dimethylformamide, tetrahydrofuran, 1,4-dioxane and the like to provide a compound of the formula (30). Alternatively, a compound of the formula (29) is reacted with carbon tetrabromide in the presence of triphenylphosphine in a solvent such as methylene chloride, dichloroethane, tetrahydrofuran, 1,4-dioxane, N,N-dimethylformamide, tetrahydrofuran, 1,4-dioxane and the like, optionally with heating, optionally with microwave irradiation, to provide a compound of the formula (30). A compound of the formula (30) is reacted with a compound of the formula (31), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (32).

Compounds of formula (37) may be prepared according to the process outlined in Scheme 7.

Scheme 7

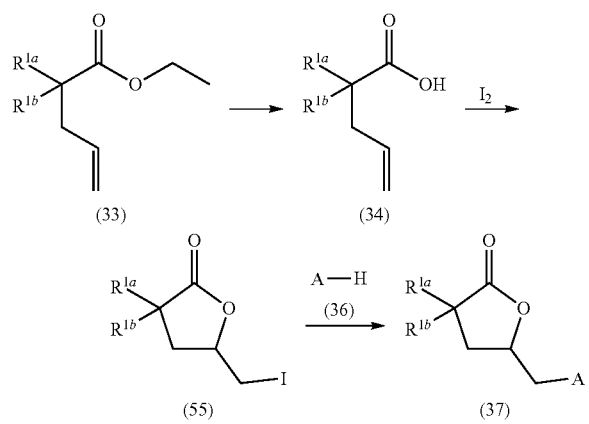

A compound of the formula (33) is reacted with a base such as sodium hydroxide, potassium hydroxide, lithium hydroxide, sodium carbonate, potassium carbonate, lithium carbonate and the like, in the presence of a solvent such as methanol, ethanol, isopropanol, water, and the like, optionally with heating, optionally with microwave irradiation to provide a compound of the formula (34). A compound of the formula (34) is then reacted with iodine in the presence of a base such as sodium bicarbonate, potassium bicarbonate, lithium bicarbonate, sodium carbonate, potassium carbonate, lithium bicarbonate, sodium hydroxide, potassium hydroxide, lithium hydroxide, and the like, in the presence of a solvent such as tetrahydrofuran, ethyl ether, 1,4-dioxane, and the like to provide a compound of the formula (35). A compound of the formula (35) is reacted with a compound of the formula (36), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (37).

Compounds of formula (46) may be prepared according to the process outlined in Scheme 8.

Scheme 8

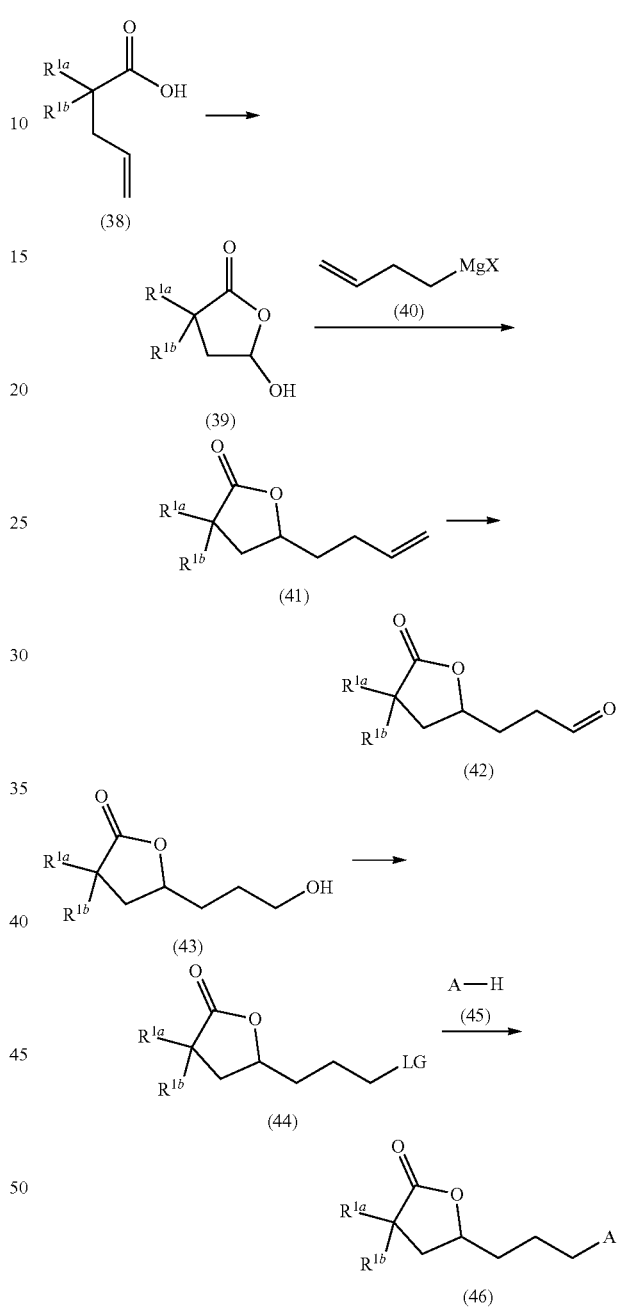

A compound of the formula (38) is reacted with ruthenium chloride in the presence of sodium periodate in a solvent such as acetonitrile, methanol, ethanol, isopropanol, and the like, to provide a compound of the formula (39). A compound of the formula (39) is reacted with a compound of the formula (40), a known compound or compound prepared by known methods, wherein x is a halogen, in the presence of a solvent such as ethyl ether, tetrahydrofuran, 1,4-dioxane and the like to provide a compound of the formula (41). A compound of the formula (41) is reacted with ruthenium chloride in the presence of sodium periodate in a solvent such as acetonitrile, methanol, ethanol, isopropanol, and the like, to provide a compound of the formula (42). A compound of the formula (42) is reacted with a reducing agent such as lithium borohydride, sodium borohydride, sodium cyanoborohydride and the like, in a solvent such as methanol, ethanol, isopropanol, acetonitrile, and the like to provide a compound of the formula (42). A compound of the formula (43) is then converted to a compound of the formula (44), wherein LG is a leaving group such as mesylate, tosylate, nosylate, bromide, and the like, using methods that are known to one skilled in the art. Thus, a compound of the formula (43) is treated with a sulfonyl chloride such as methanesulfonyl chloride, toluenesulfonyl chloride p-nitrophenyl sulfonyl chloride, and the like, in the presence of a base such as triethylamine, diisopropyl amine, pyridine, 2,6-lutidine, and the like, in an organic solvent such as methylene chloride, dichloroethane, tetrahydrofuran, 1,4-dioxane, N,N-dimethylformamide, tetrahydrofuran, 1,4-dioxane and the like to provide a compound of the formula (44). Alternatively, a compound of the formula (43) is reacted with carbon tetrabromide in the presence of triphenylphosphine in a solvent such as methylene chloride, dichloroethane, tetrahydrofuran, 1,4-dioxane, N,N-dimethylformamide, tetrahydrofuran, 1,4-dioxane and the like, optionally with heating, optionally with microwave irradiation, to provide a compound of the formula (44). A compound of the formula (44) is reacted with a compound of the formula (45), a known compound or compound prepared by known methods, in an organic solvent such as tetrahydrofuran, 1,4-dioxane, 1,2-dimethoxyethane, dimethylformamide, dimethylacetamide, and the like, optionally in the presence of a base such as triethylamine, diisopropylethylamine, pyridine, 2,6 lutidine, and the like, optionally with heating, optionally with microwave irradiation to provide a compound of the formula (46).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

EXAMPLES

The practice of the invention is illustrated by the following non-limiting examples. The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

In the examples that follow, $^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 m) with a 2996 diode array detector from 210-400 nm.

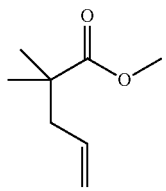

Example 1: Preparation of methyl 2,2-dimethylpent-4-enoate: This reaction was performed in oven-dried glassware under a nitrogen atmosphere. To a well-stirred solution of freshly prepared lithium diisopropylamide (1M, 1.10 equiv) in dry 35 ml tetrahydrofuran, isobutyric acid methyl ester (3.32 g, 32.6 mmol, 1.0 equiv) was added dropwise during 0.5 hours at −78° C. The mixture was allowed to stir at this temperature for 30 min followed by the addition of allyl bromide (5.35 g, 44.0 mmol) and Hexamethylphosphoramide (HMPA) (2.91 g, 16.3 mmol) dropwise over 0.5 h. The reaction mixture was stirred overnight at room temperature, quenched with 10% HCl (while cooling in ice bath) until acidic (pH=2). The organic layer was separated and the aqueous layer was extracted with hexanes (3×100 mL). The extract was washed with 10% NaHCO$_3$ (200 mL) and brine (200 mL). The solution was then dried over MgSO$_4$, concentrated in vacuo and distilled to give pure product. $^1$H NMR (400 MHz, CDCl$_3$) δ 5.73 (dd, J=9.4, 17.7, 1H), 5.04 (dd, J=1.9, 13.5, 2H), 4.12 (q, J=7.1, 2H), 2.28 (d, J=7.4, 2H), 1.25 (t, J=7.1, 3H), 1.17 (s, 6H); $^{13}$C NMR (101 MHz, CDCl$_3$) δ 177.42, 134.42, 117.88, 77.68, 77.36, 77.04, 60.35, 44.91, 42.25, 24.92, 14.35

The following compounds can be prepared by the procedure of methyl 2,2-dimethylpent-4-enoate. The skilled practitioner will know how to substitute the appropriate reagents, starting materials and purification methods known to those skilled in the art, in order to prepare the compounds provided herein.

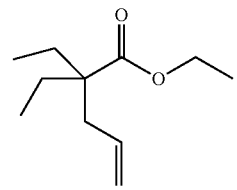

Example 2: Preparation of Ethyl 2,2-diethylpent-4-enoate: The title compound was prepared according to the procedure for methyl 2,2-dimethylpent-4-enoate, except 2-ethyl-butyric acid ethyl ester was substituted for isobutyric acid methyl ester $^1$H NMR (300 MHz, CDCl$_3$) δ 5.68 (dd, J=9.9, 17.2, 1H), 5.16-4.97 (m, 2H), 4.14 (q, J=7.1, 2H), 2.33 (d, J=7.4, 2H), 1.59 (dt, J=6.5, 7.5, 5H), 1.26 (t, J=7.1, 3H), 0.80 (t, J=7.5, 6H)

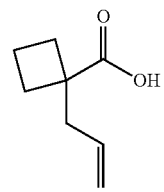

Example 3: Preparation of 1-allylcyclobutanecarboxylic acid: This reaction was performed in oven-dried glassware under a nitrogen atmosphere. To a well-stirred solution of freshly prepared lithium diisopropylamide (1M, 10.76 mmol, 2.30 equiv) in dry 107 ml tetrahydrofuran, cyclobutanecarboxylic acid (4.68 g, 46.8 mmol, 1.0 equiv) was added dropwise during 0.5 hours at 0° C. The mixture was heated to 50° C. for 6 hours, then cooled to 0° C. followed by the addition of NaI (0.697 g, 4.68 mmol, 0.1 equiv) in one portion and a mixture of allyl bromide (7.58 g, 63.2 mmol, 1.35 equiv) and HMPA (4.18 g, 23.4 mmol, 0.5 equiv) dropwise over 0.5 hr. The reaction mixture was stirred overnight at room temperature, quenched with 10% HCl (while cooling in ice bath) until acidic (pH=2). The organic layer was separated and the aqueous layer was extracted with ether (3×250 mL). The organic phases were combined and washed with brine. The solution was then dried over $MgSO_4$ and concentrated in vacuo to afford a crude oil which was purified through flash chromatography (silica; ethyl acetate/hexanes, 1%~10%). $^1$H NMR (400 MHz, $CDCl_3$) δ 5.77 (ddt, J=7.1, 10.2, 17.2, 1H), 5.17-4.99 (m, 2H), 2.59-2.38 (m, 4H), 2.07-1.84 (m, 4H). $^{13}$C NMR (101 MHz, $CDCl_3$) δ 184.04, 133.90, 118.19, 47.20, 41.74, 29.57, 15.65; Rf, 0.43 (Hexane:Ethyl Acetate 10:1); HRMS (CI): [M+H], calcd for $C_3H_{13}O_2$, 141.0916; found 141.0911.

The following compounds can be prepared by the procedure of 1-allylcyclobutanecarboxylic acid. The skilled practitioner will know how to substitute the appropriate reagents, starting materials and purification methods known to those skilled in the art, in order to prepare the compounds provided herein.

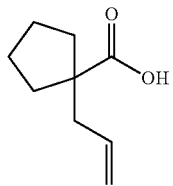

Example 4: Preparation of 1-allylcyclopentanecarboxylic acid: The title compound was prepared according to the procedure for 1-allylcyclobutanecarboxylic acid, except cyclopentane carboxylic acid was substituted for cyclobutanecarboxylic acid: $^1$H NMR (400 MHz, $CDCl_3$) δ 5.77 (ddt, J=7.2, 10.2, 17.4, 1H), 5.17-4.94 (m, 2H), 2.38 (d, J=7.2, 2H), 2.20-2.02 (m, 2H), 1.79-1.47 (m, 6H). $^{13}$C NMR (101 MHz, $CDCl_3$) δ 184.94, 134.96, 118.02, 53.75, 42.96, 35.89, 25.47. Rf, 0.50 (Hexane:Ethyl Acetate 10:1); HRMS (CI): [M+H], calcd for $C_9H_{15}O_2$, 155.1072; found 155.1068.

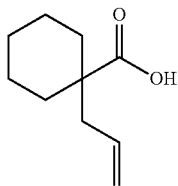

Example 5: Preparation of 1-allylcyclohexanecarboxylic acid: The title compound was prepared according to the procedure for 1-allylcyclobutanecarboxylic acid, except cyclohexane carboxylic acid was substituted for cyclobutanecarboxylic acid: $^1$H NMR (400 MHz, $CDCl_3$) δ 12.13 (broad, 1H), 5.83-5.63 (m, 1H), 5.12-5.00 (m, 2H), 2.27 (m, 2H), 2.04 (m, 2H), 1.66-1.50 (m, 3H), 1.49-1.33 (m, 2H), 1.33-1.17 (m, 3H).

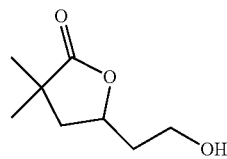

Example 6: Preparation of 5-(2-Hydroxy-ethyl)-3,3-dimethyl-dihydro-furan-2-one: A mixture of glacial acetic acid (28.6 g, 477 mmol, 53.6 equiv), paraformaldehyde (0.80 g, 26.7 mmol, 3.0 equiv) and $H_2SO_4$ (0.5 g, 4.45 mmol, 0.57 equiv) was stirred for 30 min at 70° C. before methyl 2,2-dimethylpent-4-enoate (1.26 g, 8.9 mmol, 1.0 equiv) was added dropwise during 10 min. The reaction mixture was then maintained at 70~80° C. and allowed to stir overnight. Acetic acid was removed under reduced pressure and the reaction was quenched with 10% $NaHCO_3$ solution. The mixture was then extracted with ethyl acetate (3×50 mL) and the combined organic phase was concentrated in vacuo to give a crude oil. The crude oil was used for next step without further purification.

A mixture of the crude oil (200 mg, 1.0 mmol, 1 equiv) and 30% NaOH (800 mg NaOH, 20 mmol, 20 equiv) aqueous solution was refluxed for 2 hours. The mixture was cooled in an ice bath and excess 30% $H_2SO_4$ was added until acidic (pH<2). The resulting mixture was extracted with ethyl acetate (3×25 mL), the combined organic phase was washed with 10% $NaHCO_3$, (50 mL), brine (50 mL), dried over $MgSO_4$ and concentrated in vacuo to give a crude product which was further purified by column chromatography (Ethyl acetate/Hexanes, 10%~60%) $^1$H NMR (400 MHz, $CDCl_3$) δ 4.70-4.60 (m, 1H), 3.90-3.78 (m, 2H), 2.22 (dd, J=5.9, 12.7, 1H), 1.98-1.87 (m, 2H), 1.80 (dd, J=5.9, 12.7, 1H), 1.28 (d, J=4.8, 6H). $^{13}$C NMR (101 MHz, $CDCl_3$) δ 182.26, 75.01, 59.58, 43.93, 40.62, 38.69, 25.31, 24.61; Rf, 0.34 (Hexane:Ethyl Acetate 1:1); Anal. Calcd for $C_8H_{14}O_3$: C, 60.74; H, 8.92. Found: C, 60.47; H, 8.86.

The following compounds can be prepared by the procedure of 5-(2-Hydroxy-ethyl)-3,3-dimethyl-dihydro-furan-2-one. The skilled practitioner will know how to substitute the appropriate reagents, starting materials and purification methods known to those skilled in the art, in order to prepare the compounds provided herein.

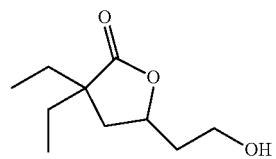

Example 7: Preparation of 3,3-diethyl-5-(2-hydroxyethyl) dihydrofuran-2(3H)-one: The title compound was prepared according to the procedure for 5-(2-Hydroxy-ethyl)-3,3-dimethyl-dihydro-furan-2-one, except ethyl 2,2-diethylpent-4-enoate was substituted for methyl 2,2-dimethylpent-4-enoate: $^1$H NMR (400 MHz, $CDCl_3$) δ 4.62 (dtd, J=5.3, 7.3, 9.5, 1H), 3.78 (t, J=6.1, 2H), 3.20 (s, 1H), 2.19 (dd, J=6.8, 13.1, 1H), 1.97-1.81 (m, 3H), 1.70-1.56 (m, 4H), 0.93 (dt, J=7.5, 20.7, 6H); $^{13}$C NMR (101 MHz, $CDCl_3$) δ 181.46, 75.10, 58.91, 48.77, 39.13, 37.76, 29.21, 28.30, 8.83, 8.73; Rf, 0.36 (Hexane:Ethyl Acetate 5:2); Anal. Calcd for $C_{10}H_{13}O_3$: C, 64.49; H, 9.74. Found: C, 64.20; H, 9.57.

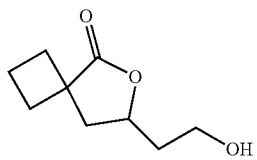 [SMILES: O=C1OC(CCO)CC12CCC2]

Example 8: Preparation of 7-(2-hydroxyethyl)-6-oxaspiro[3.4]octan-5-one: The title compound was prepared according to the procedure for 5-(2-Hydroxy-ethyl)-3,3-dimethyl-dihydro-furan-2-one, except 1-allylcyclobutanecarboxylic acid was substituted for methyl 2,2-dimethylpent-4-enoate: $^1$H NMR (400 MHz, CDCl$_3$) δ 4.60-4.50 (m, 1H), 3.82 (t, J=5.9, 2H), 2.61-2.40 (m, 3H), 2.19-1.96 (m, 5H). 1.92-185 (m, 2H); $^{13}$C NMR (101 MHz, CDCl$_3$) δ 181.25, 75.46, 59.66, 44.62, 42.42, 38.47, 31.95, 29.64, 16.79; Rf, 0.40 (Hexane:Ethyl Acetate 1:2); calcd for C$_9$H$_{15}$O$_3$, 171.1021; found 171.1016.

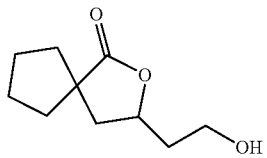 [SMILES: O=C1OC(CCO)CC12CCCC2]

Example 9: Preparation of 3-(2-hydroxyethyl)-2-oxaspiro[4.4]nonan-1-one: The title compound was prepared according to the procedure for 5-(2-Hydroxy-ethyl)-3,3-dimethyl-dihydro-furan-2-one, except 1-allylcyclopentanecarboxylic acid was substituted for methyl 2,2-dimethylpent-4-enoate: $^1$H NMR (400 MHz, CDCl$_3$) δ 4.65-4.56 (m, 1H), 3.84-3.76 (m, 2H), 2.74 (s, 1H), 2.28 (dd, J=5.8, 12.6, 1H), 2.20-2.10 (m, 1H), 2.00-1.56 (m, 10H); $^{13}$C NMR (101 MHz, CDCl$_3$) δ 183.02, 75.77, 59.20, 50.35, 43.41, 38.41, 37.49, 36.93, 25.67, 25.58; Rf, 0.46 (Hexane:Ethyl Acetate 1:2); HRMS (CI): [M+H], calcd for C$_{10}$H$_{7}$O$_3$, 185.1178; found 185.1171.

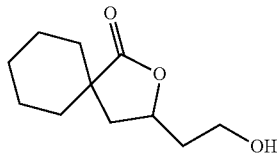 [SMILES: O=C1OC(CCO)CC12CCCCC2]

Example 10: Preparation of 3-(2-hydroxyethyl)-2-oxaspiro[4.5]decan-1-one: The title compound was prepared according to the procedure for 5-(2-Hydroxy-ethyl)-3,3-dimethyl-dihydro-furan-2-one, except 1-allylcyclohexanecarboxylic acid was substituted for methyl 2,2-dimethylpent-4-enoate: $^1$H NMR (400 MHz, CDCl$_3$) δ 4.62 (m, 1H), 3.82 (t, J=5.9, 2H), 2.43 (dd, J=6.2, 12.9, 1H), 2.22 (s, 1H), 2.00-1.17 (m, 13H). $^{13}$C NMR (101 MHz, CDCl$_3$) δ 181.96, 75.37, 59.55, 45.13, 39.88, 38.91, 34.54, 31.71, 25.57, 22.42, 22.36; Rf, 0.46 (Hexane:Ethyl Acetate 1:2); Anal. Calcd for C$_{11}$H$_{18}$O$_3$: C, 66.64; H, 9.15. Found: C, 66.48; H, 9.17.

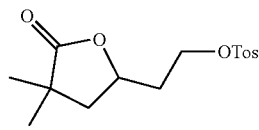

Example 11: Preparation of 2-(4,4-dimethyl-5-oxotetrahydrofuran-2-yl)ethyl 4-methylbenzenesulfonate: To a stirred solution of 5-(2-Hydroxy-ethyl)-3,3-dimethyl-dihydro-furan-2-one (0.316 g, 2 mmol, 1.0 equiv) and triethylamine (0.152 g, 1.5 mmol, 1.5 equiv) in dry dichloromethane, a solution of p-TosCl (0.475 g, 2.5 mmol, 1.25 equiv) in dichloromethane was added drop wise at 0° C. The resulting mixture was stirred at 0° C. for 1 hour and allowed to stir overnight at room temperature. Then, the reaction mixture was diluted with dichloromethane (50 mL), washed with 10% HCl, brine, dried over MgSO$_4$ and concentrated in vacuo to afford yellowish oil. This crude product was then purified by flash chromatography (silica gel; Ethyl acetate/Hexanes, 0%~40%) to afford desired tosylate. $^1$H NMR (300 MHz, CDCl$_3$) δ 7.72 (m, 2H), 7.29 (m, 2H), 4.39 (m, 1H), 4.10 (m, 2H), 2.38 (s, 3H), 2.09 (m, 1H), 1.93 (m, 2H), 1.65 (m, 1H), 1.16 (d, J=4.8, 6H); $^{13}$C NMR (101 MHz, CDCl$_3$) $^{13}$C NMR (101 MHz, CDCl$_3$) δ 181.26, 145.16, 132.53, 130.03, 127.84, 77.68, 77.36, 77.04, 72.93, 66.83, 42.99, 40.23, 34.97, 24.82, 24.12, 21.57; HRMS (CI): [M+H] 313.1; Anal. Calcd for C$_{15}$H$_{20}$O$_5$S: C, 57.67; H, 6.45. Found: C, 57.85; H, 6.63.

The following compounds can be prepared by the procedure of 2-(4,4-dimethyl-5-oxotetrahydrofuran-2-yl)ethyl 4-methylbenzenesulfonate. The skilled practitioner will know how to substitute the appropriate reagents, starting materials and purification methods known to those skilled in the art, in order to prepare the compounds provided herein.

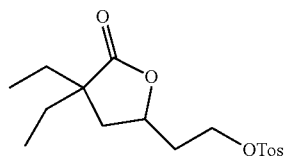

Example 12: Preparation of 2-(4,4-diethyl-5-oxotetrahydrofuran-2-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3,3-diethyl-5-(2-hydroxyethyl)dihydrofuran-2(3H)-one was substituted for 5-(2-Hydroxy-ethyl)-3,3-dimethyl-dihydro-furan-2-one: $^1$H NMR (300 MHz, CDCl$_3$) δ 7.79 (d, J=8.3 Hz, 2H), 7.36 (d, J=8.0 Hz, 2H), 4.55-4.33 (m, 1H), 4.14 (dd, J=6.5, 13.3 Hz, 3H), 2.46 (s, 3H), 2.21-1.84 (m, 3H), 1.83-1.68 (m, 1H), 1.58 (t, J=7.4 Hz, 4H), 0.89 (dt, J=7.5, 18.0 Hz, 6H); $^{13}$C NMR (101 MHz, CDCl$_3$) δ 180.33, 145.30, 132.72, 130.15, 128.03, 77.68, 77.36, 77.04, 73.18, 66.95, 48.67, 37.53, 35.82, 29.14, 28.23, 21.76, 8.81, 8.74. Anal. Calcd for C$_{17}$H$_{24}$O$_5$S: C, 59.98; H, 7.11. Found: C, 60.27; H, 7.25.

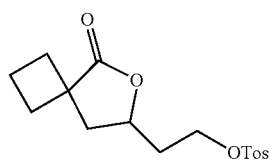

Example 13: Preparation of 2-(5-oxo-6-oxaspiro[3.4]octan-7-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 7-(2-hydroxyethyl)-6-oxaspiro[3.4]octan-5-one was substituted for 5-(2-Hydroxy-ethyl)-3,3-dimethyl-dihydro-furan-2-one: $^1$H NMR (400 MHz, CDCl$_3$) δ 7.77 (d, J=8.3 Hz, 2H), 7.35 (d, J=8.0 Hz, 2H), 4.37 (tdd, J=8.8, 6.0, 4.3 Hz, 1H), 4.21-4.05 (m, 2H), 2.57-2.32 (m, 6H), 2.19-1.82 (m, 7H); $^{13}$C NMR (101 MHz, CDCl$_3$) δ 180.41, 145.24, 132.68, 130.10, 128.02, 73.38, 66.76, 44.33, 41.79, 35.10, 31.72, 29.28, 21.76, 16.51.

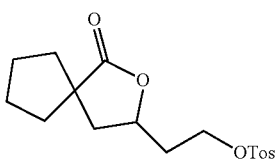

Example 14: Preparation of 2-(1-oxo-2-oxaspiro[4.4]nonan-3-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3-(2-hydroxyethyl)-2-oxaspiro[4.4]nonan-1-one was substituted for 5-(2-Hydroxy-ethyl)-3,3-dimethyl-dihydro-furan-2-one: $^1$H NMR (400 MHz, CDCl$_3$) δ 7.79 (d, J=8.3 Hz, 2H), 7.36 (d, J=8.0 Hz, 2H), 4.51-4.35 (m, 1H), 4.25-4.06 (m, 2H), 2.45 (s, 3H), 2.28-2.08 (m, 2H), 2.08-1.91 (m, 2H), 1.87-1.52 (m, 9H); $^{13}$C NMR (101 MHz, CDCl$_3$) δ 181.90, 145.26, 132.76, 130.12, 128.07, 73.71, 66.85, 50.19, 43.07, 37.44, 36.81, 35.19, 25.61, 25.50, 21.79.

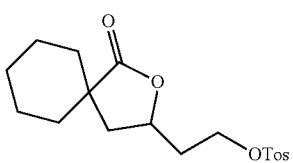

Example 15: Preparation of 2-(1-oxo-2-oxaspiro[4.5]decan-3-yl)ethyl 4-methylbenzenesulfonate: The title compound was prepared according to the procedure for 2-(4,4-dimethyl-5-oxotetrahydrofuran-2-yl)ethyl 4-methylbenzenesulfonate, except 3-(2-hydroxyethyl)-2-oxaspiro[4.5]decan-1-one was substituted for 5-(2-Hydroxy-ethyl)-3,3-dimethyl-dihydro-furan-2-one: $^1$H NMR (400 MHz, CDCl$_3$) δ 7.79 (d, J=8.3 Hz, 2H), 7.36 (d, J=8.0 Hz, 2H), 4.51-4.38 (m, 1H), 4.26-4.12 (m, 2H), 2.45 (s, 3H), 2.36 (dd, J=12.9, 6.2 Hz, 1H), 2.12-1.87 (m, 2H), 1.85-1.68 (m, 3H), 1.65-1.50 (m, 5H), 1.43-1.14 (m, 3H); $^{13}$C NMR (101 MHz, CDCl$_3$) δ 180.97, 145.27, 132.76, 130.12, 128.07, 73.28, 66.85, 44.96, 39.48, 35.58, 34.35, 31.52, 25.37, 22.23, 22.16, 21.80.

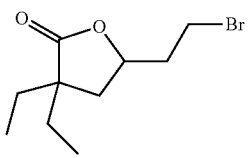

Example 16: Preparation of 5-(2-bromoethyl)-3,3-diethyldihydrofuran-2(3H)-one: To a solution of 3,3-diethyl-5-(2-hydroxyethyl)dihydrofuran-2(3H)-one (8.03 g, 43.0 mmol, 1 eq.) in tetrahydrofuran (143 mL) was added triphenylphosphine (16.94 g, 64.6 mmol, 1.5 eq.). The resulting solution was cooled to 0° C. and carbon tetrabromide (21.44 g, 64.6 mmol, 1.5 eq.) was added in one portion. The reaction was allowed to stir at 22° C. overnight. The reaction mixture was diluted with ether and filtered and concentrated onto Celite in vacuo and further purified by column chromatography (ethyl acetate/hexanes, 0%~30%, solid load). $^1$H NMR (400 MHz, CDCl$_3$) δ4.60 (m, 1H), 3.53 (dd, J=5.5, 7.6 Hz, 2H), 2.27-2.07 (m, 3H), 1.82 (dd, J=9.3, 13.0 Hz, 1H), 1.69-1.57 (m, 4H), 0.93 (dt, J=7.5, 25.7 Hz, 6H).

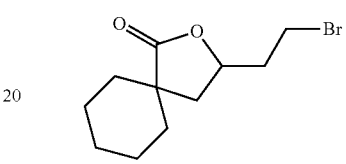

Example 17: Preparation of 3-(2-bromoethyl)-2-oxaspiro[4.5]decan-1-one: The title compound was prepared according to the procedure for 5-(2-bromoethyl)-3,3-diethyldihydrofuran-2(3H)-one, except 3-(2-hydroxyethyl)-2-oxaspiro[4.5]decan-1-one was substituted for 3,3-diethyl-5-(2-hydroxyethyl)dihydrofuran-2(3H)-one: $^1$H NMR (400 MHz, CDCl$_3$) δ4.61 (m, 1H), 3.53 (dd, J=5.5, 7.6 Hz, 2H), 2.44 (dd, J=6.4, 12.9 Hz, 1H), 2.29-2.07 (m, 2H), 1.88-1.70 (m, 3H), 1.69-1.54 (m, 4H), 1.53-1.44 (m, 1H), 1.44-1.18 (m, 3H).

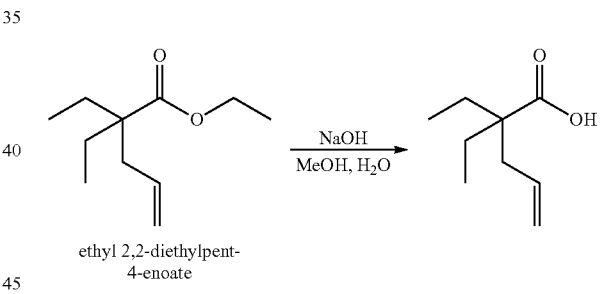

ethyl 2,2-diethylpent-4-enoate

Example 18: Preparation of 2,2-diethylpent-4-enoic acid: Ethyl 2,2-diethylpent-4-enoate (0.2 g, 0.28 mmol) is mixed with NaOH (0.4 g, 10 mmol), MeOH (2.5 mL) and H$_2$O (2.5 mL) in a microwave vial. The mixture is then heated in a microwave reactor at 160° C. for 2 hours. The mixture was then acidified with 10% HCl, washed with ether (3×30 ml). The combined organic phase was dried over MgSO$_4$ and concentrated in vacuo to give a crude product which was used in the next step without further purification.

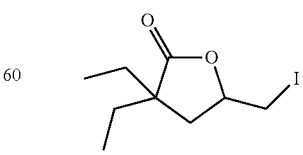

Example 19: Preparation of 3,3-diethyl-5-(iodomethyl)dihydrofuran-2(3H)-one: 2,2-diethylpent-4-enoic acid (1.77 g, 11.67 mmol) is stirred with tetrahydrofuran (34 mL), ether (12 mL) and saturated NaHCO$_3$ solution (57 mL). The mixture is protected from sunlight. I2 was dissolved in 12 mL of tetrahydrofuran and added to the mixture in one portion at 0° C. The mixture was allowed to stir overnight at room temperature. Saturated sodium thiosulfate is added to the mixture to quench the reaction. The mixture was extracted with ethyl acetate (3×50 mL). The combined organic phase was dried over MgSO$_4$ and concentrated in vacuo to give a crude oil which was purified by flash chromatography (silica gel; Ethyl acetate/Hexanes, 0%~25%). $^1$H NMR (400 MHz, CDCl$_3$) δ 4.42 (dtd, J=9.0, 7.3, 4.6 Hz, 1H), 3.41 (dd, J=10.2, 4.6 Hz, 1H), 3.23 (dd, J=10.2, 7.5 Hz, 1H), 2.25 (dd, J=13.3, 6.9 Hz, 1H), 1.86 (dd, J=13.3, 9.1 Hz, 1H), 1.63 (m, 4H), 0.94 (dt, J=10.4, 7.5 Hz, 6H). MS (LC/MS, M+H$^+$): 283.0

The following compounds can be prepared by the procedure of 3,3-diethyl-5-(iodomethyl)dihydrofuran-2(3H)-one. The skilled practitioner will know how to substitute the appropriate reagents, starting materials and purification methods known to those skilled in the art, in order to prepare the compounds provided herein.

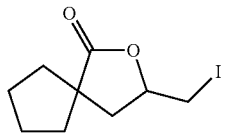 [SMILES: O=C1OC(CI)CC12CCCC2]

Example 20: Preparation of 3-(iodomethyl)-2-oxaspiro[4.4]nonan-1-one: The title compound was prepared according to the procedure for 3,3-diethyl-5-(iodomethyl)dihydrofuran-2(3H)-one, except 1-allylcyclopentanecarboxylic acid was substituted for 2,2-diethylpent-4-enoic acid: $^1$H NMR (400 MHz, CDCl$_3$) δ 4.48-4.34 (m, 1H), 3.39 (dd, J=10.2, 4.9 Hz, 1H), 3.23 (dd, J=10.2, 7.5 Hz, 1H), 2.35 (dd, J=12.9, 6.1 Hz, 1H), 2.20-2.04 (m, 1H), 1.93-1.54 (m, 8H); $^{13}$C NMR (101 MHz, CDCl$_3$) δ 181.57, 75.96, 50.71, 43.44, 37.84, 36.89, 25.45, 25.36, 7.02; MS (LC/MS, M+H$^+$): 281.0

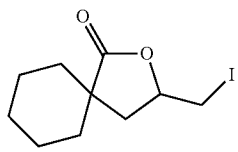 [SMILES: O=C1OC(CI)CC12CCCCC2]

Example 21: Preparation of 3-(iodomethyl)-2-oxaspiro[4.5]decan-1-one: The title compound was prepared according to the procedure for 3,3-diethyl-5-(iodomethyl)dihydrofuran-2(3H)-one, except 1-allylcyclohexanecarboxylic acid was substituted for 2,2-diethylpent-4-enoic acid: $^1$H NMR (400 MHz, CDCl$_3$) δ 4.42 (dtd, J=9.2, 6.9, 4.6 Hz, 1H), 3.41 (dd, J=10.3, 4.6 Hz, 1H), 3.26 (dd, J=10.2, 7.3 Hz, 1H), 2.50 (dd, J=13.1, 6.5 Hz, 1H), 1.85-1.49 (m, 8H), 1.44-1.20 (m, 3H); MS (LC/MS, M+H$^+$): 295.0

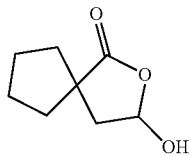 [SMILES: O=C1OC(O)CC12CCCC2]

Example 22: Preparation of 3-hydroxy-2-oxaspiro[4.4]nonan-1-one: To a stirred mixture of 1-allylcyclopentanecarboxylic acid (10.93 g, 71 mmol, 1 equiv), RuCl$_3$ stock solution (0.514 g, 0.035M in water, 0.035 equiv) and CH$_3$CN (500 mL), NaIO$_4$ (30.8 g, 142 mmol, 2.04 equiv) was added in portions over a period of 30 min at room temperature. The suspension was allowed to stir at room temperature for another 30 min. The reaction was quenched with saturated aqueous solution of Na$_2$S$_2$O$_3$ and the two layers were separated. The aqueous layer was extracted with ethyl acetate (3×200 mL). The combined organic layer was washed with brine, dried over anhydrous MgSO$_4$, filtered, and concentrated. The residue was purified by flash column chromatography (silica gel; Ethyl acetate/Hexanes, 10%~50%) to give desired product. $^1$H NMR (400 MHz, CDCl$_3$) δ 5.87 (s, 1H), 5.28 (s, 1H), 2.06 (dd, J=35.1, 28.9 Hz, 4H), 1.90-1.44 (m, 6H); $^{13}$C NMR (101 MHz, CDCl$_3$) δ 183.20, 49.58, 43.94, 38.28, 25.42.

The following compounds can be prepared by the procedure of 3-hydroxy-2-oxaspiro[4.4]nonan-1-one. The skilled practitioner will know how to substitute the appropriate reagents, starting materials and purification methods known to those skilled in the art, in order to prepare the compounds provided herein.

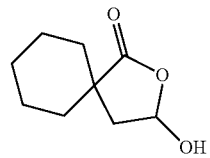 [SMILES: O=C1OC(O)CC12CCCCC2]

Example 23: Preparation of 3-hydroxy-2-oxaspiro[4.5]decan-1-one: The title compound was prepared according to the procedure for 3-hydroxy-2-oxaspiro[4.4]nonan-1-one, except 1-allylcyclohexanecarboxylic acid was substituted for 1-allylcyclopentanecarboxylic acid: $^1$H NMR (400 MHz, CDCl$_3$) δ 5.86 (t, J=4.5 Hz, 1H), 4.47 (broad, 1H), 2.18 (m, 2H), 1.83-1.43 (m, 7H), 1.32 (d, J=5.8 Hz, 3H); $^{13}$C NMR (101 MHz, CDCl$_3$) δ 181.91, 96.88, 44.52, 40.54, 34.06, 25.28, 22.23.

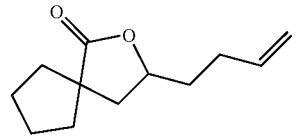

Example 24: Preparation of 3-(but-3-en-1-yl)-2-oxaspiro[4.4]nonan-1-one: This reaction was performed in oven-dried glassware under a nitrogen atmosphere. To a well-stirred solution of freshly prepared but-1-ene magnesium bromide Grignard reagent (96 mmol, 1M, 3 equiv) in dry ether, 3-hydroxy-2-oxaspiro[4.4]nonan-1-one (5.0 g, 32.0 mmol, 1.0 equiv) was added dropwise during 0.5 hours at 0° C. The reaction mixture was stirred overnight at room temperature, quenched with 10% HCl (while cooling in ice bath) until acidic (pH=2). The organic layer was separated and the aqueous layer was extracted with ethyl acetate (3×200 mL). The extract was washed with 10% NaHCO$_3$ (100 mL) and brine (200 mL). The solution was then dried over MgSO$_4$, concentrated in vacuo and purified by flash column chromatography (silica gel; Ethyl acetate/Hexanes, 0%~25%) to give desired product. $^1$H NMR (400 MHz, CDCl$_3$) δ 5.79 (ddt, J=16.9, 10.2, 6.7 Hz, 1H), 5.15-4.88 (m, 2H), 4.36 (ddt, J=9.7, 7.9, 5.5 Hz, 1H), 2.18 (m, 4H), 1.93-1.46 (m, 10H); $^{13}$C NMR (101 MHz, CDCl$_3$) δ 182.55, 137.26, 115.62, 77.19, 50.28, 43.24, 37.51, 36.91, 34.83, 29.70, 25.56, 25.47.

The following compounds can be prepared by the procedure of 3-(but-3-en-1-yl)-2-oxaspiro[4.4]nonan-1-one. The skilled practitioner will know how to substitute the appropriate reagents, starting materials and purification methods known to those skilled in the art, in order to prepare the compounds provided herein.

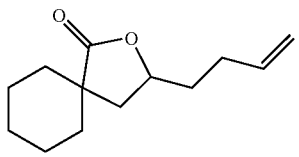

Example 25: Preparation of 3-(but-3-en-1-yl)-2-oxaspiro [4.5]decan-1-one: The title compound was prepared according to the procedure for 3-(but-3-en-1-yl)-2-oxaspiro[4.4] nonan-1-one, except 3-hydroxy-2-oxaspiro[4.5]decan-1-one was substituted for 3-hydroxy-2-oxaspiro[4.4]nonan-1-one: $^1$H NMR (400 MHz, CDCl$_3$) δ 5.80 (ddt, J=16.9, 10.2, 6.6 Hz, 1H), 5.17-4.89 (m, 2H), 4.48-4.31 (m, 1H), 2.36 (dd, J=12.9, 6.3 Hz, 1H), 2.30-2.08 (m, 2H), 1.87-1.17 (m, 13H); $^{13}$C NMR (101 MHz, CDCl$_3$) δ 181.68, 137.31, 115.67, 76.77, 45.04, 39.55, 35.31, 34.43, 31.70, 29.75, 25.42, 22.29, 22.22

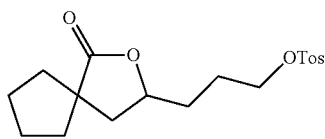

Example 26: Preparation of 3-(1-oxo-2-oxaspiro[4.4] nonan-3-yl)propyl 4-methylbenzenesulfonate: To a stirred mixture of 3-(but-3-en-1-yl)-2-oxaspiro[4.4]nonan-1-one (0.194 g, 1 mmol, 1 equiv), RuCl$_3$ stock solution (7.2 mg, 0.035M in water, 0.035 equiv) and CH$_3$CN (6 mL), NaIO$_4$ (434 mg, 2.04 mmol, 2.04 equiv) was added in portions over a period of 5 min at room temperature. The suspension was allowed to stir at room temperature for another 30 min. The reaction was quenched with saturated aqueous solution of Na$_2$S$_2$O$_3$ and the two layers were separated. The aqueous layer was extracted with ethyl acetate (3×20 mL). The combined organic layer was washed with brine, dried over anhydrous MgSO$_4$, filtered, and concentrated. The crude aldehyde was used for the next step without further purification.

This reaction was performed in oven-dried glassware under a nitrogen atmosphere. To a well-stirred solution of the crude aldehyde (0.196 g, 1 mmol, 1 equiv) in dry methanol, NaBH$_4$ (74 mg, 2.0 mmol, 2 equiv) was added to the mixture in one portion at 0° C. The reaction mixture was stirred at room temperature for another 1 h, quenched with brine (while cooling in ice bath). The organic layer was separated and the aqueous layer was extracted with ethyl acetate (3×20 mL). The combined organic phase was then dried over MgSO$_4$, concentrated in vacuo. The crude alcohol was used for the next step without further purification.

To a stirred solution of the crude alcohol (0.396 g, 2 mmol, 1.0 equiv) and Et$_3$N (0.303 g, 3 mmol, 1.5 equiv) in dry dichloromethane, a solution of p-TosCl (0.475 g, 2.5 mmol, 1.25 equiv) in dichloromethane was added drop wise at 0° C. The resulting mixture was stirred at 0° C. for 1 hour and allowed to stir overnight at room temperature. Then, the reaction mixture was diluted with dichloromethane (50 mL), washed with 10% HCl, brine, dried over MgSO$_4$ and concentrated in vacuo to afford yellowish oil. This crude product was then purified by flash chromatography (silica gel; Ethyl acetate/Hexanes, 0%~40%) to afford desired tosylate. $^1$H NMR (400 MHz, CDCl$_3$) δ 7.82-7.71 (m, 2H), 7.35 (m, 2H), 4.37-4.23 (m, 1H), 4.06 (qdd, J=10.0, 6.7, 5.2 Hz, 2H), 2.45 (s, 3H), 2.15 (m, 2H), 1.92-1.50 (m, 12H); $^{13}$C NMR (101 MHz, CDCl$_3$) δ 182.29, 145.03, 133.05, 130.04, 128.00, 76.90, 69.91, 50.24, 43.20, 37.53, 36.92, 31.74, 25.59, 25.49, 25.37, 21.76.

The following compounds can be prepared by the procedure of 3-(1-oxo-2-oxaspiro[4.4]nonan-3-yl)propyl 4-methylbenzenesulfonate. The skilled practitioner will know how to substitute the appropriate reagents, starting materials and purification methods known to those skilled in the art, in order to prepare the compounds provided herein.

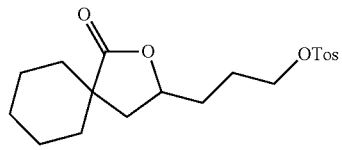

Example 27: Preparation of 3-(1-oxo-2-oxaspiro[4.5]decan-3-yl)propyl 4-methylbenzenesulfonate: The title compound was prepared according to the procedure for 3-(1-oxo-2-oxaspiro[4.4]nonan-3-yl)propyl 4-methylbenzenesulfonate, except 3-(but-3-en-1-yl)-2-oxaspiro[4.5]decan-1-one was substituted for 3-(but-3-en-1-yl)-2-oxaspiro[4.4]nonan-1-one: $^1$H NMR (400 MHz, CDCl$_3$) δ 7.78 (d, J=8.3 Hz, 2H), 7.35 (d, J=8.0 Hz, 2H), 4.39-4.26 (m, 1H), 4.16-3.97 (m, 2H), 2.44 (s, 3H), 2.32 (dt, J=15.8, 7.9 Hz, 1H), 1.98-1.13 (m, 16H); $^{13}$C NMR (101 MHz, CDCl$_3$) δ 181.36, 145.03, 133.05, 130.03, 127.99, 76.46, 69.91, 44.97, 39.54, 34.40, 32.15, 31.68, 25.37, 25.36, 22.25, 22.18, 21.76

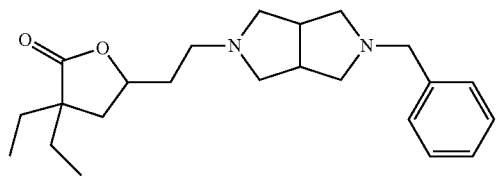 [SMILES: CCC1(CC)CC(CCN2CC3CN(Cc4ccccc4)CC3C2)OC1=O]

Example 28: Preparation of 5-(2-(5-benzylhexahydropyrrolo[3,4-c]pyrrol-2(1H)-yl)ethyl)-3,3-diethyldihydrofuran-2(3H)-one: A solution of 5-(2-bromoethyl)-3,3-diethyldihydrofuran-2(3H)-one (0.400 g, 1.53 mmol, 1 eq.), acetonitrile (8 mL), 2-benzyloctahydropyrrolo[3,4-c]pyrrole (0.340 g, 1.68 mmol, 1.1 eq.) and K$_2$CO$_3$ (1.05 g, 7.65 mmol, 5 eq.) was heated and stirred at 80° C. for 24 hours. The resulting mixture was then filtered and concentrated in vacuo to give a crude residue that was further purified by column chromatography (methanol/dichloromethane, 0%~10%). $^1$H NMR (400 MHz, CDCl$_3$) δ7.25-7.14 (m, 4H), 7.14-7.06 (m, 1H), 4.38 (m, 1H), 3.46 (s, 2H), 2.64-2.48 (m, 6H), 2.48-

2.38 (m, 2H), 2.28-2.13 (m, 4H), 2.02 (dd, J=6.8, 13.0 Hz, 1H), 1.87-1.59 (m, 3H), 1.58-1.44 (m, 4H), 0.83 (dt, J=7.3, 21.4 Hz, 6H); MS (LC/MS, M+H⁺): m/z 371.2

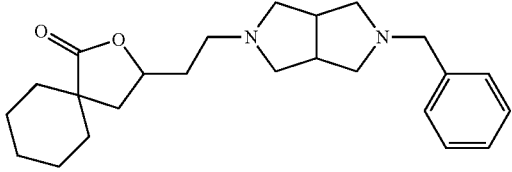 [SMILES: O=C1OC(CCN2CC3CN(Cc4ccccc4)CC3C2)CC12CCCCC2]

Example 29: Preparation of 3-(2-(5-benzylhexahydropyrrolo[3,4-c]pyrrol-2(1H)-yl)ethyl)-2-oxaspiro[4.5]decan-1-one: The title compound was prepared according to the procedure for 5-(2-(5-benzylhexahydropyrrolo[3,4-c]pyrrol-2(1H)-yl)ethyl)-3,3-diethyldihydrofuran-2(3H)-one, except 3-(2-bromoethyl)-2-oxaspiro[4.5]decan-1-one was substituted for 5-(2-bromoethyl)-3,3-diethyldihydrofuran-2(3H)-one: ¹H NMR (400 MHz, CDCl₃) δ7.26-7.17 (m, 4H), 7.17-7.10 (m, 1H), 4.40 (m, 1H), 3.50 (s, 2H), 2.69-2.52 (m, 6H), 2.49 (t, J=7.4 Hz, 2H), 2.30 (dd, J=6.3, 12.8 Hz, 1H), 2.27-2.16 (m, 4H), 1.88-1.61 (m, 5H), 1.61-1.45 (m, 4H), 1.44-1.37 (m, 1H), 1.36-1.07 (m, 3H); MS (LC/MS, M+H⁺): m/z 383.2

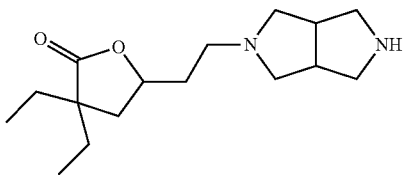 [SMILES: CCC1(CC)CC(CCN2CC3CNCC3C2)OC1=O]

Example 30: Preparation of 3,3-diethyl-5-(2-(hexahydropyrrolo[3,4-c]pyrrol-2(1H)-yl)ethyl)dihydrofuran-2(3H)-one: A mixture of 5-(2-(5-benzylhexahydropyrrolo[3,4-c]pyrrol-2(1H)-yl)ethyl)-3,3-diethyldihydrofuran-2(3H)-one (540 mg, 1.46 mmol, 1 eq.), Pd/C (108 mg, 20% wt) and MeOH (5.0 mL) was stirred at 22° C. under 1 atm of H₂ (filled balloon) for 3 days. The mixture was filtered through a plug of Celite, washed with MeOH (50 mL) and concentrated in vacuo to give a crude product that was used in following steps without further purification. ¹H NMR (400 MHz, CDCl₃) δ4.42 (m, 1H), 2.83 (b, 1H), 2.69 (m, 2H), 2.55-2.39 (m, 4H), 2.33 (m, 2H), 2.26 (t, J=7.0 Hz, 2H), 2.14 (dd, J=1.7, 9.0 Hz, 2H), 1.91 (dd, J=6.7, 13.0 Hz, 1H), 1.71-1.47 (m, 3H), 1.45-1.32 (m, 4H), 0.69 (dt, J=7.4, 19.2 Hz, 6H); MS (LC/MS, M+H⁺): m/z 281.2

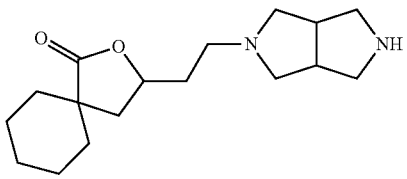 [SMILES: O=C1OC(CCN2CC3CNCC3C2)CC12CCCCC2]

Example 31: Preparation of 3-(2-(hexahydropyrrolo[3,4-c]pyrrol-2(1H)-yl)ethyl)-2-oxaspiro[4.5]decan-1-one: The title compound was prepared according to the procedure for 3,3-diethyl-5-(2-(hexahydropyrrolo[3,4-c]pyrrol-2(1H)-yl)ethyl)dihydrofuran-2(3H)-one, except 3-(2-(5-benzylhexahydropyrrolo[3,4-c]pyrrol-2(1H)-yl)ethyl)-2-oxaspiro[4.5]decan-1-one was substituted for 5-(2-(5-benzylhexahydropyrrolo[3,4-c]pyrrol-2(1H)-yl)ethyl)-3,3-diethyldihydrofuran-2(3H)-one: ¹H NMR (400 MHz, CDCl₃) δ4.55 (m, 1H), 2.94 (m, 2H), 2.82-2.63 (m, 5H), 2.63-2.46 (m, 3H), 2.42 (m, 2H), 1.97-1.60 (m, 8H), 1.59-1.43 (m, 3H), 1.43-1.22 (m, 4H); MS (LC/MS, M+H⁺): m/z 293.2

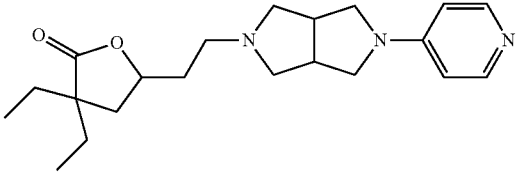 [SMILES: CCC1(CC)CC(CCN2CC3CN(c4ccncc4)CC3C2)OC1=O]

Example 32: Preparation of 3,3-diethyl-5-(2-(5-(pyridin-4-yl)hexahydropyrrolo[3,4-c]pyrrol-2(1H)-yl)ethyl)dihydrofuran-2(3H)-one: A solution of 3,3-diethyl-5-(2-(hexahydropyrrolo[3,4-c]pyrrol-2(1H)-yl)ethyl)dihydrofuran-2(3H)-one (0.180 g, 0.642 mmol, 1 eq.), 1-butanol (6.4 mL), 4-bromopyridine hydrochloride (0.249 g, 1.28 mmol, 2.0 eq.) and triethylamine (0.325 g, 3.21 mmol, 5 eq.) was heated and stirred at 120° C. for 24 hours. The resulting solution was concentrated in vacuo to give a crude residue that was further purified by column chromatography (methanol/dichloromethane, 0%~10%, w/0.1% NH₄OH). ¹H NMR (400 MHz, CDCl₃) δ8.13 (dd, J=1.4, 3.5 Hz, 2H), 6.32 (dd, J=1.5, 3.5 Hz, 2H), 4.37 (m, 1H), 3.45 (dd, J=8.3, 9.2 Hz, 2H), 3.12 (dt, J=3.4, 9.9 Hz, 2H), 2.90 (m, 2H), 2.62 (m, 2H), 2.50 (t, J=7.4 Hz, 2H), 2.46 (m, 2H), 2.02 (dd, J=6.8, 13.0 Hz, 1H), 1.85-1.61 (m, 3H), 1.52 (q, J=7.5 Hz, 4H), 0.82 (dt, J=5.7, 13.2 Hz, 6H); MS (LC/MS, M+H⁺): m/z 358.2

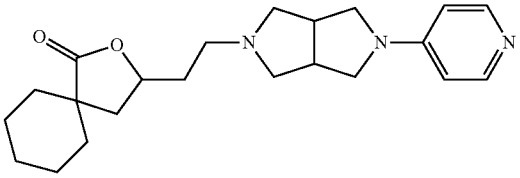

Example 33: Preparation of 3-(2-(5-(pyridin-4-yl)hexahydropyrrolo[3,4-c]pyrrol-2(1H)-yl)ethyl)-2-oxaspiro[4.5]decan-1-one: The title compound was prepared according to the procedure for 3,3-diethyl-5-(2-(5-(pyridin-4-yl)hexahydropyrrolo[3,4-c]pyrrol-2(1H)-yl)ethyl)dihydrofuran-2(3H)-one, except 3-(2-(hexahydropyrrolo[3,4-c]pyrrol-2(1H)-yl)ethyl)-2-oxaspiro[4.5]decan-1-one was substituted for 3,3-diethyl-5-(2-(hexahydropyrrolo[3,4-c]pyrrol-2(1H)-yl)ethyl)dihydrofuran-2(3H)-one: ¹H NMR (400 MHz, CDCl₃) δ8.13 (d, J=5.6 Hz, 2H), 6.33 (d, J=6.2 Hz, 2H), 4.38 (m, 1H), 3.46 (m, 2H), 3.13 (dt, J=3.7, 10.0 Hz, 2H), 2.91 (m, 2H), 2.68-2.57 (m, 2H), 2.55-2.41 (m, 4H), 2.28 (dd, J=6.2, 12.8 Hz, 1H), 1.95-1.43 (m, 9H), 1.43-1.33 (m, 1H), 1.32-1.04 (m, 3H); MS (LC/MS, M+H⁺): m/z 370.2.

Example 34: Preparation of 1-(benzyloxy)-2-bromobenzene: To a solution of 2-bromophenol (1.0 g, 5.78 mmol, 1.01 eq.) in acetonitrile (14 mL) was added benzyl bromide (0.975 g, 5.7 mmol, 1.0 eq.) and K₂CO₃ (1.09 g, 7.87 mmol, 1.38 eq.). This mixture was allowed to stir at 22° C. overnight. The reaction was filtered and concentrated in vacuo to give a crude residue that was further purified by column chromatography (hexanes/ethyl acetate, 0%~10%). ¹H NMR (400 MHz, CDCl₃) δ7.60 (dd, J=1.6, 7.8 Hz, 1H), 7.51 (m, 2H), 7.42 (t, J=7.6 Hz, 2H), 7.35 (m, 1H), 7.29-7.22 (m, 1H), 6.97 (dd, J=1.2 8.3 Hz, 1H), 6.88 (td, J=1.3, 7.6 Hz, 1H), 5.19 (s, 2H).

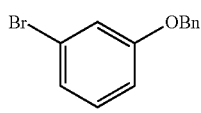

Example 35: Preparation of 1-(benzyloxy)-3-bromobenzene: The title compound was prepared according to the procedure for 1-(benzyloxy)-2-bromobenzene, except 3-bromophenol was substituted for 2-bromophenol: ¹H NMR (400 MHz, CDCl₃) δ7.50-7.34 (m, 5H), 7.23-7.10 (m, 3H), 6.95 (m, 1H), 5.08 (s, 2H).

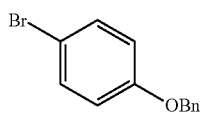

Example 36: Preparation of 1-(benzyloxy)-4-bromobenzene: The title compound was prepared according to the procedure for 1-(benzyloxy)-2-bromobenzene, except 4-bromophenol was substituted for 2-bromophenol: ¹H NMR (400 MHz, CDCl₃) δ7.51-7.33 (m, 7H), 6.91 (d, J=9.1 Hz, 2H), 5.08 (s, 2H).

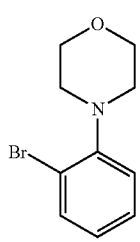

Example 37: Preparation of 4-(2-bromophenyl)morpholine: This reaction was performed in oven-dried glassware under a nitrogen atmosphere. To a solution of 1,2-dibromobenzene (1.0 g, 4.24 mmol, 1.0 eq.) and morpholine (0.370 g, 4.24 mmol, 1.0 eq.) in anhydrous toluene (10.6 mL) was added the following in this order: Pd₂(dba)₃ (0.097 g, 5 mol %), BINAP (0.197 g, 7.5 mol %), and NaOtBu (0.448 g, 5.08 mmol, 1.2 eq.). The resulting mixture was allowed to stir at 80° C. overnight, under a sweep of N₂. The reaction mixture was cooled to 22° C. and then filtered through a plug of Celite. The collected filtrate was concentrated in vacuo to give a crude residue that was further purified by column chromatography (hexanes/ethyl acetate, 0%~20%). ¹H NMR (400 MHz, CDCl₃) δ7.55 (dd, J=1.5, 7.9 Hz, 1H), 7.25 (td, J=1.4, 7.8 Hz, 1H), 7.00 (dd, J=1.4, 8.0 Hz, 1H), 6.89 (td, J=1.4, 7.7 Hz, 1H), 3.83 (m, 4H), 2.99 (m, 4H); MS (LC/MS, M+H⁺): m/z 241.9, 243.8

Example 38: Preparation of tert-butyl 6-phenyl-2,6-diazaspiro[3.3]heptane-2-carboxylate: This reaction was performed in oven-dried glassware under a nitrogen atmosphere. To a solution of 2,6-diazaspiro[3.3]heptane-2-carboxylic acid tert-butyl ester hemioxylate (0.300 g, 1.23 mmol, 1.1 eq.) and bromobenzene (0.176 g, 1.12 mmol, 1.0 eq.) in anhydrous toluene (14 mL) was added the following in this order: Pd₂(dba)₃ (0.030 g, 2.5 mol %), BINAP (0.0450 g, 1.5/Pd), triethylamine (0.125 g, 1.23 mmol, 1.1 eq.) and NaOtBu (0.355 g, 3.69 mmol, 3.3 eq.). The resulting mixture was allowed to stir at 110° C. overnight, under a sweep of N₂. The reaction mixture was cooled to 22° C. and then filtered through a plug of Celite. The collected filtrate was concentrated in vacuo to give a crude residue that was further purified by column chromatography (hexanes/ethyl acetate, 0%~30%). ¹H NMR (400 MHz, CDCl₃) δ7.21 (m, 2H), 6.93 (m, 1H), 6.74 (d, J=8.3 Hz, 2H), 4.23 (s, 4H), 4.19 (s, 4H), 1.38 (s, 9H); MS (LC/MS, M+H⁺): m/z 275.2

Example 39: Preparation of tert-butyl 6-(pyridin-4-yl)-2,6-diazaspiro[3.3]heptane-2-carboxylate: The title compound was prepared according to the procedure for tert-butyl 6-phenyl-2,6-diazaspiro[3.3]heptane-2-carboxylate, except 4-bromopyridine hydrochloride was substituted for bromobenzene and 2 equivalents of triethylamine was utilized: ¹H NMR (400 MHz, CDCl₃) δ8.09 (d, J=6.5 Hz, 2H), 6.28 (d, J=6.7 Hz, 2H), 4.12 (s, 4H), 4.06 (s, 4H), 1.37 (s, 9H); MS (LC/MS, M+H⁺): m/z 276.2

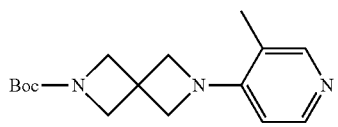 [SMILES: Cc1cnccc1N1CC2(CN(C(=O)OC(C)(C)C)C2)C1]

Example 40: Preparation of tert-butyl 6-(3-methylpyridin-4-yl)-2,6-diazaspiro[3.3]heptane-2-carboxylate: The title compound was prepared according to the procedure for tert-butyl 6-phenyl-2,6-diazaspiro[3.3]heptane-2-carboxylate, except 4-bromo-3-methylpyridine hydrochloride was substituted for bromobenzene and 2 equivalents of triethylamine was utilized: ¹H NMR (400 MHz, CDCl₃) δ8.05 (d, J=5.5 Hz, 1H), 7.94 (s, 1H), 6.12 (d, J=5.4 Hz, 1H), 4.08 (s, 4H), 4.02 (s, 4H), 2.10 (s, 3H) 1.37 (s, 9H); MS (LC/MS, M+H⁺): m/z 290.2

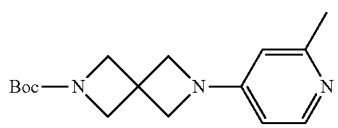 [SMILES: Cc1cc(N2CC3(CN(C(=O)OC(C)(C)C)C3)C2)ccn1]

Example 41: Preparation of tert-butyl 6-(2-methylpyridin-4-yl)-2,6-diazaspiro[3.3]heptane-2-carboxylate: The title compound was prepared according to the procedure for tert-butyl 6-phenyl-2,6-diazaspiro[3.3]heptane-2-carboxylate, except 4-bromo-2-methylpyridine was substituted for bromobenzene: $^1$H NMR (400 MHz, CDCl$_3$) δ8.05 (d, J=5.5 Hz, 1H), 6.07-6.00 (m, 2H), 4.02 (s, 4H), 3.95 (s, 4H), 2.35 (s, 3H), 1.37 (s, 9H); MS (LC/MS, M+H$^+$): m/z 290.2

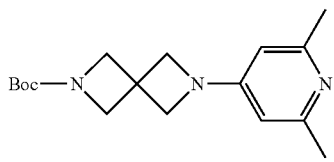 [SMILES: Cc1cc(N2CC3(CN(C(=O)OC(C)(C)C)C3)C2)cc(C)n1]

Example 42: Preparation of tert-butyl 6-(2,6-dimethylpyridin-4-yl)-2,6-diazaspiro[3.3]heptane-2-carboxylate: The title compound was prepared according to the procedure for tert-butyl 6-phenyl-2,6-diazaspiro[3.3]heptane-2-carboxylate, except 4-bromo-2,6-dimethylpyridine was substituted for bromobenzene: $^1$H NMR (400 MHz, CDCl$_3$) δ 5.90 (s, 2H), 4.01 (s, 4H), 3.92 (s, 4H), 2.32 (s, 6H), 1.37 (s, 9H); MS (LC/MS, M+H*j m/z 304.2

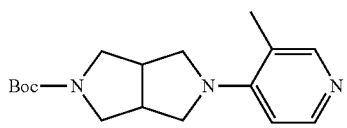 [SMILES: Cc1cnccc1N1CC2CN(C(=O)OC(C)(C)C)CC2C1]

Example 43: Preparation of tert-butyl 5-(3-methylpyridin-4-yl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate, 4-bromo-3-methylpyridine hydrochloride was substituted for bromobenzene and 2 equivalents of triethylamine was utilized: $^1$H NMR (400 MHz, CDCl$_3$) δ8.03 (d, J=5.8 Hz, 1H), 7.97 (s, 1H), 6.37 (d, J=5.8 Hz, 1H), 3.64-3.44 (m, 4H), 3.33-3.10 (m, 4H), 2.86 (b, 2H), 2.24 (s, 3H), 1.38 (s, 9H); MS (LC/MS, M+H$^+$): m/z 304.2

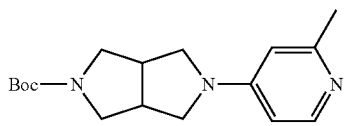

Example 44: Preparation of tert-butyl 5-(2-methylpyridin-4-yl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 4-bromo-2-methylpyridine was substituted for bromobenzene: $^1$H NMR (400 MHz, CDCl$_3$) δ7.99 (d, J=5.9 Hz, 1H), 6.13 (d, J=2.2 Hz, 1H), 6.09 (dd, J=2.4, 5.8 Hz, 1H), 3.54 (dd, J=7.2, 11.2 Hz, 2H), 3.42 (b, 2H), 3.21 (m, 1H), 3.17-2.99 (m, 3H), 2.88 (b, 2H), 2.32 (s, 3H), 1.36 (s, 9H); MS (LC/MS, M+H$^+$): m/z 304.2

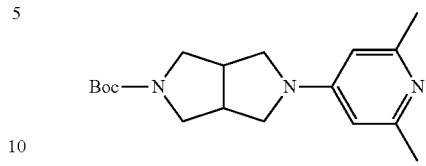

Example 45: Preparation of tert-butyl 5-(2,6-dimethylpyridin-4-yl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 4-bromo-2,6-dimethylpyridine was substituted for bromobenzene: $^1$H NMR (400 MHz, CDCl$_3$) δ5.98 (s, 2H), 3.52 (m, 2H), 3.41 (m, 2H), 3.21 (m, 1H), 3.16-2.99 (m, 3H), 2.86 (b, 2H), 2.29 (s, 6H), 1.34 (s, 9H); MS (LC/MS, M+H$^+$): m/z 318.2.

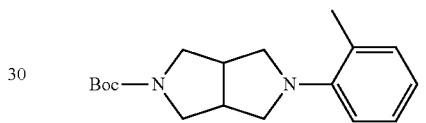

Example 46: Preparation of tert-butyl 5-(o-tolyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-2-methylbenzene was substituted for bromobenzene: $^1$H NMR (400 MHz, CDCl$_3$) δ7.18-7.10 (m, 2H), 6.96-6.89 (m, 2H), 3.69 (b, 2H), 3.36 (b, 2H), 3.18 (b, 2H), 3.05 (b, 2H), 2.91 (b, 2H), 2.33 (s, 3H), 1.52 (s, 9H); MS (LC/MS, M+H$^+$): m/z 303.2

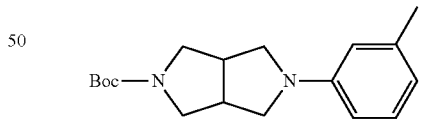

Example 47: Preparation of tert-butyl 5-(m-tolyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-3-methylbenzene was substituted for bromobenzene: $^1$H NMR (400 MHz, CDCl$_3$) δ7.17 (t, J=7.8 Hz, 1H), 6.59 (d, J=7.5 Hz, 1H), 6.46-6.37 (m, 2H), 3.68 (b, 2H), 3.52 (b, 2H), 3.42 (m, 1H), 3.29 (m, 1H), 3.23 (m, 2H), 2.97 (b, 2H), 2.38 (s, 3H), 1.54 (s, 9H); MS (LC/MS, M+H$^+$): m/z 303.2

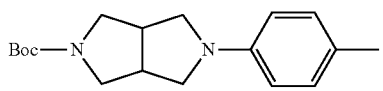

Example 48: Preparation of tert-butyl 5-(p-tolyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-4-methylbenzene was substituted for bromobenzene: $^1$H NMR (400 MHz, CDCl$_3$) δ7.09 (d, J=8.1 Hz, 2H), 6.52 (d, J=8.5 Hz, 2H), 3.68 (m, 2H), 3.57 (b, 2H), 3.42 (m, 1H), 3.28 (m, 1H), 3.21 (m, 2H), 3.00 (b, 2H), 2.30 (s, 3H), 1.51 (s, 9H); MS (LC/MS, M+H$^+$): m/z 303.2.

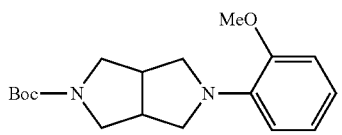

Example 49: Preparation of tert-butyl 5-(2-methoxyphenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-2-methoxybenzene was substituted for bromobenzene: $^1$H NMR (400 MHz, CDCl$_3$) δ6.91-6.78 (m, 3H), 6.76-6.67 (m, 1H), 3.80 (s, 3H), 3.61 (b, 2H), 3.45 (b, 2H), 3.40-3.22 (m, 2H), 3.14 (b, 2H), 2.90 (b, 2H), 1.46 (s, 9H); MS (LC/MS, M+H$^+$): m/z 319.2.

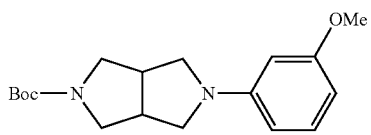 [SMILES: COc1cccc(N2CC3CN(C(=O)OC(C)(C)C)CC3C2)c1]

Example 50: Preparation of tert-butyl 5-(3-methoxyphenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-3-methoxybenzene was substituted for bromobenzene: $^1$H NMR (400 MHz, CDCl$_3$) δ7.13 (t, J=8.1 Hz, 1H), 6.29 (dd, J=2.2, 8.1 Hz, 1H), 6.18 (dd, J=1.8, 8.1 Hz, 1H), 6.10 (t, J=2.2 Hz, 1H), 3.79 (s, 3H), 3.63 (m, 2H), 3.50 (m, 2H), 3.37 (m, 1H), 3.30-3.11 (m, 3H), 2.95 (b, 2H), 1.48 (s, 9H); MS (LC/MS, M+H$^+$): m/z 319.2

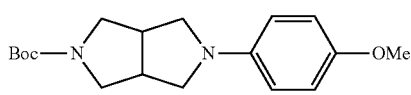 [SMILES: COc1ccc(N2CC3CN(C(=O)OC(C)(C)C)CC3C2)cc1]

Example 51: Preparation of tert-butyl 5-(4-methoxyphenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 1-bromo-4-methoxybenzene was substituted for bromobenzene: $^1$H NMR (400 MHz, CDCl$_3$) δ6.83 (d, J=9.0 Hz, 2H), 6.50 (d, J=9.0 Hz, 2H), 3.73 (s, 3H), 3.62 (m, 2H), 3.48-3.29 (m, 3H), 3.23 (m, 1H), 3.12 (dd, J=3.5, 9.3 Hz, 2H), 2.93 (b, 2H), 1.46 (s, 9H); MS (LC/MS, M+H$^+$): m/z 319.2.

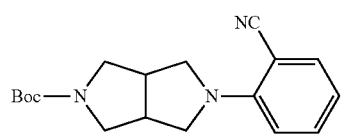

Example 52: Preparation of tert-butyl 5-(2-cyanophenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 2-bromobenzonitrile was substituted for bromobenzene: $^1$H NMR (400 MHz, CDCl$_3$) δ7.39 (dd, J=1.6, 7.8 Hz, 1H), 7.30 (m, 1H), 6.66 (t, J=7.5 Hz, 1H), 6.59 (d, J=8.5 Hz, 1H), 3.80 (m, 2H), 3.61 (m, 2H), 3.52 (m, 1H), 3.44 (m, 1H), 3.28 (m, 2H), 2.95 (b, 2H), 1.42 (s, 9H); MS (LC/MS, M+H$^+$): m/z 314.2.

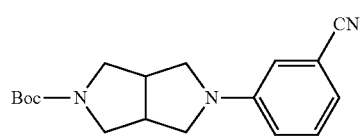 [SMILES: CC(C)(C)OC(=O)N1CC2CN(c3cccc(C#N)c3)CC2C1]

Example 53: Preparation of tert-butyl 5-(3-cyanophenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 3-bromobenzonitrile was substituted for bromobenzene: $^1$H NMR (400 MHz, CDCl$_3$) δ7.22 (m, 1H), 6.88 (d, J=7.5 Hz, 1H), 6.71-6.64 (m, 2H), 3.62 (m, 2H), 3.49 (m, 2H), 3.31 (m, 1H), 3.23 (m, 1H), 3.16 (dd, J=3.9, 9.7 Hz, 2H), 2.99 (b, 2H), 1.42 (s, 9H); MS (LC/MS, M+H$^+$): m/z 314.2

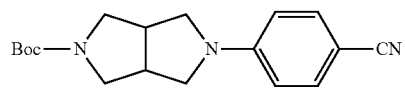 [SMILES: CC(C)(C)OC(=O)N1CC2CN(c3ccc(C#N)cc3)CC2C1]

Example 54: Preparation of tert-butyl 5-(4-cyanophenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3]heptane-2-carboxylic acid tert-butyl ester hemioxylate and 4-bromobenzonitrile was substituted for bromobenzene: ¹H NMR (400 MHz, CDCl₃) δ7.35 (d, J=8.9 Hz, 2H), 6.41 (d, J=8.9 Hz, 2H), 3.57 (m, 2H), 3.50 (m, 2H), 3.26 (m, 1H), 3.21-3.06 (m, 3H), 2.95 (b, 2H), 1.37 (s, 9H); MS (LC/MS, M+H⁺): m/z 314.2.

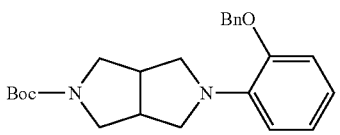

Example 55: Preparation of tert-butyl 5-(2-(benzyloxy) phenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3] heptane-2-carboxylic acid tert-butyl ester hemioxylate and 1-(benzyloxy)-2-bromobenzene was substituted for bromobenzene: ¹H NMR (400 MHz, CDCl₃) δ7.36-7.23 (m, 4H), 7.20 (m, 1H), 6.79 (m, 2H), 6.72 (m, 1H), 6.65 (m, 1H), 4.94 (s, 2H), 3.50 (b, 2H), 3.33 (m, 2H), 3.27-3.02 (m, 3H), 2.76 (b, 2H), 1.35 (s, 9H); MS (LC/MS, M+H⁺): m/z 395.2.

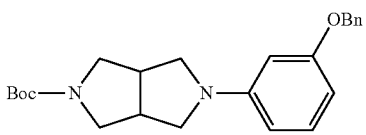 [SMILES: CC(C)(C)OC(=O)N1CC2CN(c3cccc(OCc4ccccc4)c3)CC2C1]

Example 56: Preparation of tert-butyl 5-(3-(benzyloxy) phenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3] heptane-2-carboxylic acid tert-butyl ester hemioxylate and 1-(benzyloxy)-3-bromobenzene was substituted for bromobenzene: ¹H NMR (400 MHz, CDCl₃) δ7.47 (m, 2H), 7.41 (t, J=7.6 Hz, 2H), 7.34 (m, 1H), 7.17 (t, J=8.2 Hz, 1H), 6.39 (dd, J=1.7, 8.0 Hz, 1H), 6.23 (m, 2H), 5.08 (s, 2H), 3.66 (m, 2H), 3.53 (m, 2H), 3.40 (m, 1H), 3.33-3.14 (m, 3H), 2.99 (b, 2H), 1.49 (s, 9H); MS (LC/MS, M+H⁺): m/z 395.2.

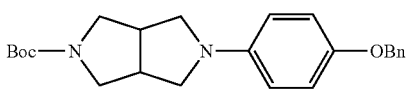

Example 57: Preparation of tert-butyl 5-(4-(benzyloxy) phenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3] heptane-2-carboxylic acid tert-butyl ester hemioxylate and 1-(benzyloxy)-4-bromobenzene was substituted for bromobenzene: ¹H NMR (400 MHz, CDCl₃) δ7.46 (m, 2H), 7.40 (t, J=7.8 Hz, 2H), 7.34 (m, 1H), 6.95 (d, J=9.0 Hz, 2H), 6.54 (d, J=8.8 Hz, 2H), 5.03 (s, 2H), 3.67 (b, 2H), 3.47 (b, 2H), 3.40 (m, 1H), 3.28 (m, 1H), 3.18 (dd, J=3.4, 9.3 Hz, 2H), 2.99 (b, 2H), 1.50 (s, 9H); MS (LC/MS, M+H⁺): m/z 395.2.

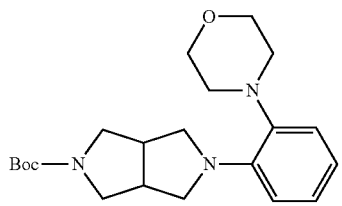 [SMILES: CC(C)(C)OC(=O)N1CC2CN(c3ccccc3N3CCOCC3)CC2C1]

Example 58: Preparation of tert-butyl 5-(2-morpholino-phenyl)hexahydropyrrolo[3,4-c]pyrrole-2(1H)-carboxylate: The title compound was prepared according to the procedure for tert-butyl 6-phenyl-2,6-diazaspiro[3.3]heptane-2-carboxylate, except tert-butyl hexahydropyrrolo[3,4-c]pyrrole-2(1H)-carboxylate was substituted for 2,6-diazaspiro[3.3] heptane-2-carboxylic acid tert-butyl ester hemioxylate and 4-(2-bromophenyl)morpholine was substituted for bromobenzene: ¹H NMR (400 MHz, CDCl₃) δ7.04-6.89 (m, 3H), 6.85 (d, J=7.8 Hz, 1H), 3.85 (t, J=4.5 Hz, 4H), 3.62 (b, 2H), 3.48-3.21 (m, 6H), 3.04 (t, J=4.5 Hz, 4H), 2.92 (b, 2H), 1.48 (s, 9H); MS (LC/MS, M+H⁺): m/z 374.2.

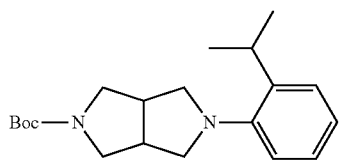 [SMILES: CC(C)c1ccccc1N1CC2CN(C(=O)OC(C)(C)C)CC2C1]

Example 59: Preparation of 2-benzyl-5-(2-isopropylphe-nyl)octahydropyrrolo[3,4-c]pyrrole: The title compound was prepared according to the procedure for tert-butyl 6-phenyl-2,6-diazaspiro[3.3]heptane-2-carboxylate, except 2-benzyloctahydropyrrolo[3,4-c]pyrrole was substituted for 2,6-diazaspiro[3.3]heptane-2-carboxylic acid tert-butyl ester hemioxylate and 1-bromo-2-isopropylbenzene was substituted for bromobenzene. The product was purified by column chromatography (dichloromethane/MeOH, 0%~5%). ¹H NMR (400 MHz, CDCl₃) δ7.54-7.33 (m, 6H), 7.32-7.11 (m, 3H), 3.77 (s, 2H), 3.65 (sept, J=6.9 Hz, 1H), 3.15 (m, 2H), 3.09-2.99 (m, 4H), 2.96 (m, 2H), 2.47 (dd, J=4.9, 8.8 Hz, 2H), 1.39 (d, J=6.9 Hz, 9H) MS (LC/MS, M+H⁺): m/z 321.2.

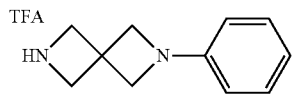 [SMILES: c1ccc(N2CC3(CNC3)C2)cc1]

Example 60: Preparation of 2-phenyl-2,6-diazaspiro[3.3] heptane trifluoroacetate: To a solution of tert-butyl 6-phenyl-2,6-diazaspiro[3.3]heptane-2-carboxylate (0.054 g, 0.196 mmol, 1 eq.) in dichloromethane (1 mL) at 0° C. was added trifluoroacetic acid (1 mL). The reaction was allowed to stir at 22° C. for 30 minutes before being diluted with MeOH and concentrated in vacuo to afford the product as a TFA salt. MS (LC/MS, M+H⁺): m/z 175.2.

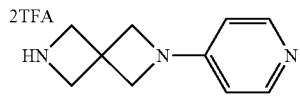

Example 61: Preparation of 2-(pyridin-4-yl)-2,6-diazaspiro[3.3]heptane ditrifluoroacetate: The title compound was prepared according to the procedure for 2-phenyl-2,6-diazaspiro[3.3]heptane trifluoroacetate, except tert-butyl 6-(pyridin-4-yl)-2,6-diazaspiro[3.3]heptane-2-carboxylate was substituted for tert-butyl 6-phenyl-2,6-diazaspiro[3.3]heptane-2-carboxylate: MS (LC/MS, M+H$^+$): m/z 176.2.

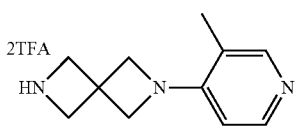

Example 62: Preparation of 2-(3-methylpyridin-4-yl)-2,6-diazaspiro[3.3]heptane ditrifluoroacetate: The title compound was prepared according to the procedure for 2-phenyl-2,6-diazaspiro[3.3]heptane trifluoroacetate, except tert-butyl 6-(3-methylpyridin-4-yl)-2,6-diazaspiro[3.3]heptane-2-carboxylate was substituted for tert-butyl 6-phenyl-2,6-diazaspiro[3.3]heptane-2-carboxylate: MS (LC/MS, M+H$^+$): m/z 190.2.

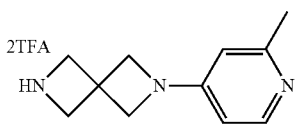

Example 63: Preparation of 2-(2-methylpyridin-4-yl)-2,6-diazaspiro[3.3]heptane ditrifluoroacetate: The title compound was prepared according to the procedure for 2-phenyl-2,6-diazaspiro[3.3]heptane trifluoroacetate, except tert-butyl 6-(2-methylpyridin-4-yl)-2,6-diazaspiro[3.3]heptane-2-carboxylate was substituted for tert-butyl 6-phenyl-2,6-diazaspiro[3.3]heptane-2-carboxylate: MS (LC/MS, M+H$^+$): m/z 190.2.

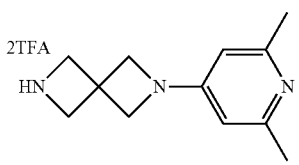

Example 64: Preparation of 2-(2,6-dimethylpyridin-4-yl)-2,6-diazaspiro[3.3]heptane: The title compound was prepared according to the procedure for 2-phenyl-2,6-diazaspiro[3.3]heptane trifluoroacetate, except tert-butyl 6-(2,6-dimethylpyridin-4-yl)-2,6-diazaspiro[3.3]heptane-2-carboxylate was substituted for tert-butyl 6-phenyl-2,6-diazaspiro[3.3]heptane-2-carboxylate: MS (LC/MS, M+H$^+$): m/z 204.2.

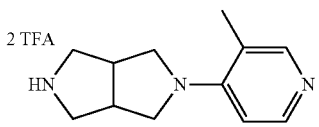

Example 65: Preparation of 2-(3-methylpyridin-4-yl)octahydropyrrolo[3,4-c]pyrrole ditrifluoroacetate: The title compound was prepared according to the procedure for 2-phenyl-2,6-diazaspiro[3.3]heptane trifluoroacetate, except tert-butyl 5-(3-methylpyridin-4-yl)hexahydropyrrolo[3,4-c]pyrrole-2(1H)-carboxylate was substituted for tert-butyl 6-phenyl-2,6-diazaspiro[3.3]heptane-2-carboxylate: MS (LC/MS, M+H$^+$): m/z 204.2.

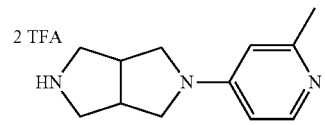

Example 66: Preparation of 2-(2-methylpyridin-4-yl)octahydropyrrolo[3,4-c]pyrrole ditrifluoroacetate: The title compound was prepared according to the procedure for 2-phenyl-2,6-diazaspiro[3.3]heptane trifluoroacetate, except tert-butyl 5-(2-methylpyridin-4-yl)hexahydropyrrolo[3,4-c]pyrrole-2(1H)-carboxylate was substituted for tert-butyl 6-phenyl-2,6-diazaspiro[3.3]heptane-2-carboxylate: MS (LC/MS, M+H$^+$): m/z 204.2.

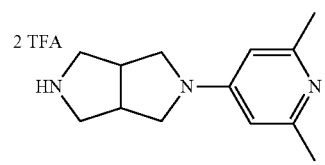 [SMILES: Cc1cc(N2CC3CNCC3C2)cc(C)n1]

Example 67: Preparation of 2-(2,6-dimethylpyridin-4-yl)octahydropyrrolo[3,4-c]pyrrole: The title compound was prepared according to the procedure for 2-phenyl-2,6-diazaspiro[3.3]heptane trifluoroacetate, except tert-butyl 5-(2,6-dimethylpyridin-4-yl)hexahydropyrrolo[3,4-c]pyrrole-2(1H)-carboxylate was substituted for tert-butyl 6-phenyl-2,6-diazaspiro[3.3]heptane-2-carboxylate: MS (LC/MS, M+H$^+$): m/z 218.2.

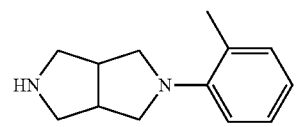

Example 68: Preparation of 2-(o-tolyl)octahydropyrrolo[3,4-c]pyrrole: To a solution of tert-butyl 5-(o-tolyl)hexahydropyrrolo[3,4-c]pyrrole-2(1H)-carboxylate (0.490 g, 1.62 mmol, 1 eq.) in dichloromethane (4 mL) at 0° C. was added trifluoroacetic acid (2 mL). The reaction was allowed to stir at 22° C. for 30 minutes before being diluted with MeOH and concentrated in vacuo to afford the product as a TFA salt. The salt was then suspended in sat. NaHCO$_3$ solution and the free based product was extracted with methylene chloride (3×15 mL). The combined organic layers were dried over Na$_2$SO$_4$, filtered and concentration in vacuo to afford the product as a free base: MS (LC/MS, M+H$^+$): m/z 203.2.

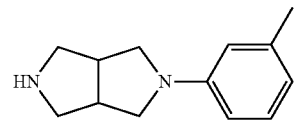

Example 69: Preparation of 2-(m-tolyl)octahydropyrrolo[3,4-c]pyrrole: The title compound was prepared according to the procedure for 2-(o-tolyl)octahydropyrrolo[3,4-c]pyrrole, except tert-butyl 5-(m-tolyl)hexahydropyrrolo[3,4-c]pyrrole-2(1H)-carboxylate was substituted for tert-butyl 5-(m-tolyl)hexahydropyrrolo[3,4-c]pyrrole-2(1H)-carboxylate: MS (LC/MS, M+H$^+$): m/z 203.2.

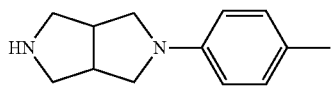

Example 70: Preparation of 2-(p-tolyl)octahydropyrrolo[3,4-c]pyrrole: The title compound was prepared according to the procedure for 2-(o-tolyl)octahydropyrrolo[3,4-c]pyrrole, except 5-(p-tolyl)hexahydropyrrolo[3,4-c]pyrrole-2(1H)-carboxylate was substituted for tert-butyl 5-(o-tolyl)hexahydropyrrolo[3,4-c]pyrrole-2(1H)-carboxylate: MS (LC/MS, M+H$^+$): m/z 203.2

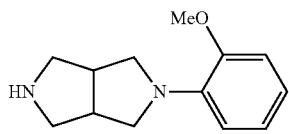 [SMILES: COc1ccccc1N1CC2CNCC2C1]

Example 71: Preparation of 2-(2-methoxyphenyl)octahydropyrrolo[3,4-c]pyrrole: The title compound was prepared according to the procedure for 2-(o-tolyl)octahydropyrrolo[3,4-c]pyrrole, except tert-butyl 5-(2-methoxyphenyl)hexahydropyrrolo[3,4-c]pyrrole-2(1H)-carboxylate was substituted for tert-butyl 5-(o-tolyl)hexahydropyrrolo[3,4-c]pyrrole-2(1H)-carboxylate: MS (LC/MS, M+H$^+$): m/z 219.2.

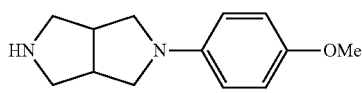

Example 72: Preparation of 2-(4-methoxyphenyl)octahydropyrrolo[3,4-c]pyrrole: The title compound was prepared according to the procedure for 2-(o-tolyl)octahydropyrrolo[3,4-c]pyrrole, except tert-butyl 5-(4-methoxyphenyl)hexahydropyrrolo[3,4-c]pyrrole-2(1H)-carboxylate was substituted for tert-butyl 5-(o-tolyl)hexahydropyrrolo[3,4-c]pyrrole-2(1H)-carboxylate: MS (LC/MS, M+H$^+$): m/z 219.2.

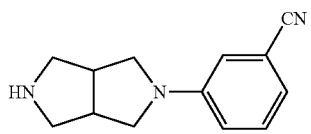 [SMILES: N#Cc1cccc(N2CC3CNCC3C2)c1]

Example 73: Preparation of 3-(hexahydropyrrolo[3,4-c]pyrrol-2(1H)-yl)benzonitrile: The title compound was prepared according to the procedure for 2-(o-tolyl)octahydropyrrolo[3,4-c]pyrrole, except tert-butyl 5-(3-cyanophenyl)hexahydropyrrolo[3,4-c]pyrrole-2(1H)-carboxylate was substituted for tert-butyl 5-(o-tolyl)hexahydropyrrolo[3,4-c]pyrrole-2(1H)-carboxylate: MS (LC/MS, M+H$^+$): m/z 214.2

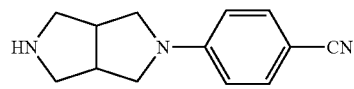 [SMILES: N#Cc1ccc(N2CC3CNCC3C2)cc1]

Example 74: Preparation of 4-(hexahydropyrrolo[3,4-c]pyrrol-2(1H)-yl)benzonitrile: The title compound was prepared according to the procedure for 2-(o-tolyl)octahydropyrrolo[3,4-c]pyrrole, except tert-butyl 5-(4-cyanophenyl)hexahydropyrrolo[3,4-c]pyrrole-2(1H)-carboxylate was substituted for tert-butyl 5-(o-tolyl)hexahydropyrrolo[3,4-c]pyrrole-2(1H)-carboxylate: MS (LC/MS, M+H$^+$): m/z 214.2.

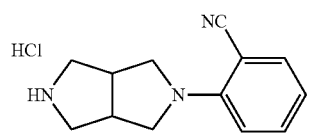 [SMILES: Cl ; N#Cc1ccccc1N1CC2CNCC2C1]

Example 75: Preparation of 2-(hexahydropyrrolo[3,4-c]pyrrol-2(1H)-yl)benzonitrile hydrochloride: To a solution of tert-butyl 5-(2-cyanophenyl)hexahydropyrrolo[3,4-c]pyrrole-2(1H)-carboxylate (0.408 g, 1.30 mmol, 1 eq.) in MeOH (1 mL) at 0° C. was added 1M methanolic HCl (3 mL). The reaction was allowed to stir at 22° C. overnight before being diluted with MeOH and concentrated in vacuo to afford the product as a HCl salt. MS (LC/MS, M+H$^+$): m/z 214.2.

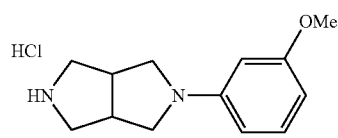 [SMILES: Cl ; COc1cccc(N2CC3CNCC3C2)c1]

Example 76: Preparation of 2-(3-methoxyphenyl)octahydropyrrolo[3,4-c]pyrrole hydrochloride: The title compound was prepared according to the procedure for 2-(hexahydropyrrolo[3,4-c]pyrrol-2(1H)-yl)benzonitrile hydrochloride, except tert-butyl 5-(3-methoxyphenyl)hexahydropyrrolo[3,4-c]pyrrole-2(1H)-carboxylate was substituted for tert-butyl 5-(2-cyanophenyl)hexahydropyrrolo[3,4-c]pyrrole-2(1H)-carboxylate: MS (LC/MS, M+H$^+$): m/z 219.2.

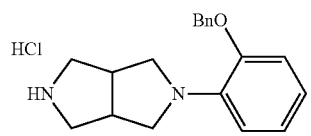 [SMILES: Cl ; c1ccc(COc2ccccc2N2CC3CNCC3C2)cc1]

Example 77: Preparation of 2-(2-(benzyloxy)phenyl)octahydropyrrolo[3,4-c]pyrrole hydrochloride: The title compound was prepared according to the procedure for 2-(hexahydropyrrolo[3,4-c]pyrrol-2(1H)-yl)benzonitrile hydrochloride, except tert-butyl 5-(2-(benzyloxy)phenyl)hexahydropyrrolo[3,4-c]pyrrole-2(1H)-carboxylate was substituted for tert-butyl 5-(2-cyanophenyl)hexahydropyrrolo[3,4-c]pyrrole-2(1H)-carboxylate: MS (LC/MS, M+H$^+$): m/z 295.2.

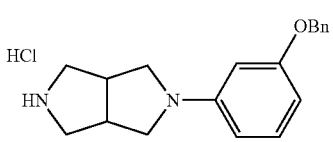 [SMILES: Cl ; c1ccc(COc2cccc(N3CC4CNCC4C3)c2)cc1]

Example 78: Preparation of 2-(3-(benzyloxy)phenyl)octahydropyrrolo[3,4-c]pyrrole hydrochloride: The title compound was prepared according to the procedure for 2-(hexahydropyrrolo[3,4-c]pyrrol-2(1H)-yl)benzonitrile hydrochloride, except tert-butyl 5-(3-(benzyloxy)phenyl)hexahydropyrrolo[3,4-c]pyrrole-2(1H)-carboxylate was substituted for tert-butyl 5-(2-cyanophenyl)hexahydropyrrolo[3,4-c]pyrrole-2(1H)-carboxylate: MS (LC/MS, M+H$^+$): m/z 295.2.

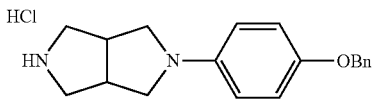

Example 79: Preparation of 2-(4-(benzyloxy)phenyl)octahydropyrrolo[3,4-c]pyrrole hydrochloride: The title compound was prepared according to the procedure for 2-(hexahydropyrrolo[3,4-c]pyrrol-2(1H)-yl)benzonitrile hydrochloride, except tert-butyl 5-(4-(benzyloxy)phenyl)hexahydropyrrolo[3,4-c]pyrrole-2(1H)-carboxylate was substituted for tert-butyl 5-(2-cyanophenyl)hexahydropyrrolo[3,4-c]pyrrole-2(1H)-carboxylate: MS (LC/MS, M+H$^+$): m/z 295.2.

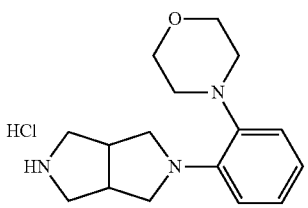 [SMILES: Cl ; c1ccc(N2CC3CNCC3C2)c(N2CCOCC2)c1]

Example 80: Preparation of 4-(2-(hexahydropyrrolo[3,4-c]pyrrol-2(1H)-yl)phenyl)morpholine hydrochloride: The title compound was prepared according to the procedure for 2-(hexahydropyrrolo[3,4-c]pyrrol-2(1H)-yl)benzonitrile hydrochloride, except tert-butyl 5-(2-morpholinophenyl)hexahydropyrrolo[3,4-c]pyrrole-2(1H)-carboxylate was substituted for tert-butyl 5-(2-cyanophenyl)hexahydropyrrolo[3,4-c]pyrrole-2(1H)-carboxylate: MS (LC/MS, M+H$^+$): m/z 274.2.

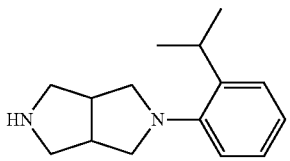 [SMILES: CC(C)c1ccccc1N1CC2CNCC2C1]

Example 81: Preparation of 2-(2-isopropylphenyl)octahydropyrrolo[3,4-c]pyrrole: To a dry round bottom flask, 0.04 g of 10% Pd/C (20% wt) was added and wet with a small amount of ethyl acetate. Following, a solution of 2-benzyl-5-(2-isopropylphenyl)octahydropyrrolo[3,4-c]pyrrole (0.20 g, 0.624 mmol, 1 eq.) in MeOH (2.1 mL) was added slowly to the Pd/C containing round bottom flask. This system was then flushed 3× with H$_2$, using a balloon filled with H$_2$. The reaction was allowed to stir under 1 atm H$_2$ for 5 days at room temperature. The Pd/C was removed via filtration through a plug of Celite. The filtrate was concentrated in vacuo to afford a crude oil of 2-(2-isopropylphenyl)octahydropyrrolo[3,4-c]pyrrole which was used in the next step without further purification. MS (LC/MS, M+H$^+$): m/z 231.2.

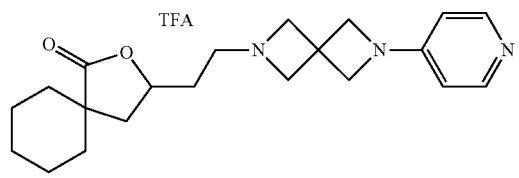 [SMILES: O=C1OC(CCN2CC3(C2)CN(c2ccncc2)C3)CC12CCCCC2]

Example 82: Preparation of 3-(2-(6-(pyridin-4-yl)-2,6-diazaspiro[3.3]heptan-2-yl)ethyl)-2-oxaspiro[4.5]decan-1-one trifluoroacetate: A mixture of 3-(2-bromoethyl)-2-oxaspiro[4.5]decan-1-one (0.057 g, 0.221 mmol, 1 eq.), acetonitrile (2 mL), 2-(pyridin-4-yl)-2,6-diazaspiro[3.3]heptane ditrifluoroacetate (0.098 g, 0.266 mmol, 1.2 eq.) and K$_2$CO$_3$ (0.153 g, 1.11 mmol, 5 eq.) was refluxed and stirred for 3 days. The resulting mixture was then filtered and concentrated in vacuo to give a crude residue that was first purified by column chromatography (methanol/dichloromethane, 0%~10% w/0.1% NH$_4$OH). The resulting fractions were further purified by column chromatography on a C18 column. (acetonitrile/H$_2$O, 0%~100%, w/0.1% TFA) $^1$H NMR (400 MHz, MeOD) δ8.11 (d, J=7.4 Hz, 2H), 6.67 (d, J=7.1 Hz, 2H), 4.70-4.17 (b, 9H), 3.44 (m, 2H), 2.54 (dd, J=6.2, 12.9 Hz, 1H), 2.10-1.99 (m, 1H), 1.98-1.86 (m, 1H), 1.83-1.61 (m, 6H), 1.60-1.44 (m, 3H), 1.43-1.21 (m, 2H); MS (LC/MS, M+H$^+$): =356.2.

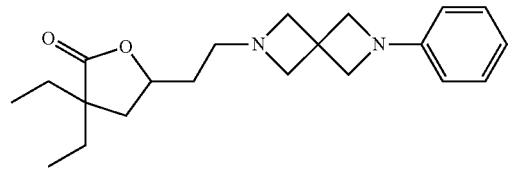 [SMILES: CCC1(CC)CC(CCN2CC3(C2)CN(c2ccccc2)C3)OC1=O]

Example 83: Preparation of 3,3-diethyl-5-(2-(6-phenyl-2,6-diazaspiro[3.3]heptan-2-yl)ethyl)dihydrofuran-2(3H)-one: A mixture of 5-(2-bromoethyl)-3,3-diethyldihydrofuran-2(3H)-one (0.080 g, 0.324 mmol, 1 eq.), acetonitrile (2 mL), 2-phenyl-2,6-diazaspiro[3.3]heptane trifluoroacetate (0.288 g, 0.389 mmol, 1.2 eq.) and K$_2$CO$_3$ (0.224 g, 1.62 mmol, 5 eq.) was refluxed and stirred for 3 days. The resulting mixture was then filtered and concentrated in vacuo to give a crude residue that was first purified by column chromatography (methanol/dichloromethane, 0%~10%). $^1$H NMR (400 MHz, CDCl$_3$) δ7.13 (m, 2H), 6.67 (t, J=7.4 Hz, 1H), 6.37 (d, J=8.2 Hz, 2H), 4.36 (m, 1H), 3.85 (s, 4H), 3.29 (s, 4H), 2.48 (t, J=7.1 Hz, 2H), 2.04 (dd, J=6.7, 13.0 Hz, 1H), 1.71 (dd, J=9.4, 13.1 Hz, 1H), 1.67-1.43 (m, 6H), 1.83-1.61 (m, 6H), 0.85 (dt, J=7.5, 21.9 Hz, 6H); MS (LC/MS, M+H$^+$): 343.2.

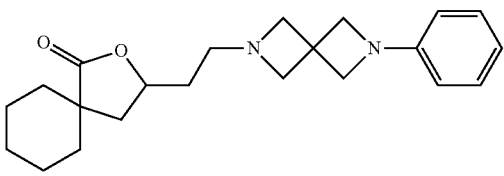 [SMILES: O=C1OC(CCN2CC3(C2)CN(c2ccccc2)C3)CC12CCCCC2]

Example 84: Preparation of 3-(2-(6-phenyl-2,6-diazaspiro[3.3]heptan-2-yl)ethyl)-2-oxaspiro[4.5]decan-1-one: The title compound was prepared according to the procedure for 3,3-diethyl-5-(2-(6-phenyl-2,6-diazaspiro[3.3]heptan-2-yl)ethyl)dihydrofuran-2(3H)-one, except 3-(2-bromoethyl)-2-oxaspiro[4.5]decan-1-one was substituted for 5-(2-bromoethyl)-3,3-diethyldihydrofuran-2(3H)-one: $^1$H NMR (400 MHz, CDCl$_3$) δ7.13 (m, 2H), 6.67 (t, J=7.4 Hz, 1H), 6.37 (d, J=8.5 Hz, 2H), 4.38 (m, 1H), 3.86 (s, 4H), 3.29 (s, 4H), 2.50 (t, J=7.9 Hz, 2H), 2.30 (dd, J=6.2, 12.9 Hz, 1H), 1.81-1.45 (m, 9H), 1.45-1.37 (m, 1H), 1.37-1.08 (m, 3H); MS (LC/MS, M+H$^+$): m/z 355.2.

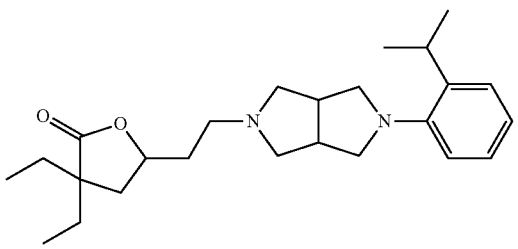 [SMILES: CCC1(CC)CC(CCN2CC3CN(c4ccccc4C(C)C)CC3C2)OC1=O]

Example 85: Preparation of 3,3-diethyl-5-(2-(5-(2-isopropylphenyl)hexahydropyrrolo[3,4-c]pyrrol-2(1H)-yl)ethyl)dihydrofuran-2(3H)-one: The title compound was prepared according to the procedure for 3,3-diethyl-5-(2-(6-phenyl-2,6-diazaspiro[3.3]heptan-2-yl)ethyl)dihydrofuran-2(3H)-one, except 2-(2-isopropylphenyl)octahydropyrrolo[3,4-c]pyrrole was substituted for 2-phenyl-2,6-diazaspiro[3.3]heptane trifluoroacetate: $^1$H NMR (400 MHz, CDCl$_3$) δ7.18 (dd, J=1.5, 7.4 Hz, 1H), 7.10-6.90 (m, 3H), 4.43 (m, 1H), 3.38 (sept, J=6.9 Hz, 1H), 3.01-2.84 (m, 4H), 2.83-2.66 (m, 4H), 2.52 (t, J=6.8 Hz, 2H), 2.19 (m, 2H), 2.06 (dd, J=6.8, 13.1 Hz, 1H), 1.91-1.67 (m, 3H), 1.63-1.44 (m, 4H), 1.15 (d, J=6.9 Hz, 6H), 0.86 (dt, J=7.3, 19.3 Hz, 6H); MS (LC/MS, M+H$^+$): m/z 399.2.

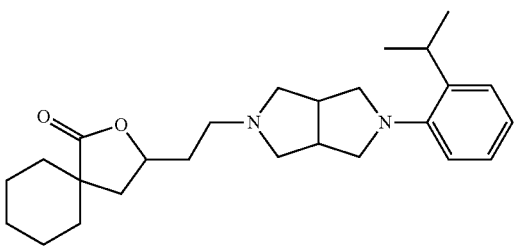 [SMILES: CC(C)c1ccccc1N1CC2CN(CCC3CC4(CCCCC4)C(=O)O3)CC2C1]

Example 86: Preparation of 3-(2-(5-(2-isopropylphenyl)hexahydropyrrolo[3,4-c]pyrrol-2(1H)-yl)ethyl)-2-oxaspiro[4.5]decan-1-one: The title compound was prepared according to the procedure for 3,3-diethyl-5-(2-(6-phenyl-2,6-diazaspiro[3.3]heptan-2-yl)ethyl)dihydrofuran-2(3H)-one, except 3-(2-bromoethyl)-2-oxaspiro[4.5]decan-1-one was substituted for 5-(2-bromoethyl)-3,3-diethyldihydrofuran-2(3H)-one and 2-(2-isopropylphenyl)octahydropyrrolo[3,4-c]pyrrole was substituted for 2-phenyl-2,6-diazaspiro[3.3]heptane trifluoroacetate: $^1$H NMR (400 MHz, CDCl$_3$) δ7.18 (dd, J=1.5, 7.0 Hz, 1H), 7.09-6.94 (m, 3H), 4.44 (m, 1H), 3.37 (sept, J=6.8 Hz, 1H), 2.99-2.83 (m, 4H), 2.82-2.66 (m, 4H), 2.52 (t, J=7.2 Hz, 2H), 2.32 (dd, J=6.3, 12.7 Hz, 1H), 2.24-2.12 (m, 2H), 1.93-1.81 (m, 1H), 1.80-1.46 (m, 8H), 1.46-1.37 (m, 1H), 1.37-1.04 (m, 9H) MS (LC/MS, M+H$^+$): m/z 411.2.

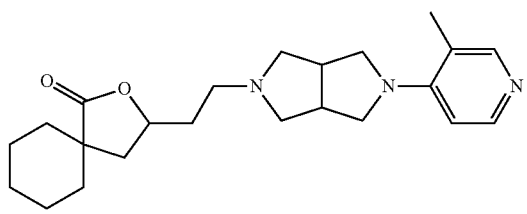 [SMILES: Cc1cnccc1N1CC2CN(CCC3CC4(CCCCC4)C(=O)O3)CC2C1]

Example 87: Preparation of 3-(2-(5-(3-methylpyridin-4-yl)hexahydropyrrolo[3,4-c]pyrrol-2(1H)-yl)ethyl)-2-oxaspiro[4.5]decan-1-one: A mixture of 3-(2-bromoethyl)-2-oxaspiro[4.5]decan-1-one (0.100 g, 0.383 mmol, 1 eq.), acetonitrile (4 mL), 2-(3-methylpyridin-4-yl)octahydropyrrolo[3,4-c]pyrrole ditrifluoroacetate (0.299 g, 0.766 mmol, 2 eq.) and K$_2$CO$_3$ (0.264 g, 1.91 mmol, 5 eq.) was refluxed and stirred for 3 days. The resulting mixture was then filtered and concentrated in vacuo to give a crude residue that was first purified by column chromatography on a C18 column. (acetonitrile/H$_2$O, 0%~100%, w/0.1% NH$_4$OH). The resulting fractions were further purified by column chromatography (methanol/dichloromethane, 0%~10% w/0.1% NH$_4$OH). $^1$H NMR (400 MHz, CDCl$_3$) δ8.06 (d, J=18.7 Hz, 2H), 6.49 (d, J=4.7 Hz, 1H), 4.38 (m, 1H), 3.20 (m, 2H), 3.04 (m, 2H), 2.83-2.66 (m, 4H), 2.47 (m, 2H), 2.35-2.21 (m, 3H), 2.17 (s, 3H), 1.85-1.74 (m, 1H), 1.74-1.40 (m, 8H), 1.40-1.32 (m, 1H), 1.31-1.02 (m, 3H); MS (LC/MS, M+H$^+$): m/z 384.2.

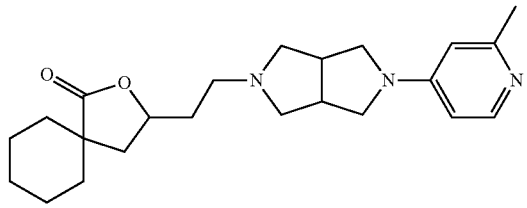 [SMILES: Cc1cc(N2CC3CN(CCC4CC5(CCCCC5)C(=O)O4)CC3C2)ccn1]

Example 88: Preparation of 3-(2-(5-(2-methylpyridin-4-yl)hexahydropyrrolo[3,4-c]pyrrol-2(1H)-yl)ethyl)-2-oxaspiro[4.5]decan-1-one: The title compound was prepared according to the procedure for 3-(2-(5-(3-methylpyridin-4-yl)hexahydropyrrolo[3,4-c]pyrrol-2(1H)-yl)ethyl)-2-oxaspiro[4.5]decan-1-one, except 2-(2-methylpyridin-4-yl)octahydropyrrolo[3,4-c]pyrrole ditrifluoroacetate was substituted for 2-(3-methylpyridin-4-yl)octahydropyrrolo[3,4-c]pyrrole ditrifluoroacetate: $^1$H NMR (400 MHz, CDCl$_3$) δ7.99 (d, J=5.4 Hz, 1H), 6.23-6.07 (m, 2H), 4.35 (m, 1H), 3.40 (t, J=8.5 Hz, 2H), 3.08 (dt, J=3.3, 9.9 Hz, 2H), 2.85 (b, 2H), 2.65-2.53 (m, 2H), 2.52-2.36 (m, 4H), 2.32 (s, 3H), 2.25 (dd, J=6.3, 12.8 Hz, 1H), 1.84-1.39 (m, 9H), 1.39-1.29 (m, 1H), 1.28-1.01 (m, 3H); MS (LC/MS, M+H$^+$): m/z 384.2

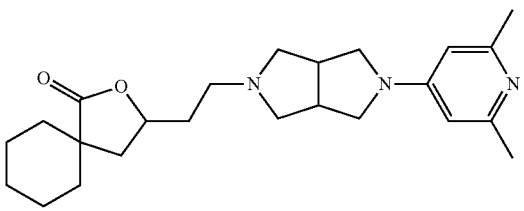 [SMILES: Cc1cc(N2CC3CN(CCC4CC5(CCCCC5)C(=O)O4)CC3C2)cc(C)n1]

Example 89: Preparation of 3-(2-(5-(2,6-dimethylpyridin-4-yl)hexahydropyrrolo[3,4-c]pyrrol-2(1H)-yl)ethyl)-2-oxaspiro[4.5]decan-1-one: The title compound was prepared according to the procedure for 3-(2-(5-(3-methylpyridin-4-yl)hexahydropyrrolo[3,4-c]pyrrol-2(1H)-yl)ethyl)-2-oxaspiro[4.5]decan-1-one, except 2-(2,6-dimethylpyridin-4-yl)octahydropyrrolo[3,4-c]pyrroleditrifluoroacetate was substituted for 2-(3-methylpyridin-4-yl)octahydropyrrolo[3,4-c]pyrrole ditrifluoroacetate: $^1$H NMR (400 MHz, CDCl$_3$) δ6.02 (s, 2H), 4.35 (m, 1H), 3.38 (m, 2H), 3.08 (dt, J=3.1, 9.9 Hz, 2H), 2.84 (b, 2H), 2.68-2.53 (m, 2H), 2.53-2.36 (m, 4H), 2.36-2.17 (m, 7H), 1.84-1.39 (m, 9H), 1.38-1.30 (m, 1H), 1.28-0.97 (m, 3H); MS (LC/MS, M+H$^+$): m/z 398.2.

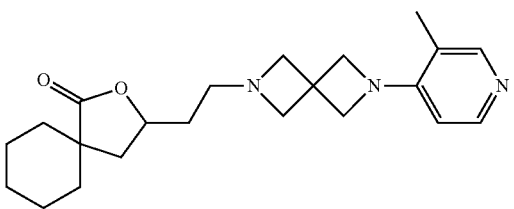 [SMILES: Cc1cnccc1N1CC2(CN(CCC3CC4(CCCCC4)C(=O)O3)C2)C1]

Example 90: Preparation of 3-(2-(6-(3-methylpyridin-4-yl)-2,6-diazaspiro[3.3]heptan-2-yl)ethyl)-2-oxaspiro[4.5]decan-1-one: The title compound was prepared according to the procedure for 3-(2-(5-(3-methylpyridin-4-yl)hexahydropyrrolo[3,4-c]pyrrol-2(1H)-yl)ethyl)-2-oxaspiro[4.5]decan-1-one, except 2-(3-methylpyridin-4-yl)-2,6-diazaspiro[3.3]heptane ditrifluoroacetate was substituted for 2-(3-methylpyridin-4-yl)octahydropyrrolo[3,4-c]pyrrole ditrifluoroacetate: $^1$H NMR (400 MHz, CDCl$_3$) δ8.02 (d, J=5.2 Hz, 1H), 7.90 (s, 1H), 6.11 (d, J=5.6 Hz, 1H), 4.38 (m, 1H), 4.06 (s, 4H), 3.29 (s, 4H), 2.49 (t, J=7.8 Hz, 2H), 2.30 (dd, J=6.2, 12.9 Hz, 1H), 2.11 (s, 3H), 1.83-1.45 (m, 9H), 1.45-1.37 (m, 1H), 1.37-1.08 (m, 3H); MS (LC/MS, M+H$^+$): m/z 370.2.

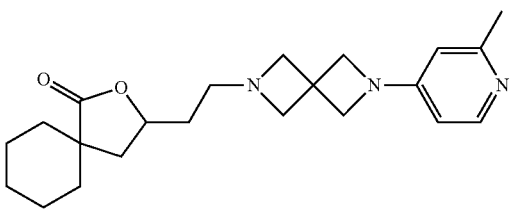 [SMILES: Cc1cc(N2CC3(CN(CCC4CC5(CCCCC5)C(=O)O4)C3)C2)ccn1]

Example 91: Preparation of 3-(2-(6-(2-methylpyridin-4-yl)-2,6-diazaspiro[3.3]heptan-2-yl)ethyl)-2-oxaspiro[4.5]decan-1-one: The title compound was prepared according to the procedure for 3-(2-(5-(3-methylpyridin-4-yl)hexahydropyrrolo[3,4-c]pyrrol-2(1H)-yl)ethyl)-2-oxaspiro[4.5]decan-1-one, except 2-(2-methylpyridin-4-yl)-2,6-diazaspiro[3.3]heptane ditrifluoroacetate was substituted for 2-(3-methylpyridin-4-yl)octahydropyrrolo[3,4-c]pyrrole ditrifluoroacetate: $^1$H NMR (400 MHz, CDCl$_3$) δ8.03 (d, J=5.4 Hz, 1H), 6.07-5.97 (m, 2H), 4.38 (m, 1H), 3.91 (s, 4H), 3.28 (s, 4H), 2.55-2.41 (m, 2H), 2.34 (s, 3H), 2.30 (dd, J=6.2, 12.8 Hz, 1H), 1.82-1.45 (m, 9H), 1.45-1.37 (m, 1H), 1.37-1.07 (m, 3H); MS (LC/MS, M+H$^+$): m/z 370.2.

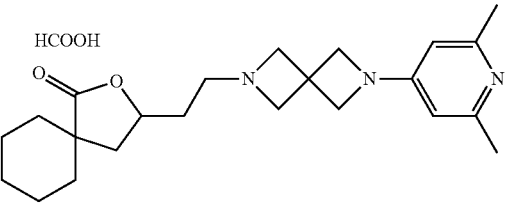 [SMILES: Cc1cc(N2CC3(CN(CCC4CC5(CCCCC5)C(=O)O4)C3)C2)cc(C)n1 ; "HCOOH"]

Example 92: Preparation of 3-(2-(6-(2,6-dimethylpyridin-4-yl)-2,6-diazaspiro[3.3]heptan-2-yl)ethyl)-2-oxaspiro[4.5]decan-1-one: The title compound was prepared according to the procedure for 3-(2-(5-(3-methylpyridin-4-yl)hexahydropyrrolo[3,4-c]pyrrol-2(1H)-yl)ethyl)-2-oxaspiro[4.5]decan-1-one, except 2-(2,6-dimethylpyridin-4-yl)-2,6-diazaspiro[3.3]heptane ditrifluoroacetate was substituted for 2-(3-methylpyridin-4-yl)octahydropyrrolo[3,4-c]pyrrole ditrifluoroacetate. A third purification was need via column chromatography on a C18 column. (acetonitrile/H$_2$O, 0%~100%, w/0.1% HCOOH): $^1$H NMR (400 MHz, CDCl$_3$) δ5.97 (s, 2H), 4.45 (m, 1H), 4.21 (s, 4H), 3.55 (s, 4H), 2.70 (m, 2H), 2.57 (s, 6H), 2.40 (dd, J=6.2, 12.7 Hz, 1H), 1.91-1.54 (m, 9H), 1.54-1.45 (m, 1H), 1.45-1.13 (m, 3H); MS (LC/MS, M+H$^+$): m/z 384.2.

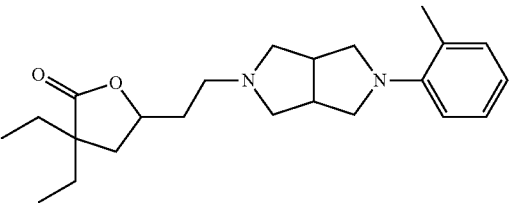 [SMILES: CCC1(CC)CC(CCN2CC3CN(c4ccccc4C)CC3C2)OC1=O]

Example 93: Preparation of 3,3-diethyl-5-(2-(5-(o-tolyl)hexahydropyrrolo[3,4-c]pyrrol-2(1H)-yl)ethyl)dihydrofuran-2(3H)-one: A mixture of 5-(2-bromoethyl)-3,3-diethyldihydrofuran-2(3H)-one (0.075 g, 0.301 mmol, 1 eq.), acetonitrile (3 mL), 2-(o-tolyl)octahydropyrrolo[3,4-c]pyrrole (0.073 g, 0.361 mmol, 1.2 eq.) and N,N-diisopropylethyl amine (0.116 g, 0.903 mmol, 3 eq.) was microwaved at 120° C. for 4 hrs. The resulting solution was concentrated in vacuo to give a crude residue that was first purified by column chromatography (methanol/dichloromethane, 0%~10%). $^1$H NMR (400 MHz, CDCl$_3$) δ7.15 (m, 2H), 6.96 (m, 2H), 4.50 (m, 1H), 3.08-2.92 (m, 6H), 2.86 (b, 2H), 2.60 (t, J=6.9 Hz, 2H), 2.37-2.24 (m, 5H), 2.14 (dd, J=6.7, 13.0 Hz, 1H), 1.99-1.75 (m, 3H), 1.64 (m, 4H), 0.94 (dt, J=7.4, 18.1 Hz, 6H); MS (LC/MS, M+H$^+$): m/z 371.2.

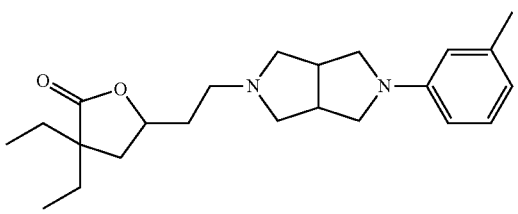

Example 94: Preparation of 3,3-diethyl-5-(2-(5-(m-tolyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(m-tolyl)octahydropyrrolo[3,4-c]pyrrole was substituted for 2-(o-tolyl)octahydropyrrolo[3,4-c]pyrrole: $^1$H NMR (400 MHz, CDCl$_3$) δ7.13 (t, J=8.0 Hz, 1H), 6.58 (d, J=7.4 Hz, 1H), 6.53-6.45 (m, 2H), 4.47 (m, 1H), 3.37 (m, 2H), 3.18 (dt, J=2.8, 9.4 Hz, 2H), 2.95 (b, 2H), 2.86 (m, 2H), 2.59 (t, J=7.0 Hz, 2H), 2.41 (dd, J=4.0, 8.9 Hz, 2H), 2.33 (s, 3H), 2.12 (dd, J=6.6, 13.0 Hz, 1H), 1.97-1.73 (m, 3H), 1.62 (q, J=7.5 Hz, 4H), 0.92 (dt, J=7.5, 14.8 Hz, 6H); MS (LC/MS, M+H$^+$): m/z 371.2.

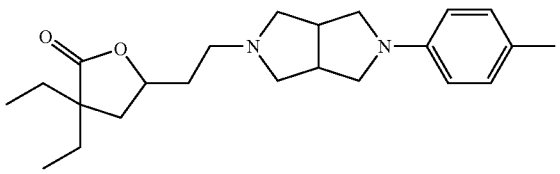 [SMILES: CCC1(CC)CC(CCN2CC3CN(c4ccc(C)cc4)CC3C2)OC1=O]

Example 95: Preparation of 3,3-diethyl-5-(2-(5-(p-tolyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(p-tolyl)octahydropyrrolo[3,4-c]pyrrole was substituted for 2-(o-tolyl)octahydropyrrolo[3,4-c]pyrrole: $^1$H NMR (400 MHz, CDCl$_3$) δ6.89 (d, J=8.4 Hz, 2H), 6.45 (d, J=8.4 Hz, 2H), 4.32 (m, 1H), 3.17 (m, 2H), 2.99 (dt, J=3.0, 9.2 Hz, 2H), 2.78 (b, 2H), 2.70 (m, 2H), 2.42 (t, J=6.9 Hz, 2H), 2.42 (dd, J=4.0, 8.8 Hz, 2H), 2.11 (s, 3H), 2.97 (dd, J=6.8, 13.0 Hz, 1H), 1.81-1.57 (m, 3H), 1.45 (q, J=7.2 Hz, 4H), 0.76 (dt, J=7.5, 14.7 Hz, 6H); MS (LC/MS, M+H$^+$): m/z 371.2.

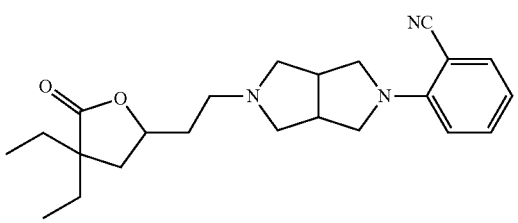 [SMILES: CCC1(CC)CC(CCN2CC3CN(c4ccccc4C#N)CC3C2)OC1=O]

Example 96: Preparation of 2-(5-(2-(4,4-diethyl-5-oxotetrahydrofuran-2-yl)ethyl)hexahydropyrrolo[3,4-c]pyrrol-2(1H)-yl)benzonitrile: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(hexahydropyrrolo[3,4-c]pyrrol-2(1H)-yl)benzonitrile hydrochloride was substituted for 2-(o-tolyl)octahydropyrrolo[3,4-c]pyrrole: $^1$H NMR (400 MHz, CDCl$_3$) δ7.45 (dd, J=1.5, 7.6 Hz, 1H), 7.36 (m, 1H), 6.81-6.68 (m, 2H), 4.45 (m, 1H), 3.62 (m, 2H), 3.45 (td, J=2.0, 8.6 Hz, 2H), 2.92 (b, 2H), 2.74 (m, 2H), 2.63-2.53 (m, 2H), 2.52-2.46 (m, 2H), 2.11 (dd, J=6.8, 13.0 Hz, 1H), 1.94-1.70 (m, 3H), 1.58 (qd, J=2.6, 7.4 Hz, 4H), 0.88 (dt, J=7.3, 14.8 Hz, 6H); MS (LC/MS, M+H$^+$): m/z 382.2.

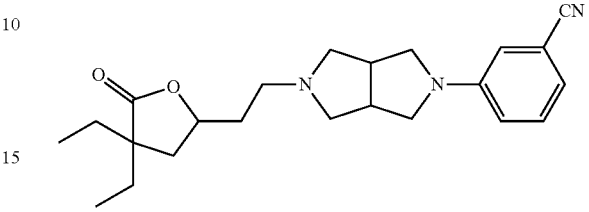

Example 97: Preparation of 3-(5-(2-(4,4-diethyl-5-oxotetrahydrofuran-2-yl)ethyl)hexahydropyrrolo[3,4-c]pyrrol-2(1H)-yl)benzonitrile: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 3-(hexahydropyrrolo[3,4-c]pyrrol-2(1H)-yl)benzonitrile was substituted for 2-(o-tolyl)octahydropyrrolo[3,4-c]pyrrole: $^1$H NMR (400 MHz, CDCl$_3$) δ7.26 (m, 1H), 6.95 (d, J=7.5 Hz, 1H), 6.82-6.75 (m, 2H), 4.44 (m, 1H), 3.44 (t, J=8.7 Hz, 2H), 3.15 (dt, J=3.8, 9.4 Hz, 2H), 2.98 (b, 2H), 2.73 (m, 2H), 2.57 (t, J=7.0 Hz, 2H), 2.50 (dd, J=3.1, 9.1 Hz, 2H), 2.10 (dd, J=6.8, 12.9 Hz, 1H), 1.94-1.70 (m, 3H), 1.59 (q, J=7.3 Hz, 4H), 0.89 (dt, J=5.4, 14.9 Hz, 6H); MS (LC/MS, M+H$^+$): m/z 382.2.

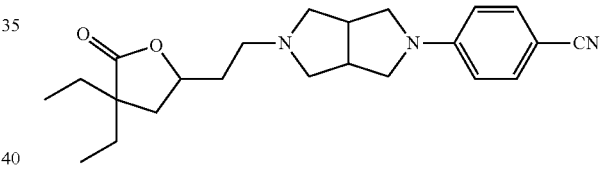

Example 98: Preparation of 4-(5-(2-(4,4-diethyl-5-oxotetrahydrofuran-2-yl)ethyl)hexahydropyrrolo[3,4-c]pyrrol-2(1H)-yl)benzonitrile: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 4-(hexahydropyrrolo[3,4-c]pyrrol-2(1H)-yl)benzonitrile was substituted for 2-(o-tolyl)octahydropyrrolo[3,4-c]pyrrole: $^1$H NMR (400 MHz, CDCl$_3$) δ7.44 (d, J=8.9 Hz, 2H), 6.54 (d, J=8.7 Hz, 2H), 4.44 (m, 1H), 3.55 (t, J=9.0 Hz, 2H), 3.23 (dt, J=3.6, 9.9 Hz, 2H), 3.00 (b, 2H), 2.72 (m, 2H), 2.64-2.50 (m, 4H), 2.10 (dd, J=6.7, 13.1 Hz, 1H), 1.94-1.71 (m, 3H), 1.59 (q, J=7.5 Hz, 4H), 0.89 (dt, J=5.1, 14.9 Hz, 6H); MS (LC/MS, M+H$^+$): m/z 382.2.

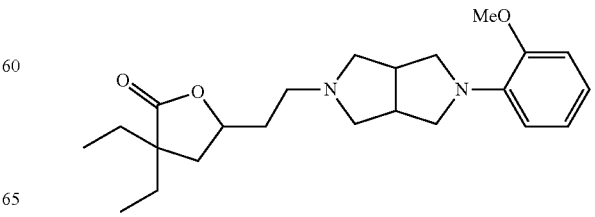

Example 99: Preparation of 3,3-diethyl-5-(2-(5-(2-methoxyphenyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(2-methoxyphenyl)octahydropyrrolo[3,4-c]pyrrole was substituted for 2-(o-tolyl)octahydropyrrolo[3,4-c]pyrrole: $^1$H NMR (400 MHz, CDCl$_3$) δ6.83-6.61 (m, 4H), 4.34 (m, 1H), 3.71 (s, 3H), 3.23 (q, J=7.5 Hz, 2H), 2.86 (m, 2H), 2.72 (b, 2H), 2.58 (b, 2H), 2.44 (m, 2H), 2.31 (dt, J=3.2, 8.8 Hz, 2H), 1.98 (dd, J=6.8, 13.1 Hz, 1H), 1.84-1.73 (m, 1H), 1.73-1.58 (m, 2H), 1.47 (qd, J=1.5, 7.5 Hz, 4H), 0.77 (dt, J=7.3, 15.8 Hz, 6H); MS (LC/MS, M+H$^+$): m/z 387.2.

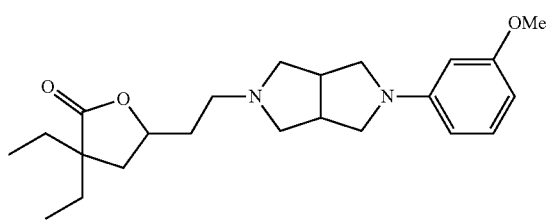 [SMILES: CCC1(CC)CC(CCN2CC3CN(c4cccc(OC)c4)CC3C2)OC1=O]

Example 100: Preparation of 3,3-diethyl-5-(2-(5-(3-methoxyphenyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(3-methoxyphenyl)octahydropyrrolo[3,4-c]pyrrole was substituted for 2-(o-tolyl)octahydropyrrolo[3,4-c]pyrrole: $^1$H NMR (400 MHz, CDCl$_3$) δ7.14 (t, J=8.2 Hz, 1H), 6.30 (m, 2H), 6.20 (t, J=2.2 Hz, 1H), 4.46 (m, 1H), 3.79 (s, 3H), 3.38 (t, J=8.2 Hz, 2H), 3.17 (dt, J=3.0, 9.5 Hz, 2H), 2.94 (b, 2H), 2.86-2.77 (m, 2H), 2.57 (t, J=7.1 Hz, 2H), 2.42 (dd, J=3.9, 9.0 Hz, 2H), 2.11 (dd, J=6.8, 13.0 Hz, 1H), 1.95-1.72 (m, 3H), 1.61 (qd, J=1.5, 7.5 Hz, 4H), 0.91 (dt, J=7.4, 14.8 Hz, 6H); MS (LC/MS, M+H$^+$): m/z 387.2.

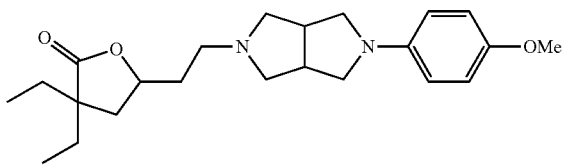 [SMILES: CCC1(CC)CC(CCN2CC3CN(c4ccc(OC)cc4)CC3C2)OC1=O]

Example 101: Preparation of 3,3-diethyl-5-(2-(5-(4-methoxyphenyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(4-methoxyphenyl)octahydropyrrolo[3,4-c]pyrrole was substituted for 2-(o-tolyl)octahydropyrrolo[3,4-c]pyrrole: $^1$H NMR (400 MHz, CDCl$_3$) δ6.83 (d, J=9.0 Hz, 2H), 6.65 (d, J=9.0 Hz, 2H), 4.46 (m, 1H), 3.76 (s, 3H), 3.28 (m, 2H), 3.10 (dt, J=3.2, 9.1 Hz, 2H), 2.92 (b, 2H), 2.84 (b, 2H), 2.63-2.51 (m, 2H), 2.39 (dd, J=4.0, 8.7 Hz, 2H), 2.11 (dd, J=6.8, 13.0 Hz, 1H), 1.97-1.71 (m, 3H), 1.61 (qd, J=1.3, 7.4 Hz, 4H), 0.91 (dt, J=7.3, 14.8 Hz, 6H); MS (LC/MS, M+H$^+$): m/z 387.2.

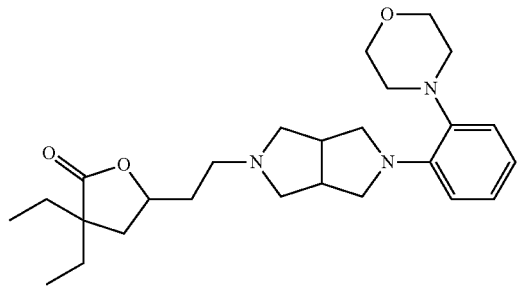 [SMILES: CCC1(CC)CC(CCN2CC3CN(c4ccccc4N4CCOCC4)CC3C2)OC1=O]

Example 102: Preparation of 3,3-diethyl-5-(2-(5-(2-morpholinophenyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 4-(2-(hexahydropyrrolo[3,4-c]pyrrol-2(1H)-yl)phenyl)morpholine hydrochloride was substituted for 2-(o-tolyl)octahydropyrrolo[3,4-c]pyrrole: $^1$H NMR (400 MHz, CDCl$_3$) δ7.05-6.94 (m, 3H), 6.91-6.83 (m, 1H), 4.49 (m, 1H) 3.85 (t, J=4.7 Hz, 4H), 3.68-3.42 (m, 4H), 3.22-2.84 (m, 10H), 2.61 (b, 2H), 2.30 (b, 1H), 2.19 (dd, J=6.7, 13.2 Hz, 1H), 2.05-1.90 (m, 1H), 1.84 (dd, J=9.3, 13.2 Hz, 1H), 1.67-1.56 (m, 4H), 0.91 (dt, J=7.3, 16.5 Hz, 6H); MS (LC/MS, M+H$^+$): m/z 442.2.

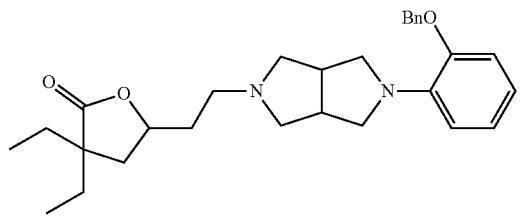 [SMILES: CCC1(CC)CC(CCN2CC3CN(c4ccccc4OCc4ccccc4)CC3C2)OC1=O]

Example 103: Preparation of 5-(2-(5-(2-(benzyloxy)phenyl)hexahydropyrrolo[3,4-c]pyrrol-2(1H)-yl)ethyl)-3,3-diethyldihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(2-(benzyloxy)phenyl)octahydropyrrolo[3,4-c]pyrrole hydrochloride was substituted for 2-(o-tolyl)octahydropyrrolo[3,4-c]pyrrole: $^1$H NMR (400 MHz, CDCl$_3$) δ7.46-7.29 (m, 5H), 7.01-6.86 (m, 3H), 6.81 (dd, J=1.4, 7.7 Hz, 1H), 5.03 (s, 2H), 4.43 (m, 1H), 3.61 (b, 2H), 3.36 (t, J=10.6 Hz, 2H), 3.17-2.97 (m, 3H), 2.91 (td, J=5.3, 12.2 Hz, 1H), 2.86-2.73 (m, 2H), 2.58-2.37 (m, 2H), 2.30 (m, 1H), 2.17 (dd, J=6.7, 13.1 Hz, 1H), 1.92-1.73 (m, 2H), 1.61 (q, J=7.4 Hz, 4H), 0.91 (dt, J=7.0, 13.9 Hz, 6H); MS (LC/MS, M+H$^+$): m/z 463.2.

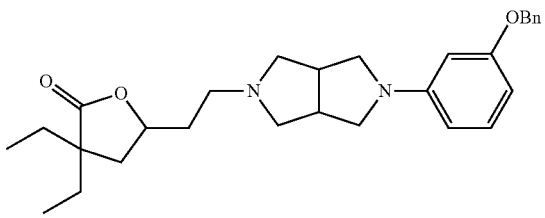 [SMILES: CCC1(CC)CC(CCN2CC3CN(c4cccc(OCc5ccccc5)c4)CC3C2)OC1=O]

Example 104: Preparation of 5-(2-(5-(3-(benzyloxy)phenyl)hexahydropyrrolo[3,4-c]pyrrol-2(1H)-yl)ethyl)-3,3-diethyldihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(3-(benzyloxy)phenyl)octahydropyrrolo[3,4-c]pyrrole hydrochloride was substituted for 2-(o-tolyl)octahydropyrrolo[3,4-c]pyrrole: $^1$H NMR (400 MHz, CDCl$_3$) δ7.39-7.33 (m, 2H), 7.33-7.26 (m, 2H), 7.26-7.20 (m, 1H), 7.05 (m, 1H), 6.29 (dd, J=1.7, 8.1 Hz, 1H), 6.24-6.18 (m, 2H), 4.96 (s, 2H), 4.37 (m, 1H), 3.28 (m, 2H), 3.08 (dt, J=2.9, 9.3 Hz, 2H), 2.93-2.81 (m, 2H), 2.81-2.69 (m, 2H), 2.50 (t, J=7.2 Hz, 2H), 2.33 (dd, J 3.9, 8.9 Hz, 2H), 2.02 (dd, J=6.7, 13.0 Hz, 1H), 1.87-1.63 (m, 3H), 1.52 (qd, J=1.2, 7.4 Hz, 4H), 0.82 (dt, J=7.4, 14.9 Hz, 6H); MS (LC/MS, M+H$^+$): m/z 463.2.

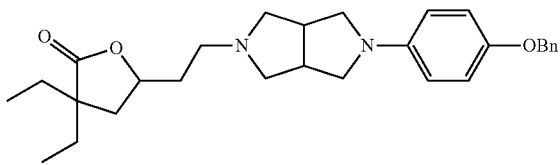 [SMILES: CCC1(CC)CC(CCN2CC3CN(c4ccc(OCc5ccccc5)cc4)CC3C2)OC1=O]

Example 105: Preparation of 5-(2-(5-(4-(benzyloxy)phenyl)hexahydropyrrolo[3,4-c]pyrrol-2(1H)-yl)ethyl)-3,3-diethyldihydrofuran-2(3H)-one: The title compound was prepared according to the procedure for 3,3-diethyl-5-(2-(5-(o-tolyl)hexahydropyrrolo[3,4-c]pyrrol-2(1H)-yl)ethyl)dihydrofuran-2(3H)-one, except 2-(4-(benzyloxy)phenyl)octahydropyrrolo[3,4-c]pyrrole hydrochloride was substituted for 2-(o-tolyl)octahydropyrrolo[3,4-c]pyrrole: $^1$H NMR (400 MHz, CDCl$_3$) δ7.37-7.31 (m, 2H), 7.31-7.25 (m, 2H), 7.24-7.18 (m, 1H), 6.81 (d, J=9.0 Hz, 2H), 6.55 (d, J=9.0 Hz, 2H), 4.92 (s, 2H), 4.37 (m, 1H), 3.19 (m, 2H), 3.01 (dt, J=3.1, 9.3 Hz, 2H), 2.89-2.80 (m, 2H), 2.80-2.70 (m, 2H), 2.48 (t, J=6.9 Hz, 2H), 2.29 (dd, J 3.9, 8.6 Hz, 2H), 2.02 (dd, J=6.7, 13.1 Hz, 1H), 1.87-1.62 (m, 3H), 1.52 (q, J=7.3 Hz, 4H), 0.82 (dt, J=7.5, 14.5 Hz, 6H); MS (LC/MS, M+H$^+$): m/z 463.2.

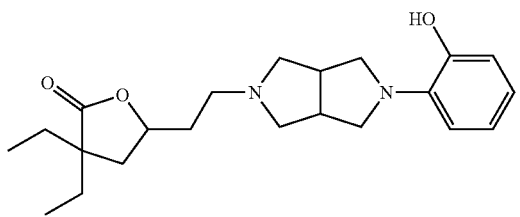 [SMILES: CCC1(CC)CC(CCN2CC3CN(c4ccccc4O)CC3C2)OC1=O]

Example 106: Preparation of 3,3-diethyl-5-(2-(5-(2-hydroxyphenyl)hexahydropyrrolo[3,4-c]pyrrol-2(1H)-yl)ethyl)dihydrofuran-2(3H)-one: To a dry round bottom flask, 0.013 g of 10% Pd/C (20% wt) was added and wet with a small amount of ethyl acetate. Following, a solution of 5-(2-(5-(2-(benzyloxy)phenyl)hexahydropyrrolo[3,4-c]pyrrol-2(1H)-yl)ethyl)-3,3-diethyldihydrofuran-2(3H)-one (0.065 g, 0.140 mmol, 1 eq.) in MeOH (1.5 mL) was added slowly to the Pd/C containing round bottom flask. This system was then flushed 3× with H$_2$, using a balloon filled with H$_2$. The reaction was allowed to stir under 1 atm H$_2$ for overnight at room temperature. The Pd/C was removed via filtration through a plug of Celite. The filtrate was concentrated in vacuo to give a crude residue that was first purified by column chromatography (methanol/dichloromethane, 0%~10%). $^1$H NMR (400 MHz, CDCl$_3$) δ7.13 (dd, J=1.3, 7.8 Hz, 1H), 7.05 (td, J=1.3, 7.7 Hz, 1H), 6.93 (dd, J=1.3, 8.1 Hz, 1H), 6.85 (td, J=1.4, 7.7 Hz, 1H), 4.52 (m, 1H), 3.12-3.00 (m, 2H), 2.98-2.74 (m, 6H), 2.65 (t, J=7.3 Hz, 2H), 2.58-2.46 (m, 2H), 2.16 (dd, J=6.7, 13.1 Hz, 1H), 2.00-1.76 (m, 3H), 1.64 (q, J=7.5 Hz, 4H), 0.95 (dt, J=7.4, 22.8 Hz, 6H); MS (LC/MS, M+H$^+$): m/z 373.2.

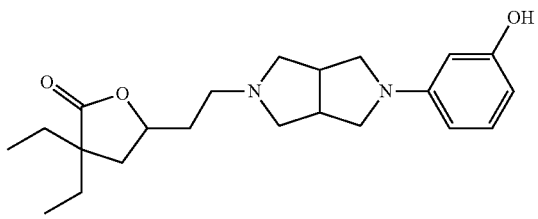

Example 107: Preparation of 3,3-diethyl-5-(2-(5-(3-hydroxyphenyl)hexahydropyrrolo[3,4-c]pyrrol-2(1H)-yl)ethyl)dihydrofuran-2(3H)-one: The title compound was prepared according to the procedure for 3,3-diethyl-5-(2-(5-(2-hydroxyphenyl)hexahydropyrrolo[3,4-c]pyrrol-2(1H)-yl)ethyl)dihydrofuran-2(3H)-one, except 5-(2-(5-(3-(benzyloxy)phenyl) hexahydropyrrolo[3,4-c]pyrrol-2(1H)-yl)ethyl)-3,3-diethyldihydrofuran-2(3H)-one was substituted for 5-(2-(5-(2-(benzyloxy)phenyl)hexahydropyrrolo[3,4-c]pyrrol-2(1H)-yl)ethyl)-3,3-diethyldihydrofuran-2(3H)-one: $^1$H NMR (400 MHz, CDCl$_3$) δ6.85 (t, J=8.1 Hz, 1H), 6.00 (td, J=1.8, 7.6 Hz, 2H), 5.91 (t, J=2.3 Hz, 1H), 4.24 (m, 1H), 3.18-3.05 (m, 2H), 2.97 (d, J=9.2 Hz, 2H), 2.83-2.64 (m, 4H), 2.44 (t, J=7.3 Hz, 2H), 2.25 (m, 2H), 1.91 (dd, J=6.7, 13.1 Hz, 1H), 1.77-1.53 (m, 3H), 1.40 (q, J=7.4 Hz, 4H), 0.70 (dt, J=7.4, 15.6 Hz, 6H); MS (LC/MS, M+H$^+$): m/z 373.2.

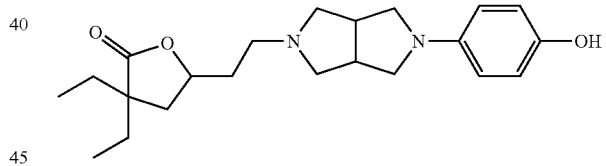

Example 108: Preparation of 3,3-diethyl-5-(2-(5-(4-hydroxyphenyl)hexahydropyrrolo[3,4-c]pyrrol-2(1H)-yl)ethyl)dihydrofuran-2(3H)-one trifluoroacetate: The title compound was prepared according to the procedure for 3,3-diethyl-5-(2-(5-(2-hydroxyphenyl)hexahydropyrrolo[3,4-c]pyrrol-2(1H)-yl)ethyl)dihydrofuran-2(3H)-one, except 5-(2-(5-(4-(benzyloxy)phenyl)hexahydropyrrolo[3,4-c]pyrrol-2(1H)-yl)ethyl)-3,3-diethyldihydrofuran-2(3H)-one was substituted for 5-(2-(5-(2-(benzyloxy)phenyl)hexahydropyrrolo[3,4-c]pyrrol-2(1H)-yl)ethyl)-3,3-diethyldihydrofuran-2(3H)-one and the reaction time was extended to 3 days. A second purification was need via column chromatography on a C18 column. (acetonitrile/H$_2$O, 0%-100%, w/0.1% TFA): $^1$H NMR (400 MHz, MeOD) δ6.78-6.67 (m, 4H), 4.54 (m, 1H), 3.69 (b, 2H), 3.45 (dd, J=7.2, 9.6 Hz, 2H), 3.40-3.09 (m, 6H), 2.98 (m, 2H), 2.28 (dd, J=6.7, 13.2 Hz, 1H), 2.20-1.97 (m, 2H), 1.91 (dd, J=9.4, 13.2 Hz, 1H), 1.74-1.52 (m, 4H), 0.94 (dt, J=5.0, 14.9 Hz, 6H); MS (LC/MS, M+H$^+$): m/z 373.2.

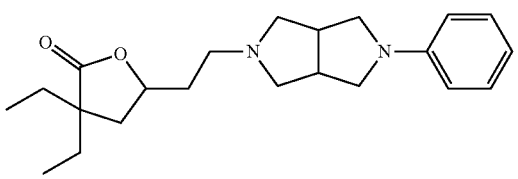 [SMILES: CCC1(CC)CC(CCN2CC3CN(c4ccccc4)CC3C2)OC1=O]

Example 109: Preparation of 3,3-diethyl-5-(2-(5-phenyl-hexahydropyrrolo[3,4-c]pyrrol-2(1H)-yl)ethyl)dihydrofuran-2(3H)-one: The title compound was prepared according to the procedure for 3,3-diethyl-5-(2-(6-phenyl-2,6-diazaspiro[3.3]heptan-2-yl)ethyl)dihydrofuran-2(3H)-one, except 2-phenyloctahydropyrrolo[3,4-c]pyrrole dihydrochloride was substituted for 2-phenyl-2,6-diazaspiro[3.3]heptane trifluoroacetate: $^1$H NMR (400 MHz, CDCl$_3$) δ7.14 (m, 2H), 6.64 (t, J=7.2 Hz, 1H), 6.57 (d, J=8.5 Hz, 2H), 4.37 (m, 1H), 3.29 (t, J=8.1 Hz, 2H), 3.08 (dt, J=2.7, 9.3 Hz, 2H), 2.92-2.79 (b, 2H), 2.78-2.65 (m, 2H), 2.47 (t, J=6.9 Hz, 2H), 2.32 (dd, J=4.0, 8.9 Hz, 2H), 2.02 (dd, J=6.7, 13.1 Hz, 1H), 1.87-1.61 (m, 3H), 1.51 (q, J=7.3 Hz, 4H), 0.81 (dt, J=7.5, 13.9 Hz, 6H); MS (LC/MS, M+H$^+$): m/z 357.2

Formulations

The present invention also relates to compositions or formulations which comprise the sigma-2 receptor binders and sigma-2 receptor activity modulators according to the present invention. In general, the compositions of the present invention comprise an effective amount of one or more compounds of the disclosure and salts thereof according to the present invention which are effective for providing modulation of sigma-2 receptor activity; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in Remington's Pharmaceutical Sciences, 17th edition, ed. Alfonoso R. Gennaro, Mack Publishing Company, Easton, PA (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known sigma-2 receptor activity modulators. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and *arachis* oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.]

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention; and one or more excipients.

Procedures

The following procedure may be utilized in evaluating and selecting compounds as sigma-2 receptor binders and sigma-2 receptor activity modulators.

Radiolabel Binding Studies for the sigma-2 receptor:

A solution of the compound of the disclosure to be tested is prepared as a 1-mg/ml stock in Assay Buffer or DMSO according to its solubility. A similar stock of the reference compound Haloperidol is also prepared as a positive control. Eleven dilutions (5× assay concentration) of the compound of the disclosure and Haloperidol are prepared in the Assay Buffer by serial dilution to yield final corresponding assay concentrations ranging from 10 pM to 10 µM.

A stock concentration of 5 nM $^3$H-1,3-di-(2-tolyl)guanidine ($^3$H-DTG) is prepared in 50 mM Tris-HCl, 10 mM $MgCl_2$, 1 mM EDTA, pH 7.4 (Assay Buffer). Aliquots (50 µl) of radioligand are dispensed into the wells of a 96-well plate containing 100 µl of Assay Buffer. Duplicate 50-µl aliquots of the compound of the disclosure test and Haloperidol positive control reference compound serial dilutions are added.

Membrane fractions of cells expressing recombinant sigma-2 receptors (50 µL) are dispensed into each well. The membranes are prepared from stably transfected cell lines expressing sigma-2 receptors cultured on 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; the membrane preparations are resuspended in 3 ml of chilled Assay Buffer and homogenized by several passages through a 26 gauge needle before using in the assay.

The 250-µl reactions are incubated at room temperature for 1.5 hours, then harvested by rapid filtration onto 0.3% polyethyleneimine-treated, 96-well filter mats using a 96-well Filtermate harvester. Four rapid 500-µl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y = \text{bottom} + [(\text{top} - \text{bottom})/(1 + 10 \times -\log IC_{50})]$$

where bottom equals the residual radioligand binding measured in the presence of 10 µM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki = IC_{50}/(1 + [\text{ligand}]/KD)$$

where [ligand] equals the assay radioligand concentration and KD equals the affinity constant of the radioligand for the target receptor.

Compounds of the disclosure are also screened at a single concentration of 10 µM using the same method described for the Radiolabel Binding Studies for sigma-2 receptors to determine the percent inhibition of $^3$H-DTG binding.

Results for representative compounds according to the present invention are listed in Table 21.

TABLE 21
Radiolabel Binding Studies for the sigma-2 receptors results for exemplary compounds of the disclosure
| Entry | Structure | Sigma-2 IC$_{50}$ (nm) |
|---|---|---|
| 1 | 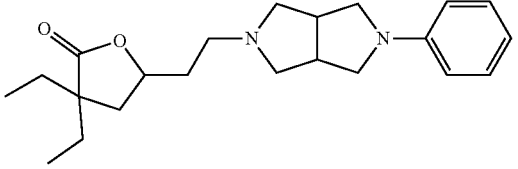 [SMILES: CCC1(CC)CC(CCN2CC3CN(c4ccccc4)CC3C2)OC1=O] | 3.5 |
| 2 | 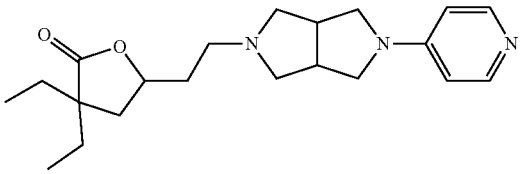 [SMILES: CCC1(CC)CC(CCN2CC3CN(c4ccncc4)CC3C2)OC1=O] | 29 |
| 3 | 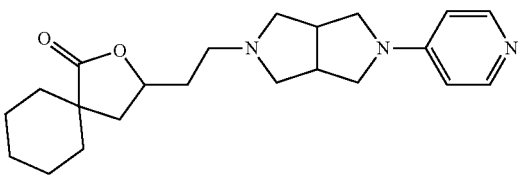 [SMILES: O=C1OC(CCN2CC3CN(c4ccncc4)CC3C2)CC12CCCCC2] | 39 |
| 4 | 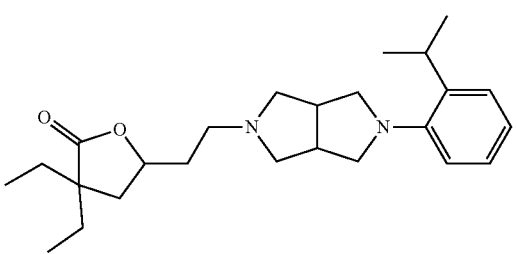 [SMILES: CCC1(CC)CC(CCN2CC3CN(c4ccccc4C(C)C)CC3C2)OC1=O] | 2.0 |
| 5 | 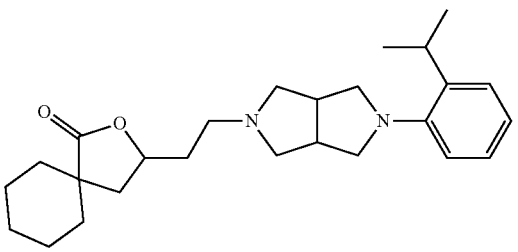 [SMILES: CC(C)c1ccccc1N1CC2CN(CCC3CC4(CCCCC4)C(=O)O3)CC2C1] | 2.4 |
| 6 | 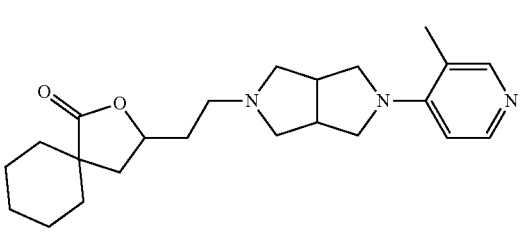 [SMILES: Cc1cnccc1N1CC2CN(CCC3CC4(CCCCC4)C(=O)O3)CC2C1] | 3.9 |
| 7 | 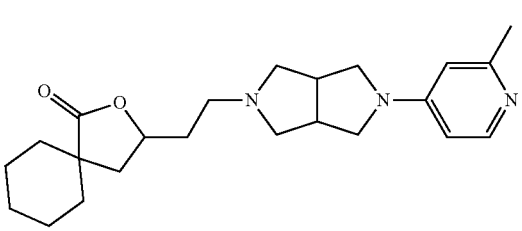 [SMILES: Cc1cc(N2CC3CN(CCC4CC5(CCCCC5)C(=O)O4)CC3C2)ccn1] | 11 |

TABLE 21-continued

Radiolabel Binding Studies for the sigma-2 receptors results for exemplary compounds of the disclosure

| Entry | Structure | Sigma-2 IC$_{50}$ (nm) |
|---|---|---|
| 8 | 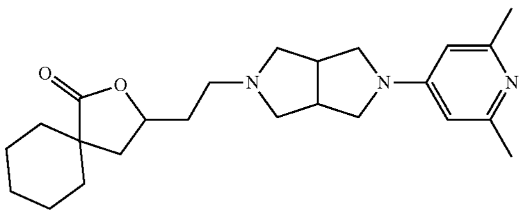 [SMILES: Cc1cc(N2CC3CN(CCC4CC5(CCCCC5)C(=O)O4)CC3C2)cc(C)n1] | 24 |
| 9 | 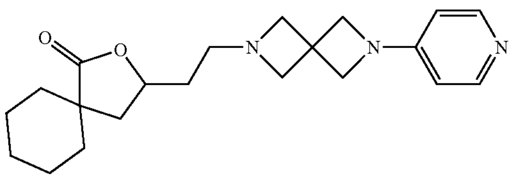 [SMILES: O=C1OC(CCN2CC3(C2)CN(c2ccncc2)C3)CC12CCCCC2] | 34 |
| 10 | 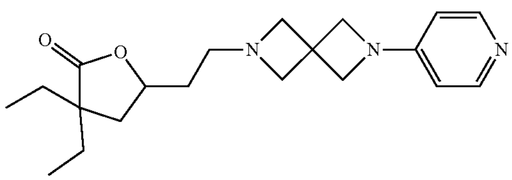 [SMILES: CCC1(CC)CC(CCN2CC3(C2)CN(c2ccncc2)C3)OC1=O] | 59 |
| 11 | 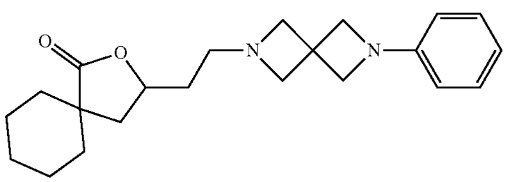 [SMILES: O=C1OC(CCN2CC3(C2)CN(c2ccccc2)C3)CC12CCCCC2] | 30 |
| 12 | 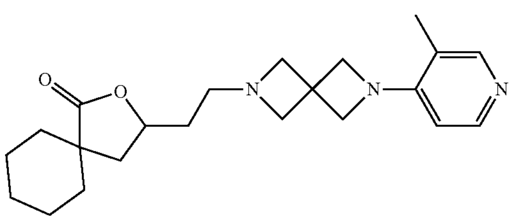 [SMILES: Cc1cnccc1N1CC2(CN(CCC3CC4(CCCCC4)C(=O)O3)C2)C1] | 3.9 |
| 13 | 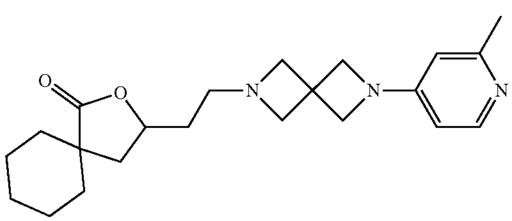 [SMILES: Cc1cc(N2CC3(CN(CCC4CC5(CCCCC5)C(=O)O4)C3)C2)ccn1] | 1.2 |
| 14 | 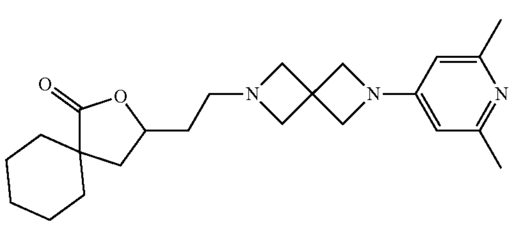 [SMILES: Cc1cc(N2CC3(CN(CCC4CC5(CCCCC5)C(=O)O4)C3)C2)cc(C)n1] | 1.5 |

TABLE 21-continued

Radiolabel Binding Studies for the sigma-2 receptors results for exemplary compounds of the disclosure

| Entry | Structure | Sigma-2 IC$_{50}$ (nm) |
|---|---|---|
| 15 | 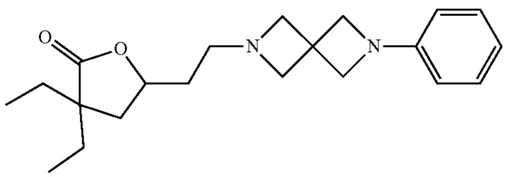 [SMILES: CCC1(CC)CC(CCN2CC3(C2)CN(c2ccccc2)C3)OC1=O] | 53 |
| 16 | 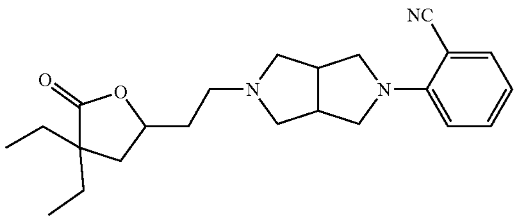 [SMILES: CCC1(CC)CC(CCN2CC3CN(c4ccccc4C#N)CC3C2)OC1=O] | 6.8 |
| 17 | 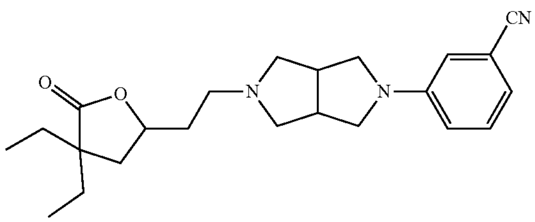 [SMILES: CCC1(CC)CC(CCN2CC3CN(c4cccc(C#N)c4)CC3C2)OC1=O] | 7.0 |
| 18 | 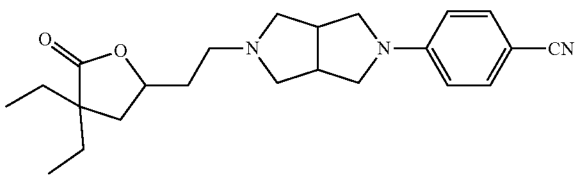 | 9.6 |
| 19 | 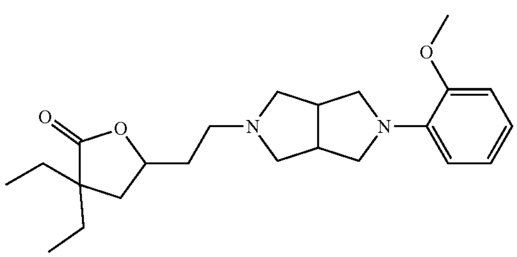 [SMILES: CCC1(CC)CC(CCN2CC3CN(c4ccccc4OC)CC3C2)OC1=O] | 6.5 |
| 20 | 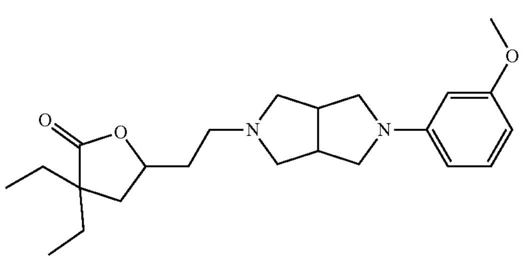 [SMILES: CCC1(CC)CC(CCN2CC3CN(c4cccc(OC)c4)CC3C2)OC1=O] | 25 |
| 21 | 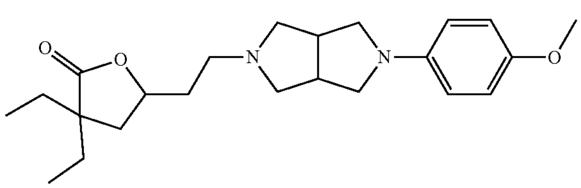 [SMILES: CCC1(CC)CC(CCN2CC3CN(c4ccc(OC)cc4)CC3C2)OC1=O] | 22 |

What is claimed is:

1. A compound having formula (VIII):

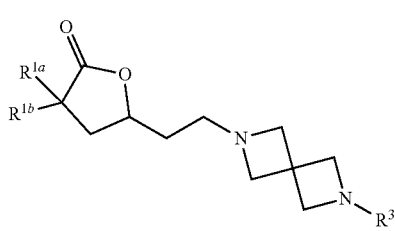

or a pharmaceutically acceptable salt thereof, wherein:
$R^{1a}$ and $R^{1b}$ are each independently selected from the group consisting of hydrogen, $C_{1-6}$ linear alkyl, and $C_{1-6}$ branched alkyl, $R^{1a}$ and $R^{1b}$ may be taken together with the atom to which they are bound to form a cyclohexyl; and
$R^3$ is optionally substituted phenyl or optionally substituted pyridyl.

2. The compound of claim 1, wherein $R^{1a}$ and $R^{1b}$ are each independently $C_{1-6}$ linear alkyl or $C_{1-6}$ branched alkyl.

3. The compound of claim 2, wherein $R^{1a}$ and $R^{1b}$ are each independently methyl or ethyl.

4. The compound of claim 1, wherein $R^3$ is selected from a group consisting of phenyl, 4-OH-phenyl, 3-OH-phenyl, 2-OH-phenyl, 4-CH₃-phenyl, 3-CH₃-phenyl, 2-CH₃-phenyl, 4-OCH₃-phenyl, 3-OCH₃-phenyl, 2-OCH₃-phenyl, 4-CN-phenyl, 3-CN-phenyl, 2-CN-phenyl, 4-F-phenyl, 3-F-phenyl, 2-F-phenyl, 4-Cl-phenyl, 3-Cl-phenyl, 2-Cl-phenyl, 4-OCF₃-phenyl, 3-OCF₃-phenyl, 2-OCF₃-phenyl, 4-isopropyl-phenyl, 3-isopropyl-phenyl, 2-isopropyl-phenyl, 4-cyclopropyl-phenyl, 3-cyclopropyl-phenyl, 2-cyclopropyl-phenyl, 4-morpholino-phenyl, 3-morpholino-phenyl, 2-morpholino-phenyl, 2-pyridyl, 3-pyridyl, 4-pyridyl, 2-CH₃-4-pyridyl, 3-CH₃-4-pyridyl, 3,5-dimethylpyridin-4-yl, 2,6-dimethylpyridin-4-yl, 2-CF₃-phenyl, 3-CF₃-phenyl, 4-CF₃-phenyl, 2-NH₂-phenyl, 3-NH₂-phenyl, 4-NH₂-phenyl, 2-tBu-phenyl, 3-tBu-phenyl, 4-tBu-phenyl, 2-NO₂-phenyl, 3-NO₂-phenyl, 4-NO₂-phenyl, 2-SCH₃-phenyl, 3-SCH₃-phenyl, 4-SCH₃-phenyl, 2-SO₂CH₃-phenyl, 3-SO₂CH₃-phenyl, 4-SO₂CH₃-phenyl, 2-SO₂NH₂-phenyl, 3-SO₂NH₂-phenyl, 4-SO₂NH₂-phenyl, 2-CO₂NH₂-phenyl, 3-CO₂NH₂-phenyl, 4-CO₂NH₂-phenyl, 2-Br-phenyl, 3-Br-phenyl, 4-Br-phenyl, 2,3-di-CH₃-phenyl, 2,4-di-CH₃-phenyl, 2,5-di-CH₃-phenyl, 2,6-di-CH₃-phenyl, 3,4-di-CH₃-phenyl, 3,5-di-CH₃-phenyl, 2,3-di-Cl-phenyl, 2,4-di-Cl-phenyl, 2,5-di-Cl-phenyl, 2,6-di-Cl-phenyl, 3,4-di-Cl-phenyl, 3,5-di-Cl-phenyl, 2-morpholino-4-CH₃-phenyl, 2-morpholino-4-CN-phenyl, 2-morpholino-4-OH-phenyl, 2,3-dimethylpyridin-4-yl, and 3,6-dimethylpyridin-4-yl.

5. The compound of claim 4, wherein $R^3$ is unsubstituted phenyl, 4-pyridyl, 3-CH₃-4-pyridyl, 2-CH₃-4-pyridyl, or 2,6-dimethylpyridin-4-yl.

6. The compound of claim 1, wherein the compound is selected from a group consisting of

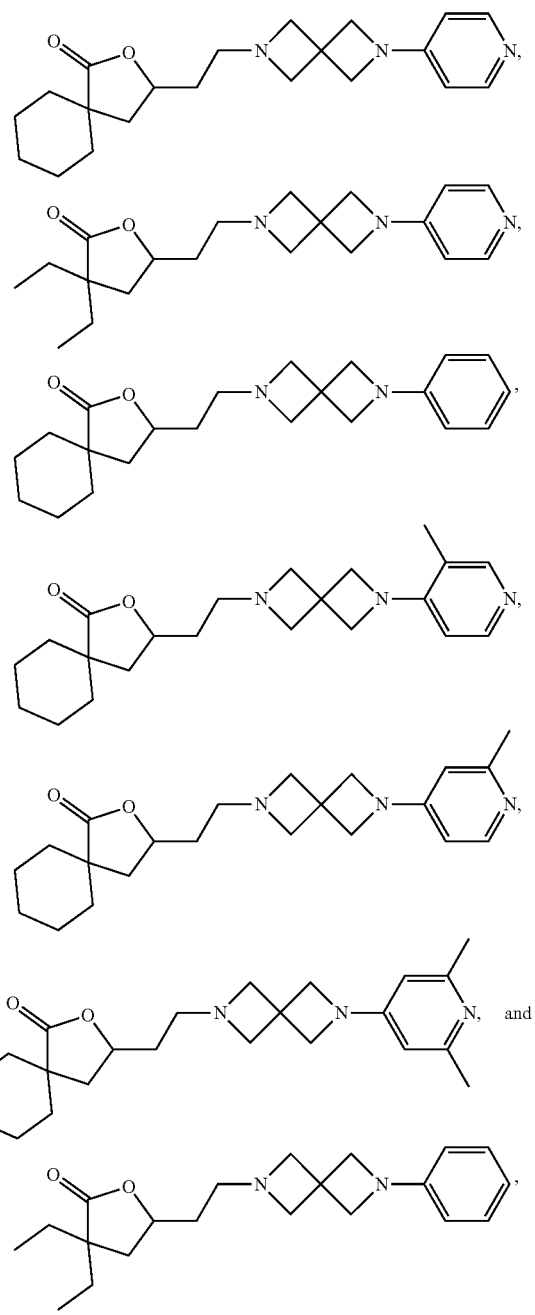

or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 11,820,774 B2 |
| APPLICATION NO. | : 17/154761 |
| DATED | : November 21, 2023 |
| INVENTOR(S) | : Benjamin E. Blass, Daniel J. Canney and Kevin M. Blattner |

It is certified that error appears in the above-identified patent and that said Letters Patent is hereby corrected as shown below:

In the Specification

Column 1, delete Lines 19-23
Replace with --This invention was made with government support under HHSN-271-2008-00025-C, and R41 AG052249-01 awarded by the National Institutes of Health. The government has certain rights in the invention.--

Signed and Sealed this
Twenty-third Day of April, 2024

Katherine Kelly Vidal
*Director of the United States Patent and Trademark Office*